US009669399B2

(12) United States Patent
Shekhar et al.

(10) Patent No.: US 9,669,399 B2
(45) Date of Patent: *Jun. 6, 2017

(54) PHOSPHINE LIGANDS FOR CATALYTIC REACTIONS

(71) Applicant: AbbVie Inc., North Chicago, IL (US)

(72) Inventors: Shashank Shekhar, Vernon Hills, IL (US); Thaddeus S. Franczyk, Lake Villa, IL (US); David M. Barnes, Bristol, WI (US); Travis B. Dunn, Gurnee, IL (US); Anthony R. Haight, Wadsworth, IL (US); Vincent S. Chan, Evanston, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/164,002

(22) Filed: May 25, 2016

(65) Prior Publication Data

US 2016/0263566 A1 Sep. 15, 2016

Related U.S. Application Data

(63) Continuation of application No. 14/834,420, filed on Aug. 24, 2015, now Pat. No. 9,381,508, which is a
(Continued)

(51) Int. Cl.
| | | |
|---|---|---|
| *C07F 9/6568* | (2006.01) | |
| *C07C 303/40* | (2006.01) | |
| *B01J 31/24* | (2006.01) | |
| *C07D 209/12* | (2006.01) | |
| *C07D 213/76* | (2006.01) | |
| *C07D 239/54* | (2006.01) | |
| *C07C 253/30* | (2006.01) | |
| *C07C 201/10* | (2006.01) | |
| *C07D 209/34* | (2006.01) | |
| *C07D 265/30* | (2006.01) | |
| *C07C 1/30* | (2006.01) | |
| *C07C 17/093* | (2006.01) | |

(Continued)

(52) U.S. Cl.
CPC ......... *B01J 31/2423* (2013.01); *B01J 31/249* (2013.01); *B01J 31/2419* (2013.01); *B01J 31/2438* (2013.01); *B01J 31/2466* (2013.01); *B01J 31/2485* (2013.01); *C07C 1/26* (2013.01); *C07C 1/30* (2013.01); *C07C 1/321* (2013.01); *C07C 17/093* (2013.01); *C07C 17/2635* (2013.01); *C07C 17/361* (2013.01); *C07C 41/01* (2013.01); *C07C 41/30* (2013.01); *C07C 45/61* (2013.01); *C07C 45/68* (2013.01); *C07C 45/71* (2013.01); *C07C 201/10* (2013.01); *C07C 253/14* (2013.01); *C07C 253/30* (2013.01); *C07C 273/1854* (2013.01); *C07C 273/1863* (2013.01); *C07C 303/36* (2013.01); *C07C 303/40* (2013.01); *C07C 319/14* (2013.01); *C07D 209/12* (2013.01); *C07D 209/34* (2013.01); *C07D 209/42* (2013.01); *C07D 213/76* (2013.01); *C07D 239/54* (2013.01); *C07D 265/30* (2013.01); *C07D 295/033* (2013.01); *C07F 1/02* (2013.01); *C07F 5/025* (2013.01); *C07F 5/04* (2013.01); *C07F 9/4021* (2013.01); *C07F 9/4841* (2013.01); *C07F 9/505* (2013.01); *C07F 9/509* (2013.01); *C07F 9/5072* (2013.01); *C07F 9/5722* (2013.01); *C07F 9/65036* (2013.01); *C07F 9/65583* (2013.01); *C07F 9/65683* (2013.01); *C07F 9/657163* (2013.01); *B01J 31/189* (2013.01); *B01J 2231/4211* (2013.01); *B01J 2231/4227* (2013.01); *B01J 2231/4277* (2013.01); *B01J 2231/4283* (2013.01); *B01J 2231/4288* (2013.01); *B01J 2231/4294* (2013.01); *B01J 2231/44* (2013.01); *B01J 2531/0205* (2013.01); *B01J 2531/0266* (2013.01); *B01J 2531/0288* (2013.01); *B01J 2531/824* (2013.01); *B01J 2540/10* (2013.01); *B01J 2540/40* (2013.01); *C07C 2531/24* (2013.01); *C07C 2531/26* (2013.01); *Y02P 20/52* (2015.11)

(58) Field of Classification Search
CPC ..................... C07F 9/65683; C07C 303/40
See application file for complete search history.

(56) References Cited

U.S. PATENT DOCUMENTS 4,239,888 A 12/1980 Miller
4,588,729 A 5/1986 Teranishi et al.
(Continued)

FOREIGN PATENT DOCUMENTS

DE 19920847 A1 11/2000
EP 0647648 A1 4/1995
(Continued)

OTHER PUBLICATIONS

Alcaraz L., et al., "Novel N-aryl and N-heteroaryl Sulfamide Synthesis Via Palladium Cross Coupling," Organic Letters, 2004, vol. 6 (16), pp. 2705-2708.
(Continued)

*Primary Examiner* — Joseph Kosack
(74) *Attorney, Agent, or Firm* — Neal, Gerber & Eisenberg LLP

(57) ABSTRACT

The disclosure is directed to: (a) phosphacycle ligands; (b) catalyst compositions comprising phosphacycle ligands; and (c) methods of using such phosphacycle ligands and catalyst compositions in bond forming reactions.

20 Claims, No Drawings

Related U.S. Application Data continuation of application No. 14/611,943, filed on Feb. 2, 2015, now Pat. No. 9,200,021, which is a continuation of application No. 13/591,117, filed on Aug. 21, 2012, now Pat. No. 8,975,443, which is a continuation-in-part of application No. 13/184,425, filed on Jul. 15, 2011, now Pat. No. 8,841,487.

(60) Provisional application No. 61/365,293, filed on Jul. 16, 2010.

(51) Int. Cl.

| | |
|---|---|
| C07C 41/01 | (2006.01) |
| C07C 45/71 | (2006.01) |
| C07C 253/14 | (2006.01) |
| C07C 273/18 | (2006.01) |
| C07C 303/36 | (2006.01) |
| C07C 319/14 | (2006.01) |
| C07D 209/42 | (2006.01) |
| C07D 295/033 | (2006.01) |
| C07F 5/02 | (2006.01) |
| C07F 9/40 | (2006.01) |
| C07C 1/32 | (2006.01) |
| C07C 45/68 | (2006.01) |
| C07F 1/02 | (2006.01) |
| C07F 9/50 | (2006.01) |
| C07C 1/26 | (2006.01) |
| C07C 17/263 | (2006.01) |
| C07C 17/361 | (2006.01) |
| C07C 41/30 | (2006.01) |
| C07C 45/61 | (2006.01) |
| C07F 5/04 | (2006.01) |
| C07F 9/48 | (2006.01) |
| C07F 9/572 | (2006.01) |
| C07F 9/6503 | (2006.01) |
| C07F 9/6558 | (2006.01) |
| C07F 9/6571 | (2006.01) |
| B01J 31/18 | (2006.01) |

(56) References Cited

U.S. PATENT DOCUMENTS

| | | |
|---|---|---|
| 4,731,472 A | 3/1988 | Pietruszkiewicz et al. |
| 4,873,238 A | 10/1989 | Kinney et al. |
| 4,958,023 A | 9/1990 | Kinney et al. |
| 5,084,084 A | 1/1992 | Satow et al. |
| 5,127,935 A | 7/1992 | Satow et al. |
| 5,154,755 A | 10/1992 | Satow et al. |
| 5,162,326 A | 11/1992 | Naka et al. |
| 5,164,396 A | 11/1992 | Grosscurt et al. |
| 5,455,377 A | 10/1995 | Ronchi et al. |
| 5,508,438 A | 4/1996 | Broger et al. |
| 6,031,105 A | 2/2000 | Wright |
| 6,307,087 B1 | 10/2001 | Buchwald et al. |
| 6,380,387 B1 | 4/2002 | Sidduri et al. |
| 6,395,916 B1 | 5/2002 | Buchwald et al. |
| 6,537,948 B1 | 3/2003 | Tohyama et al. |
| 6,867,310 B1 | 3/2005 | Buchwald et al. |
| 6,946,560 B2 | 9/2005 | Buchwald et al. |
| 7,026,498 B2 | 4/2006 | Buchwald et al. |
| 7,223,879 B2 | 5/2007 | Buchwald et al. |
| 7,247,731 B2 | 7/2007 | Buchwald et al. |
| 7,560,582 B2 | 7/2009 | Buchwald et al. |
| 7,560,596 B2 | 7/2009 | Buchwald et al. |
| 7,858,784 B2 | 12/2010 | Buchwald et al. |
| 8,158,631 B2 | 4/2012 | Chin et al. |
| 8,415,351 B2 | 4/2013 | Wagner et al. |
| 8,501,238 B2 | 8/2013 | Flentge et al. |
| 8,841,487 B2 * | 9/2014 | Shekhar .............. B01J 31/2423 548/111 |
| 8,975,443 B2 * | 3/2015 | Shekhar .............. B01J 31/2423 549/221 |
| 9,200,021 B2 * | 12/2015 | Shekhar .............. B01J 31/2423 |
| 9,266,913 B2 * | 2/2016 | Shekhar .............. B01J 31/2423 |
| 9,381,508 B2 * | 7/2016 | Shekhar .............. C07C 1/30 |
| 2004/0106512 A1 | 6/2004 | Mackewitz et al. |
| 2005/0143349 A1 | 6/2005 | Bridges |
| 2005/0143422 A1 | 6/2005 | Levin et al. |
| 2006/0142269 A1 | 6/2006 | Dykes |
| 2009/0287016 A1 | 11/2009 | Buchwald et al. |
| 2010/0204218 A1 | 8/2010 | Takahashi et al. |
| 2011/0005533 A1 | 1/2011 | Evans |
| 2011/0015401 A1 | 1/2011 | Buchwald et al. |
| 2011/0213176 A1 | 9/2011 | Ishii et al. |
| 2012/0014913 A1 | 1/2012 | Shekhar et al. |
| 2012/0022252 A1 | 1/2012 | Shekhar et al. |
| 2013/0165673 A1 | 6/2013 | Bailly et al. |

FOREIGN PATENT DOCUMENTS

| | | |
|---|---|---|
| JP | 5213755 A | 8/1993 |
| JP | H0736069 A | 2/1995 |
| WO | WO-9209545 A2 | 6/1992 |
| WO | WO-9502567 A1 | 1/1995 |
| WO | WO-9705117 A1 | 2/1997 |
| WO | WO-9718179 A1 | 5/1997 |
| WO | WO-9815515 A1 | 4/1998 |
| WO | WO-9824429 A1 | 6/1998 |
| WO | WO-9918057 A1 | 4/1999 |
| WO | WO-9928290 A1 | 6/1999 |
| WO | WO-9943643 A2 | 9/1999 |
| WO | WO-0004865 A2 | 2/2000 |
| WO | WO-0005199 A1 | 2/2000 |
| WO | WO-0002887 B1 | 8/2000 |
| WO | WO-0119761 A2 | 3/2001 |
| WO | WO-0138337 A2 | 5/2001 |
| WO | WO-0142179 A1 | 6/2001 |
| WO | WO-0142225 A2 | 6/2001 |
| WO | WO-0190121 A2 | 11/2001 |
| WO | WO-0204445 A1 | 1/2002 |
| WO | WO-0142225 A3 | 2/2002 |
| WO | WO-0246150 A2 | 6/2002 |
| WO | WO-02085838 A1 | 10/2002 |
| WO | WO-03013502 A1 | 2/2003 |
| WO | WO-03053971 A1 | 7/2003 |
| WO | WO-03066570 A1 | 8/2003 |
| WO | WO-03074169 A2 | 9/2003 |
| WO | WO-2004013094 A2 | 2/2004 |
| WO | WO-2004018414 A2 | 3/2004 |
| WO | WO-2004018428 A1 | 3/2004 |
| WO | WO-2004018461 A2 | 3/2004 |
| WO | WO-2004031195 A1 | 4/2004 |
| WO | WO-2004052939 A2 | 6/2004 |
| WO | WO-2005021500 A1 | 3/2005 |
| WO | WO-2005065683 A1 | 7/2005 |
| WO | WO-2005079378 A2 | 9/2005 |
| WO | WO-2006051378 A1 | 5/2006 |
| WO | WO-2006064218 A1 | 6/2006 |
| WO | WO-2006066174 A1 | 6/2006 |
| WO | WO-2006074315 A2 | 7/2006 |
| WO | WO-2006095263 A1 | 9/2006 |
| WO | WO-2006097817 A1 | 9/2006 |
| WO | WO-2007133637 A2 | 11/2007 |
| WO | WO-2009010454 A2 | 1/2009 |
| WO | WO-2009039127 A1 | 3/2009 |
| WO | WO-2009039134 A1 | 3/2009 |
| WO | WO-2009039135 A1 | 3/2009 |
| WO | WO-2009076622 A2 | 6/2009 |
| WO | WO-2010010017 A1 | 1/2010 |
| WO | WO-2010051926 A2 | 5/2010 |
| WO | WO-2010111348 A1 | 9/2010 |
| WO | WO-2011008618 A1 | 1/2011 |
| WO | WO-2011008725 A2 | 1/2011 |
| WO | WO-2011071840 A1 | 6/2011 |
| WO | WO-2011072275 A2 | 6/2011 |
| WO | WO-2011082400 A2 | 7/2011 |

(56) References Cited

FOREIGN PATENT DOCUMENTS

| WO | WO-2011133795 A2 | 10/2011 |
|----|------------------|---------|
| WO | WO-2011146358 A1 | 11/2011 |

OTHER PUBLICATIONS

Anderson S., et al., "Benzofuran Trimers for Organic Electroluminescence," Chemistry—A European Journal, 2004, vol. 10 (2), pp. 518-527.
Ansel H.C., et al., Ansel's Pharmaceutical Dosage forms and Drug Delivery Systems, 8th Edition, Lippincott Williams & Wilkins, 2005, Table of Contents.
Audisio D., et al., "A Convenient and Expeditious Synthesis of 3-(n-substituted) Aminocoumarins Via Palladium-catalyzed Buchwald-hartwig Coupling Reaction," Tetrahedron Letters, 2007, vol. 48 (39), pp. 6928-6932.
Aulton M.E., ed., The Design of Dosage Forms : in Pharmaceutics: The Science of Dosage Form Design, 2nd Edition, Churchill Livingstone, 2004, Table of Contents.
Austin W.B., et al., "Facile Synthesis of Ethynylated Benzoic Acid Derivatives and Aromatic Compounds via Ethynyltrimethylsilane," Journal of Organic Chemistry, 1981, vol. 46 (11), pp. 2280-2286.
Baltrushis R.S., et al., "Bromo Derivatives of 1-(4-hydroxyphenyl)dihydrouracil and -(4-hhydroxyphenyl)-5- or -6-Methyldihydrouracils," Chemistry of Heterocyclic Compounds, 1982, vol. 18 (9), pp. 1251-1254.
Bates R.W., et al., "Synthesis of Phenolic Natural Products Using Palladium Catalyzed Coupling Reactions," Tetrahedron, 1995, vol. 51 (30), pp. 8199-8212.
Bhuyan R., et al., "Efficient Copper-Catalyzed Benzylic Amidation With Anhydrous Chloramine-T," Organic Letters , 2007, vol. 9 (20), pp. 3957-3959.
Blight K.J., et al., "Efficient Initiation of HCV RNA Replication in Cell Culture," 2000, vol. 290 (5498), pp. 1972-1974.
Blight K.J., et al., "Efficient Replication of Hepatitis C Virus Genotype 1 a RNAs in Cell Culture," 2003, vol. 77 (5), pp. 3181-3190.
Bonnaventure I., et al., "Probing the Importance of the Hemilabile Site of Bis(phosphine) Monoxide Ligands in the Copper-Catalyzed Addition of Diethylzinc to N-Phosphinoylimines: Discovery of New Effective Chiral Ligands," The Journal of Organic Chemistry, 2008, vol. 73 (16), pp. 6330-6340.
Burk M.J., et al., "C2-symmetric bis(phospholanes) and their use in highly enantioselective hydrogenation reactions," Journal of the American Chemical Society , 1991, vol. 113 (22), pp. 8518-8519.
Burk M.J., et al., "Modular Phospholane Ligands in Asymmetric Catalysis," Accounts of Chemical Research , 2000, vol. 33 (6), pp. 363-372.
Burk M.J., et al., "Preparation and Use of C2-Symmetric Bis(phospholanes): Production of a-amino Acid Derivatives via Highly Enantioselective Hydrogenation Reactions," Journal of the American Chemical Society , 1993, vol. 115, pp. 10125-10138.
Burton G., et al., "Palladium-catalyzed Intermolecular Coupling of Aryl Chlorides and Sulfonamides Under Microwave Irradiation," Organic Letters, 2003, vol. 5 (23), pp. 4373-4376.
Chan J., et al., "Rh(li)-Catalyzed Intermolecular Oxidative Sulfamidation of Aldehydes: A Mild Efficient Synthesis of N-Sulfonylcarboxamides," Journal of the American Chemical Society , 2007, vol. 129 (46), pp. 14106-14107.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
Diaz A.A., et al., "Facile Synthesis of Unsymmetrical 9-phospha- and 9-arsafluorenes," Inorganic Chemistry, 2006, vol. 45 (14), pp. 5568-5575.

Driver M.S., et al., "Carbon-Nitrogen-Bond-Forming Reductive Elimination of Arylamines from Palladium(II) Phosphine Complexes," Journal of the American Chemical Society , 1997, vol. 119 (35), pp. 8232-8245.
Erre G., et al., "Novel Rhodium Catalyst for Asymmetric Hydrofomylation of Styrene: Study of Electronic and Steric Effects of Phosphorus Seven-Membered Ring Ligands," Journal of Molecular Catalysis A: Chemical, 2008, vol. 280, pp. 148-155.
Fleury-Bregeot N., et al., "Stereospecific Synthesis, Structural Characterisation and Resolution of 2-Phospha[3]ferrocenophane Derivatives—a New Chiral Scaffold," European Journal of Inorganic Chemistry, 2007, pp. 3853-3862.
Fors B.P., et al., "An Efficient System for the Pd-Catalyzed Cross-Coupling of Amides and Aryl Chlorides," Tetrahedron, 2009, vol. 65 (33) , pp. 6576-6583.
Fors B.P., et al., "Water-Mediated Catalyst Preactivation: An Efficient Protocol for C-N Cross-Coupling Reactions," Organic Letters, 2008, vol. 10 (16), pp. 3505-3508.
Giner X., et al., "(Triphenyl Phosphite)Gold(I)-Catalyzed Intermolecular Hydroamination of Alkenes and 1,3-Dienes," Organic Letters, 2008, vol. 10 (14), pp. 2919-2922.
Gravel M., et al., "Practical Procedure for the Preparation of Functionalized (E)-1-Alkenylboronic Acids Including the Unprecedented 1-Alkoxycarbonyl Derivatives," 2004, vol. 36 (6), pp. 573-579.
Hartwig J.F., "Electronic Effects on Reductive Elimination to Form Carbon-carbon and Carbon-heteroatom Bonds from Palladium(ii) Complexes," Inorganic Chemistry, 2007, vol. 46 (6), pp. 1936-1947.
Hellwinkel D., "Bis(2,2'-biphenylylene)phosphorane and the Bis(2,2'-biphenylylene)phosphoranyl Radical," Angewandte Chemie International Edition, 1966, vol. 5 (11), pp. 968.
Hicks J.D., et al., "Pd-catalyzed N-arylation of Secondary Acyclic Amides: Catalyst Development, Scope, and Computational Study," Journal of the American Chemical Society, 2009, vol. 131 (46), pp. 16720-16734.
Hilfiker R., et al., "Relevance of Solid-state Properties for Pharmaceutical Products," Polymorphism, 2006, pp. 1-19.
Hocher T., et al., "Novel [2]ferrocenophanes: Syntheses, redox properties and molecular structures of [Fe{(n5-C5H4)CMe2}2PR] (R=Ph, Cy)," Polyhedron, 2005, vol. 24 (11), pp. 1340-1346.
Hogermeier J., et al., "Nine Times Fluoride can be Good for your Syntheses. Not just Cheaper: Nonafluorobutanesulfonates as Intermediates for Transition Metal-catalyzed Reactions," Advanced Synthesis & Catalysis , 2009, vol. 351 (17), pp. 2747-2763.
Huang X., et al., "Expanding Pd-Catalyzed C—N Bond-Forming Processes: the First Amidation of Aryl Sulfonates, Aqueous Amination, and Complementarity with Cu-Catalyzed Reactions," Journal of the American Chemical Society, 2003, vol. 125 (22), pp. 6653-6655.
Ikawa T., et al., "Pd-catalyzed Amidation of Aryl Chlorides Using Monodentate Biaryl Phosphine Ligands: a Kinetic, Computational, and Synthetic Investigation," Journal of the American Chemical Society, 2007, vol. 129 (43), pp. 13001-13007.
International Preliminary Report on Patentability and Written Opinion for Application No. PCT/US2008/076576, mailed on Feb. 12, 2010, 38 pages.
International Preliminary Report on Patentability and Written Opinion for Application No. PCT/US2008/076592, mailed on Mar. 24, 2010, 7 pages.
International Preliminary Report on Patentability and Written Opinion for Application No. PCT/US2008/076594, mailed on Mar. 24, 2010, 7 pp.
International Search Report and Written Opinion for Application No. PCT/US2011/044282, mailed on Dec. 5, 2011, 11 pages.
International Search Report and Written Opinion for Application No. PCT/US2013/056061, mailed on Feb. 3, 2014, 18 pages.
International Search Report for Application No. PCT/US2008/076576, mailed on Dec. 22, 2008, 4 pages.
International Search Report for Application No. PCT/US2008/076592, mailed on Feb. 16, 2009, 2 pages.
International Search Report for Application No. PCT/US2008/076594, mailed on Dec. 30, 2008, 2 pages.

(56) References Cited

OTHER PUBLICATIONS

International Search Report for Application No. PCT/US2011/044283, mailed on Jan. 30, 2012.
Jacobsen M.F., et al., "Efficient N-Arylation and N-Alkenylation of the Five DNA/RNA Nucleobases," Journal of Organic Chemistry, 2006, vol. 71 (24), pp. 9183-9190.
Jiang H., et al., "Organocatalytic Preparation of Simple B-Hydroxy and B-Amino Esters: Low Catalyst Loadings and Gram-Scale Synthesis," Organic Letters, 2010, vol. 12 (21), pp. 5052-5055.
Kadyrov R., et al., "Efficient Enantioselective Synthesis of Optically Active Diols by Asymmetric Hydrogenation with Modular Chiral Metal Catalysts," Angewandte Chemie International Edition, 2009, vol. 48 (41), pp. 7556-7559.
King J.F., et al., "Tert-Butyl Cation Formation in the Hydrolysis of 2-Methyl-2-propanesulfonyl Chloride, the Simplest Tertiary Alkanesulfonyl Chloride," The Journal of Organic Chemistry, 1995, vol. 60 (9), pp. 2831-2834.
Knopfel T.F., et al., "The First Conjugate Addition Reaction of Terminal Alkynes Catalytic in Copper: Conjugate Addition of Alkynes in Water," Journal of the American Chemical Society, 2003, vol. 125 (20), pp. 6054-6055.
Koch U., et al., "2-(2-Thienyl)-5,6-dihydroxy-4-carboxypyrimidines as Inhibitors of the Hepatitis C Virus NS5B Polymerase: Discovery, SAR, Modeling, and Mutagenesis," Journal of Medicinal Chemistry, 2006, vol. 49 (5), pp. 1693-1705.
Kolesinska B., et al., "The Umpolung of Substituent Effect in Nucleophilic Aromatic Substitution. A New Approach to the Synthesis of N, N-Disubstituted Melamines (Triazine Triskelions) Under Mild Reaction Conditions," Tetrahedron, 2009, vol. 65 (18), pp. 3573-3576.
Kurz L., et al., "Stereospecific Functionalization of (R)-(−)-1,1'-Bl-2.Naphthol Triflate," Tetrahedron Letters, 1990, vol. 31 (44), pp. 6321-6324.
Kuwabe S.I., et al., "Palladium-Catalyzed Intramolecular C—O Bond Formation," Journal of the American Chemical Society, 2001, vol. 123 (49), pp. 12202-12206.
Lal G.S. et al., "A Convenient Synthesis of 5-Fluoropyrimidines Using 1-(Chloromethyl)-4-fluoro-1,4-diazabicyclo[2.2.2]octane Bis(tetrafluoroborate)-SELECTFLUOR Reagent," J. Org. Chem, vol. 60 (22), pp. 7340-2, 1995.
Li Z., et al., "Brønsted Acid Catalyzed Addition of Phenols, Carboxylic Acids, and Tosylamides to Simple Olefins," Organic Letters, 2006, vol. 8 (19), pp. 4175-4178.
Liu Z., et al., "Facile N-Arylation of Amines and Sulfonamides and O-Arylation of Phenols and Arenecarboxylic Acids," The Journal of Organic Chemistry, 2006, vol. 71 (8), pp. 3198-3209.
Lohmann V., et al., "Replication of Subgenomic Hepatitis C Virus RNAs in a Hepatoma Cell Line," Science, 1999, vol. 285 (5424), pp. 110-113.
Mann G., et al., "Carbon-Sulfur Bond-Forming Reductive Elimination Involving sp-, sp2-, and sp3-Hybridized Carbon. Mechanism, Steric Effects, and Electronic Effects on Sulfide Formation," Journal of the American Chemical Society, 1998, vol. 120 (36), pp. 9205-9219.
Marcotullio M.C., et al., "A New, Simple Synthesis of N-Tosyl Pyrrolidines and Piperidines," Synthesis, 2006, vol. 16 (16), pp. 2760-2766.
Maruyama T., et al., "A New Method for the Synthesis of N-phenyluracil and -pyrimidine Nucleosides," Journal of the Chemical Society, Perkin Transactions 1, 1995, pp. 733-734.
Mathe C., et al., "L-nucleoside Enantiomers as Antivirals Drugs: A Mini-review," Antiviral Research, 2006, vol. 71, pp. 276-281.
Mathew J.S., et al., "Investigations of Pd-catalyzed Arx Coupling Reactions Informed by Reaction Progress Kinetic Analysis," The Journal of Organic Chemistry, 2006, vol. 71 (13), pp. 4711-4722.
Messaoudi S., et al., "Rapid Access to 3-(N-substituted)-aminoquinolin-2(1H)-ones using Palladium-catalyzed C—N Bond Coupling Reaction," Tetrahedron, 2007, vol. 63 (41), pp. 10202-10210.
Miller M.W., et al., "Anticoccidial Activity of 1-Phenyluracils," Journal of Medicinal Chemistry, 1983, vol. 26 (7), pp. 1075-1076.
Morrison J.F., et al., "Approaches to the Study and Analysis of the Inhibition of Enzymes by Slow- and Tight-Binding Inhibitors," Comments Molecular Cellular Biophysics, 1985, vol. 2(6), pp. 347-368.
Ohira S., "Methanolysis of Dimethyl (1-Diazo-2-Oxopropyl)Phosphonate: Generation of Dimethyl(DiazoMethyl)Phosphonate and Reaction with Carbonyl Compounds," Synthetic Communications, 1989, vol. 19 (3-4), pp. 561-564.
Ohta T., et al., "Asymmetric Hydrogenation of Olefins With Aprotic Oxygen Functionalities Catalyzed by BINAP-Ru(11) Complexes ," The Journal of Organic Chemistry, 1995, vol. 60, pp. 357-363.
Onitsuka K., et al., "Living Polymerization of Bulky Aryl Isocyanide with Arylrhodium Complexes," Organometallics, 2006, vol. 25 (5), pp. 1270-1278.
Opposition filed by "Asociacion de Laboratorios Farmaceuticos, Alafar" received from Ecuadorian Patent Office, through Providence notified on Apr. 1, 2009, 3 pages.
Pelletier G., et al., "Copper-Catalyzed Amidation of Allylic and Benzylic C—H Bonds," Organic Letters, 2006, vol. 8 (26), pp. 6031-6034.
Pineschi M., et al., "Facile Regio- and Stereoselective Carboncarbon Coupling of Phenol Derivatives with Aryl Aziridines," Organic Letters, 2006, vol. 8 (12), pp. 2627-2630.
Remington J.P., ed., Pharmaceutical Sciences, 15th Edition, Mack Publishing Company, 1975, pp. 411-415.
Saget T., et al., "Chiral Monodentate Phosphines and Bulky Carboxylic Acids: Cooperative Effects in Palladium-Catalyzed Enantioselective C(sp(3) )-H Functionalization," Angewandte Chemie International Edition, 2012, vol. 51 (9), pp. 2238-2242.
Saha B., et al., "Syntheses and Applications of 2-phosphino-2'-alkoxy-1,1'-binaphthyl Ligands. Development of a Working Model for Asymmetric Induction in Hydrovinylation Reactions," Journal of Organic Chemistry, 2007, vol. 72 (7), pp. 2357-2363.
Saito T., et al., "Possible Association of Beta2- and Beta3-Adrenergic Receptor Gene Polymorphisms With Susceptibility to Breast Cancer," Breast Cancer Research, 2001, vol. 3 (4), pp. 264-269.
Santana L., et al., "A Slightly Shorter Route to Carbocyclic Nucleosides. Synthesis of (±)-trans- I [2-(Hydroxymethyl)cyclopentylmethyl]uracil," Journal of Heterocyclic Chemistry, 1999, vol. 36, pp. 293-295.
Sasaki S., et al., "Synthesis, Structure, and Redox Properties of the Extremely Crowded Triarylpnictogens: Tris(2,4,6-triisopropylphenyl)phosphine, Arsine, Stibine, and Bismuthine," Tetrahedron Letters, 2004, vol. 45 (50), pp. 9193-9196.
Scozzafava A., et al., "Anticancer and Antiviral Sulfonamides," Current Medicinal Chemistry, 2003, vol. 10 (11), pp. 925-953.
Shah S., et al., "Three Different Fates for Phosphinidenes Generated by Photocleavage of Phospha-Wittig Reagents Arp=PMe3," Journal of the American Chemical Society, 2001, vol. 123 (28), pp. 6925-6926.
Shekhar S., et al., "A General Method for Palladium-catalyzed Reactions of Primary Sulfonamides with Aryl Nonaflates," Journal of Organic Chemistry, 2011, vol. 76 (11), pp. 4552-4563.
Shekhar S., et al., A General Method for Pd-Catalyzed Reactions of Primary Sulfonamides with Aryl Nonaflates, Supporting Information, Table of Contents.
Shen Q., et al., "Lewis Acid Acceleration of C—N Bond-forming Reductive Elimination from Heteroarylpalladium Complexes and Catalytic Amidation of Heteroaryl Bromides," Journal of the American Chemical Society, 2007, vol. 129 (25), pp. 7734-7735.
Shirakawa E., et al., "Reduction of Alkynes into 1,2-dideuterioalkenes with Hexamethyldisilane and Deuterium Oxide in the Presence of a Palladium Catalyst," Chemical Communications, 2005, pp. 5885-5886.
Supplementary International Search Report for Application No. PCT/US2008/076576, mailed on Jan. 14, 2010, 2 pages.
Suzuki A., "Recent Advances in the Cross-Coupling Reactions of Organoboron Derivates with Organic Electrophiles, 1995-1998," Journal of Organometallic Chemistry, 1999, vol. 576, pp. 147-168.

(56) References Cited

OTHER PUBLICATIONS

Taylor W.P., et al., "Quiescent Affinity Inactivators of Protein Tyrosine Phosphatases," Bioorganic & Medicinal Chemistry, 1996, vol. 4 (9), pp. 1515-1520.

Tschan M.J., et al., "Efficient Bulky Phosphines for the Selective Telomerization of 1,3-Butadiene with Methanol," Journal of the American Chemical Society, 2010, vol. 132 (18), pp. 6463-6473.

Ueki H., et al., "Efficient Large-Scale Synthesis of Picolinic Acid-Derived Nickel(II) Complexes of Glycine," European Journal of Organic Chemistry, 2003, vol. 2003 (10), pp. 1954-1957.

Ueno Y., et al., "Synthesis and Properties of Nucleic Acid Analogues Consisting of a Benzene-Phosphate Backbone," Journal of Organic Chemistry, 2005, vol. 70 (20), pp. 7925-7935.

Van Aller R.T., et al., "A Study of Aliphatic Sulfonyl Compounds. VIII. The Thermal Decomposition of Trimethylmethanesulfonyl Chloride," The Journal of Organic Chemistry, 1966, vol. 31 (7), pp. 2357-2365.

Voituriez A., et al., "2-Phospha[3]ferrocenophanes with Planar Chirality: Synthesis and Use in Enantioselective Organocatalytic [3+2] Cyclizations," Journal of the American Chemical Society, 2008, vol. 130 (43), pp. 14030-14031.

Wallace D.J., et al., "Palladium-catalyzed Amidation of Enol Triflates: a New Synthesis of Enamides," Organic Letters, 2003, vol. 5 (24), pp. 4749-4752.

Wang Z., et al., "FeCl2-Catalyzed Aminobromination of Alkenes Using Amides or Sulfonamides and NBS as the Nitrogen and Bromine Sources," Synlett, 2008, vol. 17, pp. 2667-2668.

Widenhoefer R.A., et al., "Electronic Dependence of C—O Reductive Elimination from Palladium (Aryl)neopentoxide Complexes," Journal of the American Chemical Society, 1998, vol. 120 (26), pp. 6504-6511.

Widhalm M., et al., "Rigid P-Chiral Mono and Diphosphines. Configurative Stability and P-Inversion Barrier," Tetrahedron: Asymmetry, 2006, vol. 17 (9), pp. 1355-1369.

Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.

Written Opinion for Application No. PCT/US2011/044283, mailed on Jan. 16, 2013, 7 pages.

Yamashita M., et al., "Trans Influence on the Rate of Reductive Elimination. Reductive Elimination of Amines from Isomeric Arylpalladium Amides with Unsymmetrical Coordination Spheres," Journal of the American Chemical Society, 2003, vol. 125 (52), pp. 16347-16360.

Yang., et al., Synlett, 2009, pp. 1167-1171.

Yin J., et al., "Palladium-catalyzed Intermolecular Coupling of Aryl Halides and Amides," Organic Letters, 2000, vol. 2 (8), pp. 1101-1104.

Yin J., et al., "Pd-Catalyzed Intermolecular Amidation of Aryl Halides. The Discovery that Xantphos Can Be Trans-Chelating in a Palladium Complex," Journal of the American Chemical Society, vol. 124, pp. 6043-6048.

Zhang J., et al., "Gold(I)-Catalyzed Intra- and Intermolecular Hydroamination of Unactivated Olefins," Journal of the American Chemical Society, 2006, vol. 128 (6), pp. 1798-1799.

Zhou T., et al., "Hypervalent Iodine in Synthesis: Part 86. Selective Copper-catalyzed N-monoarylation and N1, N3 Diarylation of Uracil and its Derivatives with Diaryliodonium Salts," Helvetica Chimica Acta, 2005, vol. 88 (2), pp. 290-296.

Herrbach A. et al., "Asymmetric Synthesis of an Axially Chiral Antimitotic Biaryl via an Atropo-Enantioselective Suzuki Cross-Coupling," Journal of Organic Chem., 2003, 68(12), pp. 4897-4905.

Li W. et al., "3,4-Disubstituted benzofuran P1' MMP-13 inhibitors: Optimization of selectivity and reduction of protein binding," Bioorg. Med. Chem. Lett., 2009, 19, pp. 4546-4550.

Suwandi L.S. et al., "Synthesis and antitumor activities of 3-modified 2-methoxyestradiol analogs," Bioorg. Med. Chem. Lett., 2009, 19, pp. 6459-6462.

Rosen et al., "Mild Pd-Catalyzed N-Arylation of Methanesulfonamide and Related Nucleophiles: Avoiding Potentially Genotoxic Reagents and Byproducts," Org. Lett., 2011, 13(10):2564-2567.

* cited by examiner

PHOSPHINE LIGANDS FOR CATALYTIC REACTIONS

CROSS-REFERENCE TO RELATED APPLICATIONS

This application is a continuation of U.S. application Ser. No. 14/834,420, filed on Aug. 24, 2015, which is a continuation of U.S. application Ser. No. 14/611,943, now U.S. Pat. No. 9,200,021, filed on Feb. 2, 2015, which is a continuation of U.S. application Ser. No. 13/591,117, now U.S. Pat. No. 8,975,443, filed Aug. 21, 2012, which is a continuation-in-part of U.S. application Ser. No. 13/184,425, now U.S. Pat. No. 8,841,487, filed Jul. 15, 2011, which claims priority to U.S. Provisional Application No. 61/365,293 filed Jul. 16, 2010, the entire contents of which are incorporated herein by reference.

BACKGROUND

Transition metal catalyst complexes play important roles in organic synthesis. These complexes contain a central transition metal such as palladium as well as ligands that associate with the metal. The catalysts are used in a wide variety of carbon-carbon and carbon-heteroatom bond forming reactions.

The properties of the catalysts are recognized as being influenced by the nature of the central metal and also by the structure of the ligands. The structure of the ligands is believed to have an effect on rate constants and regioselectivity of the reactions, for example. Phosphine ligands including trivalent phosphorus are known for use with transition metals such as palladium. However, current ligands still require significant catalyst loading and are not optimal in either reaction completion or reaction rate. There is therefore a need for new and more effective phosphine ligands.

SUMMARY

Phosphacycles suitable for use as ligands for transition metal catalyst systems include those represented by the general formula I,

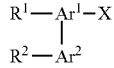

(I)

or a salt thereof, wherein, $Ar^1$ and $Ar^2$ are each independently aryl or heteroaryl, and wherein $Ar^1$ and $Ar^2$ are each independently optionally substituted with one or more $R^1$ and $R^2$, respectively;

$R^1$ and $R^2$ are independently selected at each occurrence from the group consisting of hydrogen; amino; hydroxyl; cyano; halo; alkyl; alkenyl; alkynyl; haloalkyl; haloalkoxy; oxoalkyl; alkoxy; aryloxy; heteroaryloxy; arylamino; heteroarylamino; alkylamino; dialkylamino; cycloalkyl optionally substituted with alkyl, alkenyl, alkynyl, alkoxy, cyano, halo, haloalkyl or haloalkoxy; cycloalkyloxy optionally substituted with alkyl, alkenyl, alkynyl, alkoxy, cyano, halo, haloalkyl or haloalkoxy; 5- or 6-membered heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; hydroxyalkoxy; alkoxyalkyl; aminoalkyl; N-alkylaminoalkyl; N,N-dialkylaminoalkyl; N,N,N-trialkylammoniumalkyl; $L^1$-C(O)—$OR^{1'}$, $L^1$-P(O)—$(OR^{1'})_2$, or $L^1$-S(O)$_2OR^{1'}$, wherein $L^1$ is a bond or alkylene, and $R^{1'}$ is selected from the group consisting of hydrogen, alkyl and hydroxyalkyl; $L^2$-O—C(O)—$R^{2'}$ wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; sulfate; alkylthio; thioalkyl; and a ring containing an alkylene or —O—$(CH_2)_m$—O— formed by the joining together of any two $R^1$ or any two $R^2$ or an $R^1$ and an $R^2$, wherein m is 1, 2, 3 or 4;

X is a phosphine of formula (Ia):

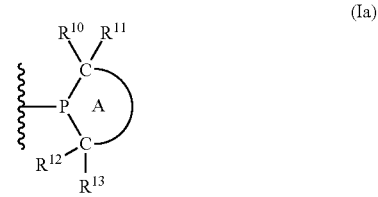

(Ia)

wherein ring A is a monocyclic heterocyclic ring, bicyclic heterocyclic ring, or tricyclic heterocyclic ring, and wherein ring A includes 0 to 9 ring atoms in addition to the phosphorus and 2 carbon ring atoms of formula (Ia), wherein said ring atoms are each independently selected from the group consisting of carbon, oxygen, nitrogen, phosphorus and sulfur; or X is a phosphine of formula (Ib):

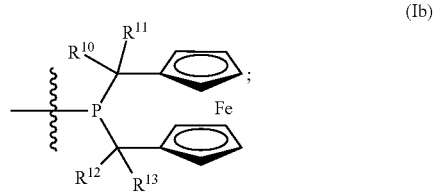

(Ib)

X is a phosphine fused to $Ar^1$ to give a compound of formula (Ic):

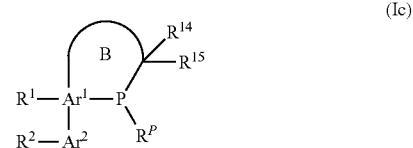

(Ic)

wherein, ring B is a phosphorus heterocyclic ring with 0 to 5 ring atoms in addition to the phosphorus and carbon ring atoms of formula (Ic), wherein said ring atoms are each independently selected from the group consisting of carbon, oxygen, nitrogen, phosphorus and sulfur, and wherein the ring atoms of ring A and ring B are each independently optionally substituted with one or more substituents selected from the group consisting of alkenyl;

alkoxy; alkoxyalkyl; alkyl; alkylamino; alkylthio; alkynyl; aminoalkyl; N-alkylaminoalkyl; N,N-dialkylaminoalkyl; N,N,N-trialkylammoniumalkyl; arylalkyl optionally substituted with alkyl, alkenyl, alkynyl, alkoxy, cyano, halo, haloalkyl or haloalkoxy; cycloalkyl optionally substituted with alkyl, alkenyl, alkynyl, alkoxy, cyano, halo, haloalkyl or haloalkoxy; dialkylamino; halo; haloalkyl; fluoroalkyl; $C_{5-6}$ heteroaryl optionally substituted with alkyl, alkenyl, alkynyl, alkoxy, cyano, halo, haloalkyl or haloalkoxy; heterocycloalkyl optionally substituted with alkyl, alkenyl, alkynyl, alkoxy, cyano, halo, haloalkyl or haloalkoxy; hydroxy; hydroxyalkyl; oxo; an exocyclic double bond optionally substituted with alkyl, alkenyl, alkynyl, aryl, cycloalkyl, heterocyclyl, or heteroaryl; a 3- to 7-membered spiro ring containing zero, one, or two heteroatoms; phenyl optionally substituted with alkyl, alkenyl, alkynyl, alkoxy, cyano, halo, haloalkyl or haloalkoxy; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl or hydroxyalkyl; $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; and $L^7$-$NR^{8'}$—S(O)$_2$—$R^{9'}$, wherein $L^7$ is a bond or alkylene, $R^{8'}$ is hydrogen or alkyl, and $R^{9'}$ is alkyl or hydroxyalkyl;

$R^P$ is selected from the group consisting of alkyl, alkenyl, alkynyl, cycloalkyl, aryl, and heteroaryl, wherein $R^P$ is optionally substituted with alkyl, alkenyl, alkynyl, alkoxy, cyano, halo, haloalkyl or haloalkoxy, or $R^P$ is a bridging group between the phosphorus and another B ring atom, wherein $R^P$ is selected from the group consisting of alkylene, alkenylene, alkynylene, and —$(CR^{41}R^{42}$—O$)_q$—, wherein $R^{41}$ and $R^{42}$ are each independently hydrogen or alkyl, and wherein q is 1 or 2, and wherein $R^P$ is optionally substituted with alkyl, alkenyl, alkynyl, alkoxy, cyano, halo, haloalkyl or haloalkoxy;

as to $R^{10}$, $R^{11}$, $R^{12}$, and $R^{13}$ in formulae (Ia) and (Ib), $R^{10}$ or $R^{11}$ together with $R^{12}$ or $R^3$ form a ring; or $R^{10}$ and $R^{11}$ together with the carbon atom to which they are attached form a spirocyclic ring and/or $R^{12}$ and $R^{13}$ together with the carbon atom to which they are attached form a spirocyclic ring; or one or more of $R^{10}$, $R^{11}$, $R^{12}$ and $R^{13}$ form a ring together with a ring substituent of ring A; wherein, if any of substituents $R^{10}$, $R^{11}$, $R^{12}$, and $R^{13}$ do not form a ring, said substituents are each independently selected from the group consisting of hydrogen; alkyl; alkenyl; haloalkyl; alkynyl; oxoalkyl; cycloalkyl optionally substituted with alkyl, alkenyl, alkynyl, alkoxy, cyano, halo, haloalkyl or haloalkoxy; heterocyclyl optionally substituted with alkyl, alkenyl, alkynyl, alkoxy, cyano, halo, haloalkyl or haloalkoxy; $C_{5-6}$ heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; alkoxyalkyl; aminoalkyl; N-alkylaminoalkyl; N,N-dialkylaminoalkyl; N,N,N-trialkylammoniumalkyl; thioalkyl; $L^{13}$-C(O)—$OR^{14'}$, $L^{13}$-P(O)—$(OR^{14'})_2$, or $L^{13}$-S(O)$_2$—$OR^{14'}$, wherein $L^{13}$ is a bond or alkylene, and $R^{14'}$ is selected from the group consisting of hydrogen, alkyl and hydroxyalkyl; $L^{15}$-O—C(O)—$R^{16'}$, wherein $L^{15}$ is alkylene and $R^{16'}$ is alkyl or hydroxyalkyl; $L^1$-C(O)—$NR^{18'}R^{19'}$, wherein $L^{17}$ is a bond or alkylene, and $R^{18'}$ and $R^{19'}$ are each independently selected from the group consisting of hydrogen, alkyl, and hydroxyalkyl; and $L^{20}$-$NR^{21'}$—C(O)—$R^{22'}$, wherein $L^{20}$ is alkylene, $R^{21'}$ is hydrogen or alkyl, and $R^{22'}$ is alkyl or hydroxyalkyl; and as to $R^{14}$ and $R^{15}$, $R^{14}$ and $R^{15}$ together with the carbon atom to which they are attached form a spirocyclic ring; or one or more of $R^{14}$ and $R^{15}$ form a ring together with a ring atom or ring substituent of ring B, wherein if any of substituents $R^{14}$ and $R^{15}$ do not form a ring, said substituents are each independently selected from the group consisting of hydrogen; alkyl; alkenyl; haloalkyl; alkynyl; oxoalkyl; cycloalkyl optionally substituted with alkyl, alkenyl, alkynyl, alkoxy, cyano, halo, haloalkyl or haloalkoxy; heterocyclyl optionally substituted with alkyl, alkenyl, alkynyl, alkoxy, cyano, halo, haloalkyl or haloalkoxy; $C_{5-6}$ heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; alkoxyalkyl; aminoalkyl; N-alkylaminoalkyl; N,N-dialkylaminoalkyl; N,N,N-trialkylammoniumalkyl; thioalkyl; $L^{13}$-C(O)—$OR^{14'}$, $L^{13}$-P(O)—$(OR^{14'})_2$, or $L^{13}$-S(O)$_2$—$OR^{14'}$ wherein $L^{13}$ is a bond or alkylene, and $R^{14'}$ is selected from the group consisting of hydrogen, alkyl, and hydroxyalkyl; $L^{15}$-O—C(O)—$R^{16'}$ wherein $L^{15}$ is alkylene, and $R^{16'}$ is alkyl or hydroxyalkyl; $L^{17}$-C(O)—$NR^{18'}R^{19'}$, wherein $L^{17}$ is a bond or alkylene and $R^{18'}$ and $R^{19'}$ are each independently selected from the group consisting of hydrogen, alkyl, and hydroxyalkyl; and $L^{20}$-$NR^{21'}$—C(O)—$R^{22'}$, wherein $L^{20}$ is alkylene, $R^{21'}$ is hydrogen or alkyl, and $R^{22'}$ is alkyl or hydroxyalkyl.

The disclosure is directed to catalyst compositions comprising a ligand of formula (I) and one or more transition metal compounds.

The disclosure is directed to catalyst compositions comprising a ligand of formula (I) covalently bonded to a solid catalyst support.

The disclosure is directed to methods of performing a bond-forming reaction comprising catalyzing said reaction with a ligand of formula (I), wherein the bond-forming reaction is selected from the group consisting of carbon-nitrogen, carbon-oxygen, carbon-carbon, carbon-sulfur, carbon-phosphorus, carbon-boron, carbon-fluorine and carbon-hydrogen.

The disclosure is directed to methods of forming a bond in a chemical reaction comprising catalyzing said reaction with a ligand of formula (I), wherein the bond is selected from the group consisting of a carbon-nitrogen bond, a carbon-oxygen bond, a carbon-carbon bond, a carbon-sulfur bond, a carbon-phosphorus bond, a carbon-boron bond, a carbon-fluorine bond and a carbon-hydrogen bond.

The disclosure is also directed to methods of synthesizing phosphacylces such as a method comprising metalation of a biaryl halide to form a biaryl lithium species; reacting a chlorophosphate with said biaryl lithium species to form biaryl phosphonate; reduction of second product to form primary phosphine; and reacting primary phosphine with a divinylketone.

Further benefits of this disclosure will be apparent to one skilled in the art.

DETAILED DESCRIPTION

This detailed description is intended only to acquaint others skilled in the art with this disclosure, its principles, and its practical application so that others skilled in the art may adapt and apply the disclosure in its numerous forms, as they may be best suited to the requirements of a particular use. This description and its specific examples are intended for purposes of illustration only. This disclosure, therefore, is not limited to the embodiments described in this patent application, and may be variously modified

DEFINITIONS

"Alkyl" refers to a straight or branched chain hydrocarbyl group of formula —($C_nH_{2n+1}$). In an embodiment, n is 1 to 12, so that the alkyl has from 1 to 12 carbon atoms and is called as a $C_1$-$C_{12}$ alkyl. Similarly, in some embodiments, alkyl is a $C_1$-$C_{10}$ alkyl group, a $C_1$-$C_6$ alkyl group, or a $C_1$-$C_4$ alkyl group. Examples of alkyl groups include methyl, ethyl, propyl, isopropyl, butyl, isobutyl, t-butyl, pentyl, hexyl, heptyl, octyl, nonyl, decyl, and so on.

"Alkylene" is a hydrocarbyl group containing two points of attachment on different carbons. An examples is ethylene represented by —($CH_2CH_2$)—. "Alkylidene" is a hydrocarbyl group containing two points of attachment on the same carbon. An example is ethylidene represented by —CH($CH_3$)—.

"Alkenyl" refers to a straight or branched hydrocarbyl group with at least one site of unsaturation, i.e. a carbon-carbon, $sp^2$ double bond. The general formula is —($C_nH_{2n-1}$). In an embodiment, alkenyl has from 2 to 12 carbon atoms, represented as $C_2$-$C_{12}$ alkenyl. In some embodiments, alkenyl is a $C_2$-$C_{10}$ alkenyl group or a $C_2$-$C_6$ alkenyl group. Examples of alkenyl group include ethylene or vinyl (—CH=$CH_2$), allyl (—$CH_2$CH=$CH_2$), and 5-hexenyl (—$CH_2CH_2CH_2CH_2$CH=$CH_2$).

"Alkenylene" means a divalent group derived from a straight or branched chain hydrocarbon and contains at least one carbon-carbon double. "$C_2$-$C_6$ alkenylene" means an alkenylene group containing 2-6 carbon atoms. Representative examples of alkenylene include, but are not limited to, —CH=CH— and —$CH_2$CH=CH—.

"Oxoalkyl" is a substituted alkyl group wherein at least one of the carbon atoms of an alkyl group is substituted with an oxo group, being a double bond to an oxygen, also known as a carbonyl. An oxoalkyl group thus has ketone or aldehyde functionality. If the oxo substitution is on the first atom bonded to the respective ring, the group can be called as "alkanoyl" or "acyl," being the group RC(O)— where R is an alkyl group as defined herein. In various embodiments, "oxoalkyl" is a $C_1$-$C_{10}$ oxoalkyl group, a $C_1$-$C_6$ oxoalkyl group, or a $C_1$-$C_3$ oxoalkyl group.

"Alkoxy" is RO— where R is alkyl. Non-limiting examples of alkoxy groups include a $C_1$-$C_{10}$ alkoxy group, a $C_1$-$C_6$ alkoxy group, or a $C_1$-$C_3$ alkoxy group methoxy, ethoxy and propoxy.

"Alkoxyalkyl" refers to an alkyl moiety substituted with an alkoxy group. Embodiments can be named by combining the designations of alkoxy and alkyl. So for example, there can be ($C_1$-$C_6$)alkoxy-($C_1$-$C_{10}$)alkyl and the like. Examples of alkoxyalkyl groups include methoxymethyl, methoxyethyl, methoxypropyl, ethoxyethyl, and so on.

"Alkoxycarbonyl" is ROC(O)—, where R is an alkyl group as defined herein. In various embodiments, R is a $C_1$-$C_{10}$ alkyl group or a $C_1$-$C_6$ alkyl group.

"Alkylamino" is RNH— and "dialkylamino" is $R_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, and butylamino. Examples of dialkylamino groups include dimethylamino, diethylamino, methylethylamino, and methylpropylamino.

"Alkynyl" refers to a straight or branched carbon-chain group with at least one carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—$CH_2$C≡CH).

"Alkynylene" refers to a straight or branched chain hydrocarbon of from 2 to 10 carbon atoms containing at least one triple bond. Representative examples of alkynylene include, but are not limited to, —C≡C—, —$CH_2$C≡C—, —CH($CH_3$)$CH_2$C≡C—, —C≡C$CH_2$—, and —C≡CCH($CH_3$)$CH_2$—.

"Alkylthio" is —SR and "alkylseleno" is —SeR, where R is alkyl as defined herein.

"Alkylsulfate" and "arylsulfate" are —O—S($O_2$)—OR where R is alkyl or aryl, respectively.

"Alkylsulfonate" and "arylsulfonate" are —S($O_2$)—OR where R is alkyl or aryl, respectively.

"Alkylsulfonyl" and "arylsulfonyl" are —S($O_2$)—R, where R is alkyl or aryl, respectively.

"Alkylsulfonamido" is —N(R')—S(O)$_2$—R, where R is alkyl and where R' is H or alkyl. "Arylsulfonamido" is —N(R')—S(O)$_2$—R, where R is aryl and where R' is H or alkyl.

"Amino" (alone or in combination with another term(s)) means —$NH_2$.

"Aminoalkyl" is an alkyl group substituted with an amino group —$NH_2$. "N-alkylaminoalkyl" means aminoalkyl in which there is an alkyl group substituted for one of the hydrogens of the amino group. "Dialkylaminoalkyl" or "N,N-dialkylaminoalkyl" means aminoalkyl in which there is an alkyl group substituted for both of the hydrogens of the amino group. The two substituted alkyl groups can be the same or different. "Trialkylammoniumalkyl" or "N,N,N-trialkylammoniumalkyl" means aminoalkyl in which there are three alkyl group substituted on the nitrogen of the amino group resulting in a net positive charge. The three substituted alkyl groups can be the same of different. Examples of alkylaminoalkyl groups include methylaminomethyl and ethylaminomethyl. Examples of N,N-dialkylaminoalkyl groups include dimethylaminomethyl and diethylaminomethyl. Examples of N,N,N-trialkyammoniumalkyl include trimethylammoniummethyl and diethylmethylammoniummethyl.

"Aryl" refers to any monocyclic or bicyclic carbon ring of up to 7 atoms in each ring, wherein at least one ring is aromatic. Aryl encompasses a ring system of up to 14 carbons atoms that includes a carbocyclic aromatic group fused with a 5- or 6-membered cycloalkyl group. Examples of aryl groups include, but are not limited to, phenyl, naphthyl, tetrahydronaphthyl and indanyl.

"Arylalkyl" refers to an aryl group, as defined herein, appended to the parent molecular moiety through an alkyl group, as defined herein. For example, "aryl-$C_1$-$C_6$ alkyl" or "aryl-$C_1$-$C_8$ alkyl" contains an aryl moiety attached to an alkyl chain of from one to six, or from one to eight carbon atoms, respectively. Representative examples of arylalkyl include, but are not limited to, benzyl, 2-phenylethyl, 3-phenylpropyl, and 2-naphth-2-ylethyl.

"Arylamino" is RNH—, where R is aryl.

"Aryloxy" is RO—, where R is aryl. "Arylthio" is RS—, where R is aryl.

"Carbamoyl" is the group $NH_2$—C(O)—; the nitrogen can be substituted with alkyl groups. N-(alkyl)carbamoyl is RNH—C(O)— and N,N-(alkyl)$_2$ carbamoyl is R$_2$N—C(O)—, where the R groups are alkyl as defined herein and are the same or different. In various embodiments, R is a C$_1$-C$_{10}$ alkyl group or a C$_1$-C$_6$ alkyl group.

"Cyano" as used herein, means a —CN group.

"Cycloalkyl" is a hydrocarbyl group containing at least one saturated or unsaturated ring structure which is not an aromatic ring, and attached via a ring carbon. In various embodiments, it refers to a saturated or an unsaturated but not aromatic C$_3$-C$_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkyloxy" is RO—, where R is cycloalkyl.

"Cycloalkylalkyl" refers to an alkyl moiety substituted with a cycloalkyl group, wherein cycloalkyl is as defined herein. Examples of cycloalkylalkyl groups include, but are not limited to, cyclopropylmethyl, cyclobutylmethyl, cyclopentylethyl and cyclohexylmethyl.

"Fluoroalkyl" refers to an alkyl moiety substituted with one or more fluorine atoms. Examples of fluoroalkyl groups include —CF$_3$ and —CHF$_2$.

"Halo" refers to chloro (—Cl), bromo (—Br), fluoro (—F) or iodo (—I).

"Haloalkoxy" refers to an alkoxy group substituted with one or more halo groups. Examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CCl$_3$ and —CHBr$_2$.

"Heterocyclyl" includes the heteroaryls defined below and refers to an unsaturated, saturated, or partially unsaturated single ring, two fused ring, or three fused ring group of 2 to 14 ring-carbon atoms. In addition to ring-carbon atoms, at least one ring has one or more heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Heterocyclylalkyl" is an alkyl group substituted with a heterocyclyl.

"Heterocyclyloxy" is RO—, where R is heterocyclyl.

"Heterocyclylthio" is RS—, where R is heterocyclyl.

"Heteroaryl" is a heterocyclyl where at least one ring is aromatic. In various embodiments, it refers to a single ring, two ring fused system, or three ring fused system having up to 7 atoms in each ring, wherein at least one ring is aromatic and contains from 1 to 4 heteroatoms in the ring selected from the group consisting of N, O and S. A 5-membered heteroaryl is a heteroaryl ring with 5 ring atoms. A 6-membered heteroaryl is a heteroaryl ring with 6 ring atoms. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen-containing heteroaryl.

"Heteroarylamino" is RNH—, where R is heteroaryl.

"Heteroaryloxy" is RO—, where R is heteroaryl.

"Heterocycloalkyl" is a heterocyclyl where no rings are aromatic.

"Hydroxyl" or "hydroxy" as used herein, means an —OH group.

"Hydroxyalkyl" is an alkyl group as defined herein substituted with at least one hydroxy group. Examples of hydroxyalkyl groups include, but are not limited to, hydroxymethyl, hydroxyethyl, hydroxypropyl and hydroxybutyl.

"Hydroxyalkoxy" refers to an alkoxy group substituted with a hydroxy group (—OH), wherein alkoxy is as defined herein. An example of hydroxyalkoxy is hydroxyethoxy.

"Oxo" as used herein, means a =O or carbonyl group.

"Selenoalkyl" is an alkyl group as defined herein substituted with a seleno group —SeH. "Thioalkyl" is an alkyl group as defined herein substituted with a thio group —SH.

"Silyl" is —SiR$_3$ where each R is alkyl, and the three R groups are the same or different. "Silyloxy" is —OSiR$_3$ where each R is alkyl, and the three R groups are the same or different.

"Sulfate" is —O—S(O)$_2$—OH or its salt form.

"Sulfamoyl" is —S(O)$_2$—NH$_2$. "N-(alkyl)sulfamoyl" is RNH—S(O)$_2$—; and "N,N-(alkyl)$_2$sulfamoyl" or "N,N-(dialkyl)sulfamoyl" is R$_2$N—S(O)$_2$—, where the R groups are alkyl as defined herein and are the same or different. In various embodiments, R is a C$_1$-C$_{10}$ alkyl group or a C$_1$-C$_6$ alkyl group.

"Sulfonamide" as used herein, means a Z'S(O)$_2$NZ$^2$— group, as defined herein, wherein Z$^1$ is an optionally substituted alkyl, aryl, haloalkyl, or heteroaryl as defined herein, and Z$^2$ is hydrogen or alkyl. Representative examples of sulfonamide include, but are not limited to, methanesulfonamide, trifluoromethanesulfonamide, and benzenesulfonamide.

"Sulfonic acid is —S(O)$_2$—OH. "Sulfonate" is its salt form.

When cycloalkyl, heterocyclyl, heteroaryl, phenyl, and the like are "substituted", it means there are one or more substituents other than hydrogen on the respective ring. The substituents are selected from those defined herein for the groups $R^1$, $R^2$, $R^{10}$, $R^{11}$, $R^{12}$, and $R^{13}$. "Unsubstituted" rings have no substituents other than hydrogen.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms.

Illustrating further, $C_3$-$C_6$-cycloalkyl means a saturated hydrocarbyl ring containing from 3 to 6 carbon ring atoms.

When the ligands disclosed herein have chiral centers, the disclosure includes the racemic mixture as well as the isolated optical isomers, including enantiomers and diastereomers.

R groups are named equivalently with and without subscripts or superscripts. Thus, R1 is the same as $R_1$ and $R^1$, R10 is the same as $R_{10}$ and R10, Q1 is the same as $Q_1$ and $Q^{10}$, and so on. The designation "R" is used several places in different ways. Unless the context requires, there is no intention that all the R groups are the same.

Ligands

Formula (I)—Biaryl Phosphacycles

In one embodiment, ligands for transition metal catalyst systems are selected from those of general formula (I),

(I)

wherein X is a phosphorus containing heterocyclic ring.

$Ar^1$ and $Ar^2$ are each independently aryl or heteroaryl, and $Ar^1$ and $Ar^2$ are each independently optionally substituted with one or more $R^1$ and $R^2$, respectively. $Ar^1$ and $Ar^2$ independently are substituted with $R^1$ and $R^2$, respectively, any number of times depending on, for example, stability and rules of valence.

$R^1$ and $R^2$ are independently selected at each occurrence from the group consisting of hydrogen; amino; hydroxyl; cyano; halo; alkyl; alkenyl; alkynyl; haloalkyl; haloalkoxy; oxoalkyl; alkoxy; aryloxy; heteroaryloxy; arylamino; heteroarylamino; alkylamino; dialkylamino; cycloalkyl optionally substituted with alkyl, alkenyl, alkynyl, alkoxy, cyano, halo, haloalkyl or haloalkoxy; cycloalkyloxy optionally substituted with alkyl, alkenyl, alkynyl, alkoxy, cyano, halo, haloalkyl or haloalkoxy; 5- or 6-membered heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; hydroxyalkoxy; alkoxyalkyl; aminoalkyl; N-alkylaminoalkyl; N,N-dialkylaminoalkyl; N,N,N-trialkylammoniumalkyl; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl and hydroxyalkyl; $L^2$-O—C(O)—$R^{2'}$ wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; sulfate; alkylthio; and thioalkyl; or an $R^1$ and an $R^2$ join together to form an alkylene or —O—$(CH_2)_m$—O—, wherein m is 1, 2, 3 or 4. $R^1$ and $R^2$ may be optional substituents that do not interfere with the catalytic action of the ligands when they are used in a catalyst composition in combination with transition metal compounds.

In embodiments, X is a phosphorus-containing heterocyclic ring of Formula (Ia).

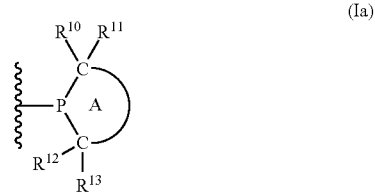

(Ia)

In the ligands where X is a phosphorus-containing heterocyclic ring of formula (Ia), a phosphorus heterocycle labeled above as ring A (a "phosphacycle") is bonded through a phosphorus atom to a substituted aromatic ring that is in turn substituted with another aromatic ring at an adjacent or ortho carbon atom to the phosphacycle. The phosphacycle contains three or more ring atoms including a phosphorus atom and two ring carbons bonded directly to the phosphorus atom. Ring A is a phosphorus monocyclic heterocyclic ring, a bicyclic heterocyclic ring, or a tricyclic heterocyclic ring, and wherein ring A includes 0 to 9 ring atoms selected from the group consisting of carbon, oxygen, nitrogen, phosphorus and sulfur in addition to the phosphorus and 2 carbon ring atoms of formula (Ia). The two ring carbons bonded to the phosphorus atom are in turn bonded to substituents $R^{10}$, $R^{11}$, $R^{12}$, and $R^{13}$ through a carbon atom. That is to say, substituents $R^{10}$, $R^{11}$, $R^{12}$, and $R^{13}$ are bonded to the phosphacycle through a carbon atom of the respective substituents. The phosphacycle also optionally contains one or more ring substituents selected from the group consisting of alkenyl; alkoxy; alkoxyalkyl; alkyl; alkylamino; alkylthio; alkynyl; aminoalkyl; N-alkylaminoalkyl; N,N-dialkylaminoalkyl; N,N,N-trialkylammoniumalkyl; arylalkyl optionally substituted with alkyl, alkenyl, alkynyl, alkoxy, cyano, halo, haloalkyl or haloalkoxy; cycloalkyl optionally substituted with alkyl, alkenyl, alkynyl, alkoxy, cyano, halo, haloalkyl or haloalkoxy; dialkylamino; halo; haloalkyl; fluoroalkyl; $C_{5-6}$ heteroaryl optionally substituted with alkyl, alkenyl, alkynyl, alkoxy, cyano, halo, haloalkyl or haloalkoxy; heterocycloalkyl optionally substituted with alkyl, alkenyl, alkynyl, alkoxy, cyano, halo, haloalkyl or haloalkoxy; hydroxy; hydroxyalkyl; oxo; an exocyclic double bond optionally substituted with alkyl, alkenyl, alkynyl, aryl, cycloalkyl, heterocyclyl, or heteroaryl; a 3- to 7-membered spiro ring containing zero, one, or two heteroatoms; phenyl optionally substituted with alkyl, alkenyl, alkynyl, alkoxy, cyano, halo, haloalkyl or haloalkoxy; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl or hydroxyalkyl; $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; and $L^7$-$NR^{8'}$—S(O)$_2$—$R^{9'}$, wherein $L^7$ is a bond or alkylene, $R^{8'}$ is hydrogen or alkyl, and $R^{9'}$ is alkyl or hydroxyalkyl.

In various embodiments, the A ring (the "phosphacycle") is a 4-, 5-, 6-, 7-, or 8-membered ring containing no hetero ring atoms except the P-atom shown in Formula (Ia). The phosphacycle can be a single ring containing no bridging atoms, or it can be a polycyclic ring such as a bicyclic or tricyclic ring containing bridging atoms.

As to $R^{10}$, $R^{11}$, $R^{12}$, and $R^{13}$ in formulae (Ia) and (Ib), $R^{10}$ or $R^{11}$ together with $R^{12}$ or $R^{13}$ form a ring; or $R^{10}$ and $R^{11}$ together with the carbon atom to which they are attached form a spirocyclic ring and/or $R^{12}$ and $R^{13}$ together with the carbon atom to which they are attached form a spirocyclic ring; or one or more of $R^{10}$, $R^{11}$, $R^{12}$ and $R^{13}$ form a ring together with a ring substituent of ring A.

If any of substituents $R^{10}$, $R^{11}$, $R^{12}$, and $R^{13}$ do not form a ring, said substituents are each independently selected from the group consisting of hydrogen; alkyl; alkenyl; haloalkyl; alkynyl; oxoalkyl; cycloalkyl optionally substituted with alkyl, alkenyl, alkynyl, alkoxy, cyano, halo, haloalkyl or haloalkoxy; heterocyclyl optionally substituted with alkyl, alkenyl, alkynyl, alkoxy, cyano, halo, haloalkyl or haloalkoxy; $C_{5-6}$ heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; alkoxyalkyl; aminoalkyl; N-alkylaminoalkyl; N,N-dialkylaminoalkyl; N,N,N-trialkylammoniumalkyl; thioalkyl; $L^{13}$-C(O)—$OR^{14'}$, $L^{13}$-P(O)—$(OR^{14'})_2$, or $L^{13}$-S(O)$_2$—$OR^{14'}$, wherein $L^{13}$ is a bond or alkylene, and $R^{14'}$ is selected from the group consisting of hydrogen, alkyl and hydroxyalkyl; $L^{15}$-O—C(O)—$R^{16'}$, wherein $L^{15}$ is alkylene and $R^{16'}$ is alkyl or hydroxyalkyl; $L^{17}$-C(O)—$NR^{18'}R^{19'}$, wherein $L^{17}$ is a bond or alkylene, and $R^{18'}$ and $R^{19'}$ are each independently selected from the group consisting of hydrogen, alkyl, and hydroxyalkyl; and $L^{20}$-$NR^{21'}$—C(O)—$R^{22'}$, wherein $L^{20}$ is alkylene, $R^{21'}$ is hydrogen or alkyl, and $R^{22'}$ is alkyl or hydroxyalkyl.

In another embodiment, X is a phosphorus-containing heterocyclic ring of Formula (Ib).

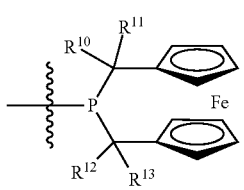

(Ib)

In these ligands, a phosphacycle is bonded through a phosphorus atom to a substituted aromatic ring that is in turn substituted with another aromatic ring at an adjacent or ortho carbon atom to the phosphacycle. The phosphacycle contains a ferrocenyl moiety in addition to a phosphorus atom and two ring carbons bonded directly to the phosphorus atom. The two ring carbons bonded to the phosphorus atom are in turn bonded to substituents $R^{10}$, $R^{11}$, $R^{12}$, and $R^{13}$ through a carbon atom. That is to say, substituents $R^{10}$, $R^{11}$, $R^{12}$, and $R^{13}$ are bonded to the phosphacycle through a carbon atom of the respective substituents. $R^{10}$, $R^{11}$, $R^{12}$, and $R^{13}$ are as described above.

In a further embodiment, X is fused to $Ar^1$ to give a compound of formula (Ic):

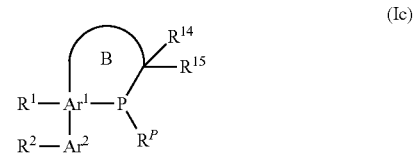

(Ic)

wherein, ring B is a phosphorus heterocyclic ring (phosphacycle) with 0 to 5 ring atoms selected from the group consisting of carbon, oxygen, nitrogen, phosphorus and sulfur in addition to the phosphorus and carbon ring atom of formula (Ic). The phosphacycle also optionally contains one or more ring substituents selected from the group consisting of alkenyl; alkoxy; alkoxyalkyl; alkyl; alkylamino; alkylthio; alkynyl; aminoalkyl; N-alkylaminoalkyl; N,N-dialkylaminoalkyl; N,N,N-trialkylammoniumalkyl; arylalkyl optionally substituted with alkyl, alkenyl, alkynyl, alkoxy, cyano, halo, haloalkyl or haloalkoxy; cycloalkyl optionally substituted with alkyl, alkenyl, alkynyl, alkoxy, cyano, halo, haloalkyl or haloalkoxy; dialkylamino; halo; haloalkyl; fluoroalkyl; $C_{5-6}$ heteroaryl optionally substituted with alkyl, alkenyl, alkynyl, alkoxy, cyano, halo, haloalkyl or haloalkoxy; heterocycloalkyl optionally substituted with alkyl, alkenyl, alkynyl, alkoxy, cyano, halo, haloalkyl or haloalkoxy; hydroxy; hydroxyalkyl; oxo; an exocyclic double bond optionally substituted with alkyl, alkenyl, alkynyl, aryl, cycloalkyl, heterocyclyl, or heteroaryl; a 3- to 7-membered spiro ring containing zero, one, or two heteroatoms; phenyl optionally substituted with alkyl, alkenyl, alkynyl, alkoxy, cyano, halo, haloalkyl or haloalkoxy; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl or hydroxyalkyl; $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; and $L^7$-$NR^{8'}$—S(O)$_2$—$R^{9'}$, wherein $L^7$ is a bond or alkylene, $R^{8'}$ is hydrogen or alkyl, and $R^{9'}$ is alkyl or hydroxyalkyl.

And as to $R^{14}$ and $R^{15}$, $R^{14}$ and $R^{15}$ together with the carbon atom to which they are attached form a spirocyclic ring; or one or more of $R^{14}$ and $R^{15}$ form a ring together with a ring substituent of ring B.

If any of substituents $R^{14}$ and $R^{15}$ do not form a ring, said substituents are each independently selected from the group consisting of hydrogen; alkyl; alkenyl; haloalkyl; alkynyl; oxoalkyl; cycloalkyl optionally substituted with alkyl, alkenyl, alkynyl, aryl, cycloalkyl, heterocyclyl, or heteroaryl; heterocyclyl optionally substituted with alkyl, alkenyl, alkynyl, alkoxy, cyano, halo, haloalkyl or haloalkoxy; $C_{5-6}$ heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; alkoxyalkyl; aminoalkyl; N-alkylaminoalkyl; N,N-dialkylaminoalkyl; N,N,N-trialkylammoniumalkyl; thioalkyl; $L^{13}$-C(O)—$OR^{14'}$, $L^{13}$-P(O)—$(OR^{14'})_2$, or $L^{13}$-S(O)$_2$—$OR^{14'}$ wherein $L^{13}$ is a bond or alkylene, and $R^{14'}$ is selected from the group consisting of hydrogen, alkyl and hydroxyalkyl; $L^{15}$-O—C(O)—$R^{16'}$ wherein $L^{15}$ is alkylene, and $R^{16'}$ is alkyl or hydroxyalkyl; $L^{17}$-C(O)—$NR^{18'}R^{19'}$, wherein $L^{17}$ is a bond or alkylene and $R^{18'}$ and $R^{19'}$ are each independently selected from the group consisting of hydrogen, alkyl, and hydroxyalkyl; and $L^{20}$-$NR^{21'}$—C(O)—$R^{22'}$, wherein $L^{20}$ is alkylene, $R^{21'}$ is hydrogen or alkyl, and $R^{22'}$ is alkyl or hydroxyalkyl.

$R^P$ is an optionally substituted alkyl, alkenyl, alkynyl, cycloalkyl, aryl, heterocyclyl, or heteroaryl; otherwise, $R^P$ is selected from the group consisting of alkylene, alkenylene, alkynylene, or —$(CR^{41}R^{42}$—O$)_q$— wherein one end is attached to the phosphorus atom of the phosphacycle and the other end is attached to a B ring atom, wherein $R^{41}$ and $R^{42}$ are each independently hydrogen or alkyl, and wherein q is 1 or 2. In other words, when $R^P$ is alkylene, alkenylene, alkynylene, or —$(CR^{41}R^{42}$—O$)_q$—, $R^P$ is a bridging group between the phosphorus atom of the phosphacycle and another ring atom of ring B.

In further embodiments, the phosphacycle X is represented by the formula (Id):

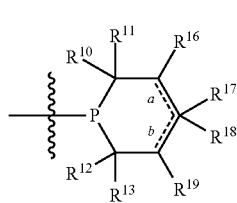
(Id)

where the groups $R^{10}$, $R^{11}$, $R^{12}$, $R^{13}$ are as described above for formula (Ia). Here the phosphacycle is a six-membered ring wherein bonds a and b are single bonds or double bonds provided wherein a and b are not simultaneously double bonds. === represents a bond that is either a single or double bond.

In the phosphacycles of formula (Id), one or more of the substituents $R^{16}$, $R^{17}$, $R^{18}$, and $R^{19}$ can optionally form a ring with substituents $R^{10}$, $R^{11}$, $R^{12}$, or $R^{13}$. If the respective substituent does not form such a ring, the following hold in illustrative embodiments: $R^{16}$ and $R^{19}$ are independently selected from H, halo, alkyl, haloalkyl, fluoroalkyl, alkenyl, and alkoxy; and $R^{17}$ and $R^{18}$ together form a carbonyl; an exocyclic double bond optionally substituted with alkyl, alkenyl, alkynyl, aryl, cycloalkyl, heterocyclyl, or heteroaryl; or a 3- to 7-membered spiro ring containing zero, one, or two heteroatoms.

Further, the alkyl, alkenyl, alkynyl, aryl, cycloalkyl, heterocyclyl, or heteroaryl with which the exocyclic double bond is substituted, as well as the exocyclic spiro ring optionally formed by $R^{17}$ and $R^{18}$ together can in turn be optionally substituted with substituents that do no interfere unacceptably with the catalytic action of the respective ligand when used in combination with transition metal compounds. In various embodiments, these optional substituents are selected from those used for groups $R^1$ and $R^2$ in non-limiting embodiments.

When $R^{17}$ and $R^{18}$ are not a carbonyl or exocyclic double bond or spiro ring as described above, in further non-limiting embodiments they are independently selected from moieties that do no interfere unacceptably with the catalytic action of the respective ligand when used in combination with transition metal compounds. In particular embodiments, $R^{17}$ and $R^{18}$ are independently selected from:

hydrogen; halo; fluoro; alkyl; alkenyl; alkynyl; haloalkyl; fluoroalkyl; alkyloxy; N-alkylamino; N,N-dialkylamino; cycloalkyl optionally substituted with alkyl, alkenyl, alkynyl, alkoxy, cyano, halo, haloalkyl or haloalkoxy; heterocycloalkyl optionally substituted with alkyl, alkenyl, alkynyl, alkoxy, cyano, halo, haloalkyl or haloalkoxy; $C_{5-6}$ heteroaryl optionally substituted with alkyl, alkenyl, alkynyl, alkoxy, cyano, halo, haloalkyl or haloalkoxy, phenyl optionally substituted with alkyl, alkenyl, alkynyl, alkoxy, cyano, halo, haloalkyl or haloalkoxy; arylalkyl optionally substituted with alkyl, alkenyl, alkynyl, alkoxy, cyano, halo, haloalkyl or haloalkoxyalkyl, alkenyl, alkynyl, aryl, cycloalkyl, heterocyclyl, or heteroaryl; hydroxyalkyl; alkoxyalkyl; aminoalkyl; N-alkylaminoalkyl; N,N-dialkylaminoalkyl; N,N,N-trialkylammoniumalkyl; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl and hydroxyalkyl $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, and $R^{5'}$ is hydrogen or alkyl, $R^{6'}$ is alkyl or hydroxyalkyl; and alkylthio;

In various embodiments, including those described above, $R^{16}$ and $R^{19}$ are hydrogen.

Illustrative phosphacycles of formula (Id) are shown in Table 1. Some have substituted or unsubstituted exocyclic double bonds, some have spiro rings, and some illustrate other substitutions for $R^{17}$ and $R^{18}$. Polycyclic rings with bridging atoms are also illustrated. The phosphacycle substituents of Table 1 are based on 6-membered ring phosphacycles. Some have chiral centers; these include, for example, 1-15, 1-16, 1-17, 1-18, 1-19, 1-20, 1-21, 1-22, 1-32, 1-33, 1-34, 1-35, 1-36, 1-42, 1-43, and 1-44.

TABLE 1

6-Membered Ring Phosphacycles

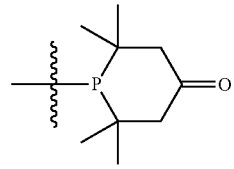
1-1

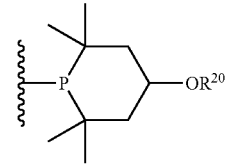
1-2

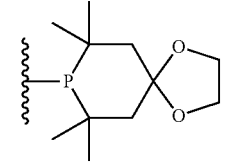 [SMILES: *P1C(C)(C)CC2(CC1(C)C)OCCO2]
1-3

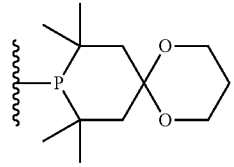 [SMILES: *P1C(C)(C)CC2(CC1(C)C)OCCCO2]
1-4

TABLE 1-continued
6-Membered Ring Phosphacycles
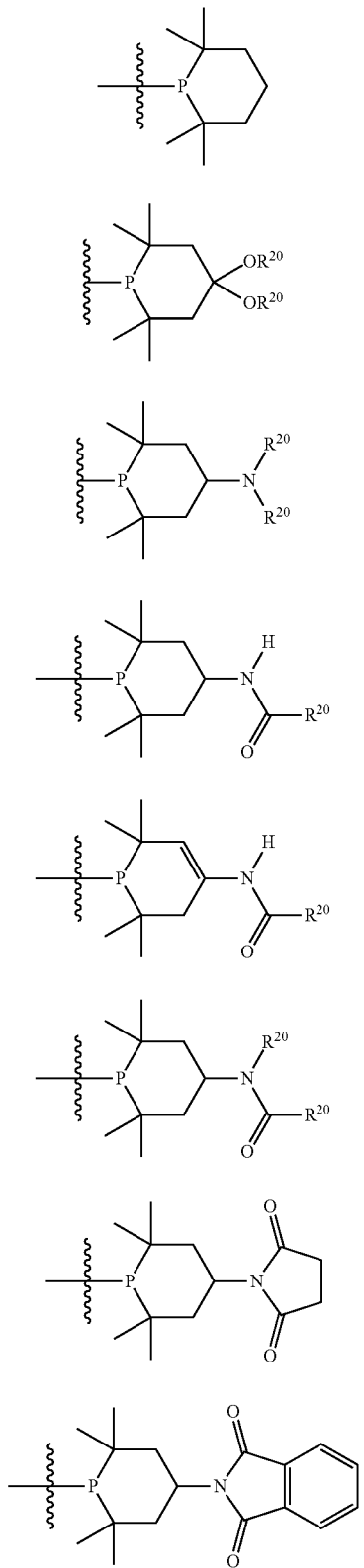
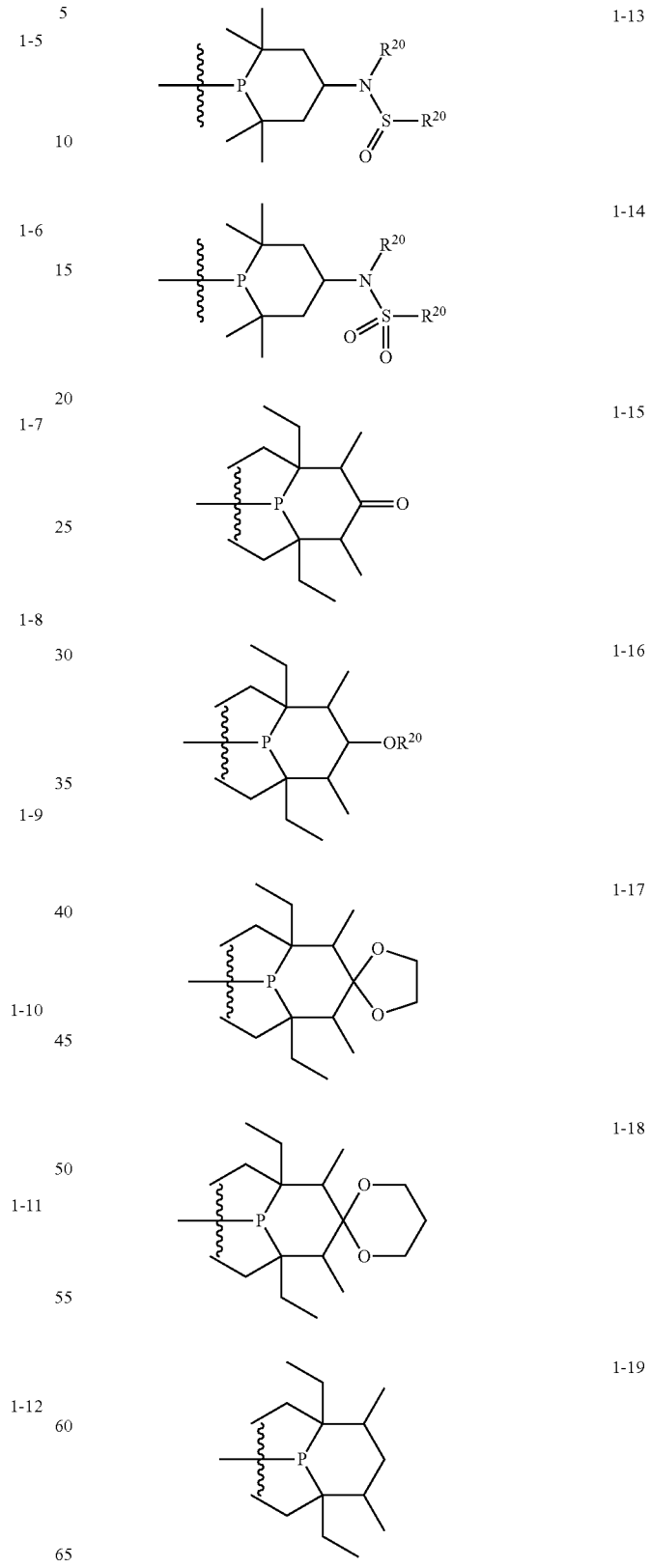

TABLE 1-continued
6-Membered Ring Phosphacycles
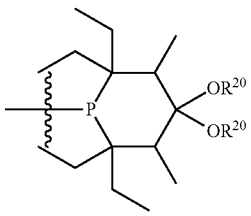 1-20
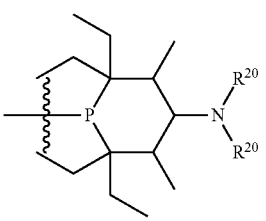 1-21
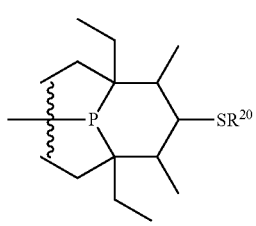 1-22
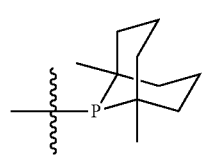 1-23
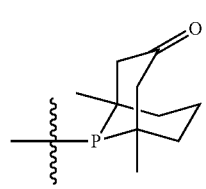 [SMILES: *P1C2(C)CCCC1(C)CC(=O)C2] 1-24
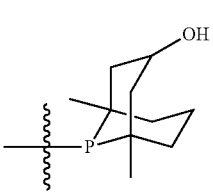 [SMILES: *P1C2(C)CCCC1(C)CC(O)C2] 1-25
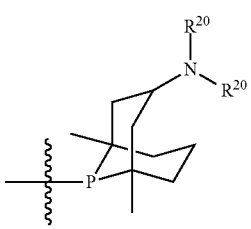 1-26
TABLE 1-continued
6-Membered Ring Phosphacycles
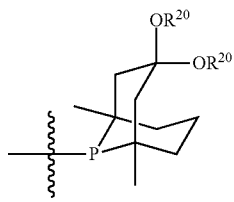 1-27
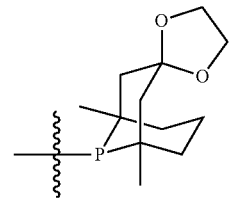 [SMILES: *P1C2(C)CCCC1(C)CC1(C2)OCCO1] 1-28
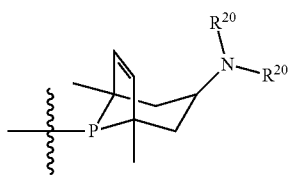 1-29
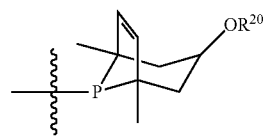 1-30
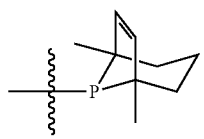 1-31
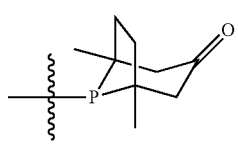 [SMILES: *P1C2(C)CCC1(C)CC(=O)C2] 1-32
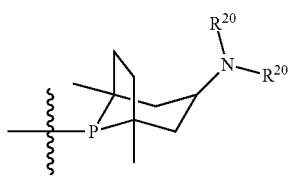 1-33
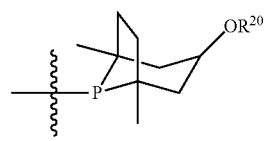 1-34
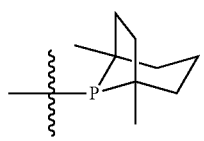 [SMILES: *P1C2(C)CCCC1(C)CC2] 1-35

TABLE 1-continued
6-Membered Ring Phosphacycles
1-36
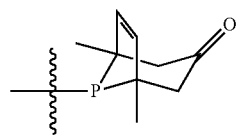 [SMILES: *P1C2(C)C=CC1(C)CC(=O)C2]
1-37
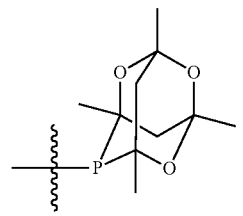 [SMILES: *P1C2(C)CC3(C)OC(C)(CC1(C)O3)O2]
1-38
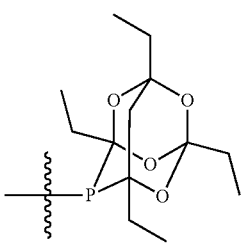 [SMILES: *P1C2(CC)CC3(CC)OC(CC)(O2)OC1(CC)O3]
1-39
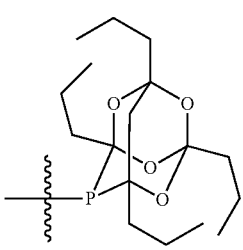 [SMILES: *P1C2(CCC)CC3(CCC)OC(CCC)(O2)OC1(CCC)O3]
1-40
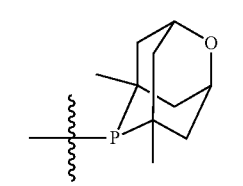 [SMILES: *P1C2(C)CC3CC1(C)CC(C2)O3]
1-41
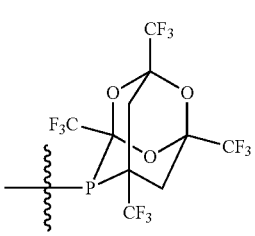 [SMILES: *P1C2(C(F)(F)F)CC3(C(F)(F)F)OC(C(F)(F)F)(C2)OC1(C(F)(F)F)O3]
1-42
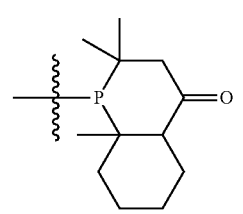 [SMILES: *P1C(C)(C)CC(=O)C2CCCCC21C]
TABLE 1-continued
6-Membered Ring Phosphacycles
1-43
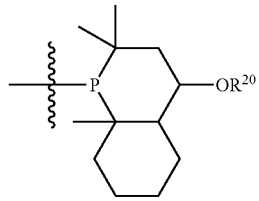
1-44
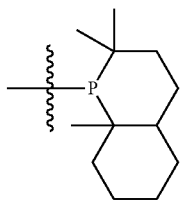 [SMILES: *P1C(C)(C)CCC2CCCCC21C]
1-45
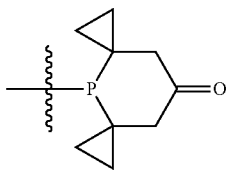 [SMILES: *P1C2(CC2)CC(=O)CC12CC2]
1-46
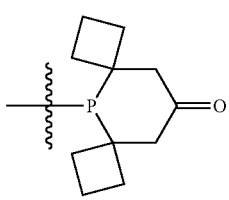 [SMILES: *P1C2(CCC2)CC(=O)CC12CCC2]
1-47
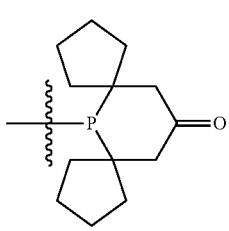 [SMILES: *P1C2(CCCC2)CC(=O)CC12CCCC2]
1-48
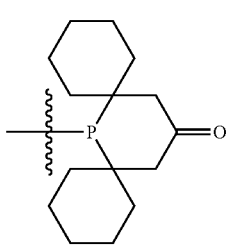 [SMILES: *P1C2(CCCCC2)CC(=O)CC12CCCCC2]
1-49
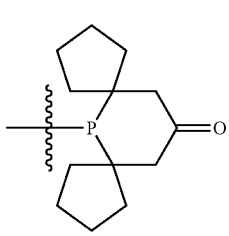 [SMILES: *P1C2(CCCC2)CC(=O)CC12CCCC2]

TABLE 1-continued
6-Membered Ring Phosphacycles
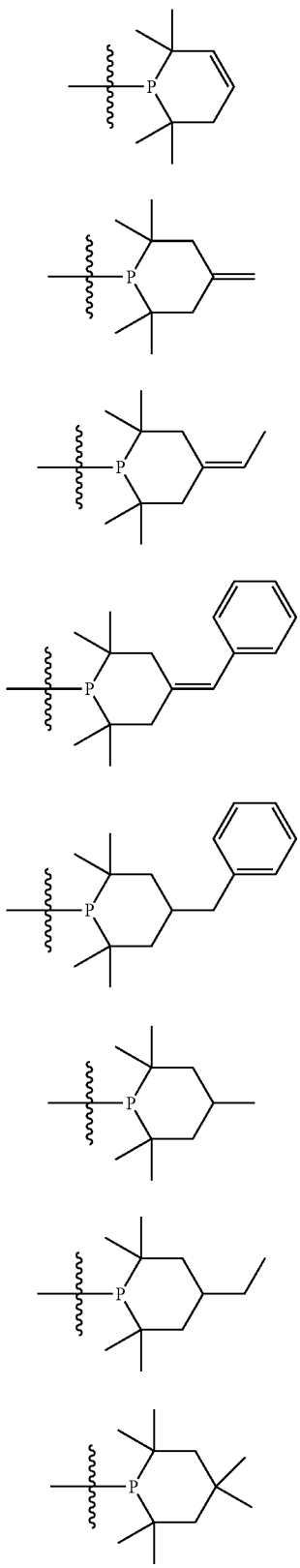
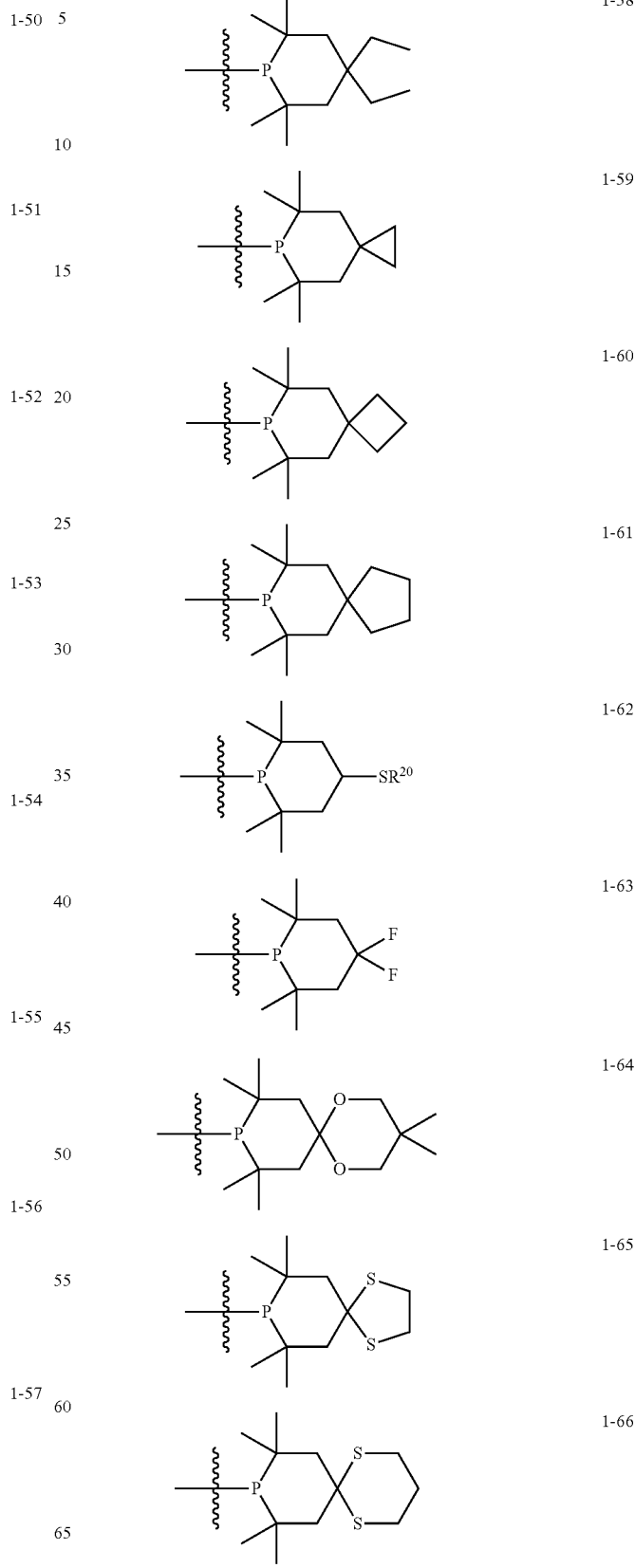

TABLE 1-continued

6-Membered Ring Phosphacycles

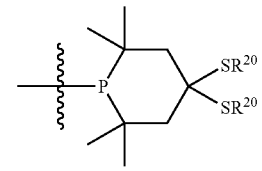

1-67

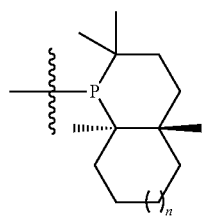

1-68

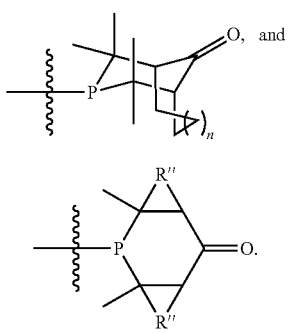

1-69

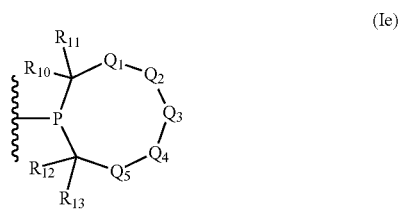

1-70 or a salt thereof, wherein R'' is selected from the group consisting of oxygen, NR$^{20}$, and C(R$^{20}$)$_2$;

R$^{20}$ is hydrogen, alkyl, aryl, heteroaryl, arylalkyl or heteroarylalkyl, wherein the aryl, heteroaryl, aryl of arylalkyl and heteroaryl of heteroarylalkyl are optionally substituted with alkyl, alkenyl, alkynyl, alkoxy, cyano, halo, haloalkyl or haloalkoxy; and n is 0, 1, or 2.

Other phosphacycles X are based on rings other than a 6-membered ring. Such phosphacycles are included in those represented by formula (Ie):

(Ie)

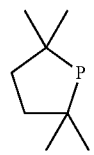

In formula (Ie), at least one of Q1, Q2, Q3, Q4, and Q5 is not a bond, so that the phosphacycle has at least four members. In addition, Q$^1$ is a bond, —O—, —S—, —N(R$^{21}$)—, =C(R$^{22}$)—, or —C(R$^{23}$)(R$^{24}$)—;

Q$^2$ is a bond, —O—, —S—, —N(R$^{25}$)—, =C(R$^{26}$)—, or —C(R$^{27}$)(R$^{28}$)—;

Q$^3$ is a bond, —O—, —S—, —N(R$^{29}$)—, =C(R$^{30}$)—, or —C(R$^{32}$)(R$^{30}$)—;

Q$^4$ is a bond, —O—, —S—, —N(R$^{33}$)—, =C(R$^{34}$)—, or —C(R$^{35}$)(R$^{36}$)—; and Q$^5$ is a bond, —O—, —S—, —N(R$^{37}$)—, =C(R$^{38}$)—, or —C(R$^{39}$)(R$^{40}$)—;

wherein R$^{10}$, R$^{11}$, R$^{12}$, R$^{13}$, and R$^{21}$ through R$^{40}$ are ring substituents.

In various embodiments, one or more of the ring substituents R$^{21}$ through R$^{40}$ form a ring with another ring substituent. If they do not form a ring, in certain embodiments the ring substituents R$^{21}$ through R$^{40}$ are independently selected from H, halo, fluoro, alkyl, haloalkyl, fluoroalkyl, alkenyl, alkynyl, alkyloxy, N-alkylamino, N,N-dialkylamino, N,N,N-trialkylammoniumalkyl; substituted or unsubstituted cycloalkyl, substituted or unsubstituted heterocycloalkyl, substituted or unsubstituted C$_{5-6}$ heteroaryl, substituted or unsubstituted phenyl; hydroxyalkyl; alkoxyalkyl; aminoalkyl; N-alkylaminoalkyl; N,N-dialkylaminoalkyl; N,N,N-trialkylammoniumalkyl; L$^1$-C(O)—OR$^{1'}$, L$^1$-P(O)—(OR$^{1'}$)$_2$, or L$^1$-S(O)$_2$—OR$^{1'}$ where R$^{1'}$ is hydrogen, alkyl or hydroxyalkyl and L$^1$ is a bond or alkylene; L$^2$-O—C(O)—R$^{2'}$ where R$^{2'}$ is alkyl or hydroxyalkyl and L$^2$ is a bond or alkylene; L$^3$-C(O)—NR$^{3'}$R$^{4'}$ where R$^{3'}$ and R$^{4'}$ are independently selected from H, alkyl, and hydroxyalkyl and wherein L$^3$ is a bond or alkylene; L$^4$-NR$^{5'}$—C(O)—R$^{6'}$ wherein R$^{5'}$ is selected from H and alkyl, R$^{6'}$ is selected from alkyl and hydroxyalkyl, and L$^4$ is a bond or alkylene; and alkylthio.

Alternatively, two ring substituents on the same ring atom Q1, Q2, Q3, Q4, or Q5 together form a carbonyl; an exocyclic double bond optionally substituted with alkyl, alkenyl, aryl, cycloalkyl, heterocyclyl, or heteroaryl; or a 3- to 7-membered spiro ring containing zero, one, or two hetero ring atoms. The optional substituents on the exocyclic double bond or spiro ring are selected from those used for groups R$^1$ and R$^2$, in non-limiting embodiments In various embodiments of formula (I), the phosphacycle X of formula (Ie) is a 4-membered, 5-membered, 7-membered, or 8-membered ring, optionally containing bridging to form a polycyclic ring.

In certain embodiments of ligands incorporating group X of formula (Ie) into the substituted biaryl structure of formula (I), the groups R$^1$ and R$^2$ are selected from H, alkyl, and alkoxy and R$^{10}$, R$^{11}$, R$^{12}$, and R$^{13}$ are selected from alkyl, aryl, and heteroaryl, or wherein R$^{10}$ or R$^{11}$ together with R$^{12}$ or R$^{13}$ form a ring.

Non-limiting examples of phosphacycles of formula (Ie) are illustrated in Table 2.

TABLE 2

4-, 5-, 7, and 8-Membered Phosphacycles.

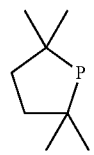

2-1

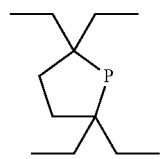

2-2

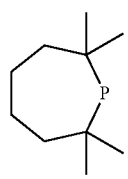

2-3

TABLE 2-continued
4-, 5-, 7, and 8-Membered Phosphacycles.
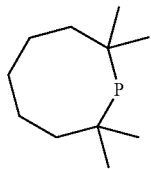
2-4
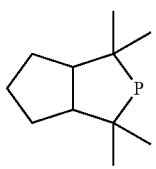
2-5
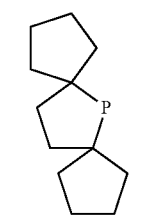
2-6
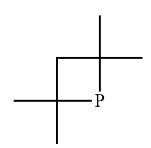
2-7
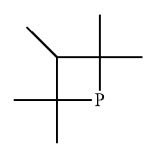
2-8
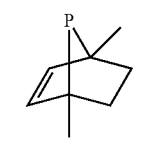
2-9
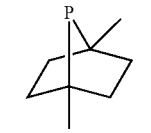
2-10
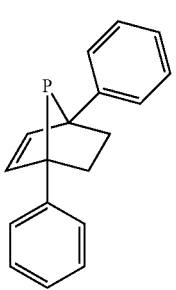
2-11
TABLE 2-continued
4-, 5-, 7, and 8-Membered Phosphacycles.
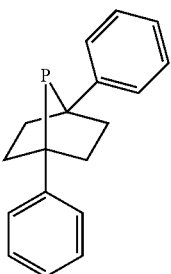
2-12
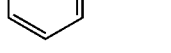
2-13
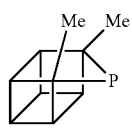
2-14
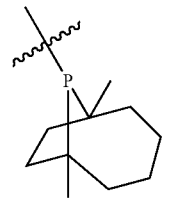 [SMILES: *P1C2(C)CCCCC1(C)CC2]
2-15
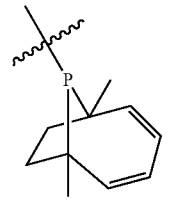 [SMILES: *P1C2(C)C=CC=CC1(C)CC2]
2-16
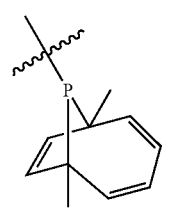 [SMILES: *P1C2(C)C=CC=CC1(C)C=C2]
2-17
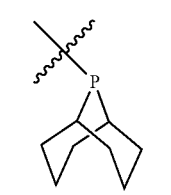 [SMILES: *P1C2CCCC1CCC2]
2-18
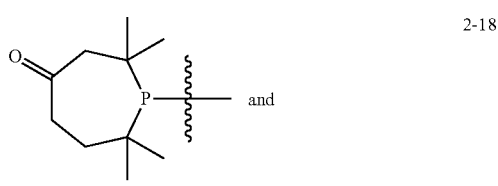 and TABLE 2-continued 4-, 5-, 7, and 8-Membered Phosphacycles.

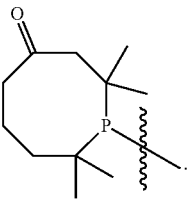 [SMILES: *P1C(C)(C)CCCC(=O)CC1(C)C]
2-19

In various embodiments, phosphacycles of formula (Ia), (Id), and (Ie), including the individual species shown in Tables 1 and 2, are substituted as group X on the $Ar^1$-$Ar^2$ group of formula (I), wherein the groups $R^1$ and $R^2$ are hydrogen or a non-hydrogen substituent. Illustrative substitution patterns on the $Ar^1$-$Ar^2$ group are given in formulae (I-1)-(I-42) in Table 3, where $R^1$ and $R^2$ are as defined herein.

TABLE 3

(I-1)

(I-2)

(I-3)

(I-4)

TABLE 3-continued

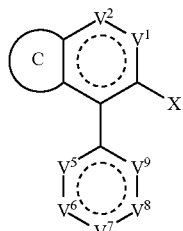
(I-5)

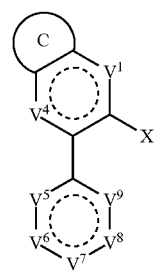
(I-6)

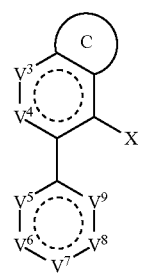
(I-7)

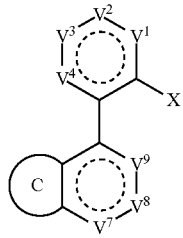
(I-8)

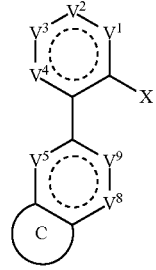
(I-9)

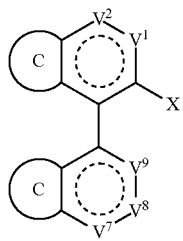
(I-10)

TABLE 3-continued
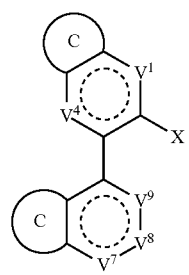
(I-11)
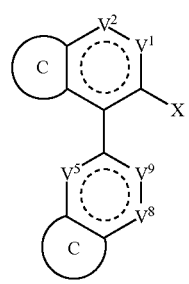
(I-12)
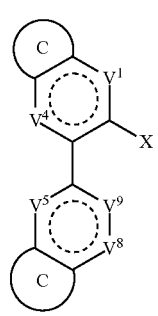
(I-13)
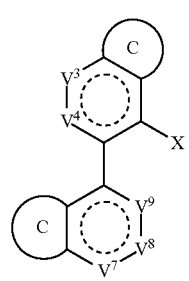
(I-14)
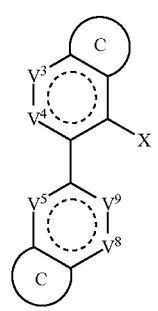
(I-15)
TABLE 3-continued
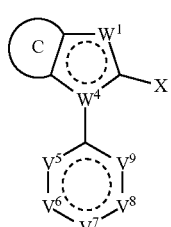
(I-16)
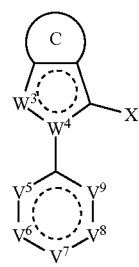
(I-17)
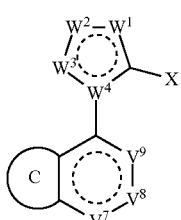
(I-18)
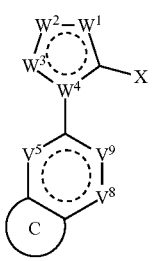
(I-19)
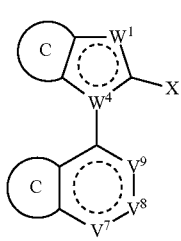
(I-20)
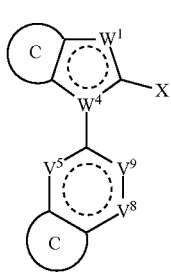
(I-21)

TABLE 3-continued
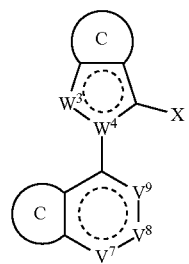 (I-22)
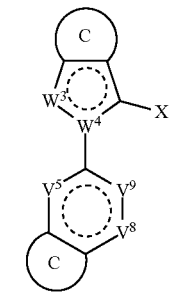 (I-23)
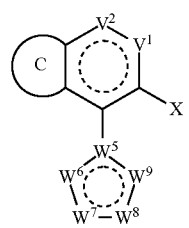 (I-24)
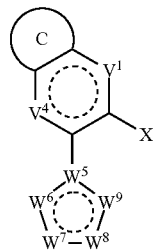 (I-25)
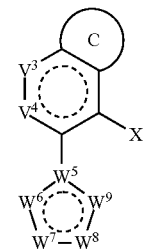 (I-26)
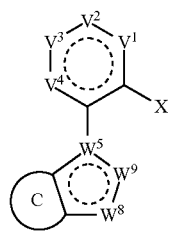 (I-27)
TABLE 3-continued
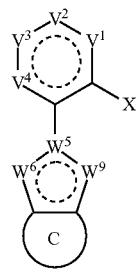 (I-28)
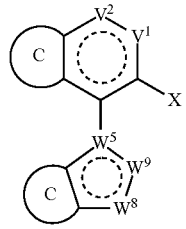 (I-29)
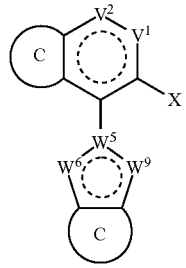 (I-30)
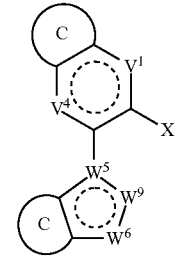 (I-31)
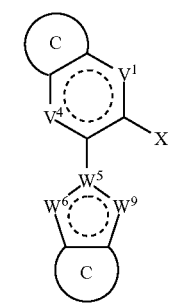 (I-32)
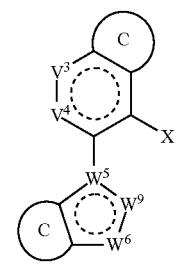 (I-33)

TABLE 3-continued (I-34) 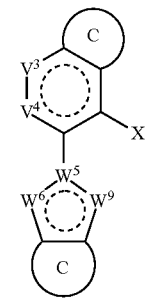

(I-35) 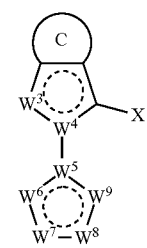

(I-36) 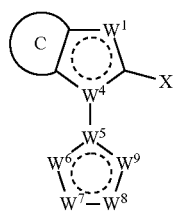

(I-37) 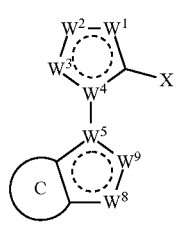

(I-38) 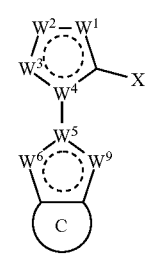

(I-39) 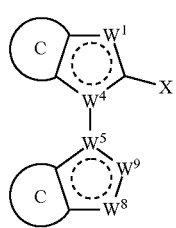

TABLE 3-continued (I-40) 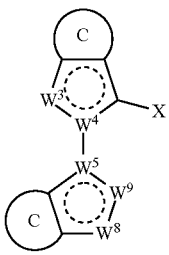

(I-41) 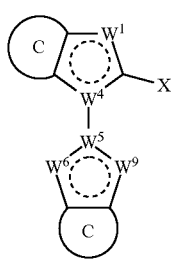

(I-42) 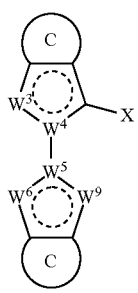

wherein X is a phosphine of formula (Ia) or (Ib);
$V^1$, $V^2$, $V^3$, and $V^4$ are independently selected from $CR^1$ or N;
$V^5$, $V^6$, $V^7$, $V^8$ and $V^9$ are independently selected from $CR^2$ or N;
$W^1$, $W^2$, an $W^3$ are independently selected from $CR^1$, $NR^1$, N or O;
$W^4$ is C or N;
$W^5$ is C or N;
$W^6$, $W^7$, $W^8$ and $W^9$ are independently selected from $CR^2$, $NR^2$, N or O;

indicates that the 5- or 6-membered ring which it is inside is aromatic; and ring C, at each occurrence, is independently a fused-aryl or fused-heteroaryl unsubstituted or substituted with $R^1$ and $R^2$, respectively, any number of times depending on, for example, stability and rules of valence.

In particular embodiments, the groups $R^1$ and $R^2$ substituted as shown in each of Formulae (I-1)-(I-42) are selected from alkyl, alkoxy, dialkylamino, haloalkyl, fluoroalkyl, and phenyl. In various embodiments, the alkyl groups are $C_1$-$C_3$ alkyl, the alkoxy are $C_1$-$C_3$ alkoxy, and the haloalkyl and fluoroalkyl and are also based on $C_1$-$C_3$ alkyl groups. Examples of alkyl include methyl, ethyl, and isopropyl. Examples of alkoxy include methoxy and isopropoxy. Examples of haloalkyl include trifluoromethyl. Examples of the dialkylamino include dimethylamino.

Sub-genera disclosed by combining Ar¹-Ar² substitution formulae (I-1)-(I-42) and phosphacycle formulae Ia, Id, and Ie are designated for convenience by referring to both formulae in the sub-genus name. So, for example, in addition to the generic ligand formulae disclosed above, a sub-genus (I-2)-(1-5) would indicate that the diaryl substitution pattern is that of formula (I-2) and the phosphacycle is that of generic formula 1-5. To further illustrate, a sub-genus denoted as (I-4)-(1-3) would be based on the substitution pattern of formula (I-4) and the phosphacycle of formula (1-3), and so on according to the pattern described. In this way a total of 3649 sub-generic structures are disclosed by combining each of formulae (I-1)-(I-42) with each of formulae Ia, Id, and Ie in turn.

Sub-generic structures for the specific phosphacycles ligands are conveniently designated by referring to the biaryl portion of the ligand depicted in Table 3, (I-1), first, then the designation of the phosphacycle in Table 1 or Table 2. Thus for example a species or sub-genus including the biaryl of formula (I-3) further substituted by the number (2-3) phosphacycle from Table 2 would be (I-3)-(2-3).

Thus, in various embodiments suitable ligands are selected from those of any of the formulae (I-1)-(I-42), wherein X is selected from any of the generic phosphacycles of formulae Ia, Id, or Ie, or is selected from any of the specific phosphacycles shown in Table 1 or Table 2. In these embodiments, the groups R¹ and R² are selected from those described above for formula (I). In various embodiments, the ligands of this paragraph are further defined as the groups R¹ and R² being selected from alkyl, alkoxy, haloalkyl (including fluoroalkyl such as trifluoromethyl), and dialklamino. In various embodiments, the alkyl groups are $C_1$-$C_3$ alkyl, the alkoxy are $C_1$-$C_3$ alkoxy, and the haloalkyl and fluoroalkyl and are also based on $C_1$-$C_3$ alkyl groups. Examples of alkyl include methyl, ethyl, and isopropyl. Examples of alkoxy include methoxy and isopropoxy. Examples of haloalkyl include trifluoromethyl. Examples of the dialkylamino group include dimethylamino.

In one embodiment, the phosphine ligand is (I-1),

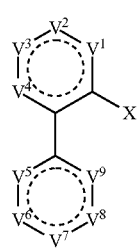

(I-1)

or a salt thereof, wherein
- $V^1$ and $V^4$ are $CR^1$, wherein $R^1$ is independently, at each occurrence, hydrogen, alkyl or alkoxy;
- $V^2$ and $V^3$ are $CR^1$, wherein $R^1$ is independently, at each occurrence, hydrogen, alkyl or alkoxy;
- $V^5$ and $V^9$ are $CR^2$, wherein $R^2$ is independently, at each occurrence, hydrogen, alkyl, alkoxy or dialkylamino;
- $V^6$ and $V^8$ are $CR^2$, wherein $R^2$ is independently, at each occurrence, hydrogen, alkyl or alkoxy;
- $V^7$ is $CR^2$, wherein $R^2$ is hydrogen or alkyl; and
- X is selected from the group consisting of 1-1, 1-2, 1-3, 1-4, 1-5, and 1-64.

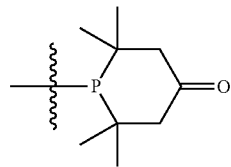

1-1

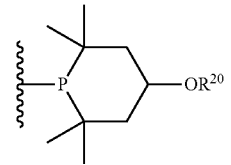

1-2

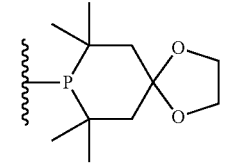

1-3

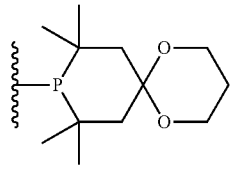

1-4

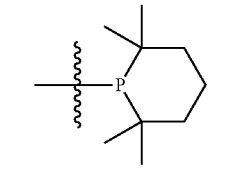

1-5

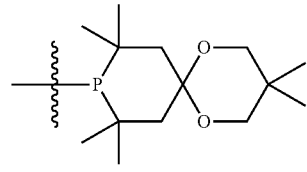

1-64

Specific embodiments may include, but are not limited to, compounds of formula (I), as defined, for example:
2,2,6,6-tetramethyl-1-(2',4',6'-triisopropylbiphenyl-2-yl) phosphinane;
2,2,6,6-tetramethyl-1-(2',4',6'-triisopropylbiphenyl-2-yl) phosphinan-4-one;
2,2,6,6-tetramethyl-1-(2',4',6'-triisopropylbiphenyl-2-yl) phosphinan-4-ol;
7,7,9,9-tetramethyl-8-(2',4',6'-triisopropylbiphenyl-2-yl)-1,4-dioxa-8-phosphaspiro[4.5]decane;
8,8,10,10-tetramethyl-9-(2',4',6'-triisopropylbiphenyl-2-yl)-1,5-dioxa-9-phosphaspiro[5.5]undecane;
3,3,8,8,10,10-hexamethyl-9-(2',4',6'-triisopropylbiphenyl-2-yl)-1,5-dioxa-9-phosphaspiro[5.5]undecane;
1-(2'-(dimethylamino)-6'-methoxybiphenyl-2-yl)-2,2,6,6-tetramethylphosphinan-4-one;
1-(2',6'-bis(dimethylamino)biphenyl-2-yl)-2,2,6,6-tetramethylphosphinan-4-one;
1-(2',6'-dimethoxybiphenyl-2-yl)-2,2,6,6-tetramethylphosphinan-4-one;
1-(2',6'-diisopropoxybiphenyl-2-yl)-2,2,6,6-tetramethylphosphinan-4-one;

1-(2'-(dimethylamino)biphenyl-2-yl)-2,2,6,6-tetramethylphosphinan-4-one;
1-(biphenyl-2-yl)-2,2,6,6-tetramethylphosphinan-4-one;
1-(1,1'-binaphthyl-2-yl)-2,2,6,6-tetramethylphosphinan-4-one;
1-(2'-methoxy-1,1'-binaphthyl-2-yl)-2,2,6,6-tetramethylphosphinan-4-one;
1-(3,6-dimethoxybiphenyl-2-yl)-2,2,6,6-tetramethylphosphinan-4-one;
1-(3,6-dimethoxy-2',4',6'-trimethylbiphenyl-2-yl)-2,2,6,6-tetramethylphosphinan-4-one;
2,2,6,6-tetramethyl-1-(2',4',6'-triisopropyl-3,6-dimethoxybiphenyl-2-yl)phosphinan-4-one;
2,2,6,6-tetramethyl-1-(2',4',6'-triisopropyl-4,5-dimethoxybiphenyl-2-yl)phosphinan-4-one;
1-(3',5'-dimethoxybiphenyl-2-yl)-2,2,6,6-tetramethylphosphinan-4-one;
1-(4'-tert-butylbiphenyl-2-yl)-2,2,6,6-tetramethylphosphinan-4-one;
6-methoxy-N,N-dimethyl-2'-(7,7,9,9-tetramethyl-1,4-dioxa-8-phosphaspiro[4.5]decan-8-yl)biphenyl-2-amine;
$N^2,N^2,N^6,N^6$-tetramethyl-2'-(7,7,9,9-tetramethyl-1,4-dioxa-8-phosphaspiro[4.5]decan-8-yl)biphenyl-2,6-diamine;
8-(2',6'-dimethoxybiphenyl-2-yl)-7,7,9,9-tetramethyl-1,4-dioxa-8-phosphaspiro[4.5]decane;
8-(2',6'-diisopropoxybiphenyl-2-yl)-7,7,9,9-tetramethyl-1,4-dioxa-8-phosphaspiro[4.5]decane;
N,N-dimethyl-2'-(7,7,9,9-tetramethyl-1,4-dioxa-8-phosphaspiro[4.5]decan-8-yl)biphenyl-2-amine;
8-(biphenyl-2-yl)-7,7,9,9-tetramethyl-1,4-dioxa-8-phosphaspiro[4.5]decane;
8-(3,6-dimethoxybiphenyl-2-yl)-7,7,9,9-tetramethyl-1,4-dioxa-8-phosphaspiro[4.5]decane;
8-(3,6-dimethoxy-2',4',6'-trimethylbiphenyl-2-yl)-7,7,9,9-tetramethyl-1,4-dioxa-8-phosphaspiro[4.5]decane;
7,7,9,9-tetramethyl-8-(2',4',6'-triisopropyl-3,6-dimethoxybiphenyl-2-yl)-1,4-dioxa-8-phosphaspiro[4.5]decane;
7,7,9,9-tetramethyl-8-(2',4',6'-triisopropyl-4,5-dimethoxybiphenyl-2-yl)-1,4-dioxa-8-phosphaspiro[4.5]decane;
8-(3',5'-dimethoxybiphenyl-2-yl)-7,7,9,9-tetramethyl-1,4-dioxa-8-phosphaspiro[4.5]decane;
8-(4'-tert-butylbiphenyl-2-yl)-7,7,9,9-tetramethyl-1,4-dioxa-8-phosphaspiro[4.5]decane; and
2,2,6,6-tetramethyl-1-(2',4',6'-triisopropyl-3,6-dimethoxybiphenyl-2-yl)phospinane.

In one embodiment, the phosphine ligand is (1-8),

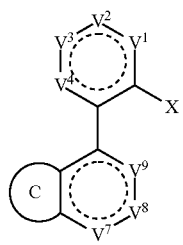

(I-8)

or a salt thereof, wherein $V^1$ and $V^2$ are each $CR^1$, wherein $R^1$ is, at each occurrence, hydrogen;

$V^3$ and $V^4$ are independently selected from $CR^1$ or N;

$V^7$ and $V^8$ are each $CR^2$, wherein $R^2$ is, at each occurrence, hydrogen;

$V^9$ is $CR^2$, wherein $R^2$ is hydrogen;

ring C at each occurrence is an unsubstituted fused-phenyl; and

X is a phosphine having a structure corresponding to a formula selected from the group consisting of formulae 1-1, 1-3 and 1-5.

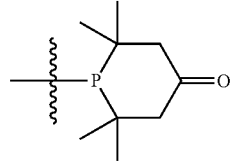

1-1

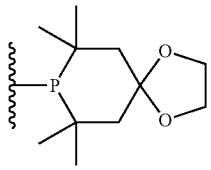

1-3

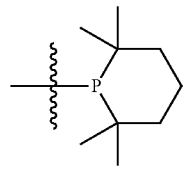

1-5

Specific embodiments contemplated as part of the invention also include, but are not limited to, compounds of formula (I), as defined, for example:

2,2,6,6-tetramethyl-1-(2-(naphthalen-1-yl)phenyl)phosphinan-4-one; and 7,7,9,9-tetramethyl-8-(4-methyl-2-(naphthalen-1-yl)phenyl)-1,4-dioxa-8-phosphaspiro[4.5]decane.

In one embodiment, the phosphine ligand is (I-10),

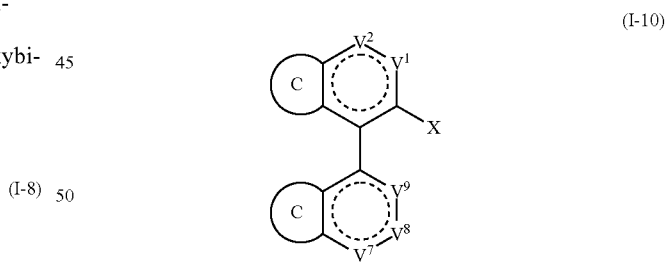

(I-10)

or a salt thereof, wherein $V^1$ and $V^2$ are each $CR^1$, wherein $R^1$ is, at each occurrence, hydrogen;

$V^7$ and $V^8$ are each $CR^2$, wherein $R^2$ is, at each occurrence, hydrogen;

$V^9$ is $CR^2$, wherein $R^2$ is hydrogen or alkoxy;

ring C at each occurrence is an unsubstituted fused-phenyl; and

X is a phosphine having a structure corresponding to a formula selected from the group consisting of formulae 1-1, 1-3, and 1-5.

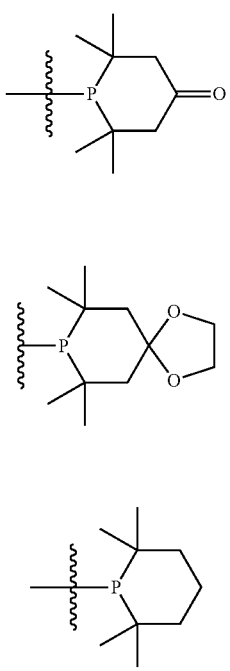

Specific embodiments contemplated as part of the invention also include, but are not limited to, compounds of formula (I), as defined, for example:

1-(1,1'-binaphthyl-2-yl)-2,2,6,6-tetramethylphosphinan-4-one;

1-(2'-methoxy-1,1'-binaphthyl-2-yl)-2,2,6,6-tetramethylphosphinan-4-one;

8-(1,1'-binaphthyl-2-yl)-7,7,9,9-tetramethyl-1,4-dioxa-8-phosphaspiro[4.5]decane; and 8-(2'-methoxy-1,1'-binaphthyl-2-yl)-7,7,9,9-tetramethyl-1,4-dioxa-8-phosphaspiro[4.5]decane.

In one embodiment, the phosphine ligand is (I-9),

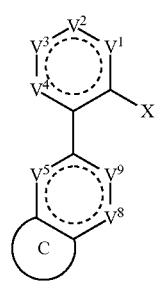

(I-9)

or a salt thereof, wherein $V^1$, $V^2$, $V^3$, and $V^4$ are each $CR^1$, wherein $R^1$, at each occurrence, is hydrogen;

$V^5$, $V^8$ and $V^9$ are each $CR^2$, wherein $R^2$, at each occurrence, is hydrogen;

ring C is an unsubstituted fused-phenyl; and

X is a phosphine having a structure corresponding to a formula selected from the group consisting of formulae 1-1, 1-3, and 1-5.

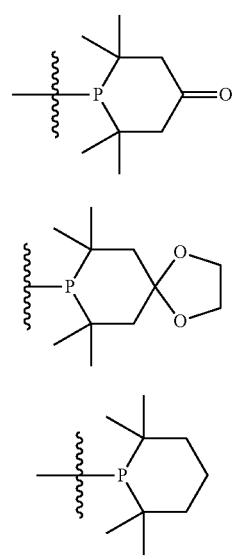

Specific embodiments contemplated as part of the invention also include, but are not limited to, compounds of formula (I), as defined, for example:

2,2,6,6-tetramethyl-1-(2-(naphthalen-2-yl)phenyl)phosphinan-4-one; and 7,7,9,9-tetramethyl-8-(2-(naphthalen-2-yl)phenyl)-1,4-dioxa-8-phosphaspiro[4.5]decane.

In one embodiment, the phosphine ligand is (I-2),

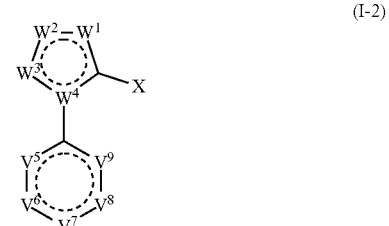

(I-2)

or a salt thereof, wherein $W^1$ and $W^2$ are each $CR^1$, wherein $R^1$, at each occurrence, is hydrogen;

$W^3$ and $W^4$ are each N;

$V^5$, $V^6$, $V^7$, $V^8$, and $V^9$ are each $CR^2$, wherein $R^2$, at each occurrence, is hydrogen; and X is a phosphine having a structure corresponding to a formula selected from the group consisting of formulae 1-1, 1-3 and 1-5.

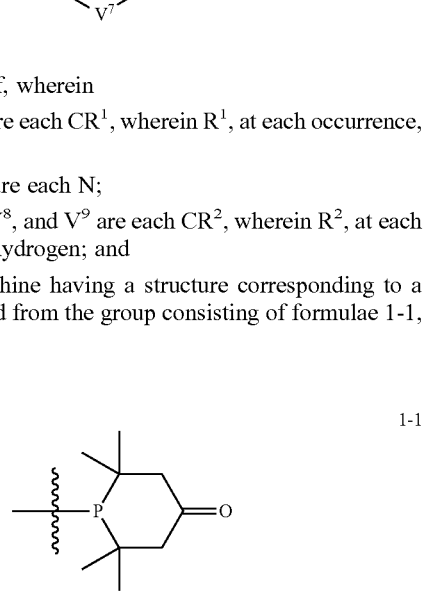

-continued

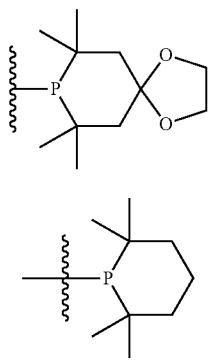
1-3

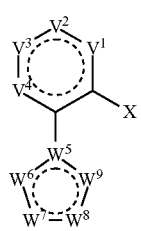
1-5

Specific embodiments contemplated as part of the invention also include, but are not limited to, compounds of formula (I), as defined, for example:

2,2,6,6-tetramethyl-1-(1-phenyl-1H-pyrazol-5-yl)phosphinan-4-one; and 1-phenyl-5-(7,7,9,9-tetramethyl-1,4-dioxa-8-phosphaspiro[4.5]decan-8-yl)-1H-pyrazole.

In one embodiment, the phosphine ligand is (I-3), (I-3)

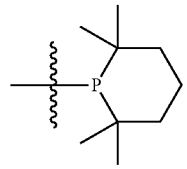

or a salt thereof, wherein $V^1$, $V^2$, $V^3$ and $V^4$ are each $CR^1$, wherein $R^1$, at each occurrence, is hydrogen;

$W^6$, $W^7$, $W^8$ and $W^9$ are each $CR^2$, wherein $R^2$, at each occurrence, is hydrogen;

$W^5$ is N; and

X is a phosphine having a structure corresponding to a formula selected from the group consisting of formulae 1-1, 1-3 and 1-5.

1-1

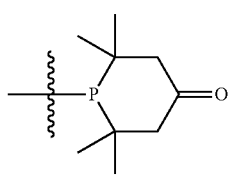

1-3

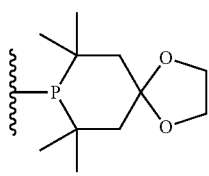

-continued 1-5

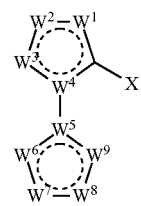

Specific embodiments contemplated as part of the invention also include, but are not limited to, compounds of formula (I), as defined, for example:

1-(2-(1H-pyrrol-1-yl)phenyl)-2,2,6,6-tetramethylphosphinan-4-one; and 1-(2-(7,7,9,9-tetramethyl-1,4-dioxa-8-phosphaspiro[4.5]decan-8-yl)phenyl)-1H-pyrrole.

In one embodiment, the phosphine ligand is (I-4), (I-4)

or a salt thereof, wherein $W^1$ and $W^2$ are each $CR^1$, wherein $R^1$, at each occurrence, is hydrogen;

$W^3$ and $W^4$ are each N;

$W^5$ is C;

$W^6$ and $W^9$ are each $CR^2$, wherein $R^2$, at each occurrence, is substituted or unsubstituted phenyl;

$W^7$ is N;

$W^8$ is $NR^2$, wherein $R^2$, at each occurrence, is phenyl optionally substituted with alkyl, alkenyl, alkynyl, alkoxy, cyano, halo, haloalkyl or haloalkoxy; and X is a phosphine having a structure corresponding to a formula selected from the group consisting of formulae 1-1, 1-3 and 1-5.

-continued 1-5

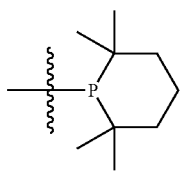

Specific embodiments contemplated as part of the invention also include, but are not limited to, compounds of formula (I), as defined, for example:
2,2,6,6-Tetramethyl-1-(1',3',5'-triphenyl-1'H-1,4'-bipyrazol-5-yl)phosphinan-4-one;
1'1',3',5'-Triphenyl-5-(7,7,9,9-tetraethyl-1,4-dioxa-8-phosphaspiro[4.5]decan-8-yl)-1'H-1,4'-bipyrazole; and
1',3',5'-Triphenyl-5-(2,2,6,6-tetramethylphosphinan-1-yl)-1'H-1,4'-bipyrazole.

In one embodiment, the phosphine ligand is (I-1), (I-1)

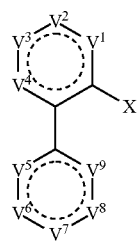

or a salt thereof, wherein
$V^1$, $V^2$, $V^3$ and $V^4$ are each $CR^1$, wherein $R^1$ is, at each occurrence, hydrogen;
$V^5$ and $V^9$ are $CR^2$, wherein $R^2$ is independently, at each occurrence, hydrogen or alkyl;
$V^6$ and $V^8$ are $CR^2$, wherein $R^2$, at each occurrence, is hydrogen;
$V^7$ is $CR^2$, wherein $R^2$ is hydrogen or alkyl; and
X is a phosphine of formula 1-37.

1-37

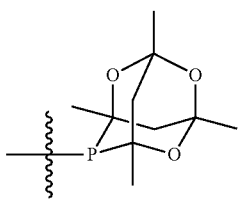

Specific embodiments contemplated as part of the invention also include, but are not limited to, compounds of formula (I), as defined, for example:
1,3,5,7-tetramethyl-8-(2',4',6'-triisopropylbiphenyl-2-yl)-2,4,6-trioxa-8-phosphatricyclo[3.3.1.1³,⁷]decane; and
8-(biphenyl-2-yl)-1,3,5,7-tetramethyl-2,4,6-trioxa-8-phosphatricyclo[3.3.1.1³,⁷]decane.

In one embodiment, the phosphine ligand is (I-1), or a salt thereof, wherein
$V^1$, $V^2$, $V^3$ and $V^4$ are each $CR^1$, wherein $R^1$ is, at each occurrence, hydrogen;
$V^5$ and $V^9$ are $CR^2$, wherein $R^2$ is independently, at each occurrence, hydrogen or alkyl;
$V^6$ and $V^8$ are $CR^2$, wherein $R^2$, at each occurrence, is hydrogen;
$V^7$ is $CR^2$, wherein $R^2$ is hydrogen or alkyl; and
X is a phosphine having a structure corresponding to a formula selected from the group consisting of formulae 2-3, 2-4, 2-18, and 2-19

2-3

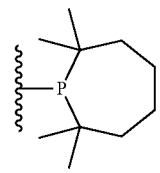

2-4

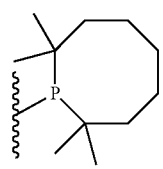

2-18

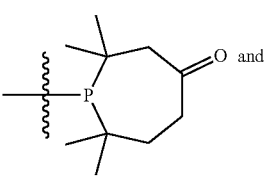

and 2-19

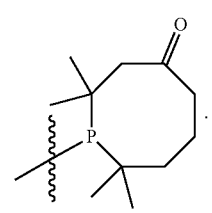

.

Specific embodiments contemplated as part of the invention also include, but are not limited to, compounds of formula (I), as defined, for example:
1-(biphenyl-2-yl)-2,2,7,7-tetramethylphosphepan-4-one;
1-(biphenyl-2-yl)-2,2,7,7-tetramethylphosphepane;
2,2,7,7-tetramethyl-1-(2',4',6'-triisopropylbiphenyl-2-yl)phosphepan-4-one;
2,2,7,7-tetramethyl-1-(2',4',6'-triisopropylbiphenyl-2-yl)phosphepane;
2,2,8,8-tetramethyl-1-(2',4',6'-triisopropylbiphenyl-2-yl)phosphocan-4-one; and
2,2,8,8-tetramethyl-1-(2',4',6'-triisopropylbiphenyl-2-yl)phosphocane.

In another embodiment, ligands are selected from those of formula (Ic), where a phosphacyclic ring is fused to the (upper) $Ar^1$ ring further substituted with $R^1$, (Ic)

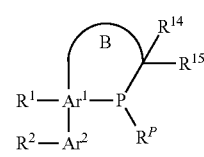

where $Ar^1$, $Ar^2$, $R^2$, $R^{14}$, $R^{15}$ and $R^P$ are as defined above. Ring B contains 0, 1, 2, or 3 heteroatoms in addition to the phosphorus bonded to the upper $Ar^1$ ring.

In one embodiment, the ligands are represented by formula (Ic-1):

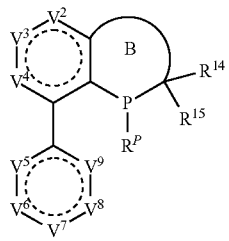

(Ic-1)

where $V^1$ through $V^9$ are as defined above.

In a further embodiment, the phosphine ligands are represented by formula (Ic-1a),

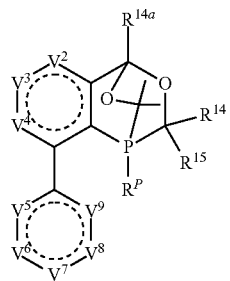

(Ic-1a)

wherein, $R^{14a}$ is alkenyl; alkoxy; alkoxyalkyl; alkyl; N-alkylamino; alkylthio; alkynyl; aminoalkyl; N-alkylaminoalkyl; N,N-dialkylaminoalkyl; N,N,N-trialkylammoniumalkyl; substituted or unsubstituted arylalkyl; substituted or unsubstituted cycloalkyl; dialkylamino; halo; haloalkyl; fluoroalkyl; substituted or unsubstituted $C_{5-6}$ heteroaryl; substituted or unsubstituted heterocycloalkyl; hydroxy; hydroxyalkyl; substituted or unsubstituted phenyl; $L^1$-C(O)—$OR^{1'}$, $L^1$-P(O)—$(OR^{1'})_2$, or $L^1$-S(O)$_2$—$OR^{1'}$ where $R^{1'}$ is hydrogen, alkyl or hydroxyalkyl and $L^1$ is a bond or alkylene; $L^2$-O—C(O)—$R^{2'}$ where $R^{2'}$ is alkyl or hydroxyalkyl and $L^2$ is a bond or alkylene; $L^3$-C(O)—$NR^{3'}R^{4'}$ where $R^{3'}$ and $R^{4'}$ are independently selected from H, alkyl, and hydroxyalkyl and wherein $L^3$ is a bond or alkylene; $L^4$-$NR^{5'}$—C(O)—$R^{6'}$ wherein $R^{5'}$ is selected from H and alkyl, $R^{6'}$ is selected from alkyl and hydroxyalkyl, and $L^4$ is a bond or alkylene; and $L^7$-$NR^{8'}$—S(O)$_2$—$R^{9'}$ wherein $R^{8'}$ is H or alkyl, $R^{9'}$ is alkyl and hydroxyalkyl, and $L^7$ is a bond or alkylene and where $V^1$ through $V^9$ are as defined above.

Phosphine ligands may include, for example, 7,7,9,9-tetramethyl-8-(2',4',6'-triisopropylbiphenyl-2-yl)-1,4-dioxa-8-phosphaspiro[4.5]decane; 2,2,6,6-tetramethyl-1-(2,4,6-triisopropylbiphenyl-2-yl)phosphinane; 8,8,10,10-tetramethyl-9-(2',4',6'-triisopropylbiphenyl-2-yl)-1,5-dioxa-9-phosphaspiro[5.5]undecane; 2,2,6,6-tetramethyl-1-(2',4',6'-triisopropylbinphenyl-2-yl)phosphinan-4-ol; 8-(2',6'-diisopropoxybiphenyl-2-yl)-7,7,9,9-tetramethyl-1,4-dioxa-8-phosphaspiro[4.5]decane; 1,3,5,7-tetramethyl-8-(2',4',6'-triisopropylbiphenyl-2-yl)-2,4,6-trioxa-8-phosphatricyclo[3.3.1.1$^{3,7}$]decane; 2,2,5,5-tetramethyl-1-(2',4',6'-triisopropyl-3,4,5,6-tetramethylbiphenyl-2-yl)phospholane; 2,2,6,6-tetramethyl-1-(2',4',6'-triisopropyl-3,4,5,6-tetramethylbiphenyl-2-yl)phosphinane; 2,2,7,7-tetramethyl-1-(2',4',6'-triisopropyl-3,4,5,6-tetramethylbiphenyl-2-yl)phosphepane; 2,2,8,8-tetramethyl-1-(2',4',6'-triisopropyl-3,4,5,6-tetramethylbiphenyl-2-yl)phosphocane; 8-(2',6'-dimethoxybiphenyl-2-yl)-7,7,9,9-tetramethyl-1,4-dioxa-8-phosphaspiro[4.5]decane; 6-methoxy-N,N-dimethyl-2'-(7,7,9,9-tetramethyl-1,4-dioxa-8-phosphaspiro[4.5]decan-8-yl)biphenyl-2-amine; 8-(2'-methoxy-1,1'-binaphthyl-2-yl)-7,7,9,9-tetramethyl-1,4-dioxa-8-phosphaspiro[4.5]decane; 8-(1,1'-binaphthyl-2-yl)-7,7,9,9-tetramethyl-1,4-dioxa-8-phosphaspiro[4.5]decane; 7,7,9,9-tetramethyl-8-(2-(naphthalen-1-yl)phenyl)-1,4-dioxa-8-phosphaspiro[4.5]decane; 7,7,9,9-tetramethyl-8-(2-(naphthalen-2-yl)phenyl)-1,4-dioxa-8-phosphaspiro[4.5]decane; 2,2,6,6-tetramethyl-1-(2,4,6'-triisopropylbiphenyl-2-yl)phosphinan-4-one; 3,3,8,8,10,10-hexamethyl-9-(2,4,6'-triisopropylbiphenyl-2-yl)-1,5-dioxa-9-phosphaspiro[5.5]undecane; 1-(2'-(dimethylamino)-6'-methoxybiphenyl-2-yl)-2,2,6,6-tetramethylphosphinan-4-one; 1-(2',6'-bis(dimethylamino)biphenyl-2-yl)-2,2,6,6-tetramethylphosphinan-4-one; 1-(2',6'-dimethoxybiphenyl-2-yl)-2,2,6,6-tetramethylphosphinan-4-one; 1-(2',6'-diisopropoxybiphenyl-2-yl)-2,2,6,6-tetramethylphosphinan-4-one; 1-(2'-(dimethylamino)biphenyl-2-yl)-2,2,6,6-tetramethylphosphinan-4-one; 1-(biphenyl-2-yl)-2,2,6,6-tetramethylphosphinan-4-one; 1-(1,1'-binaphthyl-2-yl)-2,2,6,6-tetramethylphosphinan-4-one; 1-(2'-methoxy-1,1'-binaphthyl-2-yl)-2,2,6,6-tetramethylphosphinan-4-one; 1-(3,6-dimethoxybiphenyl-2-yl)-2,2,6,6-tetramethylphosphinan-4-one; 1-(3,6-dimethoxy-2',4',6'-trimethylbiphenyl-2-yl)-2,2,6,6-tetramethylphosphinan-4-one; 2,2,6,6-tetramethyl-1-(2',4',6'-triisopropyl-3,6-dimethoxybiphenyl-2-yl)phosphinan-4-one; 2,2,6,6-tetramethyl-1-(2',4',6'-triisopropyl-4,5-dimethoxybiphenyl-2-yl)phosphinan-4-one; 1-(3',5'-dimethoxybiphenyl-2-yl)-2,2,6,6-tetramethylphosphinan-4-one; 1-(4'-tert-butylbiphenyl-2-yl)-2,2,6,6-tetramethylphosphinan-4-one; $N^2,N^2,N^6,N^6$-tetramethyl-2'-(7,7,9,9-tetramethyl-1,4-dioxa-8-phosphaspiro[4.5]decan-8-yl)biphenyl-2,6-diamine; N,N-dimethyl-2'-(7,7,9,9-tetramethyl-1,4-dioxa-8-phosphaspiro[4.5]decan-8-yl)biphenyl-2-amine; 8-(biphenyl-2-yl)-7,7,9,9-tetramethyl-1,4-dioxa-8-phosphaspiro[4.5]decane; 8-(3,6-dimethoxybiphenyl-2-yl)-7,7,9,9-tetramethyl-1,4-dioxa-8-phosphaspiro[4.5]decane; 8-(3,6-dimethoxy-2',4',6'-trimethylbiphenyl-2-yl)-7,7,9,9-tetramethyl-1,4-dioxa-8-phosphaspiro[4.5]decane; 7,7,9,9-tetramethyl-8-(2,4',6'-triisopropyl-3,6-dimethoxybiphenyl-2-yl)-1,4-dioxa-8-phosphaspiro[4.5]decane; or any other suitable phosphine.

Solid Supports—Heterogeneous Catalysts

Optionally, any of the ligand embodiments disclosed herein can be provided with a substituent that permits covalent or other attachment to a solid support to create a heterogeneous catalyst composition. This provides a convenient method to carry out various catalytic reactions by eluting starting materials and optional transition metal compounds through a column to effect contact with the catalytic ligand. Thus in various embodiments, when the substituents described contain suitable functional groups, the ligands can be covalently bound to a solid support. Functional groups include hydroxyl, carboxylic, halo, epoxy, isocyanate, sulfhydryl, vinyl, amino, imino, and so on.

Synthetic Methods

In various embodiments, ligands described herein can be synthesized from known starting materials using organic transformations known in the art. In one embodiment, a phosphorus moiety is added as a substituent to a biaryl system and is elaborated into a phosphacyclic ring in subsequent synthetic steps. In the illustrative synthetic route of Scheme A, biaryliodide or biarylbromide 2 is converted by metal-halogen exchange to its derived organolithium, which is quenched with chlorophosphate to give biarylphosphonate 3, which is in turn reduced to primary phosphine 4, for example, using lithium aluminum hydride as shown. The primary phosphine 4 then undergoes double conjugate addition to divinylketone 5 to give phosphorinanone 1b. Phosphorinanone 1b is then converted to ethylene glycol ketal 1d or to phosphine 1a under known conditions. Propanediol ketal 1c is likewise available from reaction of 1,3-propanediol with phosphorinanone 1b under the acidic conditions shown. An alcohol such as 1c is available through conventional reduction of the carbonyl group of 1b. Additional phosphacycle ligands can be synthesized from the intermediates of Scheme A and especially from the ketone 1b or the alcohol 1c by known organic transformation reactions. In this way, Scheme A provides a general method for preparing phosphacycle ligands containing a 6-membered phosphacycle ring of formula Ib.

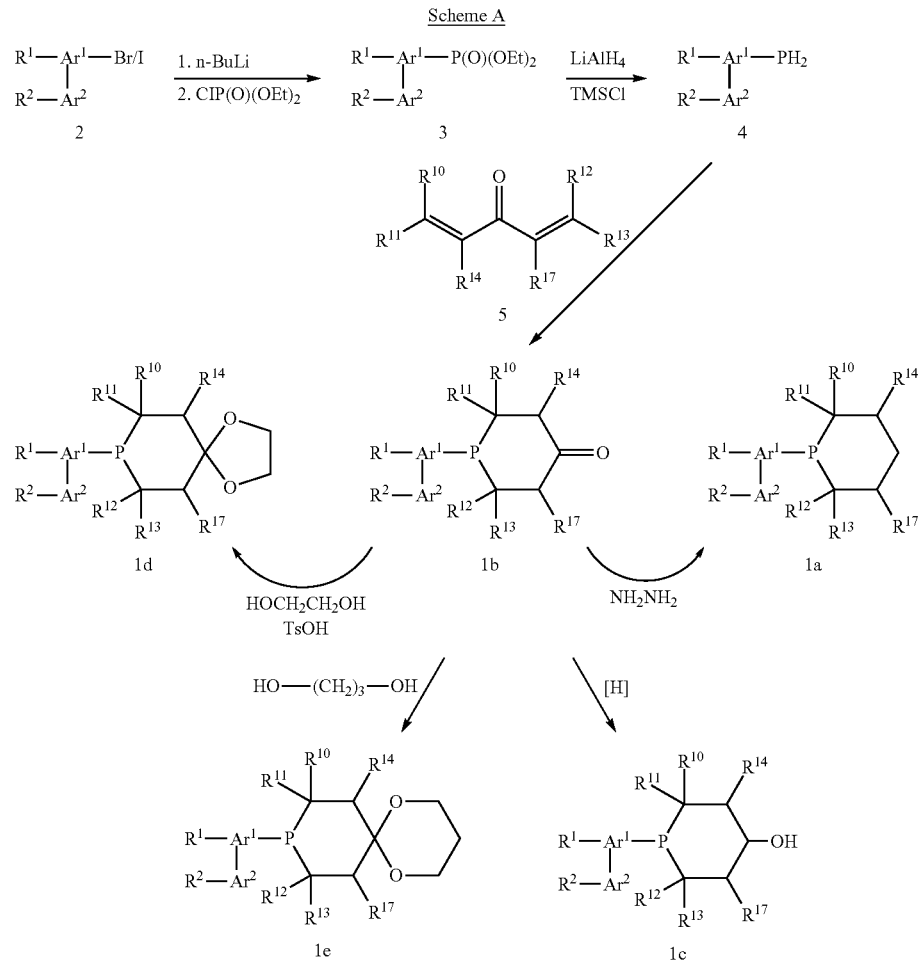

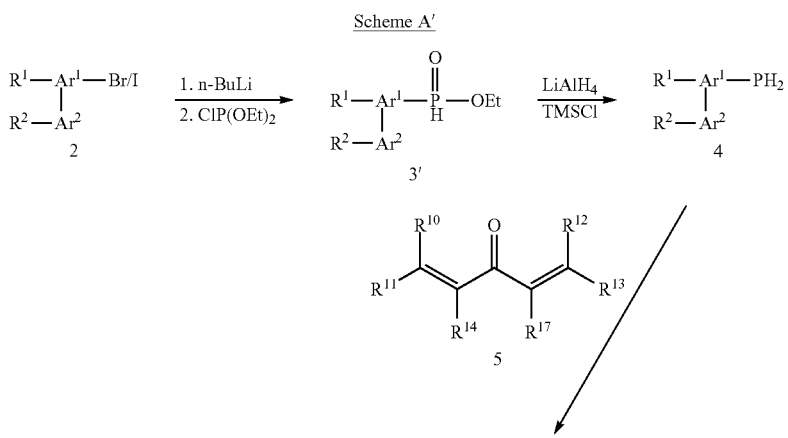

-continued

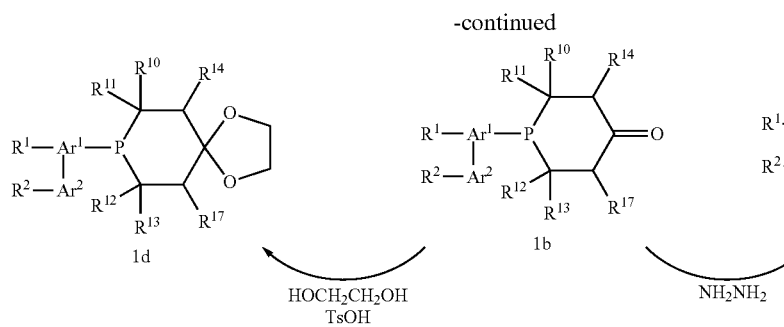

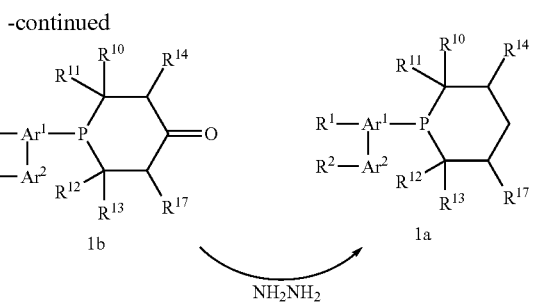

Scheme A' is a variation of Scheme A where a different phosphorylating reagent is used that generates a different first isolated intermediate 3'. Accordingly, Scheme A and Scheme A' provide general methods for preparing phosphacycle ligands containing a 6-membered phosphacycle ring of formula Ib Ketone 1b can undergo a variety of ring contraction or ring expansion reactions to produce ligands containing phosphacycles having other than 6 ring atoms. Such reactions can result in the inclusion of heteroatoms other than P into the phosphacycle ring of the ligands. Similar reactions can introduce hetero ring atoms also into a 6-membered phosphacycle ring.

In another synthetic route, the phosphacycle may be formed first, followed by coupling of the phosphacycle to a biaryl ring system. This coupling reaction can be catalyzed by one or more of the disclosed ligands. Scheme A" shows the general reaction between a biaryl system on the left and a preformed phosphacycle like that of formula (Ia). Other examples are provided in Scheme B' and in Example 2. Such an approach can also be applied to preparation of the fused phosphacycles of (Ic-1) or (Ic-1a).

Scheme A"

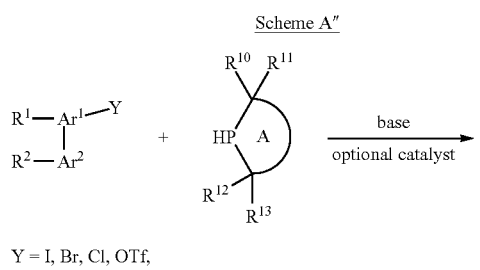

Y = I, Br, Cl, OTf, OMs, OTs, etc.

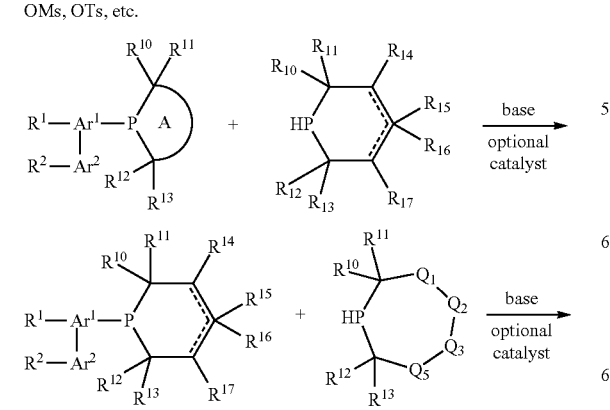

-continued

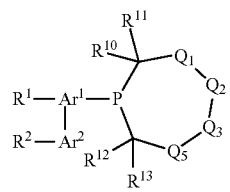

In various embodiments, methods for synthesizing the ligands involve reacting a biaryl system as in Scheme A" with the secondary phosphines shown in generic form in Scheme A" under basic conditions, optionally with a catalyst containing the ligands described herein, where the groups $R^1$ through $R^{13}$ and Q1 through Q5 are as defined herein.

Bridges between ring atoms or between ring substituents can be provided in a variety of post annelation reactions, or can be formed as the phosphacycle ring is formed. To illustrate, a trioxaphosphatricyclcodecane ring can be formed by reaction of a primary phosphine 4 under acidic conditions with a pentanedione 6 to make trioxaphosphatricyclcodecane ligand 7 according to Scheme B, where R' and R" can be any group that does not interfere with the reaction, and where for clarity of illustration R represents the biaryl radical of 4 to which the P atom is attached. Non-limiting examples of R' and R" include alkyl, haloalkyl, perfluoroalkyl, methyl, ethyl, propyl, and isopropyl. In certain embodiments, R' and R" are the same. The reaction of Scheme B is described for example in U.S. Pat. No. 3,026,327, the disclosure of which useful for background information and is hereby incorporated by reference.

Scheme B

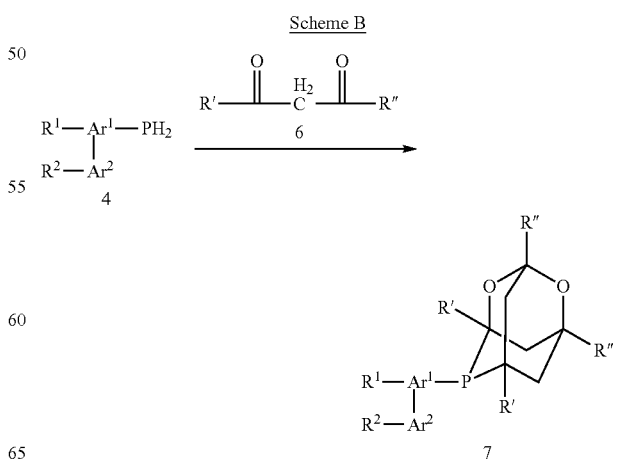

Scheme B'

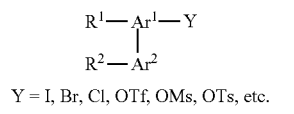

Y = I, Br, Cl, OTf, OMs, OTs, etc.

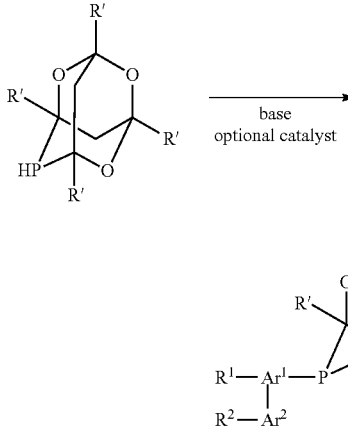

Scheme B' illustrates a method of making ligand 7 by coupling a phosphine and a biaryl starting material such as shown in Scheme A".

Scheme C

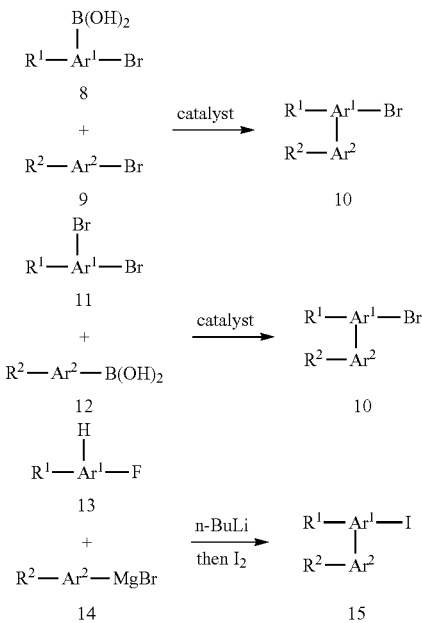

Scheme C illustrates several sequences that can be used to construct the biaryl halides used in the preparation of the ligands. A bromo-boronic acid, 8, can be coupled with an aryl bromide, 9, to give biarylbromide, 10. Similarly, a bis-bromoaryl, 11, can be coupled with a boronic acid, 12, to give biarylbromide, 10. In another sequence, aryl fluoride, 13, can be reacted first with an alkyllithium, then treated with Grignard reagent, 14, and finally treated with iodine to give biaryliodide, 15. The biaryl halides can be used in the synthetic sequences described in Schemes A, A', A", and B'.

Scheme D

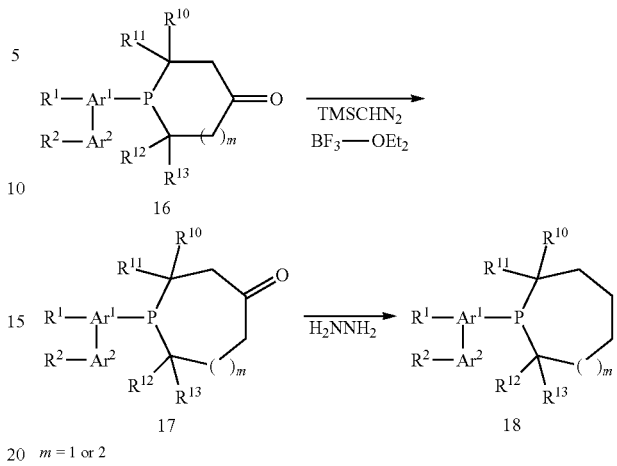

$m = 1$ or $2$

Scheme D illustrates how catalysts containing a phosphinan-4-one or phosphepan-4-one, 16, can be expanded by treatment with trimethylsilyldiazomethane to give compounds 17. Compounds 17 can be reduced as previously described to give compounds 18.

Catalyst Compositions

The ligands described herein find application in catalyst compositions in combination with transition metal compounds. In various embodiments, catalyst compositions contain a ligand described herein and a transition metal compound. Examples of transition metal compounds include those of palladium, rhodium ruthenium, platinum, gold, cobalt, iridium, copper, and nickel, as well as combinations. In various embodiments, the transition metal compound and the ligand are provided in the catalyst composition in stoichiometric amounts with respect to one another. For example, the catalyst compositions contain one mole of ligand per one mole of transition metal compound, or they may contain two moles of ligand per one mole of transition metal compound. In various embodiments, the optimum ligand to metal ratio depends on the metal source used as well as the specifics of the transformation being attempted. The stoichiometric relation between the transition metal and the ligand is an indication that catalysis proceeds through interaction of the organic starting materials with a transition metal catalyst having a phosphacycle ligand bound to a central transition metal, at least for a portion of the reaction. For this reason, the phosphine based compounds of formula I and the like are referred to as ligands.

In various embodiments, the transition metal compound is provided in the catalyst composition as a salt of a central atom. A non-limiting example of such a salt is an acetate salt. When the central atom is palladium in a preferred embodiment, a preferred transition metal compound is palladium acetate, or $Pd(OAc)_2$. A catalyst composition is then formed of a mixture of palladium acetate and a ligand compound as described herein. Other embodiments of palladium sources formally in the 2+ oxidation state include but are not limited to $PdCl_2$, $PdCl_2(CH_3CN)_2$, $[PdCl(allyl)]_2$, $[PdCl(2\text{-methyl-allyl})]_2$, $PdCl_2(PhCN)_2$, $Pd(acetylacetonate)_2$, $Pd(O_2CCF_3)_2$, $Pd(OTf)_2$, $PdBr_2$, $[Pd(CH_3CN)_4](BF_4)_2$, $PdCl_2(cyclooctadiene)$, and $PdCl_2(norbomadiene)$.

In various embodiments, the transition metal compound is in the zero valence state. An example is tris(dibenzylideneacetone)dipalladium(0), commonly abbreviated as $Pd_2$ (dba)₃. Other suitable palladium sources include palladium sources in formally the zero or other valence states. Examples include but are not limited to Pd(dba)₂, Pd₂(dba)₃.CHCl₃, and Pd(PPh₃)₄.

Catalytic Reactions

The ligands described herein exhibit utility in transition metal catalyzed reactions. In embodiments, the disclosed ligands may be combined with a variety of transition metal compounds to catalyzes a range of chemical transformations. In embodiments, compositions containing a transition metal compound and a disclosed ligand can be used to catalyze a variety of organic reactions. A non-limiting example of a reaction catalyzed by a disclosed ligand is given in Scheme E, illustrating the catalysis of a sulfonamidation reaction. As shown, an aryl nonaflate 8 is reacted with a sulfonamide 9 in the presence of a palladium catalyst and a ligand described herein to produce a sulfonamide 10 in high yield. Other reactions of interest include carbon-nitrogen, carbon-oxygen, carbon-carbon, carbon-sulfur, carbon-phosphorus, carbon-boron, carbon-fluorine and carbon-hydrogen bond-forming reactions. In non-limiting examples, the catalysts can be used to catalyze Buchwald-Hartwig type C—N bond-forming reactions and C—O bond-forming reactions including ether-forming macrocyclizations (see Scheme E, where L stands for a ligand) and the like, among other reactions. More specifically, a combination of a ligand with a transition metal compound catalyzes the following reactions:

i. Carbon-carbon bond forming reactions such as Suzuki, Stille, Heck, Negishi, Kumada, Hayashi coupling reactions.

ii. Carbon-nitrogen bond-forming reactions where aryl halides, pseudohalides, nitriles, carboxalates, ether etc. are used as electrophiles and amines, ammonia, ammonia surrogates, amides, carbamates, sulfonamides and other nitrogen containing molecules are used as nucleophiles.

iii. Carbon-oxygen bond-forming reactions where aryl halides, pseudohalides, nitriles, carboxalates, ethers, etc. are used as electrophiles and alcohols, metal hydroxides and water are used as nucleophiles.

iv. Carbon-sulfur bond-forming reactions where aryl halides, pseudohalides, nitriles, carboxalates, ethers, etc. are used as electrophiles and thiols and metal sulfides are used as nucleophiles.

v. Carbon-phosphorus bond-forming reactions where aryl halides, pseudohalides, nitriles, carboxalates, ethers, etc. are used as electrophiles and phosphines, metal phosphides and phosphites are used as nucleophiles.

vi. Carbon-carbon bond-forming reactions via C—H functionalization.

vii. Carbon-X (X=N, O, S, P) bond-forming reactions via C—H functionalization.

viii. Metal-catalyzed addition reactions to alkenes, alkynes, allenes, ketenes, etc. such as hydroamination, hydroalkoxylation, hydroamidation, etc.

ix. Metal-catalyzed carbonylation reactions.

x. Metal-catalyzed hydrogenation reactions.

xi. Alpha-arylation of ketones, aldehydes, nitriles, amides, etc.

xii. Metal-catalyzed cycloisomerization reactions.

xiii. Metal-catalyzed fluorination of aryl sulfonates.

xiv. Metal-catalyzed borolation of aryl halides.

Scheme E

C—N Cross Coupling

Palladium-catalyzed C—N cross-coupling reactions.

The disclosed ligands may be used in palladium-catalyzed C—N cross-coupling reactions such as the coupling of a wide range of optionally substituted aryl and alkyl primary sulfonamides, $H_2NSO_2R^A$, with various coupling partners, $Ar^3$-$LG_1$.

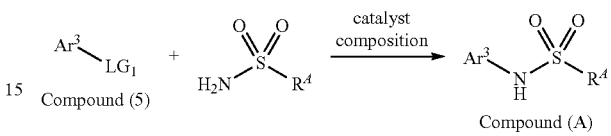

In embodiments, $Ar^3$ is optionally substituted aryl or optionally substituted heteroaryl.

$LG_1$ is a leaving group. In embodiments, $LG_1$ is selected from the group consisting of chloro, bromo, iodo and —$OSO_2R^{1a}$, wherein $R^{1a}$ is selected from the group consisting of aryl, alkyl, fluoroalkyl, -fluoroalkyl-O-fluoroalkyl, —N(alkyl)₂, —O(alkyl), —O(aryl), fluoro, imidazolyl, and isomers and homologs thereof.

In embodiments, $LG^1$ is —$OSO_2R^{1a}$, wherein $R^{1a}$ is aryl, such as p-tolyl or phenyl; alkyl such as methyl or ethyl; fluoroalkyl such as trifluoromethyl, perfluorobutyl ($C_4F_9$), or isomers of perfluorobutyl and other higher and lower homologs such as, but not limited to, perfluoropentyl, perfluorohexyl, and perfluorooctyl. In embodiments, $R^{1a}$ is -fluoroalkyl-O-fluoroalkyl such as perfluoroethoxyethyl; —N(alkyl)₂; fluoro; or imidazolyl.

In embodiments, $R^A$ is optionally substituted aryl or alkyl.

Compound (5) may be sulfonamidated in the presence of a catalyst and/or a catalyst precursor. In embodiments, the catalyst and/or a catalyst precursor is a transition metal compound. In embodiments, the transition metal catalyst or the transition metal catalyst precursor is a palladium catalyst or a palladium catalyst precursor, respectively. Palladium catalysts or palladium catalyst precursors may include, for example, tetrakis(triphenylphosphine)palladium(0), dichlorobis(tri-o-tolylphosphine)palladium(II), palladium(II) acetate, [1,1'-bis(diphenylphosphino) ferrocene]dichloropalladium(II), bis(dibenzylideneacetone) palladium(0), tris (dibenzylideneacetone) dipalladium(0), tris(dibenzylideneacetone) dipalladium(0) chloroform adduct, dichlorobis (tricyclohexylphosphine) palladium(II), dichlorobis (triphenylphosphine) palladium(II), chloro(η3-allyl) palladium(II) dimer-triphenylphosphine, palladium(II) chloride, palladium(II) bromide, bis(acetonitrile)dichloropalladium(II) and any other suitable palladium catalyst or palladium catalyst precursor. In embodiments, the palladium catalyst precursor or palladium catalyst precursor is tetrakis (triphenylphosphine) palladium(0). In embodiments, the palladium catalyst or palladium catalyst precursor is dichlorobis(tri-o-tolylphosphine) palladium(II). In embodiments, the palladium catalyst or palladium catalyst precursor is palladium(II) acetate. In embodiments, the palladium catalyst or palladium catalyst precursor is [1,1'-bis(diphenylphosphino)ferrocene]dichloro palladium(II). In embodiments, the palladium catalyst or palladium catalyst precursor is tris(dibenzylideneacetone) dipalladium(0). In embodiments, the palladium catalyst or palladium catalyst precursor is bis(dibenzylideneacetone) palladium(0). In embodiments, the palladium catalyst or palladium catalyst precursor is palladium(II) bromide. In embodiments, the palladium catalyst or palladium catalyst precursor is palladium(II) chloride. In embodiments, the palladium catalyst or palladium catalyst precursor is bis(acetonitrile)dichloropalladium(II). In embodiments, the palladium catalyst or palladium catalyst precursor is dichlorobis(tricyclohexylphosphine) palladium(II). In embodiment, the palladium catalyst or palladium catalyst precursor is dichlorobis(triphenylphosphine) palladium(II). In embodiment, the palladium catalyst or palladium catalyst precursor is chloro(η3-allyl)palladium (II) dimer-triphenylphosphine.

In embodiments, compound (5) is sulfonamidated in the presence of solvent. Solvents may include, for example, tetrahydrofuran, N,N-dimethylformamide, N,N-dimethylacetamide, N-methyl-pyrrolidone, dimethyl sulfoxide, 1,2-dimethoxyethane, 1,4-dioxane, acetonitrile, cyclopentyl methyl ether, toluene, benzene, tert-amyl alcohol, and tert-butyl alcohol, 2-methyltetrahydrofuran, ethyl acetate, isopropyl acetate, anisole, trifluorotoluene and any other suitable solvent and combinations thereof. In embodiments, the solvent is tetrahydrofuran. In embodiments, the solvent is N,N-dimethylformamide. In embodiments, the solvent is N,N-dimethylacetamide. In embodiments, the solvent is N-methylpyrrolidone. In embodiments, the solvent is dimethyl sulfoxide. In embodiments, the solvent is 1,2-dimethoxyethane. In embodiments, the solvent is 1,4-dioxane. In embodiments, the solvent is acetonitrile. In embodiments, the solvent is cyclopentyl methyl ether. In embodiments, the solvent is toluene. In embodiments, the solvent is benzene. In embodiments, the solvent is tert-amyl alcohol. In embodiments, the solvent is tert-butyl alcohol. In embodiments, the solvent is 2-methyltetrahydrofuran. In embodiments, the solvent is ethyl acetate. In embodiments, the solvent is isopropyl acetate. In embodiments, the solvent is anisole. In embodiments, the solvent is trifluorotoluene. In embodiments, the solvent is a mixture of 2-methyltetrahydrofuran and ethyl acetate. In embodiments, the solvent is a mixture of tert-amyl alcohol and dimethyl sulfoxide. In embodiments, the solvent is a 7:1 mixture of tert-amyl alcohol and dimethyl sulfoxide. In embodiments, the solvent is a 1:2 mixture of 2-methyltetrahydrofuran and ethyl acetate. In embodiments, the solvent is a 1:3 mixture of 2-methyltetrahydrofuran and ethyl acetate.

Compound (5) may be sulfonamidated in the presence of base. Bases may include, for example, potassium phosphate tribasic, cesium carbonate, potassium carbonate, sodium carbonate, sodium tert-butoxide, potassium tert-butoxide, sodium phenoxide, lithium bis(trimethylsilyl)amide, lithium diisopropylamide and any other suitable base and combinations thereof. In embodiments, the base is potassium phosphate tribasic. In embodiments, the base is potassium phosphate tribasic with a particle size (D90) less than or equal to 120 μm. In embodiments, the base is potassium phosphate tribasic hydrated with less than one molar equivalent of water. In embodiments, the base is potassium phosphate tribasic hydrated with less than 0.5 molar equivalents of water. In embodiments, the base is potassium phosphate tribasic with a particle size (D90) less than or equal to 120 μm and hydrated with less than one molar equivalent of water. In embodiments, the base is potassium phosphate tribasic with a particle size (D90) less than or equal to 120 μm and hydrated with less than 0.5 molar equivalent of water. In embodiments, the base is cesium carbonate. In embodiments, the base is potassium carbonate. In embodiments, the base is sodium carbonate. In embodiments, the base is sodium tert-butoxide. In embodiments, the base is potassium tert-butoxide. In embodiments, the base is sodium phenoxide. In embodiments, the base is lithium bis(trimethylsilyl)amide. In embodiments, the base is lithium diisopropylamide.

Compound (5) may be sulfonamidated at a temperature of from about 20° C. to about 130° C. or from about 60° C. to about 100° C. In instances where the reaction is conducted above the boiling point of the reaction solvent, the reaction is conducted in a sealed vessel suitable to contain the pressure of the reaction. In embodiments, compound (5) is sulfonamidated at a temperature of about 60° C., then about 85° C., and finally about 95° C. In embodiments, compound (5) is sulfonamidated at a temperature of about 80° C. and then about 50° C. In embodiments, compound (5) is sulfonamidated at a temperature of about 80° C. and then about 90° C.

Compound (5) may be sulfonamidated in an inert atmosphere. In embodiments, the inert atmosphere is provided by nitrogen. In embodiments, the inert atmosphere is provided by argon.

In an embodiment, compound (5) is reacted with methanesulfonamide under an argon atmosphere in t-amyl alcohol in the presence of potassium phosphate tribasic, tris(dibenzylideneacetone)dipalladium(0) and di-tert-butyl(2',4',6'-triisopropyl-3,4,5,6-tetramethylbiphenyl-2-yl)phosphine to give compound (A).

In an embodiment, compound (5) is reacted with methanesulfonamide under an argon atmosphere in t-amyl alcohol in the presence of potassium phosphate tribasic, tris(dibenzylideneacetone)dipalladium(0) and 7,7,9,9-tetramethyl-8-(2',4',6'-triisopropylbiphenyl-2-yl)-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 2,2,6,6-tetramethyl-1-(2',4',6'-triisopropylbiphenyl-2-yl)phosphinane to give compound (A).

In an embodiment, compound (5) is reacted with methanesulfonamide in t-amyl alcohol in the presence of potassium phosphate tribasic, tris(dibenzylideneacetone)dipalladium(0) and 8,8,10,10-tetramethyl-9-(2',4',6'-triisopropylbiphenyl-2-yl)-1,5-dioxa-9-phosphaspiro[5.5]undecane to give compound (A).

In an embodiment, compound (5) is reacted with methanesulfonamide in t-amyl alcohol in the presence of potassium phosphate tribasic, tris(dibenzylideneacetone)dipalladium(0) and 2,2,6,6-tetramethyl-1-(2',4',6'-triisopropylbiphenyl-2-yl)phosphinan-4-ol to give compound (A).

In an embodiment, compound (5) is reacted with methanesulfonamide in t-amyl alcohol in the presence of potassium phosphate tribasic, tris(dibenzylideneacetone)dipalladium(0) and 8-(2',6'-diisopropoxybiphenyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 1,3,5,7-tetramethyl-8-(2',4',6'-triisopropylbiphenyl-2-yl)-2,4,6-trioxa-8-phosphatricyclo[3.3.1.1$^{3,7}$]decane to give compound (A).

In an embodiment, compound (5) is reacted with methanesulfonamide in t-amyl alcohol in the presence of potassium phosphate tribasic, tris(dibenzylideneacetone)dipalladium(0) and 8-(2',6'-dimethoxybiphenyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 6-methoxy-N,N-dimethyl-2'-(7,7,9,9-tetramethyl-1,4-dioxa-8-phosphaspiro[4.5]decan-8-yl)biphenyl-2-amine to give compound (A).

In an embodiment, compound (5) is reacted with methanesulfonamide in t-amyl alcohol in the presence of potassium phosphate tribasic, tris(dibenzylideneacetone)dipalladium(0) and 8-(2'-methoxy-1,1'-binaphthyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 8-(1,1'-binaphthyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 7,7,9,9-tetramethyl-8-(2-(naphthalen-1-yl)phenyl)-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 7,7,9,9-tetramethyl-8-(2-(naphthalen-2-yl)phenyl)-1,4-dioxa-8-phosphaspiro[4.5]decane to give compound (A).

In an embodiment, compound (5) is reacted with methanesulfonamide in tetrahydrofuran in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in 2-methyltetrahydrofuran in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in ethyl acetate in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in t-amyl alcohol in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in a mixture of 2-methyltetrahydrofuran and ethyl acetate in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in a mixture of 2-methyltetrahydrofuran and ethyl acetate in the presence of potassium phosphate tribasic, tris(dibenzylideneacetone)dipalladium(0) and 7,7,9,9-tetramethyl-8-(2',4',6'-triisopropyl-3,6-dimethoxybiphenyl-2-yl)-1,4-dioxa-8-phosphaspiro[4.5]decane to give compound (A).

Palladium-catalyzed C—N cross-coupling of an aryl nonaflate with methylsulfonamide.

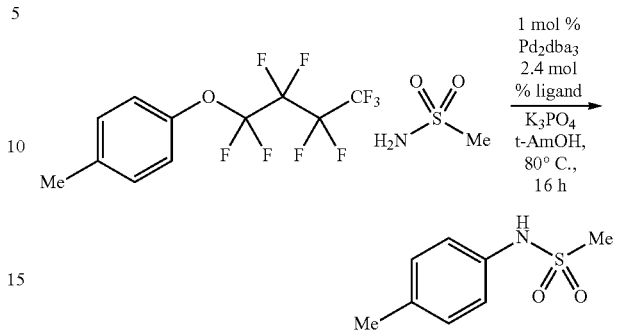

Palladium-catalyzed C—N cross-coupling of an aryl bromide with a primary amine.

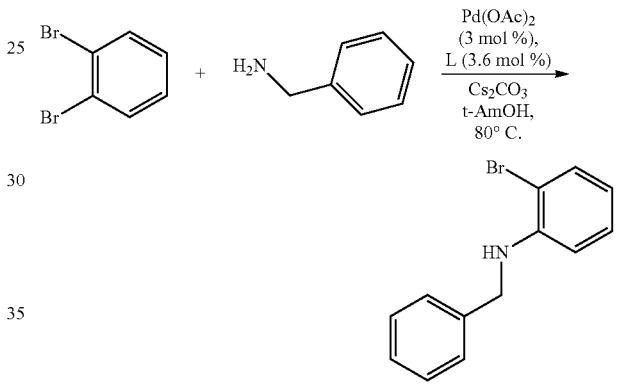

Palladium-catalyzed phenylurea coupling with an aryl chloride.

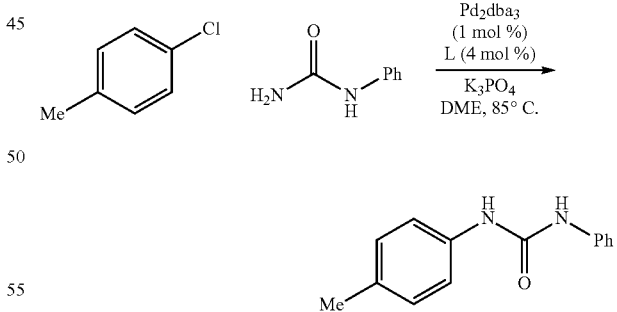

Palladium-catalyzed selective N-arylation of oxindole.

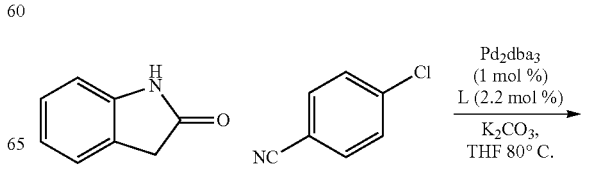

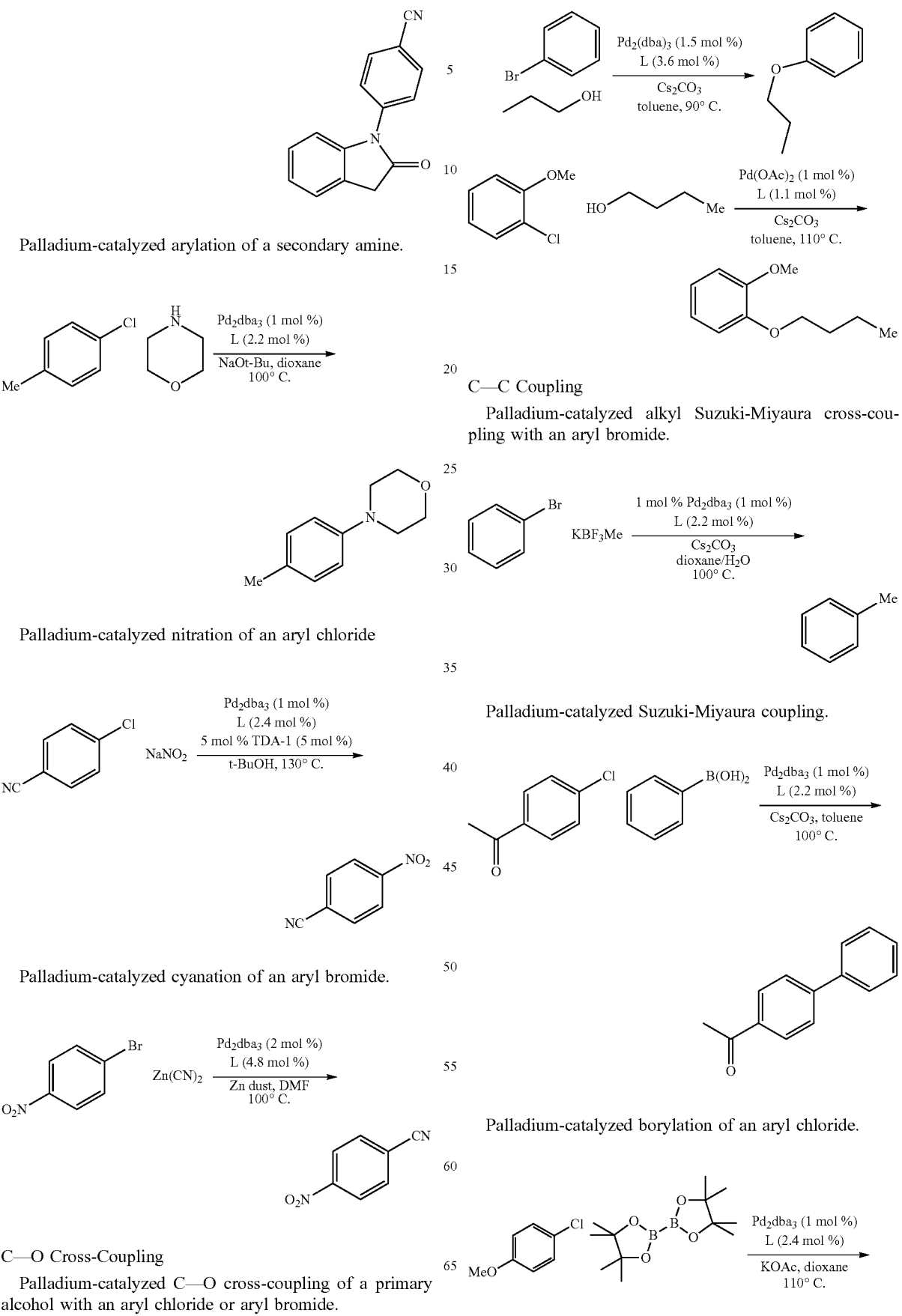

Palladium-catalyzed arylation of a secondary amine.

Palladium-catalyzed nitration of an aryl chloride

Palladium-catalyzed cyanation of an aryl bromide.

C—O Cross-Coupling

Palladium-catalyzed C—O cross-coupling of a primary alcohol with an aryl chloride or aryl bromide.

C—C Coupling

Palladium-catalyzed alkyl Suzuki-Miyaura cross-coupling with an aryl bromide.

Palladium-catalyzed Suzuki-Miyaura coupling.

Palladium-catalyzed borylation of an aryl chloride.

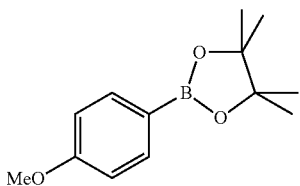

Palladium-catalyzed fluorination of an aryl trifluoromethanesulfonate.

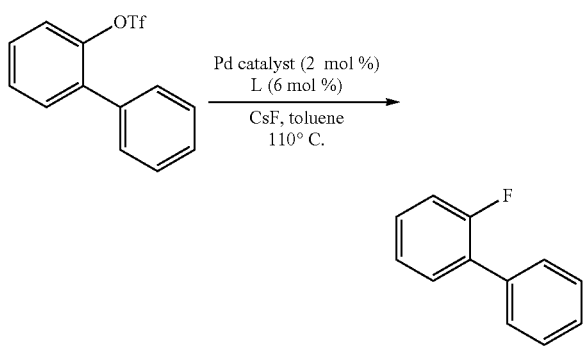

Palladium-catalyzed coupling of bromobenzene with a thiol.

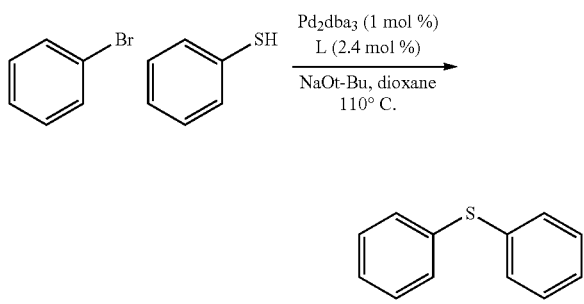

Palladium-catalyzed coupling of diethylphosphite with bromobenzene.

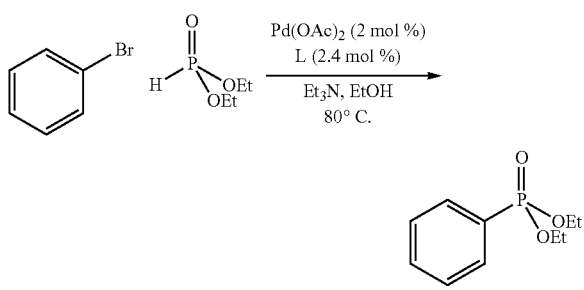

Ligands, catalyst compositions, and catalyzed reactions have been described with respect to various preferred embodiments. Further non-limiting description is given by way of the working examples in the section following.

EXAMPLES

Abbreviations: Ac for acetyl; t-AmOH for tert-amyl alcohol; $BF_3$-$Et_2O$ for boron trifluoride diethyl etherate; t-BuOH for tert-butyl alcohol; CYTOP 292® for 1,3,5,7-tetramethyl-8-phenyl-2,4,6-trioxa-8-phosphatricyclo[3.3.1.1$^{3,7}$]decane; DME for 1,2-dimethoxyethane; DMF for dimethylformamide; Et for ethyl; EtOH for ethanol; $Et_3N$ for triethylamine; HPLC for high pressure liquid chromatography; HRMS for high resolution mass specroscopy; KOAc for potassium acetate; Me for methyl; NMR for nuclear magnetic resonance; OAc for acetate; Ot-Bu for tert-butoxide; $Pd_2dba_3$ for tris(dibenzylideneacetone)dipalladium(0); Pd(OAc)$_2$ for palladium(II) acetate; PPh$_3$ for triphenylphosphine; Tf for trifluoromethanesulfonate; THF for tetrahydrofuran; TLC for thin layer chromatography; TMEDA for N,N,N',N',-tetramethylethylenediamine; TMSCl for chlorotrimethylsilane; TOF-ESI$^+$ for time-of-flight-electron spary ionization General Information.

Unless otherwise noted, reactions were performed under an inert atmosphere using standard Schlenk techniques. Glassware was oven-dried for at least 8 hours at 100° C. prior to use. NMR spectra were recorded on a 400, 500, or 600 MHz spectrometers, with $^1H$ and $^{13}C$ chemical shifts reported in parts per million (ppm) downfield from tetramethylsilane and referenced to residual proton ($^1H$) or deuterated solvent ($^{13}C$). $^{31}P$ NMR chemical shifts reported in ppm relative to 85% aqueous phosphoric acid. Thin layer chromatography (TLC) analysis of reaction mixtures was performed on EMD silica gel 60 $F_{254}$ thin layer chromatography plates. Silica gel column chromatography was performed with an Isco CombiFlash Companion® with pre-packaged Teledyne Isco RediSepRf normal phase silica columns using default flow rates (40-g: 40 mL/minutes; 80-g: 60 mL/minutes; 120-g: 85 mL/minutes). Product purities were determined using a Hewlett Packard Series 1100 HPLC and are reported as the peak area percent (a %) of the desired peak at 254 nm. The following HPLC method was used for Examples 1-16:

Mobile phase A: 0.1% perchloric acid in water.

Mobile phase B: acetonitrile.

Column: Ascentis® Express C8 2.7 μm, 4.6 mm×150 mm.

Flow rate: 1.5 mL/minutes.

Column temperature: 40° C.

Monitored at 254 nm.

| Time (minutes) | % A | % B |
|---|---|---|
| 0 | 60% | 40% |
| 8 | 5% | 95% |
| 16 | 5% | 95% |
| 17 | 60% | 40% |

Example 1

Synthesis of Ligands Containing 6-Membered Phosphacycles

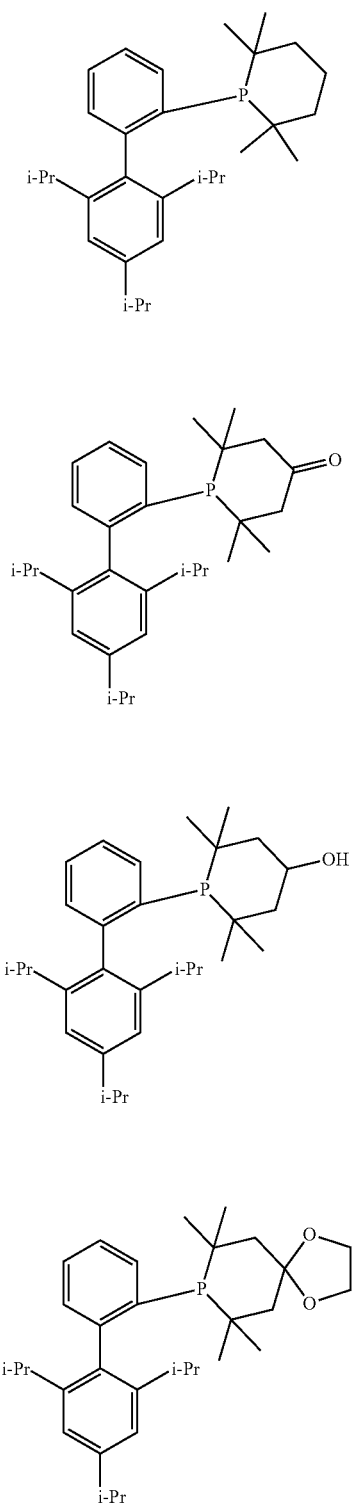

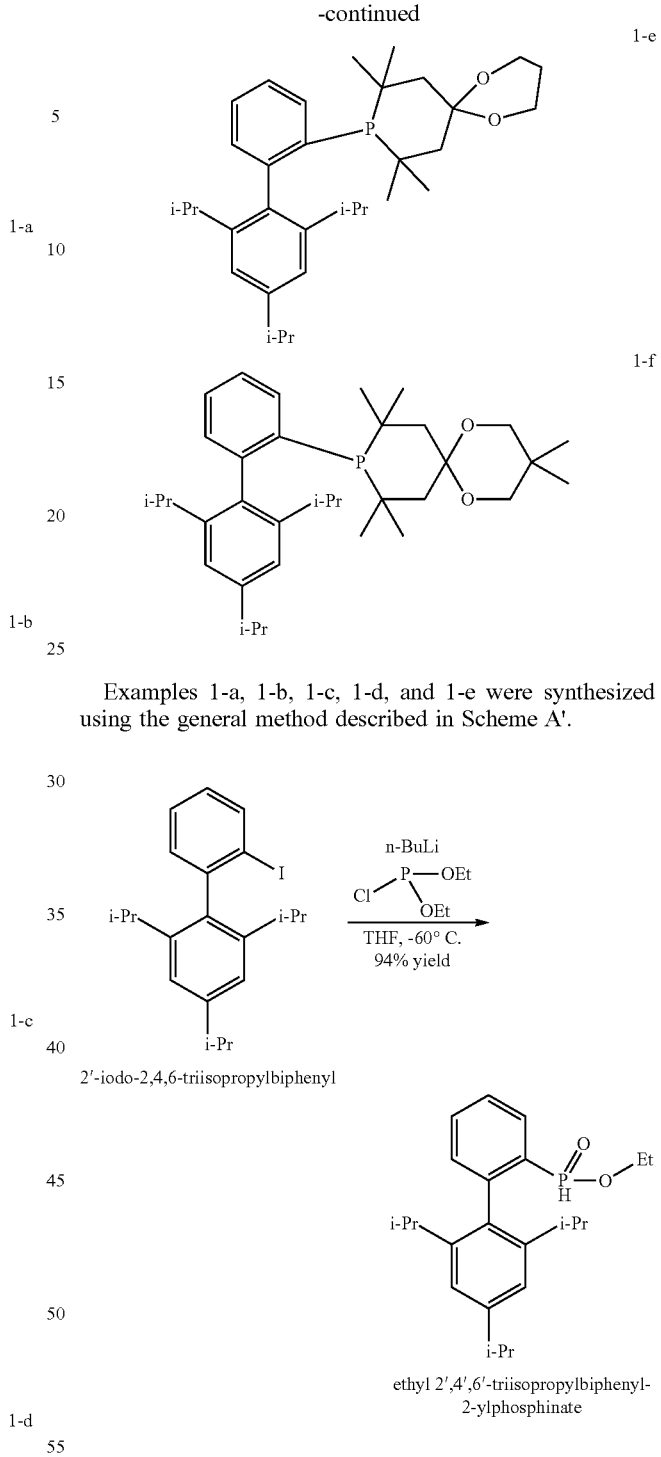

Examples 1-a, 1-b, 1-c, 1-d, and 1-e were synthesized using the general method described in Scheme A'.

Ethyl 2',4',6'-triisopropylbiphenyl-2-ylphosphinate

A 1-L 3-neck round-bottom flask was fitted with an addition funnel and the atmosphere was purged with nitrogen. Anhydrous, degassed THF (170 mL) was added to the 1-L flask and cooled to −60° C. (internal temperature). The addition funnel was charged with hexyllithium (2.38 M in hexanes, 57 mL, 135 mmol, 2.0 equiv). The hexyllithium was transferred into the cold THF over 20 min, maintaining the temperature below −40° C. The solution was re-cooled to −60° C. (internal temperature). A solution of 2'-iodo-2,4, 6-triisopropylbiphenyl (27.5 g, 67.7 mmol, 1.0 equiv) in 170 mL of anhydrous, degassed THF was transferred, via cannula, drop wise to the n-hexyllithium solution. This was done over 25 min while maintaining the temperature below −40° C. After addition, the reaction mixture was allowed to stir at −60° C. for 30 min. Diethyl chlorophosphite (19.62 mL, 135 mmol, 2.0 equiv) was added to the reaction mixture, over 10 min while maintaining the temperature below −40° C. After addition of diethyl chlorophosphite, the reaction was allowed to proceed at −60° C. for an additional 30 min. Aqueous hydrochloric acid (1 M, 338 mL, 338 mmol) was added at −60° C. The flask was removed from the cold bath and the reaction was allowed to warm to 22° C. The resultant solution was diluted with heptane (340 mL) and transferred to a separatory funnel. The layers were separated and the organic layer was assayed for product by quantitative HPLC (94% yield). The organic layer was concentrated under reduced pressure to give an oil which was used in the next reaction without further purification.

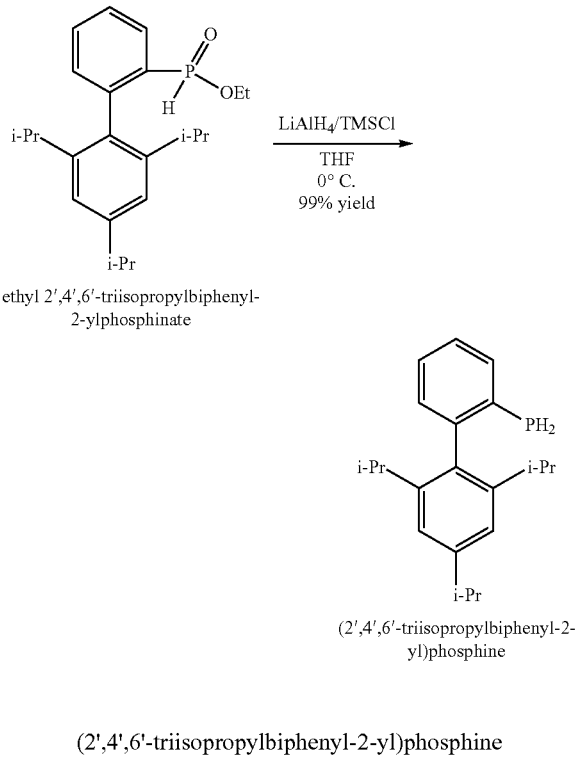

ethyl 2′,4′,6′-triisopropylbiphenyl-2-ylphosphinate (2′,4′,6′-triisopropylbiphenyl-2-yl)phosphine A 1-L 3-neck round-bottom flask was purged with nitrogen. Anhydrous, degassed THF (100 mL) was added to the flask and cooled to 0° C. (internal temperature). Lithium aluminum hydride (2.0 M in THF, 70 mL, 140 mmol, 3.0 equiv) was added to the cooled THF. Chlorotrimethylsilane (18 mL, 140 mmol, 3.0 equiv) was added by addition funnel to the LAH solution over 10 min while maintaining the internal temperature below +10° C. This solution was allowed to stir at 0° C. for 20 min.

A solution of ethyl 2′,4′,6′-triisopropylbiphenyl-2-ylphosphinate (17.5 g, 47.0 mmol, 1.0 equiv) in 100 mL of anhydrous, degassed THF was cooled to 0° C. under an atmosphere of nitrogen. The lithium aluminum hydride/chlorotrimethylsilane solution was transferred by cannula into the solution of phosphinate over 20 min. The reaction was allowed to proceed overnight with slow warming to 22° C. Prior to quench the mixture was cooled in an ice bath. The reaction was quenched by slow addition of EtOAc (23 mL, 235 mmol, 5 equiv), followed by aqueous hydrochloric acid (2 M, 250 mL, 500 mmol, 10.6 equiv). This mixture was allowed to stir for 1 h under an atmosphere of $N_2$. This mixture was diluted with EtOAc (250 mL), the layers were separated and the organic layer was washed once with a saturated solution of NaCl (100 mL). The organic solution was concentrated in vacuo to give a white solid (23.0 g) which was 66% potent (w/w by HPLC), for a 99% yield. This material was used without further purification.

Example 1-a 2,2,6,6-tetramethyl-1-(2′,4′,6′-triisopropylbiphenyl-2-yl)phosphinane

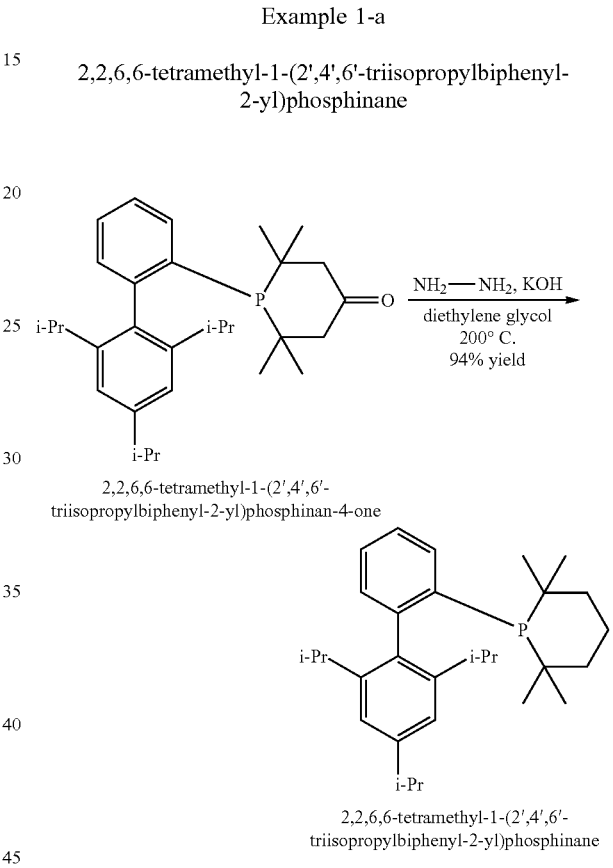

2,2,6,6-tetramethyl-1-(2′,4′,6′-triisopropylbiphenyl-2-yl)phosphinan-4-one 2,2,6,6-tetramethyl-1-(2′,4′,6′-triisopropylbiphenyl-2-yl)phosphinane A flask was charged with 1.05 g of 2,2,6,6-tetramethyl-1-(2′,4′,6′-triisopropylbiphenyl-2-yl)phosphinan-4-one (2.33 mmol, 1.0 equiv), the atmosphere was sparged with argon and 12 mL of argon-sparged diethylene glycol was added. The flask was mounted with a Dean-Stark trap and condenser to collect distillate. The mixture was charged with 1.05 mL of hydrazine hydrate (55 wt % hydrazine, 11.7 mmol, 5 equiv) and 0.77 g of potassium hydroxide (88 wt %, 12.1 mmol, 5 equiv) and the mixture was immersed in an oil bath at 115° C. under an argon atmosphere. The temperature of the bath was gradually increased to 200° C. over two hours and kept at that temperature for 5 h. The reaction mixture was cooled to room temperature under argon gas. The reaction mixture was partitioned between heptane and water. The organic solution was washed once with 0.1 M aqueous hydrochloric acid, once with 10 wt % aqueous sodium carbonate and once with water. The organic solution was concentrated in vacuo with gentle heating and the residue dried in vacuo to give 0.99 g of 2,2,6,6-tetramethyl-1-(2′,4′,6′-triisopropylbiphenyl-2-yl)phosphinane (97 area % by HPLC, 94% yield) as a white solid. $^1$H NMR ($C_6D_6$, 500

MHz), δ=0.93 (d, 6H, J=10 Hz), 1.11 (d, 6H, J=7 Hz), 1.13 (d, 6H, J=19 Hz), 1.23 (d, 6H, J=7 Hz), 1.31-1.26 (m, 2H), 1.42 (d, 6H, J=7 Hz), 1.57-1.50 (m, 1H), 1.65-1.57 (m, 1H), 1.88-1.83 (m, 2H), 2.79 (sept, 2H, J=7 Hz), 2.84 (sept, 1H, J=7 Hz), 7.12-7.11 (m, 2H), 7.22 (s, 2H), 7.27-7.24 (m, 1H), 7.98-7.93 (m, 1H); $^{31}$P NMR (C$_6$D$_6$, 202 MHz), δ ppm −0.4 (br singlet).

Example 1-b 2,2,6,6-tetramethyl-1-(2',4',6'-triisopropylbiphenyl-2-yl)phosphinan-4-one

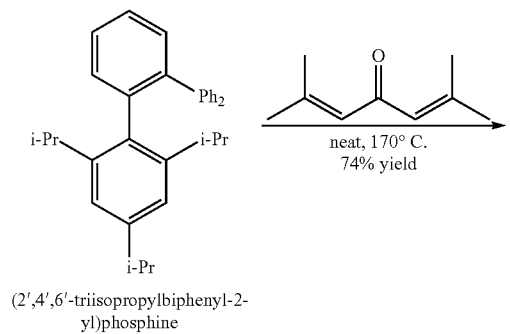

(2',4',6'-triisopropylbiphenyl-2-yl)phosphine

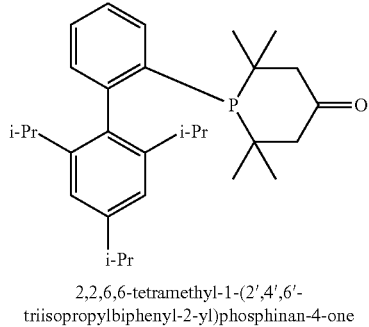

2,2,6,6-tetramethyl-1-(2',4',6'-triisopropylbiphenyl-2-yl)phosphinan-4-one

A flask was charged with 10.8 g of (2',4',6'-triisopropylbiphenyl-2-yl)phosphine (66% potent, 7.13 g, 22.8 mmol, 1.0 equiv) and 6.6 g of 2,6-dimethyl-2,5-heptadien-4-one (47.7 mmol, 2.1 equiv). The vessel was purged with argon gas and immersed in an oil bath at 170° C. with magnetic stirring. The flask was sealed with a Teflon stopcock and the reaction was allowed to proceed under a static argon atmosphere. The flask was removed from the oil bath after 14 h and the contents allowed to cool to room temperature under argon gas. Anhydrous ethanol (70 mL) was added to the unpurified solids and the solids were broken up manually. The slurry was warmed to 80° C., held for an hour, and cooled to room temperature. The product was isolated by filtration, washes with ethanol and dried in vacuo to give 7.82 g of 2,2,6,6-tetramethyl-1-(2',4',6'-triisopropylbiphenyl-2-yl)phosphinan-4-one (98 area % by HPLC, 74% yield).

Example 1-c 2,2,6,6-tetramethyl-1-(2',4',6'-triisopropylbiphenyl-2-yl)phosphinan-4-ol

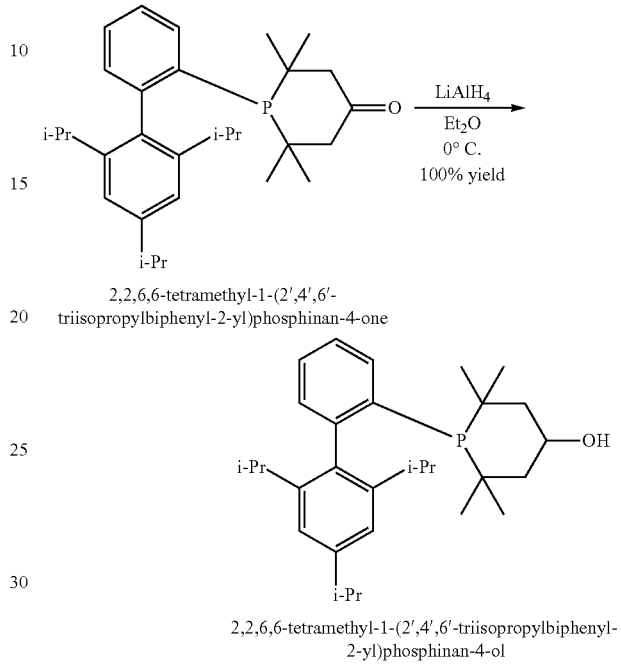

A flask was charged with 1.5 g of 2,2,6,6-tetramethyl-1-(2',4',6'-triisopropylbiphenyl-2-yl)phosphinan-4-one (3.33 mmol, 1.0 equiv). The ketone was dissolved in 16 mL of nitrogen-sparged tetrahydrofuran and cooled in an ice water bath. A solution of lithium aluminum hydride (3.33 mL, 6.66 mmol, 2 equiv, 2 M in THF) was added dropwise over 3 minutes to the solution. The solution was warmed to room temperature and stirred for 7 hours. The reaction mixture was quenched by the slow addition of aqueous hydrochloric acid (50 mL, 1 M). The solution was stirred vigorously until homogeneous. The phases were partitioned and the aqueous layer was collected. The aqueous layer was washed with ethyl acetate (4×20 mL), then the combined organic layers were washed with brine (50 mL), dried over sodium sulfate and concentrated. The resulting white solid was purified by column chromatography using an Isco CombiFlash Companion® with a Teledyne Isco RediSepRf column (40-g, flow rate: 40 mL/minute, gradient: 1 column volumes heptane, ramp up to 60:40 heptane:ethyl acetate over 7 column volumes, hold at 60:40 for 2 column volumes). The title compound was isolated as a white solid (1.32 g, 95 area % by HPLC at 254 nm, 88% yield). $^1$H NMR (400 MHz, CDCl$_3$) δ ppm 7.88-7.81 (m, 1H), 7.40-7.28 (m, 2H), 7.23-7.17 (m, 1H), 7.00 (s, 2H), 4.04 (tt, J=10.2, 3.5 Hz, 1H), 2.94 (hept, J=6.9 Hz, 1H), 2.50 (hept, J=6.7 Hz, 2H), 1.92-1.74 (m, 2H), 1.71-1.57 (m, 2H), 1.38 (d, J=3.8 Hz, 6H), 1.32 (d, J=6.9 Hz, 6H), 1.20 (d, J=6.8 Hz, 6H), 1.04 (s, 3H), 0.99 (s, 3H), 0.95 (d, J=6.7 Hz, 6H) ppm. $^{13}$C NMR (100 MHz, CDCl$_3$) δ=149.4 (d, J=36 Hz), 147.1, 145.5, 136.8 (d, J=6 Hz), 135.7 (d, J=3 Hz), 133.5 (d, J=32 Hz), 132.7 (d, J=7 Hz), 127.8, 125.0, 120.0, 66.4, 51.1 (d, J=12

Hz), 34.2, 33.7, 33.4 (d, J=4 Hz), 33.2, 30.8, 27.8 (d, J=4 Hz), 26.5, 24.3, 23.1. $^{31}$P NMR (CDCl$_3$, 202 MHz), δ ppm 0.0.

Example 1-d 7,7,9,9-tetramethyl-8-(2',4',6'-triisopropylbiphenyl-2-yl)-1,4-dioxa-8-phosphaspiro[4.5]decane

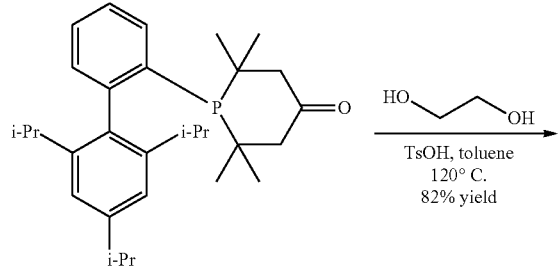

2,2,6,6-tetramethyl-1-(2',4',6'-triisopropylbiphenyl-2-yl)phosphinan-4-one

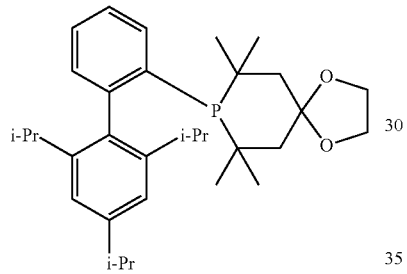

7,7,9,9-tetramethyl-8-(2',4',6'-triisopropylbiphenyl-2-yl)-1,4-dioxa-8-phosphaspiro[4.5]decane A flask was charged with 3.75 g of 2,2,6,6-tetramethyl-1-(2',4',6'-triisopropylbiphenyl-2-yl)phosphinan-4-one (8.32 mmol, 1.0 equiv) and 0.16 g of p-toluenesulfonic acid monohydrate (0.84 mmol, 0.1 equiv). The atmosphere was purged with nitrogen and the flask was charged with 80 mL of nitrogen-sparged toluene. To this solution was added 4.6 mL of ethylene glycol (83 mmol, 10 equiv). The reaction flask was equipped with a Dean-Stark trap and warmed to an internal temperature of 110° C. for 2 h under nitrogen atmosphere. The distilled toluene was collected in the Dean-Stark trap. The reaction mixture was cooled to room temperature under nitrogen gas. The reaction was quenched with 1.6 mL of aqueous 10 wt % sodium carbonate solution and partitioned between 65 mL of heptane and 35 mL of water. The organic solution was washed twice with 20 mL portions of water, concentrated in vacuo with gentle heating and the residue was chased once with heptane. The concentrate was dissolved in 35 g of methanol. Seed crystals were added to induce crystallization, the solvent was removed in vacuo and 16 mL of methanol was added to the crystalline solid. The mixture was stirred overnight at room temperature and the crystalline product was isolated by filtration, washed with methanol and dried in vacuo at 50° C. to give 3.5 g of 7,7,9,9-tetramethyl-8-(2',4',6'-triisopropylbiphenyl-2-yl)-1,4-dioxa-8-phosphaspiro[4.5]decane (96 area % by HPLC, 82% yield).

Example 1-e 8,8,10,10-tetramethyl-9-(2',4',6'-triisopropylbiphenyl-2-yl)-1,5-dioxa-9-phosphaspiro[5.5]undecane

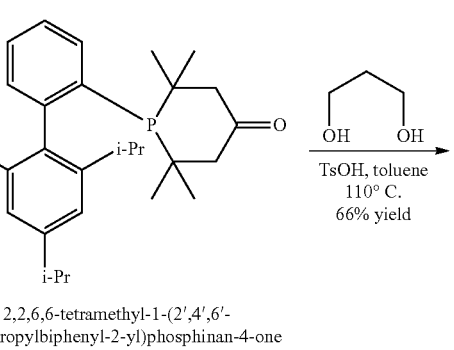

2,2,6,6-tetramethyl-1-(2',4',6'-triisopropylbiphenyl-2-yl)phosphinan-4-one

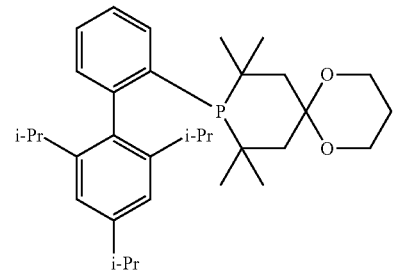

8,8,10,10-tetramethyl-9-(2',4',6'-triisopropylbiphenyl-2-yl)-1,5-dioxa-9-phosphaspiro[5.5]undecane A flask was charged with 0.40 g of 2,2,6,6-tetramethyl-1-(2',4',6'-triisopropylbiphenyl-2-yl)phosphinan-4-one (0.89 mmol, 1.0 equiv), 10 mL of argon-sparged toluene, 0.65 mL of 1,3-propanediol (8.9 mmol, 10 equiv) and 0.015 g of p-toluenesulfonic acid monohydrate (0.09 mmol, 0.1 equiv). The atmosphere was purged with argon and the reaction flask was equipped with a Dean-Stark trap and warmed in an oil bath at 125° C. for 20 h under argon atmosphere. The distilled toluene was collected in the Dean-Stark trap. The reaction mixture was cooled to room temperature, quenched with saturated aqueous sodium bicarbonate and partitioned between toluene and water. The aqueous solution was back extracted once with toluene, the combined organic solution was washed once with water, dried over potassium carbonate and concentrated in vacuo. The unpurified material was purified by flash chromatography over silica gel with gradient elution using acetone/heptane mixtures. After concentration. 0.3 g (66% yield) of 8,8,10,10-tetramethyl-9-(2',4',6'-triisopropylbiphenyl-2-yl)-1,5-dioxa-9-phosphaspiro[5.5]undecane was isolated as a solid. $^1$H NMR (C$_6$D$_6$, 500 MHz) δ ppm 1.02 (d, 6H, J=10 Hz), 1.12 (d, 6H, J=7 Hz), 1.24 (d, 6H, J=7 Hz), 1.31-1.28 (pent, 2H, J=5.5 Hz), 1.42 (d, 6H, J=20 Hz), 1.45 (d, 6H, J=7 Hz), 2.13 (d, 2H, J=14.5 Hz), 2.25 (dd, 2H, J=14.5, 6 Hz), 2.80 (sept, 2H, J=7 Hz), 2.86 (sept, 1H, J=7 Hz), 3.48 (t, 2H, J=5.5 Hz), 3.72 (t, 2H, J=5.5 Hz), 7.01 (td, 1H, J=7.5, 1.5 Hz), 7.08 (br t, 1H, J=7.5 Hz), 7.24 (s, 2H), 7.26-7.24 (m, 1H), 7.89 (br d, 1H, J=8 Hz); $^{31}$P NMR (C$_6$D$_6$, 200 MHz) δ ppm −2.7 (br singlet).

Example 1-f 3,3,8,8,10,10-hexamethyl-9-(2',4',6'-triisopropylbiphenyl-2-yl)-1,5-dioxa-9-phosphaspiro[5.5]undecane

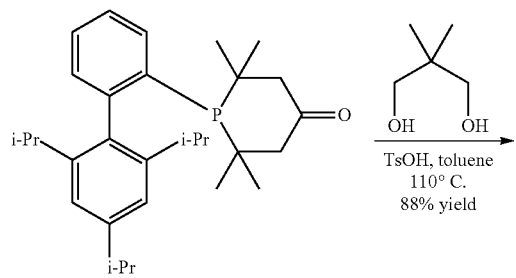

2,2,6,6-tetramethyl-1-(2',4',6'-triisopropylbiphenyl-2-yl)phosphinan-4-one

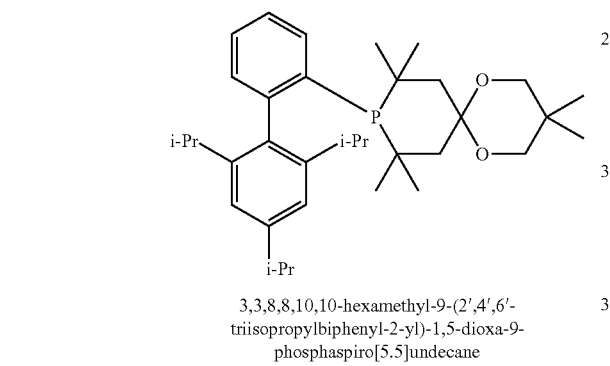

3,3,8,8,10,10-hexamethyl-9-(2',4',6'-triisopropylbiphenyl-2-yl)-1,5-dioxa-9-phosphaspiro[5.5]undecane A flask was charged with 4.0 g of 2,2,6,6-tetramethyl-1-(2',4',6'-triisopropylbiphenyl-2-yl)phosphinan-4-one (8.88 mmol, 1.0 equiv) 4.6 g of neopentyl glycol (44 mmol, 5 equiv) and 0.15 g of p-toluenesulfonic acid monohydrate (0.89 mmol, 0.1 equiv). The atmosphere was purged with argon and the flask was charged with 80 mL of argon-sparged toluene. The reaction flask was equipped with a Dean-Stark trap and warmed to an internal temperature of 110° C. for 2 h under argon atmosphere. The distilled toluene was collected in the Dean-Stark trap. The reaction mixture was cooled to room temperature under argon gas. The reaction was quenched with 1.7 mL of aqueous 10 wt % sodium carbonate solution and partitioned between 65 mL of heptane and 35 mL of water. The organic solution was washed three times with 20 mL portions of water and concentrated in vacuo with gentle heating. Anhydrous ethanol (78 g) was added to the crystalline residue and removed in vacuo with gentle heating. Anhydrous ethanol (24 mL) was added to the unpurified solids and the solids slurry was warmed to 80° C., held for an hour, and cooled to room temperature. The product was isolated by filtration, washed with ethanol and dried in vacuo at 50° C. to give 4.3 g of 3,3,8,8,10,10-hexamethyl-9-(2',4',6'-triisopropylbiphenyl-2-yl)-1,5-dioxa-9-phosphaspiro[5.5]undecane (98 area % by HPLC, 88% yield).

Example 2

Synthesis of Ligand Containing a Tricyclic Phosphacyclic Ring

Example 2a 1,3,5,7-tetramethyl-8-(2',4',6'-triisopropylbiphenyl-2-yl)-2,4,6-trioxa-8-phosphatricyclo[3.3.1.1$^{3,7}$]decane

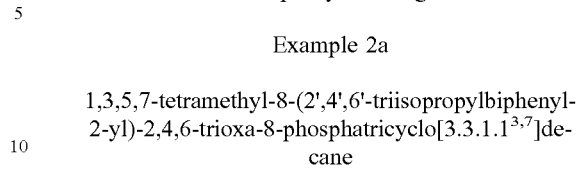

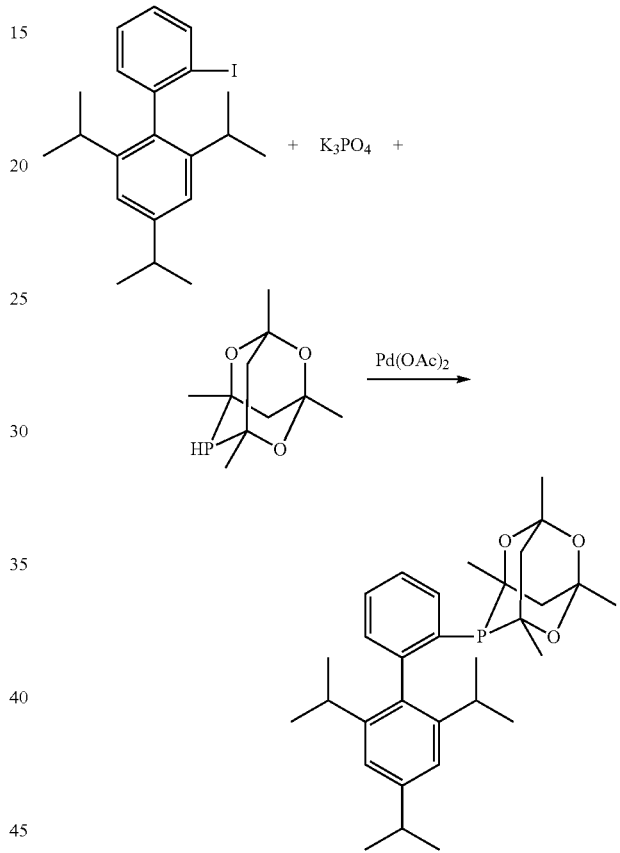

A 100-mL 3-neck round-bottom flask equipped with a magnetic stir bar and a reflux condenser was charged with potassium phosphate tribasic (1.23 g, 5.78 mmol), adamantylphosphine (1.00 g, 4.63 mmol), 2'-iodo-2,4,6-triisopropylbiphenyl (1.92 g, 1.02 mmol) and palladium acetate (10.4 mg, 0.046 mmol). The solids were purged with argon for approximately 30 min. A separate 25-mL round bottom flask was charged with diglyme (10 mL) and degassed with argon for 30 min. The degassed diglyme solution was transferred to the 100-mL 3-neck flask using a syringe. The contents of the 3-neck flask were heated to 155° C. and stirred for 18 h under a positive pressure of argon. The reaction mixture was cooled to 80° C., water (15 mL) was added and the mixture was allowed to cool down to the room temperature. Brown colored solid (2.55 g) was obtained after filtration and wash with water (20 mL). The solid obtained was transferred to a 100-mL round bottom flask, methanol (10 mL) was added and stirred under nitrogen for 30 min. Off-white solid was isolated after filtration and washed with methanol (10 mL). The off-white solid was transferred again to a separate 100-mL round bottom flask, methanol (15 mL) was added and stirred under nitrogen for 20 min. White solid isolated after filtration was washed with methanol (15 mL) and dried in vacuo to obtain 1.55 g of impure product. A portion (0.5 g) of the solid was further purified by flash chromatography using 0-2% acetone in heptane as eluent to afford 0.35 g of the desired product. $^{31}$P NMR (202 MHz, C$_6$D6): δ ppm −38.8.

Example 2b 8-(biphenyl-2-yl)-1,3,5,7-tetramethyl-2,4,6-trioxa-8-phosphatricyclo[3.3.1.1$^{3,7}$]decane

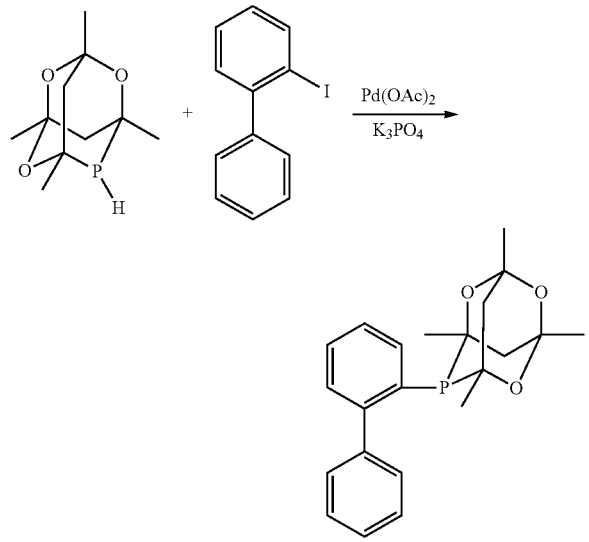

Into a dry 100-mL round-bottom flask equipped with a reflux condenser and magnetic stir bar, was placed the 1,3,5,7-tetramethyl-2,4,8-trioxa-6-phosphaadamantane (4.32 g, 19.98 mmol), milled K$_3$PO$_4$ (5.25 g, 24.73 mmol), and palladium acetate (22 mg, 0.098 mmol). The system was purged thoroughly with argon and 2-iodobiphenyl (6.16 g, 21.99 mmol) was added via syringe and degassed diglyme (40 mL) was added via cannula. The mixture was stirred at ambient temperature for about 1 hour and then heated in an oil bath at 145° C. (bath temperature) for about 8 hours under argon.

After cooling to ambient temperature, water (90 mL) was added to the mixture over about 3 minutes. The resulting solid was filtered, rinsed with water (2×20 mL), and dried in vacuo at ambient temperature to afford 7.16 g of a greenish-yellow powder. The solid was recrystallized from about 50 mL of 1:1 heptane/ethyl acetate. The recovered light green solid was dissolved in toluene (ca. 200 mL) and ethyl acetate (75 mL) and treated first with activated carbon (Darco S-51, 3.0 g) and then filtered through a plug of silica gel. After rinsing the solids with ethyl acetate, the combined filtrates were evaporated. The residue was recrystallized from t-butyl methyl ether (ca. 60 mL) to afford 3.72 g (50.6%) of pale yellow-orange crystals after drying in vacuo at 50-60° C. overnight. mp (Mettler FP-62, 0.4° C./minute) 168-169° C. $^1$H NMR (600 MHz, CDCl$_3$) δ ppm 8.34 (dt, J=7.8, 1.8 Hz, 1H), 7.25-7.43 (m, 8H), 2.02 (dd, J=13.3, 7.3 Hz, 1H), 1.89 (d, J=13.2 Hz, 1H), 1.88 (dd, J=25.8, 13.2 Hz, 1H), 1.52 (d, J=12.4 Hz, 3H), 1.43 (s, 3H), 1.41 (dd, J=13.3, 3.9 Hz, 1H), 1.32 (s, 3H), 0.90 (d, J=11.9 Hz, 3H). $^{31}$P{$^1$H}NMR (243 MHz, CDCl$_3$) δ ppm −39.1. Anal. Calcd for C$_{22}$H$_{25}$O$_3$P: C, 71.72; H, 6.84. Found: C, 71.63; H, 6.97.

Example 3

Preparation of Biaryl Halides

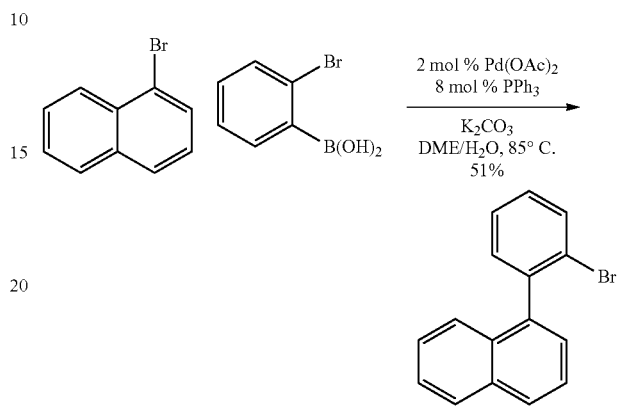

Example 3-a 1-(2-Bromophenyl)naphthalene

To a 250-mL round bottom flask equipped with a magnetic stir bar was added water (25 mL) and 1,2-dimethoxyethane (25 mL). The solution was sparged with nitrogen for 20 minutes, then potassium carbonate (6.67 g, 48.3 mmol, 3 equiv), 2-bromophenylboronic acid (3.80 g, 18.9 mmol, 0.98 equiv) and 1-bromonaphthalene (2.70 mL, 19.3 mmol, 1 equiv) were added. The flask was then purged with N$_2$ for 10 minutes before finally adding palladium(II) acetate (87 mg, 0.39 mmol, 0.02 equiv) and triphenylphosphine (405 mg, 1.55 mmol, 0.08 equiv). The reaction mixture was heated to 85° C. under a positive pressure of nitrogen for 16 hours. After cooling to room temperature, the phases were partitioned and the organic layer was collected, and the aqueous layer was washed with ethyl acetate (3×20 mL). The combined organic fractions were washed with brine (50 mL), dried over sodium sulfate, filtered, and concentrated on a rotary evaporator. The crude material was purified by column chromatography on an Isco CombiFlash system (120-g column; gradient: ramp up from heptane to 99:1 heptane:ethyl acetate over 1.5 column volumes, hold at 99:1 for 1.5 column volumes, ramp up to 92:8 heptane:ethyl acetate over 6 column volumes, hold at 92:8 for 6 column volumes) and then recrystallization from 99:1 heptane:ethanol to afford the title compound as a white solid (2.81 g, 93 area % by HPLC, 51% yield). $^1$H NMR (400 MHz, CDCl$_3$) δ ppm 7.91 (dd, J=8.3, 0.8 Hz, 2H), 7.74 (dd, J=8.0, 1.2 Hz, 1H), 7.57-7.29 (m, 8H)

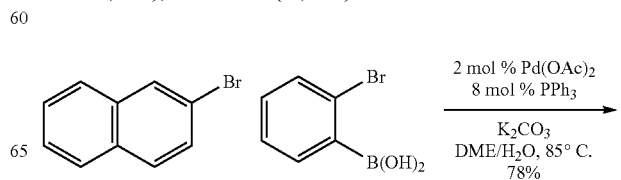

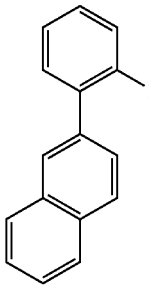

Example 3-b 2-(2-Bromophenyl)naphthalene

To a 250-mL round bottom flask equipped with a magnetic stir bar was added water (25 mL) and 1,2-dimethoxyethane (25 mL). The solution was sparged with nitrogen for 20 minutes, and then potassium carbonate (6.67 g, 48.3 mmol, 3 equiv), 2-bromophenylboronic acid (3.80 g, 18.9 mmol, 0.98 equiv) and 2-bromonaphthalene (4.00 g, 19.3 mmol, 1 equiv) were added. The flask was purged with $N_2$ for 10 minutes before finally adding palladium(II) acetate (87 mg, 0.39 mmol, 0.02 equiv) and triphenylphosphine (405 mg, 1.55 mmol, 0.08 equiv). The reaction mixture was heated to 85° C. under a positive pressure of nitrogen for 7 hours. After cooling to room temperature, the phases were partitioned and the organic layer was collected. The aqueous layer was washed with ethyl acetate (3×30 mL), and the combined organic fractions were washed with brine (60 mL), dried over sodium sulfate, filtered, and concentrated on a rotary evaporator. The crude orange oil was purified by column chromatography on an Isco CombiFlash system (120-g column; gradient: 0.5 column volumes heptane, ramp up to 99:1 heptane:dichloromethane over 0.5 column volumes, hold at 99:1 for 1 column volumes, ramp up to 92:8 heptane:dichloromethane over 7 column volumes, hold at 92:8 for 6 column volumes) to afford the title compound as a colorless oil (4.26 g, 97 area % by HPLC, 78% yield). $^1$H NMR (400 MHz, CDCl$_3$) δ ppm 7.93-7.85 (m, 4H), 7.72 (dd, J=8.0, 1.0 Hz, 1H), 7.57 (dd, J=8.5, 1.7 Hz, 1H), 7.55-7.49 (m, 2H), 7.46-7.38 (m, 2H), 7.28-7.21 (m, 1H).

Example 3-c

2-Iodo-3,6-dimethoxy-2',4',6'-trimethylbiphenyl

To an oven-dried 500-mL round bottom flask equipped with a magnetic stir bar was added 2-fluoro-1,4-dimethoxybenzene (6 g, 38.4 mmol, 1 equiv). The flask was purged with $N_2$, and anhydrous degassed tetrahydrofuran (250 mL) was added. The solution was cooled to −78° C., and n-butyllithium (15.4 mL, 38.4 mmol, 1 equiv, 2.5 M in hexanes) was added dropwise over 12 minutes The mixture was stirred for another 30 minutes, and mesitylmagnesium bromide (38.4 mL, 38.4 mmol, 1 equiv, 1 M in tetrahydrofuran) was slowly added over 16 minutes. The reaction mixture was stirred at −78° C. for an additional hour, then removed from the cold bath to warm to room temperature. After 2 hours at room temperature, the reaction mixture was cooled in an ice bath to 0° C. and added a fresh solution of iodine (46.1 mL, 46.1 mmol, 1.2 equiv, 1 M in tetrahydrofuran) was added dropwise over 10 minutes. The flask was removed from the ice bath and stirred for an additional hour. Then the reaction mixture was concentrated to afford a red oil. The oil was dissolved in dichloromethane (100 mL), washed with aqueous saturated sodium thiosulfate (2×50 mL) and brine (50 mL), dried over sodium sulfate, filtered, and concentrated to furnish a brown-yellowish oil. Purification of the crude product by column chromatography (330-g column; gradient: 1.5 column volumes heptane, ramp up to 89:11 heptane:ethyl acetate over 8 column volumes, hold at 89:11 for 2 column volumes) followed by crystallization in heptane (20 mL) and a minimal amount of methyl tert-butyl ether, filtration, washing with cold heptane, and drying under vacuum afforded the title compound (6.64 g, >99 area % by HPLC, 45% yield). $^1$H NMR (400 MHz, CDCl$_3$) δ ppm 6.99-6.96 (m, 2H), 6.94 (d, J=8.9 Hz, 1H), 6.82 (d, J=8.9 Hz, 1H), 3.90 (s, 3H), 3.69 (s, 3H), 2.37 (s, 3H), 1.93 (s, 6H). $^{13}$C NMR (100 MHz, CDCl$_3$) δ ppm 152.4, 150.9, 137.6, 136.7, 135.8, 135.3, 127.7, 110.9, 109.3, 94.5, 56.9, 56.4, 21.6, 20.1.

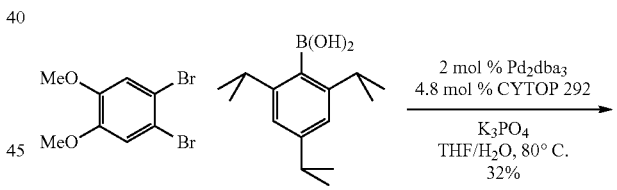

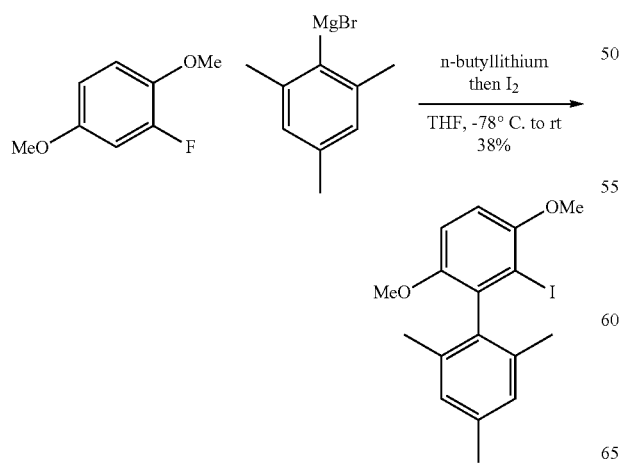

Example 3-d

2-Bromo-2',4',6'-triisopropyl-4,5-dimethoxybiphenyl

To a 100-mL round bottom flask equipped with a magnetic stir bar was added tris(dibenzylideneacetone)dipalladium(0) (198 mg, 0.216 mmol, 0.02 equiv), 1,3,5,7-tetramethyl-8-phenyl-2,4,6-trioxa-8-phosphatricyclo[3.3.1.1$^{3,7}$]decane (152 mg, 0.519 mmol, 0.048 equiv, CYTOP® 292) 2,4,6-triisopropylphenylboronic acid (4.02 g, 16.2 mmol, 1.5 equiv) and potassium phosphate (6.89 g, 32.4 mmol, 3 equiv). The flask was purged with nitrogen for 30 minutes, then anhydrous, degassed tetrahydrofuran (20 mL) was added. The reddish slurry was stirred at room temperature for 30 minutes, and then degassed water (2 mL), and 1,2-dibromo-4,5-dimethoxybenzene (3.20 g, 10.8 mmol, 1 equiv) was added. The reaction was stirred at reflux for 21 hours. The reaction mixture was cooled to room temperature and then diluted with water (30 mL). The phases were separated and the aqueous layer was washed with ethyl acetate (3×20 mL). The combined organics were washed with brine (50 mL), dried over sodium sulfate, filtered, and concentrated on a rotary evaporator. The unreacted dibromoarene was removed by recrystallization from hot methanol. The product was further purified by column chromatography on an Isco CombiFlash system (120-g column; gradient: 1 column volumes heptane, ramp up to 98:2 heptane:ethyl acetate over 0.5 column volumes, hold at 98:2 for 2 column volumes, ramp up to 90:10 heptane:ethyl acetate over 7 column volumes, hold at 90:10 for 1 column volumes) to afford the title compound as a white solid (1.47 g, 99 area % by HPLC, 32% yield). $^1$H NMR (400 MHz, CDCl$_3$) δ ppm 7.13 (s, 1H), 7.05 (s, 2H), 6.69 (s, 1H), 3.94 (s, 3H), 3.81 (s, 3H), 2.96 (hept, J=7.0 Hz, 1H), 2.52 (hept, J=6.9 Hz, 2H), 1.32 (d, J=6.9 Hz, 6H), 1.20 (d, J=6.9 Hz, 6H), 1.07 (d, J=6.8 Hz, 6H). $^{13}$C NMR (100 MHz, CDCl$_3$) δ ppm 148.0, 147.9, 147.6, 146.0, 135.3, 133.2, 120.5, 114.8, 114.8, 113.9, 56.2, 34.4, 30.9, 25.1, 24.3, 23.9.

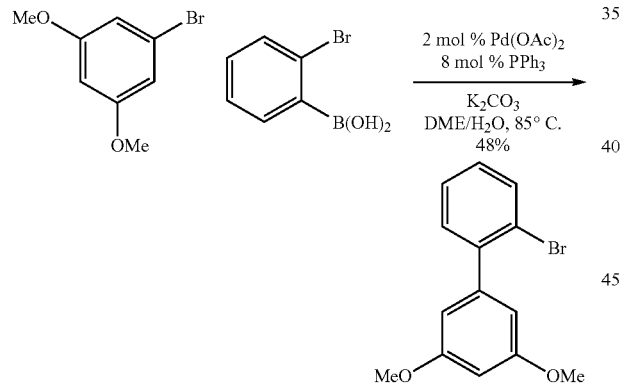

Example 3-e

2-Bromo-3',5'-dimethoxybiphenyl

To a 250-mL round bottom flask equipped with a magnetic stir bar was added water (41 mL) and 1,2-dimethoxyethane (41 mL). The solution was sparged with nitrogen for 20 minutes, and then potassium carbonate (11.1 g, 81.0 mmol, 3 equiv), 2-bromophenylboronic acid (6.35 g, 31.6 mmol, 0.98 equiv) and 1-bromo-3,5-dimethoxybenzene (7.00 g, 32.2 mmol, 1 equiv) were added. The flask was purged with N$_2$ for 10 minutes before finally adding palladium(II) acetate (145 mg, 0.645 mmol, 0.02 equiv) and triphenylphosphine (677 mg, 2.58 mmol, 0.08 equiv). The reaction mixture was heated to 85° C. under a positive pressure of nitrogen for 16 hours. After cooling to room temperature, the phases were partitioned. The organic phase was collected and the aqueous phase was washed with ethyl acetate (3×20 mL). The combined organic fractions were washed with brine (50 mL), dried over sodium sulfate, filtered, and concentrated on a rotary evaporator. The crude yellow oil was purified by column chromatography on the Isco (120-g column; gradient: 2 column volumes heptane, ramp up to 94:6 heptane:ethyl acetate over 8 column volumes, hold at 94:6 for 6 column volumes) to afford the title compound as a colorless oil (4.51 g, 94 area % by HPLC, 48% yield). $^1$H NMR (400 MHz, CDCl$_3$) δ ppm 7.68-7.62 (m, 1H), 7.40-7.31 (m, 2H), 7.24-7.15 (m, 1H), 6.55 (d, J=2.3 Hz, 2H), 6.50 (t, J=2.3 Hz, 1H), 3.83 (s, 6H). $^{13}$C NMR (100 MHz, CDCl$_3$) δ ppm 159.8, 142.6, 142.1, 132.8, 130.7, 128.5, 127.0, 122.1, 107.4, 99.6, 55.5.

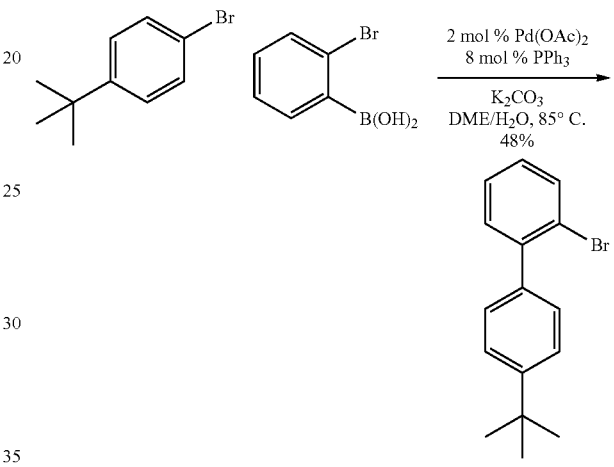

Example 3-f

2-Bromo-4'-tert-butylbiphenyl

To a 250-mL round bottom flask equipped with a magnetic stir bar was added water (41 mL) and 1,2-dimethoxyethane (41 mL). The solution was sparged with nitrogen for 20 minutes, then potassium carbonate (6.49 g, 46.9 mmol, 3 equiv), 2-bromophenylboronic acid (3.69 g, 18.4 mmol, 0.98 equiv) and 1-bromo-4-tert-butylbenzene (4.00 g, 18.8 mmol, 1 equiv) were added. The flask was then purged with N$_2$ for 10 minutes before finally adding palladium(II) acetate (84 mg, 0.375 mmol, 0.02 equiv) and triphenylphosphine (394 mg, 1.50 mmol, 0.08 equiv). The reaction mixture was heated to 85° C. under a positive pressure of nitrogen for 18 hours. After cooling to room temperature, the phases were partitioned and the organic layer was collected. The aqueous layer was washed with ethyl acetate (3×20 mL). The combined organic fractions were washed with brine (50 mL), dried over sodium sulfate, filtered, and concentrated on a rotary evaporator. The crude yellow oil was purified by column chromatography on an Isco CombiFlash system (120-g column; eluted with 14 column volumes heptane) to afford the title compound as a colorless oil (2.93 g, 67 area % by HPLC, 54% yield). $^1$H NMR (400 MHz, CDCl$_3$) δ ppm 7.68-7.64 (m, 1H), 7.48-7.42 (m, 2H), 7.39-7.31 (m, 4H), 7.21-7.15 (m, 1H), 1.39 (s, 9H).

Example 4

General Procedure for Synthesis of Diethylphosphonates

To a round-bottom flask equipped with a magnetic stir bar was added the arene (1 equiv). After purging the flask with nitrogen for 10 minutes, degassed, anhydrous tetrahydrofuran was added (0.3 M relative to arene). The resulting solution was cooled to −78° C., and then n-butyllithium (1.2 equiv, 2.5 Min hexanes) was added in a dropwise fashion. The reaction was typically stirred for 1 hour at −78° C., and then the aryllithium intermediate was quenched with diethyl chlorophosphate (1.2 equiv). The reaction was allowed to warm slowly to room temperature overnight, and then diluted with aqueous saturated sodium bicarbonate. The reaction mixture was worked up by separating the phases and washing the aqueous layer with ethyl acetate (3×). The combined organic fractions were then washed once with brine, dried over sodium sulfate, filtered, and concentrated on a rotary evaporator. The crude diethylphosphonate was purified by silica gel column chromatography on an Isco CombiFlash system as described.

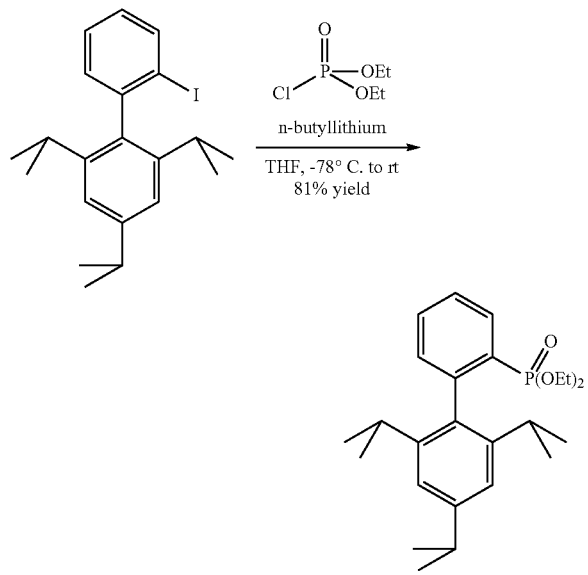

Example 4-a

Diethyl 2',4',6'-triisopropylbiphenyl-2-ylphosphonate

The titled compound was prepared as described in the general procedure for synthesis of diethylphosphonates substituting 2'-iodo-2,4,6-triisopropylbiphenyl (10.0 g, 24.6 mmol, 1 equiv), for the arene, wherein all other reagents are scaled accordingly, followed by purification via column chromatography (120-g column; gradient: 2 column volumes dichloromethane, ramp up to 92:8 dichloromethane:acetone over 8 column volumes, hold at 92:8 for 4 column volumes) (8.31 g, 97 area % by HPLC, 81% yield). $^1$H NMR (400 MHz, CDCl$_3$) δ ppm 8.02 (ddd, J=14.3, 7.7, 1.3 Hz, 1H), 7.51 (tt, J=7.5, 1.5 Hz, 1H), 7.43 (tdd, J=7.5, 3.6, 1.3 Hz, 1H), 7.24-7.15 (m, 1H), 7.02 (s, 2H), 3.86 (ddq, J=10.2, 8.7, 7.1 Hz, 2H), 3.64 (ddq, J=10.2, 8.9, 7.1 Hz, 2H), 2.93 (hept, J=6.9 Hz, 1H), 2.42 (hept, J=6.8 Hz, 2H), 1.28 (d, J=6.9 Hz, 6H), 1.21 (d, J=6.8 Hz, 6H), 1.09 (t, J=7.1 Hz, 6H), 0.97 (d, J=6.8 Hz, 6H).

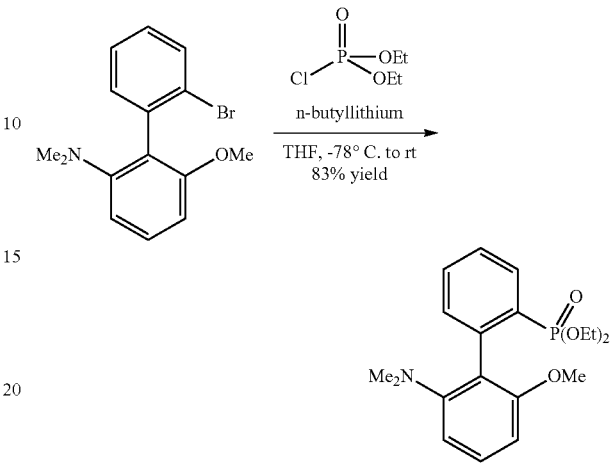

Example 4-b

Diethyl 2'-(dimethylamino)-6'-methoxybiphenyl-2-ylphosphonate

The titled compound was prepared as described in the general procedure for synthesis of diethylphosphonates substituting 2'-bromo-6-methoxy-N,N-dimethylbiphenyl-2-amine (see Buchwald S L, et al. JACS 2009; 131: 7532-7533) (3.00 g, 9.80 mmol, 1 equiv) for the arene, wherein all other reagents are scaled accordingly, followed by purification via column chromatography (80-g column; gradient: 1.5 column volumes dichloromethane, ramp up to 90:10 dichloromethane:acetone over 9.5 column volumes, hold at 90:10 for 6 column volumes) (2.97 g, 95 area % by HPLC, 83% yield). $^1$H NMR (400 MHz, CDCl$_3$) δ ppm 7.98 (ddd, J=14.1, 7.7, 1.3 Hz, 1H), 7.54 (tt, J=7.6, 1.5 Hz, 1H), 7.39 (tdd, J=7.6, 3.5, 1.3 Hz, 1H), 7.32-7.20 (m, 2H), 6.72 (dd, J=8.2, 0.7 Hz, 1H), 6.60 (d, J=8.2 Hz, 1H), 4.02-3.74 (m, 4H), 3.67 (s, 3H), 2.49 (s, 6H), 1.16 (td, J=7.1, 4.7 Hz, 6H). $^{31}$P NMR (CDCl$_3$, 202 MHz) δ ppm 15.0 (s).

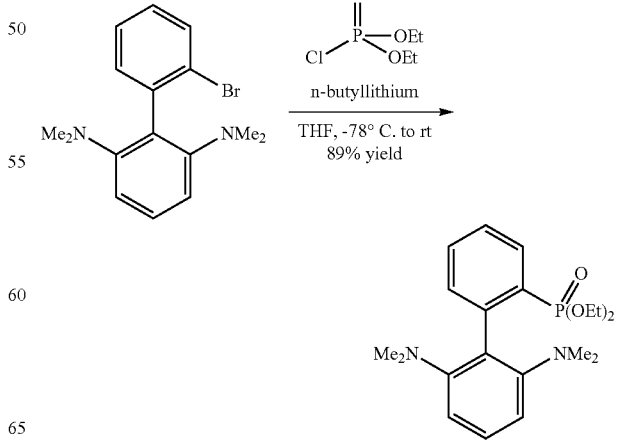

Example 4-c

Diethyl 2',6'-bis(dimethylamino)biphenyl-2-ylphosphonate

The titled compound was prepared as described in the general procedure for synthesis of diethylphosphonates substituting 2'-bromo-$N^2,N^2,N^6,N^6$-tetramethylbiphenyl-2,6-diamine (see Buchwald S L, JACS 2009; 131: 7532-7533) (5.00 g, 15.7 mmol, 1 equiv) for the arene, wherein all other reagents are scaled accordingly, followed by purification via column chromatography (120-g column; gradient: 1.5 column volumes dichloromethane, ramp up to 84:16 dichloromethane:acetone over 8 column volumes, hold at 84:16 for 6 column volumes) (5.25 g, >94 area % by HPLC, 89% yield). $^1$H NMR (500 MHz, CDCl$_3$) δ ppm 7.83 (dd, J=14.0, 7.7 Hz, 1H), 7.43 (t, J=7.5 Hz, 1H), 7.30-7.24 (m, 2H), 7.19-7.12 (m, 1H), 6.76 (d, J=8.0 Hz, 2H), 3.94-3.81 (m, 2H), 3.81-3.63 (m, 2H), 2.31 (s, 12H), 1.05 (t, J=7.0 Hz, 6H). $^{31}$P NMR (CDCl$_3$, 202 MHz) δ ppm 14.8 (s).

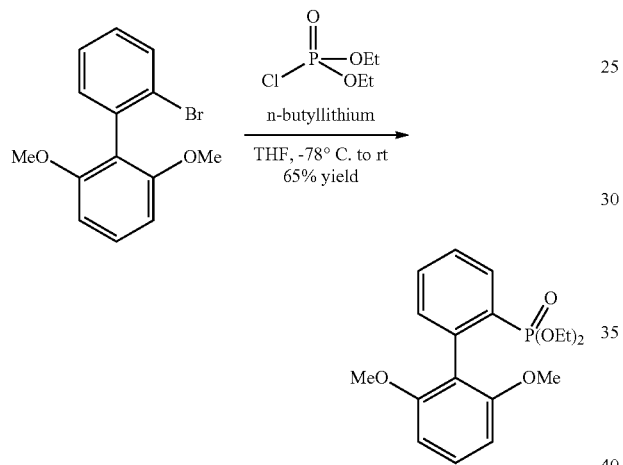

Example 4-d

Diethyl 2',6'-dimethoxybiphenyl-2-ylphosphonate

To a 250-mL round-bottom flask equipped with a magnetic stir bar was added 2'-bromo-2,6-dimethoxybiphenyl (see Buchwald S L, Journal of the American Chemical Society 2005; 127:4685-4696) (7.02 g, 24.0 mmol, 1 equiv). Degassed, anhydrous tetrahydrofuran was added (80 mL) followed by N,N,N',N'-tetramethylethylene-1,2-diamine (4.31 mL, 28.7 mmol, 1.2 equiv). The resulting solution was cooled to −78° C., and then n-butyllithium (11.5 mL, 28.7 mmol, 1.2 equiv, 2.5 Min hexanes) was added in a dropwise fashion. After the addition of 5 mL of n-butyllithium the reaction slurry could no longer be stirred. The reaction flask was warmed to 0° C. at which point the slurry became free-flowing. The remainder of the n-butyllithium (~6.5 mL) was added over the course of 10 minutes. The reaction was stirred for 90 minutes at 0° C., and then the aryllithium intermediate was quenched with diethyl chlorophosphate (4.15 mL, 28.7 mmol, 1.2 equiv). The reaction was re-cooled to −78° C. and stirred for 1 hour, then the cooling bath was removed and the flask was warmed to room temperature. At that point, the reaction solution was diluted with pH 7 phosphate buffer (100 mL). The reaction mixture was worked up by separating the phases and washing the aqueous layer with ethyl acetate (4×60 mL). The combined organic fractions were then washed once with brine (150 mL), dried over sodium sulfate, filtered, and concentrated on a rotary evaporator. The crude product was purified by column chromatography (120-g column; gradient: 1.5 column volumes dichloromethane, ramp up to 88:12 dichloromethane:acetone over 10.5 column volumes, hold at 88:12 for 6 column volumes), the product was isolated as a white solid (5.49 g, 78 area % by HPLC, 65% yield). $^1$H NMR (400 MHz, CDCl$_3$) δ ppm 8.07 (dd, J=14.1, 7.7 Hz, 1H), 7.57 (t, J=7.5 Hz, 1H), 7.46-7.37 (m, 1H), 7.30 (t, J=8.3 Hz, 1H), 7.24-7.18 (m, 1H), 6.60 (d, J=8.4 Hz, 2H), 3.98-3.77 (m, 4H), 3.70 (s, 6H), 1.17 (t, J=7.1 Hz, 6H). $^{31}$P NMR (CDCl$_3$, 202 MHz) δ ppm 15.2 (s).

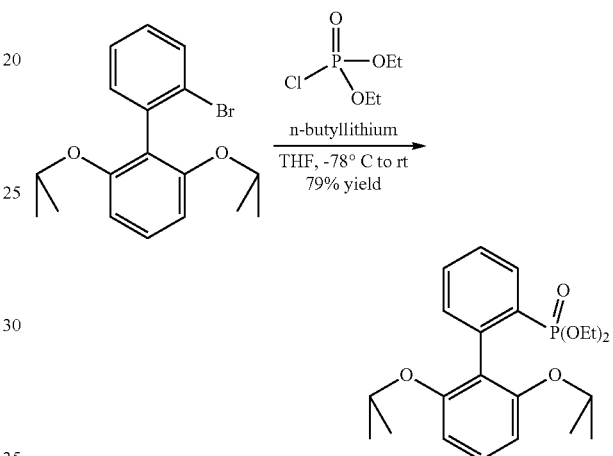

Example 4-e

Diethyl 2',6'-diisopropoxybiphenyl-2-ylphosphonate

The titled compound was prepared as described in the general procedure for synthesis of diethylphosphonates substituting 2'-bromo-2,6-diisopropoxybiphenyl (12.0 g, 34.4 mmol, 1 equiv) for the arene, wherein all other reagents are scaled accordingly, followed by purification via flash column chromatography (300-mL SiO$_2$ gel; gradient: 85:15 to 75:25 dichloromethane:acetone) (11.0 g, 79% yield). 1H NMR (400 MHz, C$_6$D6) δ ppm 8.31 (dd, J=14.0, 7.7 Hz, 1H), 7.28-7.22 (m, 2H), 7.19 (t, J=3.3 Hz, 1H), 7.15-7.07 (m, 1H), 6.51 (d, J=8.3 Hz, 2H), 4.26 (hept, J=6.1 Hz, 2H), 4.13-3.97 (m, 2H), 3.96-3.83 (m, 2H), 1.12-1.06 (m, 12H), 1.02 (d, J=6.0 Hz, 6H). $^{31}$P NMR (C$_6$D$_6$, 202 MHz) δ ppm 18.2 (s).

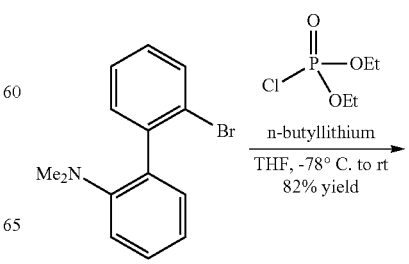

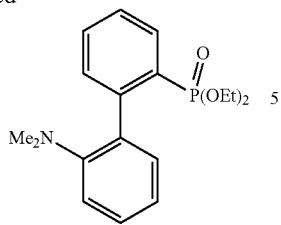

Example 4-f

Diethyl 2'-(dimethylamino)biphenyl-2-ylphosphonate

The titled compound was prepared as described in the general procedure for synthesis of diethylphosphonates substituting 2'-bromo-N,N-dimethylbiphenyl-2-amine (1.99 g, 7.21 mmol, 1 equiv) for the arene, wherein all other reagents are scaled accordingly, followed by purification via column chromatography (80-g column; gradient: 1.5 column volumes dichloromethane, ramp up to 90:10 dichloromethane:acetone over 9.5 column volumes, hold at 90:10 for 6 column volumes) (1.96 g, 96 area % by HPLC, 82% yield). $^1$H NMR (400 MHz, CDCl$_3$) δ ppm 8.00 (ddd, J=14.3, 7.7, 1.1 Hz, 1H), 7.50 (ttd, J=5.1, 3.3, 1.7 Hz, 1H), 7.47-7.34 (m, 2H), 7.32-7.22 (m, 2H), 7.04-6.92 (m, 2H), 4.05-3.87 (m, 3H), 3.80-3.62 (m, 1H), 2.52 (s, 6H), 1.18 (t, J=7.1 Hz, 3H), 1.11 (t, J=7.1 Hz, 3H). $^{31}$P NMR (CDCl$_3$, 202 MHz) δ ppm 24.8 (s).

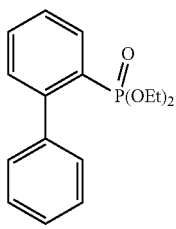

Example 4-g

Diethyl biphenyl-2-ylphosphonate

The titled compound was prepared as described in the general procedure for synthesis of diethylphosphonates substituting 2-iodobiphenyl (4 mL, 22.7 mmol, 1 equiv) for the arene, wherein all other reagents are scaled accordingly, followed by purification via column chromatography (120-g column; gradient: 1 column volumes dichloromethane, ramp up to 91:9 dichloromethane:acetone over 9 column volumes, hold at 91:9 for 6 column volumes) (5.27 g, 94 area % by HPLC, 80% yield). $^1$H NMR (400 MHz, CDCl$_3$) δ ppm 8.04 (ddd, J=14.3, 7.7, 1.3 Hz, 1H), 7.56 (tt, J=7.6, 1.5 Hz, 1H), 7.50-7.29 (m, 7H), 4.01-3.76 (m, 4H), 1.13 (t, J=7.1 Hz, 6H). $^{31}$P NMR (CDCl$_3$, 202 MHz) δ ppm 25.0 (s).

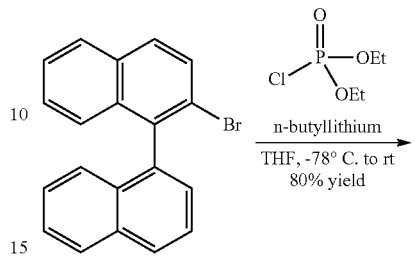

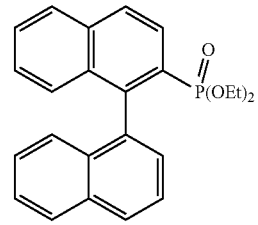

Example 4-h

Diethyl 1,1'-binaphthyl-2-ylphosphonate

The titled compound was prepared as described in the general procedure for synthesis of diethylphosphonates substituting 2-bromo-1,1'-binaphthyl (4.15 g, 12.5 mmol, 1 equiv) for the arene, wherein all other reagents are scaled accordingly, followed by purification via column chromatography (80-g column; gradient: 1.5 column volumes dichloromethane, ramp up to 91:9 dichloromethane:acetone over 9.5 column volumes, hold at 91:9 for 7 column volumes) (3.91 g, 95 area % by HPLC, 80% yield). $^1$H NMR (400 MHz, CDCl$_3$) δ ppm 8.26-8.16 (m, 1H), 8.02 (dd, J=8.4, 3.7 Hz, 1H), 7.99-7.89 (m, 3H), 7.60 (dd, J=8.2, 7.0 Hz, 1H), 7.57-7.47 (m, 2H), 7.43 (ddd, J=8.1, 6.8, 1.2 Hz, 1H), 7.29-7.15 (m, 3H), 7.08 (d, J=8.4 Hz, 1H), 3.85-3.51 (m, 4H), 0.98 (t, J=7.1 Hz, 3H), 0.75-0.70 (m, 3H). $^{13}$C NMR (100 MHz, CDCl$_3$) δ ppm 143.1 (d, J=10 Hz), 135.5 (d, J=6 Hz), 134.6 (d, J=2 Hz), 133.0, 132.8, 132.8, 128.4 (d, J=3 Hz), 128.3 (d, J=6 Hz), 127.9, 127.7, 127.6, 127.5, 127.3 (d, J=15 Hz), 126.8, 126.4, 126.4 (d, J=1 Hz), 125.6, 125.3, 125.0, 124.6, 61.8 (d, J=6 Hz), 61.6 (d, J=6 Hz), 16.3 (d, J=7 Hz), 15.8 (d, J=7 Hz). $^{31}$P NMR (CDCl$_3$, 202 MHz) δ ppm 17.5 (s).

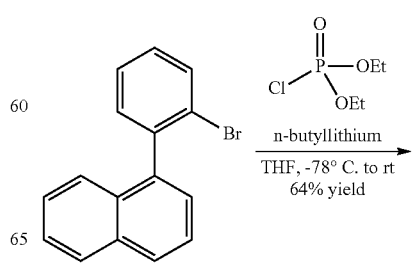

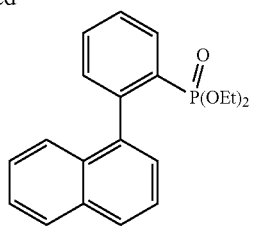

Example 4-i

Diethyl 2-(naphthalen-1-yl)phenylphosphonate

The titled compound was prepared as described in the general procedure for synthesis of diethylphosphonates substituting 1-(2-bromophenyl)naphthalene (2.78 g, 9.82 mmol, 1 equiv) for the arene, wherein all other reagents are scaled accordingly, followed by purification via column chromatography (120-g column; gradient: 1.5 column volumes dichloromethane, ramp up to 89:11 dichloromethane:acetone over 8 column volumes, hold at 89:11 for 3.5 column volumes) (2.14 g, 97 area % by HPLC, 64% yield). $^1$H NMR (400 MHz, CDCl$_3$) δ ppm 8.17 (ddd, J=14.2, 7.7, 1.4 Hz, 1H), 7.89-7.84 (m, 2H), 7.61 (tt, J=7.5, 1.5 Hz, 1H), 7.57-7.48 (m, 2H), 7.48-7.40 (m, 2H), 7.40-7.30 (m, 3H), 3.85-3.48 (m, 4H), 0.95 (t, J=7.1 Hz, 3H), 0.71 (td, J=7.0, 0.5 Hz, 3H). $^{13}$C NMR (100 MHz, CDCl$_3$) δ ppm 143.4 (d, J=9 Hz), 138.0 (d, J=4 Hz), 133.6 (d, J=10 Hz), 132.9, 132.2, 131.6 (d, J=14 Hz), 131.2 (d, J=3 Hz), 129.2, 127.6 (d, J=6 Hz), 127.3, 127.2, 126.8 (d, J=15 Hz), 126.1, 125.4, 125.2, 124.3, 61.7 (dd, J=13, 6 Hz), 16.2 (d, J=7 Hz), 15.76 (d, J=7 Hz). $^{31}$P NMR (CDCl$_3$, 202 MHz) δ ppm 14.3 (s).

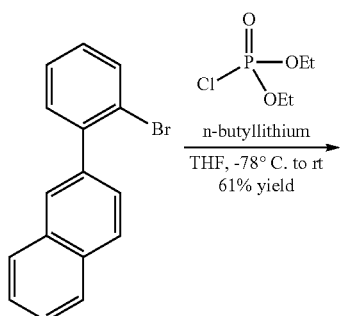

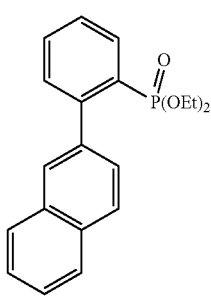

Example 4-j

Diethyl 2-(naphthalen-2-yl)phenylphosphonate

The titled compound was prepared as described in the general procedure for synthesis of diethylphosphonates substituting 2-(2-bromophenyl)naphthalene (4.25 g, 15.0 mmol, 1 equiv) for the arene, wherein all other reagents are scaled accordingly, followed by purification via column chromatography (120-g column; gradient: 1.5 column volumes dichloromethane, ramp up to 90:10 dichloromethane:acetone over 7.5 column volumes, hold at 90:10 for 4 column volumes) (3.10 g, 96 area % by HPLC, 61% yield). $^1$H NMR (400 MHz, CDCl$_3$) δ ppm 8.09 (ddd, J=14.3, 7.7, 1.2 Hz, 1H), 7.96-7.78 (m, 4H), 7.65-7.55 (m, 2H), 7.55-7.45 (m, 3H), 7.45-7.36 (m, 1H), 3.98-3.75 (m, 4H), 1.06 (t, J=7.1 Hz, 6H). $^{13}$C NMR (100 MHz, CDCl$_3$) δ ppm 145.5 (d, J=10 Hz), 138.5 (d, J=4 Hz), 133.6 (d, J=10 Hz), 132.4, 132.2, 131.6 (d, J=3 Hz), 131.2 (d, J=14 Hz), 127.9, 127.8, 127.8, 127.4, 127.3, 126.7, 126.6, 126.0, 125.8 (d, J=17 Hz), 61.8 (d, J=6 Hz), 16.3 (d, J=7 Hz). $^{31}$P NMR (CDCl$_3$, 202 MHz) δ ppm 14.8 (s).

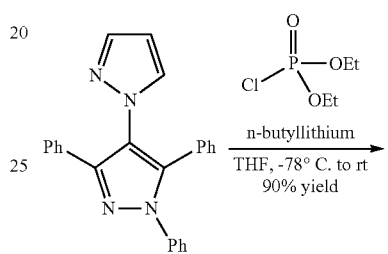

Example 4-k

Diethyl 1',3',5'-triphenyl-1'H-1,4'-bipyrazol-5-yl-phosphonate

The titled compound was prepared as described in the general procedure for synthesis of diethylphosphonates substituting 1',3',5'-triphenyl-1'H-1,4'-bipyrazole (see Sieser J E et al, Org. Proc. Res. & Devel. 2008; 12:480-489) (2.00 g, 5.52 mmol, 1 equiv) for the arene, wherein all other reagents are scaled accordingly, followed by purification via column chromatography (80-g column; gradient: 1.5 column volumes dichloromethane, ramp up to 95:5 dichloromethane: acetone over 8.5 column volumes, hold at 95:5 for 6 column volumes) (2.47 g, 99 area % by HPLC, 90% yield). $^1$H NMR (400 MHz, CDCl$_3$) δ ppm 7.76 (dd, J=1.6, 1.6 Hz, 1H), 7.36-7.22 (m, 7H), 7.22-7.05 (m, 8H), 6.85 (dd, J=2.4, 1.6 Hz, 1H), 3.75-3.49 (m, 2H), 3.34-3.16 (m, 2H), 0.85 (dt, J=8.4, 6.8 Hz, 6H). $^{13}$C NMR (100 MHz, CDCl$_3$) δ ppm 148.0, 141.2, 139.9 (d, J=17 Hz), 139.4, 135.7, 133.5, 131.0, 129.0, 128.7, 128.5, 128.1, 128.0, 127.5, 126.3, 125.0, 119.7, 116.7 (d, J=20 Hz), 62.5 (d, J=5 Hz), 62.3 (d, J=6 Hz), 16.3 (d, J=6 Hz), 16.2 (d, J=6 Hz). $^{31}$P NMR (CDCl$_3$, 202 MHz) δ ppm 11.0 (s).

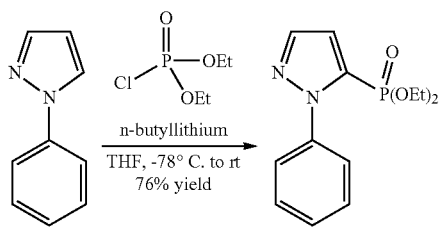

Example 4-l

Diethyl 1-phenyl-1H-pyrazol-5-ylphosphonate

The titled compound was prepared as described in the general procedure for synthesis of diethylphosphonates substituting 1-phenyl-1H-pyrazole (5.00 mL, 37.8 mmol, 1 equiv) for the arene, wherein all other reagents are scaled accordingly, followed by purification via column chromatography (120-g column; gradient: 1.5 column volumes dichloromethane, ramp up to 92:8 dichloromethane:acetone over 8.5 column volumes, hold at 92:8 for 8 column volumes) (8.34 g, 98 area % by HPLC, 79% yield). 1H NMR (400 MHz, CDCl$_3$) δ ppm 7.71 (t, J=1.7 Hz, 1H), 7.66-7.60 (m, 2H), 7.49-7.36 (m, 3H), 6.96 (dd, J=2.5, 1.9 Hz, 1H), 4.11-3.92 (m, 4H), 1.17 (td, J=7.0, 0.5 Hz, 6H). $^{13}$C NMR (100 MHz, CDCl$_3$) δ ppm 140.1, 139.3 (d, J=17 Hz), 131.6 (d, J=216 Hz), 128.4, 128.3, 125.1, 117.0 (d, J=19 Hz), 62.9 (d, J=6 Hz), 16.3 (d, J=7 Hz). $^{31}$P NMR (CDCl$_3$, 202 MHz) δ ppm 5.0 (s).

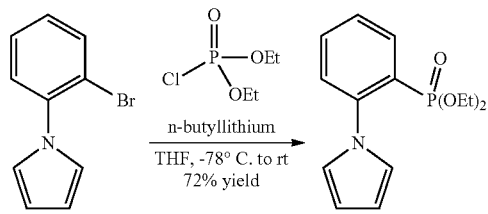

Example 4-m

Diethyl 2-(1H-pyrrol-1-yl)phenylphosphonate

The titled compound was prepared as described in the general procedure for synthesis of diethylphosphonates substituting 1-(2-bromophenyl)-1H-pyrrole (see Lautens M et al, Organic Letters 2007; 9: 1761-1764) (5.29 g, 23.8 mmol, 1 equiv) for the arene, wherein all other reagents are scaled accordingly, followed by purification via column chromatography (80-g column; gradient: 1.5 column volumes dichloromethane, ramp up to 92:8 dichloromethane:acetone over 9.5 column volumes, hold at 92:8 for 5 column volumes) (4.81 g, 97 area % by HPLC, 72% yield). $^1$H NMR (400 MHz, CDCl$_3$) δ ppm 8.04 (ddd, J=14.6, 7.7, 1.6 Hz, 1H), 7.59 (tt, J=7.7, 1.4 Hz, 1H), 7.45 (tdd, J=7.6, 3.1, 1.2 Hz, 1H), 7.39-7.29 (m, 1H), 6.97 (t, J=2.2 Hz, 2H), 6.29 (t, J=2.2 Hz, 2H), 4.09-3.89 (m, 4H), 1.23 (t, J=7.1 Hz, 6H). $^{31}$P NMR (CDCl$_3$, 202 MHz) δ ppm 15.1 (s).

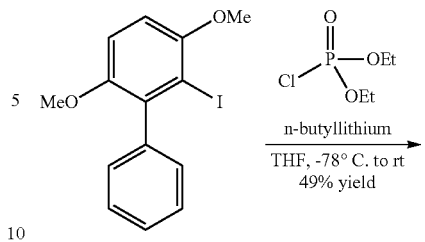

Example 4-n

Diethyl 3,6-dimethoxybiphenyl-2-ylphosphonate

The titled compound was prepared as described in the general procedure for synthesis of diethylphosphonates substituting 2-iodo-3,6-dimethoxybiphenyl (5.00 g, 14.7 mmol, 1 equiv) (see Buchwald S L et al, U.S. Pat. No. 7,858,784, Dec. 28, 2010) for the arene, wherein all other reagents are scaled accordingly, followed by purification via column chromatography (120-g column; gradient: 1 column volumes dichloromethane, ramp up to 82:18 dichloromethane:acetone over 8 column volumes, hold at 82:18 for 6 column volumes) (2.54 g, >99 area % by HPLC, 49% yield). $^1$H NMR (400 MHz, CDCl$_3$) δ ppm 7.44-7.26 (m, 5H), 7.09 (d, J=9.0 Hz, 1H), 6.98 (dd, J=9.0, 7.2 Hz, 1H), 4.02-3.91 (m, 5H), 3.75-3.66 (m, 2H), 3.64 (d, J=2.5 Hz, 3H), 1.09 (t, J=7.0 Hz, 6H). $^{13}$C NMR (100 MHz, CDCl$_3$) δ ppm 155.7, 151.0 (d, J=19 Hz), 137.4 (d, J=5 Hz), 136.2 (d, J=8 Hz), 129.6, 126.9, 126.5, 118.2 (d, J=188 Hz), 116.1 (d, J=3 Hz), 111.6 (d, J=11 Hz), 61.5 (d, J=6 Hz), 56.9, 16.4 (d, J=7 Hz). $^{31}$P NMR (CDCl$_3$, 202 MHz) δ ppm 12.4 (s).

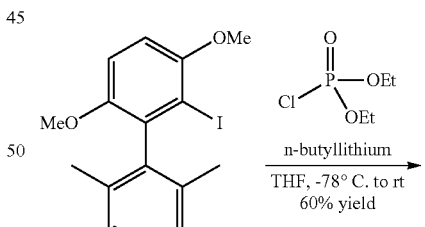

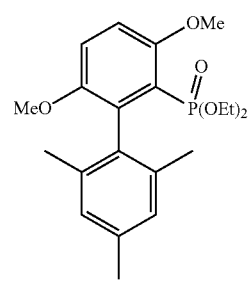

Example 4-o

Diethyl 3,6-dimethoxy-2',4',6'-trimethylbiphenyl-2-ylphosphonate

The titled compound was prepared as described in the general procedure for synthesis of diethylphosphonates substituting 2-iodo-3,6-dimethoxy-2',4',6'-trimethylbiphenyl (5.01 g, 13.1 mmol, 1 equiv) for the arene, wherein all other reagents are scaled accordingly, followed by purification via column chromatography (120-g column; gradient: 1.5 column volumes dichloromethane, ramp up to 85:15 dichloromethane:acetone over 8.5 column volumes, hold at 85:15 for 6 column volumes) (3.09 g, 88 area % by HPLC, 60% yield). $^1$H NMR (400 MHz, CDCl$_3$) δ ppm 7.07 (d, J=9.0 Hz, 1H), 6.94 (dd, J=9.0, 7.2 Hz, 1H), 6.85 (s, 2H), 4.01-3.87 (m, 5H), 3.70-3.55 (m, 5H), 2.30 (s, 3H), 1.95 (s, 6H), 1.09 (t, J=7.1 Hz, 6H). $^{13}$C NMR (100 MHz, CDCl$_3$) δ ppm 155.7, 150.5 (d, J=20 Hz), 135.6, 135.6, 134.6 (d, J=9 Hz), 134.0 (d, J=4 Hz), 127.1, 119.5, 115.5 (d, J=3 Hz), 111.1 (d, J=11 Hz), 61.4 (d, J=7 Hz), 56.7 (d, J=12 Hz), 21.4, 20.6, 16.5 (d, J=6 Hz). $^{31}$P NMR (CDCl$_3$, 202 MHz) δ ppm 12.6 (s).

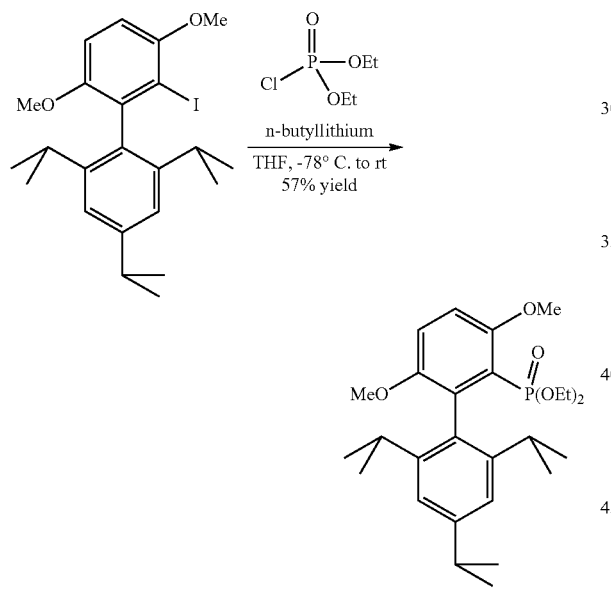

Example 4-p

Diethyl 2',4',6'-triisopropyl-3,6-dimethoxybiphenyl-2-ylphosphonate

The titled compound was prepared as described in the general procedure for synthesis of diethylphosphonates substituting 2-iodo-2',4',6'-triisopropyl-3,6-dimethoxybiphenyl (see Buchwald S L et al, JACS 2008; 130: 13552-13554) (6.00 g, 12.9 mmol, 1 equiv) for the arene, wherein all other reagents are scaled accordingly, followed by purification via column chromatography (120-g column; gradient: 1.5 column volumes dichloromethane, ramp up to 88:12 dichloromethane:acetone over 8 column volumes, hold at 88:12 for 7.5 column volumes) (3.51 g, 93 area % by HPLC, 57% yield). $^1$H NMR (400 MHz, CDCl$_3$) δ ppm 7.04-6.89 (m, 4H), 3.99-3.84 (m, 5H), 3.60 (s, 3H), 3.57-3.44 (m, 2H), 2.93 (hept, J=6.9 Hz, 1H), 2.49 (hept, J=6.8 Hz, 2H), 1.28 (d, J=6.9 Hz, 1H), 1.17 (d, J=6.8 Hz, 6H), 1.01 (dd, J=9.3, 4.9 Hz, 6H), 0.97 (d, J=6.8 Hz, 6H). $^{13}$C NMR (100 MHz, CDCl$_3$) δ ppm 155.4, 151.3 (d, J=20 Hz), 146.6, 145.7, 133.7 (d, J=8 Hz), 131.9, 119.8, 119.5 (d, J=190 Hz), 113.7 (d, J=3 Hz), 110.5 (d, J=11 Hz), 61.1 (d, J=7 Hz), 56.5, 55.5, 34.4 31.0, 24.7, 24.3, 23.7, 16.6 (d, J=6 Hz). $^{31}$P NMR (CDCl$_3$, 202 MHz) δ ppm 13.1 (s).

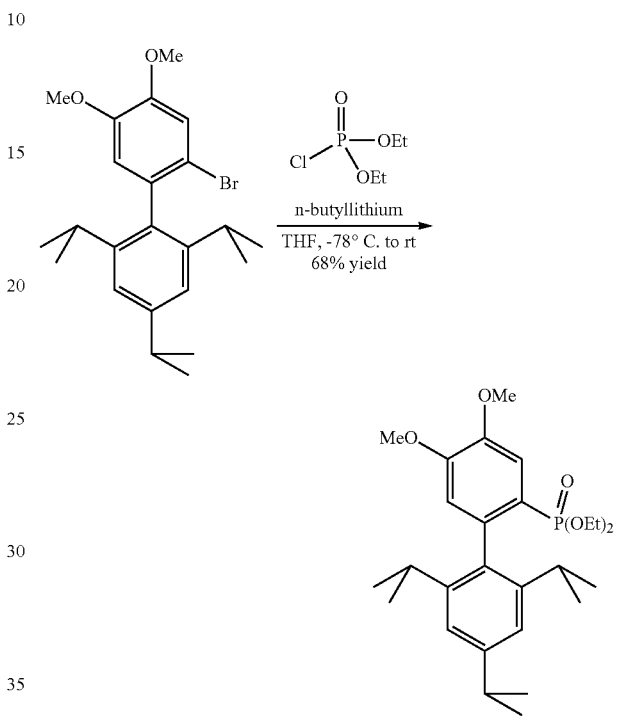

Example 4-q

Diethyl 2',4',6'-triisopropyl-4,5-dimethoxybiphenyl-2-ylphosphonate

The titled compound was prepared as described in the general procedure for synthesis of diethylphosphonates substituting 2-bromo-2',4',6'-triisopropyl-4,5-dimethoxybiphenyl (1.47 g, 3.51 mmol, 1 equiv) for the arene, wherein all other reagents are scaled accordingly, followed by purification via column chromatography (80-g column; gradient: 2 column volumes dichloromethane, ramp up to 92:8 dichloromethane:acetone over 8 column volumes, hold at 92:8 for 8 column volumes) (1.13 g, 99 area % by HPLC, 68% yield). $^1$H NMR (400 MHz, CDCl$_3$) δ ppm 7.49 (dd, J=14.9, 3.9 Hz, 1H), 7.01 (s, 2H), 6.67 (d, J=5.5 Hz, 1H), 3.98 (s, 3H), 3.91-3.78 (m, 5H), 3.66 (ddq, J=10.2, 8.7, 7.1 Hz, 2H), 2.92 (hept, J=7.0 Hz, 1H), 2.50 (hept, J=6.8 Hz, 2H), 1.28 (d, J=6.9 Hz, 6H), 1.21 (d, J=6.8 Hz, 6H), 1.07 (t, J=7.1 Hz, 6H), 1.00 (d, J=6.8 Hz, 6H). $^{13}$C NMR (100 MHz, CDCl$_3$) δ ppm 150.4 (d, J=4 Hz), 147.7, 146.8 (d, J=19 Hz), 146.3, 137.3 (d, J=10 Hz), 135.5 (d, J=3 Hz), 120.0, 119.5 (d, J=197 Hz), 116.5, 115.0 (d, J=13 Hz), 114.6 (d, J=19 Hz), 61.6 (d, J=6 Hz), 56.1 (d, J=5 Hz), 34.6, 30.9, 26.1, 24.4, 22.9, 16.5 (d, J=6 Hz). $^{31}$P NMR (CDCl$_3$, 202 MHz) δ ppm 18.3 (s).

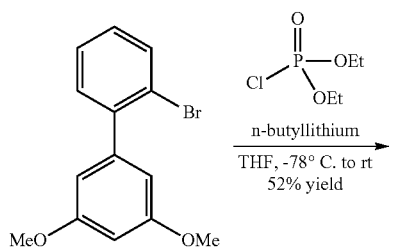

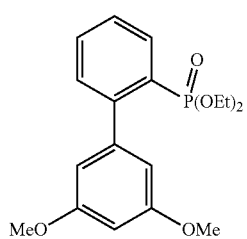

Example 4-r

Diethyl 3',5'-dimethoxybiphenyl-2-ylphosphonate

The titled compound was prepared as described in the general procedure for synthesis of diethylphosphonates substituting 2-bromo-3',5'-dimethoxybiphenyl (4.50 g, 15.4 mmol, 1 equiv) for the arene, wherein all other reagents are scaled accordingly, followed by purification via column chromatography (120-g column; gradient: 1.5 column volumes dichloromethane, ramp up to 88:12 dichloromethane:acetone over 8 column volumes, hold at 88:12 for 4 column volumes) (2.81 g, 98 area % by HPLC, 52% yield). $^1$H NMR (400 MHz, CDCl$_3$) δ ppm 8.02 (ddd, J=14.3, 7.7, 1.4 Hz, 1H), 7.54 (tt, J=7.5, 1.5 Hz, 1H), 7.46-7.38 (m, 1H), 7.38-7.32 (m, 1H), 6.63 (d, J=2.3 Hz, 2H), 6.48 (t, J=2.3 Hz, 1H), 4.03-3.84 (m, 4H), 3.82 (s, 7H), 1.17 (t, J=7.1 Hz, 6H). $^{13}$C NMR (100 MHz, CDCl$_3$) δ ppm 159.5, 145.4 (d, J=10 Hz), 142.9 (d, J=4 Hz), 133.5 (d, J=10 Hz), 131.6 (d, J=3 Hz), 130.7 (d, J=14 Hz), 126.7 (d, J=14 Hz), 126.6 (d, J=186 Hz), 107.5, 99.7, 61.9 (d, J=6 Hz), 55.5, 16.4 (d, J=7 Hz). $^{31}$P NMR (CDCl$_3$, 202 MHz) δ ppm 17.7 (s).

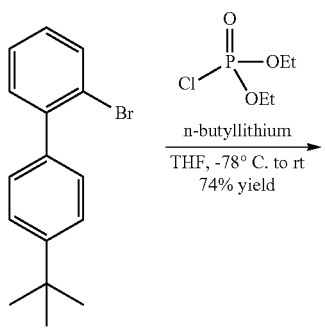

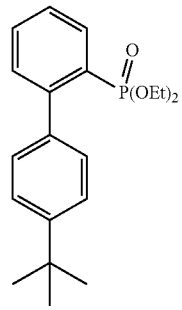

Example 4-s

Diethyl 4'-tert-butylbiphenyl-2-ylphosphonate

The titled compound was prepared as described in the general procedure for synthesis of diethylphosphonates substituting 2-bromo-4'-tert-butylbiphenyl (2.86 g, 9.89 mmol, 1 equiv) for the arene, wherein all other reagents are scaled accordingly, followed by purification via column chromatography (120-g column; gradient: 2 column volumes dichloromethane, ramp up to 92:8 dichloromethane:acetone over 8 column volumes, hold at 92:8 for 6 column volumes) (2.53 g, 96 area % by HPLC, 74% yield). $^1$H NMR (400 MHz, CDCl$_3$) δ ppm 8.02 (ddd, J=14.3, 7.7, 1.4 Hz, 1H), 7.54 (tt, J=7.6, 1.5 Hz, 1H), 7.45-7.30 (m, 6H), 3.98-3.74 (m, 4H), 1.36 (s, 9H), 1.10 (t, J=7.0 Hz, 6H). $^{13}$C NMR (100 MHz, CDCl$_3$) δ ppm 149.9, 145.6 (d, J=10 Hz), 138.2 (d, J=4 Hz), 133.4 (d, J=10 Hz), 131.5 (d, J=3 Hz), 131.1 (d, J=14 Hz), 128.7, 127.7, 126.3 (d, J=15 Hz), 124.1, 61.8 (d, J=6 Hz), 34.8, 31.6, 16.3 (d, J=7 Hz). $^{31}$P NMR (CDCl$_3$, 202 MHz) δ ppm 17.8 (s).

Example 5

General Procedure for the Phosphonate Reduction

In a round-bottom flask equipped with a magnetic stir bar and under a positive pressure of nitrogen was added anhydrous, degassed tetrahydrofuran (~1.6M relative to LiAlH$_4$) and lithium aluminum hydride (3 equiv) as a solution in tetrahydrofuran. After cooling the mixture to 0° C. in an ice bath, chlorotrimethylsilane (3 equiv) was added in a dropwise manner. The resulting solution was stirred at 0° C. A tetrahydrofuran solution (~0.7 M relative to the phosphonate) of the diethylphosphonate (1 equiv) was prepared in a separate round-bottom flask, then cooled to 0° C. in an ice bath while under a positive pressure of N$_2$. After 30 minutes, the lithium aluminum hydride/chlorotrimethylsilane solution was transferred to the solution of diethylphosphonate in a dropwise fashion by cannula using a positive pressure of nitrogen. Rapid gas evolution was observed. The reaction was stirred vigorously at 0° C. and warmed slowly to room temperature overnight. After ~16 hours, the reaction solution was cooled in an ice bath to 0° C. and quenched using either an acidic workup (method A) or by the Fieser method (method B).

Workup method A was used for air-stable phosphines without a basic functional group. The reaction mixture was quenched slowly with ethyl acetate (7.7 equiv), followed by 1 M aqueous hydrochloric acid (15 equiv). The biphasic mixture was then stirred vigorously at room temperature until the phases became clear (~1 h), at which point the phases were partitioned. The organic layer was collected, and the aqueous layer was washed with ethyl acetate (3×). The combined organic fractions were then washed once with brine, dried over sodium sulfate, filtered, and concentrated on a rotary evaporator. The isolated primary phosphines were used without further purification.

Workup method B was employed with air-sensitive phosphines and air-stable phosphines containing basic substituents. For air-sensitive substrates, the water and 15% aqueous sodium hydroxide solution used in the Fieser quench (n mL of water, n mL 15% aqueous sodium hydroxide, 3n mL water, where n=grams of LiAlH$_4$ used) were degassed by sparging with nitrogen for 30 minutes prior to use. The resulting slurry was stirred vigorously for 15 minutes. Then, using standard Schlenk technique, the air-sensitive phosphine slurry was cannula transferred into a fritted Schlenk filter under nitrogen pressure. The filtrate solution was collected in a 3-neck round-bottom flask. The reaction flask was rinsed with nitrogen-sparged dichloromethane (2×), and the wash was passed through the Schlenk filter each time. The filter cake was also rinsed with dichloromethane (2×). The combined organic fractions were concentrated in vacuo to ~10 mL, then the solution was cannula transferred into a degassed 40-mL scintillation vial with a septa-top cap. The solution was concentrated in the vial to furnish the phosphine, which was used without further purification.

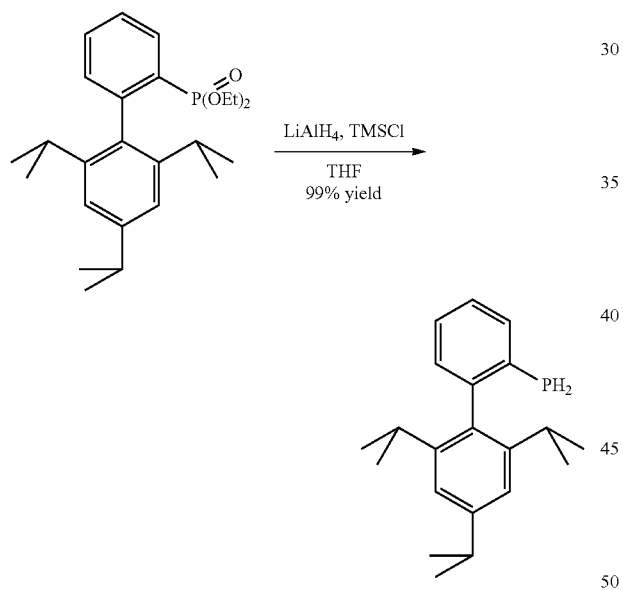

Example 5-a

Alternative Preparation of (2',4',6'-Triisopropylbiphenyl-2-yl)phosphine

The titled compound was prepared as described in the general procedure for the phosphonate reduction substituting diethyl 2',4',6'-triisopropylbiphenyl-2-ylphosphonate (8.31 g, 20.0 mmol, 1 equiv) for diethylphosphonate, wherein all other reagents were scaled accordingly, and using work up method A (15 mL ethyl acetate, 250 mL 1M aqueous hydrochloric acid) (6.20 g, 95 area % by HPLC, 99% yield). $^1$H NMR (400 MHz, CDCl$_3$) δ ppm 7.65-7.55 (m, 1H), 7.36-7.29 (m, 1H), 7.29-7.22 (m, 1H), 7.16-7.10 (m, 1H), 7.06 (s, 2H), 3.57 (d, J=203.7 Hz, 2H), 2.95 (hept, J=6.9 Hz, 1H), 2.42 (hept, J=6.8 Hz, 2H), 1.32 (d, J=6.9 Hz, 6H), 1.20 (d, J=6.9 Hz, 6H), 1.02 (d, J=6.8 Hz, 6H). $^{31}$P NMR (CDCl$_3$, 202 MHz) δ ppm −130.5 (s).

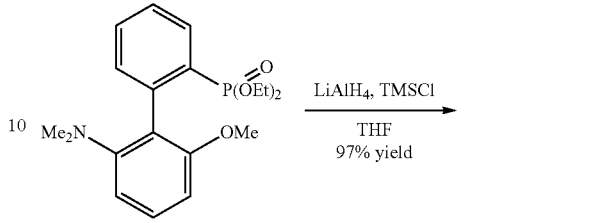

Example 5-b

6-Methoxy-N,N-dimethyl-2'-phosphinobiphenyl-2-amine

The titled compound was prepared as described in the general procedure for the phosphonate reduction substituting diethyl 2'-(dimethylamino)-6'-methoxybiphenyl-2-ylphosphonate (3.15 g, 8.67 mmol, 1 equiv) for diethylphosphonate, wherein all other reagents were scaled accordingly, and using work up method B (1 mL water, 1 mL 15% aqueous sodium hydroxide, 3 mL water) (2.17 g, 96 area % by HPLC, 97% yield). $^1$H NMR (400 MHz, CDCl$_3$) δ ppm 7.61 (dd, J=10.6, 3.8 Hz, 1H), 7.37-7.26 (m, 3H), 7.24-7.18 (m, 1H), 6.72 (t, J=8.0 Hz, 1H), 6.65 (d, J=8.2 Hz, 1H), 3.72 (s, 3H), 3.65 (dq, J=202.4, 12.1 Hz, 2H), 2.48 (s, 6H). $^{31}$P NMR (CDCl$_3$, 202 MHz) δ ppm −131.9 (s).

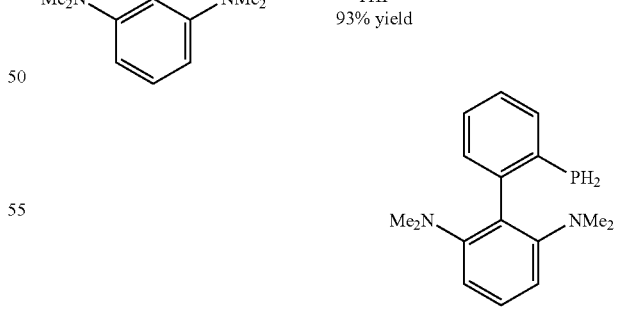

Example 5-c

N$^2$,N$^2$,N$^6$,N$^6$-tetramethyl-2'-phosphinobiphenyl-2,6-diamine

The titled compound was prepared as described in the general procedure for the phosphonate reduction substituting diethyl 2',6'-bis(dimethylamino)biphenyl-2-ylphosphonate (5.14 g, 13.7 mmol, 1 equiv) for diethylphosphonate, wherein all other reagents were scaled accordingly, and using work up method B (1.55 mL water, 1.55 mL 15% aqueous sodium hydroxide, 4.7 mL water) (3.45 g, >99 area % by HPLC, 93% yield). $^1$H NMR (400 MHz, CDCl$_3$) δ ppm 7.58 (dd, J=10.7, 4.2 Hz, 1H), 7.34 (ddd, J=12.3, 7.1, 5.1 Hz, 1H), 7.31-7.26 (m, 1H), 7.26-7.22 (m, 1H), 7.19-7.12 (m, 1H), 6.81 (d, J=8.0 Hz, 2H), 3.60 (d, J=202.4 Hz, 2H), 2.39 (s, 12H). $^{31}$P NMR (CDCl$_3$, 202 MHz) δ ppm −133.7 (s).

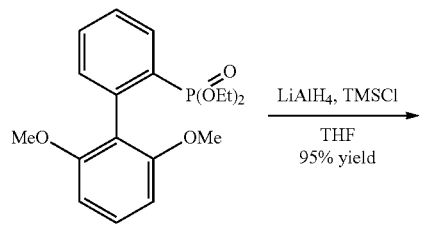

Example 5-d (2',6'-Dimethoxybiphenyl-2-yl)phosphine

The titled compound was prepared as described in the general procedure for the phosphonate reduction substituting diethyl 2',6'-dimethoxybiphenyl-2-ylphosphonate (5.40 g, 15.4 mmol, 1 equiv) for diethylphosphonate, wherein all other reagents were scaled accordingly, and using. work up method A (10 mL ethyl acetate, 100 mL 1 M aqueous hydrochloric acid) to afford the product as a white solid (3.80 g, 86 area % by HPLC, >99% yield). $^1$H NMR (400 MHz, CDCl$_3$) δ ppm 7.68-7.59 (m, 1H), 7.41-7.29 (m, 2H), 7.29-7.22 (m, 1H), 7.22-7.17 (m, 1H), 6.65 (dd, J=9.9, 4.7 Hz, 2H), 3.73 (d, J=4.7 Hz, 6H), 3.65 (d, J=203.0 Hz, 2H). $^{31}$P NMR (CDCl$_3$, 202 MHz) δ ppm −131.5 (s).

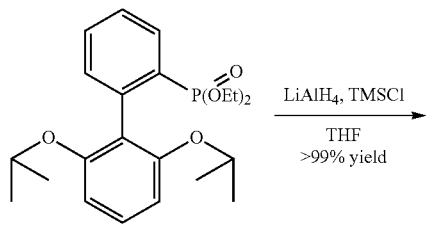

Example 5-e (2',6'-Diisopropoxybiphenyl-2-yl)phosphine

The titled compound was prepared as described in the general procedure for the phosphonate reduction substituting diethyl 2',6'-diisopropoxybiphenyl-2-ylphosphonate (3.16 g, 15.4 mmol, 1 equiv) for diethylphosphonate, wherein all other reagents were scaled accordingly, and using. work up method A (6 mL ethyl acetate, 75 mL 1 M aqueous hydrochloric acid) (2.30 g, 94 area % by HPLC, 98% yield). $^1$H NMR (400 MHz, CDCL$_3$) δ 7.63-7.53 (m, 1H), 7.34-7.27 (m, 1H), 7.25-7.13 (m, 3H), 6.63 (dd, J=6.8, 4.0 Hz, 2H), 4.33 (hept, J=6.1 Hz, 2H), 3.68 (d, J=202.7 Hz, 2H), 1.16 (d, J=6.1 Hz, 6H), 1.13 (d, J=6.0 Hz, 6H). $^{31}$P NMR (CDCl$_3$, 202 MHz) δ ppm −132.2 (s).

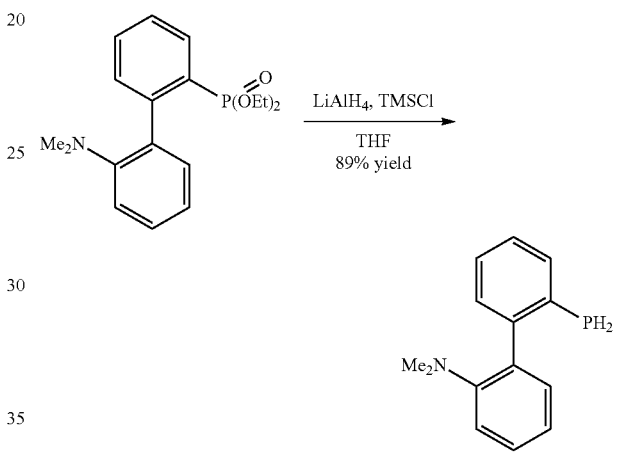

Example 5-f

N,N-Dimethyl-2'-phosphinobiphenyl-2-amine

The titled compound was prepared as described in the general procedure for the phosphonate reduction substituting diethyl 2'-(dimethylamino)biphenyl-2-ylphosphonate (1.96 g, 5.88 mmol, 1 equiv) for diethylphosphonate, wherein all other reagents were scaled accordingly, and using. the air-free work up method B (0.7 mL water, 0.7 mL 15% aqueous sodium hydroxide, 2.0 mL water) (1.20 g, 89% yield). $^1$H NMR (400 MHz, CDCl$_3$) δ ppm 7.73-7.49 (m, 1H), 7.37-7.29 (m, 3H), 7.25-7.19 (m, 1H), 7.19-7.14 (m, 1H), 7.03 (dd, J=10.6, 4.4 Hz, 2H), 4.15-3.22 (m, 2H), 2.52 (s, 6H).

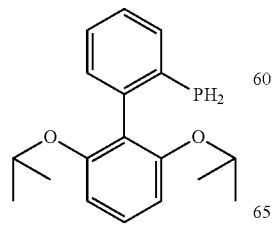

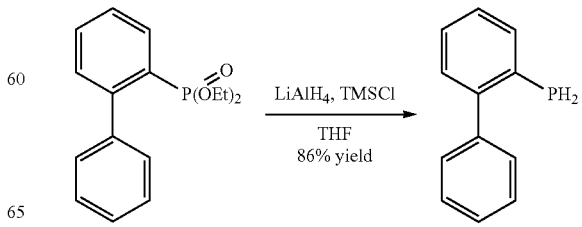

Example 5-g

Biphenyl-2-ylphosphine

The titled compound was prepared as described in the general procedure for the phosphonate reduction substituting diethyl biphenyl-2-ylphosphonate (9.00 g, 31.0 mmol, 1 equiv) for diethylphosphonate, wherein all other reagents were scaled accordingly, and using the air-free work up method B (3.5 mL water, 3.5 mL 15% aqueous sodium hydroxide, 11.5 mL water) (4.96 g, 86% yield). $^1$H NMR (400 MHz, CDCl$_3$) δ ppm 7.56-7.39 (m, 1H), 7.38-7.19 (m, 6H), 7.19-7.09 (m, 2H), 3.72 (d, J=204.4 Hz, 2H). $^{31}$P NMR (CDCl$_3$, 202 MHz) δ ppm −123.6 (t, $^1J_{PH}$=202 Hz).

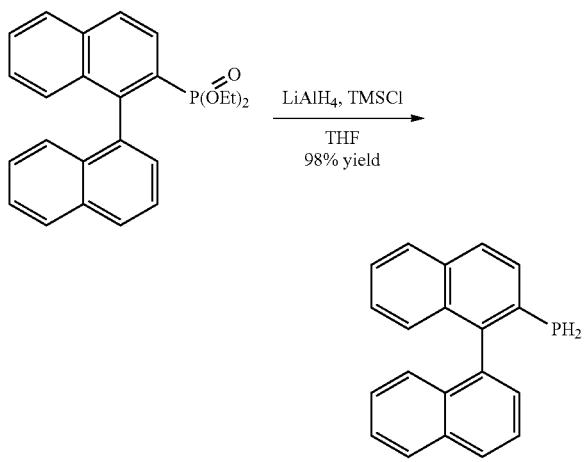

Example 5-h

1,1'-Binaphthyl-2-ylphosphine

The titled compound was prepared as described in the general procedure for the phosphonate reduction substituting diethyl 1,1'-binaphthyl-2-ylphosphonate (3.90 g, 9.99 mmol, 1 equiv) for diethylphosphonate, wherein all other reagents were scaled accordingly, and using the air-free work up method B (1.1 mL water, 1.1 mL 15% aqueous sodium hydroxide, 3.4 mL water) (2.80 g, 98% yield). $^1$H NMR (400 MHz, CDCl$_3$) δ ppm 7.93-7.84 (m, 2H), 7.78 (dd, J=12.0, 8.3 Hz, 2H), 7.67-7.57 (m, 1H), 7.53 (dt, J=10.7, 5.3 Hz, 1H), 7.44-7.28 (m, 3H), 7.23-7.13 (m, 2H), 7.08 (dd, J=16.5, 8.5 Hz, 2H), 3.57 (ddd, J=205.2, 66.6, 12.0 Hz, 2H). $^{31}$P NMR (CDCl$_3$, 202 MHz) δ ppm −126.1 (s).

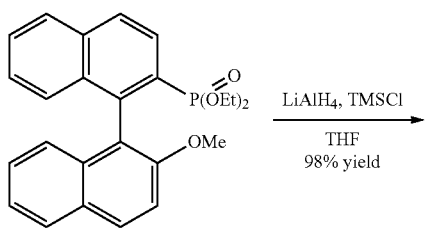

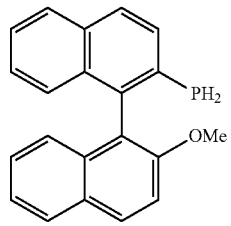

Example 5-i

(2'-Methoxy-1,1'-binaphthyl-2-yl)phosphine

The titled compound was prepared as described in the general procedure for the phosphonate reduction substituting diethyl 2'-methoxy-1,1'-binaphthyl-2-ylphosphonate (see Powell D R, et al. Journal of Organic Chemistry 1998; 63: 2338-2341) (1.23 g, 2.92 mmol, 1 equiv) for diethylphosphonate, wherein all other reagents were scaled accordingly, and using the air-free work up method B (0.3 mL water, 0.3 mL 15% aqueous sodium hydroxide, 1.0 mL water) (908 mg, 98% yield). $^1$H NMR (400 MHz, CDCL$_3$) δ 8.07-7.96 (m, 1H), 7.93-7.80 (m, 3H), 7.80-7.67 (m, 1H), 7.52-7.37 (m, 2H), 7.37-7.26 (m, 1H), 7.26-7.17 (m, 2H), 7.13 (dt, J=6.9, 1.9 Hz, 1H), 6.99-6.88 (m, 1H), 3.79 (s, 3H), 3.62 (ddd, J=204.0, 46.0, 12.1 Hz, 2H). $^{31}$P NMR (CDCl$_3$, 202 MHz) δ ppm −129.2 (s).

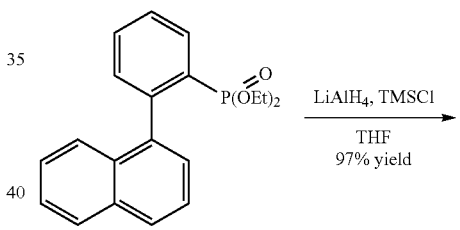

Example 5-j

(2-(Naphthalen-1-yl)phenyl)phosphine

The titled compound was prepared as described in the general procedure for the phosphonate reduction substituting diethyl 2-(naphthalen-1-yl)phenylphosphonate (2.12 g, 6.23 mmol, 1 equiv) for diethylphosphonate, wherein all other reagents were scaled accordingly, and using the air-free work up method B (0.7 mL water, 0.7 mL 15% aqueous sodium hydroxide, 2.1 mL water) (1.43 g, 97% yield). $^1$H NMR (400 MHz, CDCl$_3$) δ ppm 7.98-7.85 (m, 2H), 7.72-7.62 (m, 1H), 7.57-7.29 (m, 8H), 3.59 (ddd, J=102.0, 34.9, 12.2 Hz, 2H). $^{31}$P NMR (CDCl$_3$, 202 MHz) δ ppm −130.1 (s).

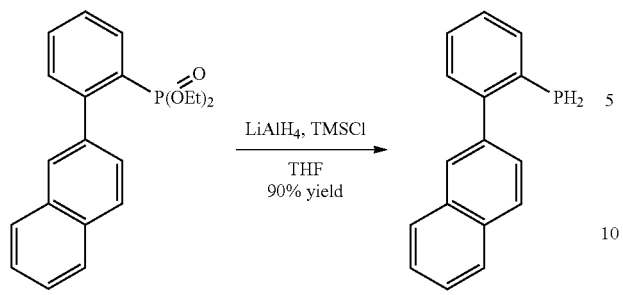

Example 5-k

(2-(Naphthalen-2-yl)phenyl)phosphine

The titled compound was prepared as described in the general procedure for the phosphonate reduction substituting diethyl 2-(naphthalen-2-yl)phenylphosphonate (3.06 g, 8.99 mmol, 1 equiv) for diethylphosphonate, wherein all other reagents were scaled accordingly, and using. the reaction air-free work up method B (1.0 mL water, 1.0 mL 15% aqueous sodium hydroxide, 3.1 mL water) (1.92 g, 90% yield). $^1$H NMR (400 MHz, CDCl$_3$) δ 7.93-7.82 (m, 3H), 7.82-7.76 (m, 1H), 7.63 (ddd, J=13.6, 4.6, 4.0 Hz, 1H), 7.54-7.45 (m, 3H), 7.40-7.31 (m, 2H), 7.31-7.22 (m, 1H), 3.85 (d, J=204.6 Hz, 2H). $^{31}$P NMR (CDCl$_3$, 202 MHz) δ ppm −126.0 (s).

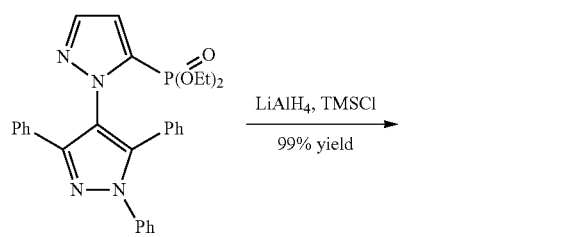

Example 5-l

1',3',5'-Triphenyl-5-phosphino-1'H-1,4'-bipyrazole

The titled compound was prepared as described in the general procedure for the phosphonate reduction substituting diethyl 1',3',5'-triphenyl-1'H-1,4'-bipyrazol-5-ylphosphonate (2.42 g, 4.85 mmol, 1 equiv) for diethylphosphonate, wherein all other reagents were scaled accordingly, and using the air-free work up method B (0.6 mL water, 0.6 mL 15% aqueous sodium hydroxide, 1.6 mL water) (1.81 g, 86 area % by HPLC, 95% yield). $^1$H NMR (400 MHz, CDCL$_3$) δ 7.76 (t, J=1.6 Hz, 1H), 7.46-7.32 (m, 6H), 7.32-7.27 (m, 4H), 7.25-7.18 (m, 3H), 7.15-7.09 (m, 2H), 6.60-6.50 (m, 1H), 3.32 (dm, J=208.4 Hz, 2H).

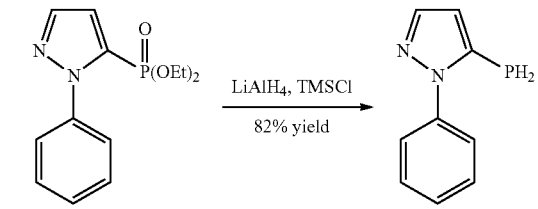

Example 5-m

1-Phenyl-5-phosphino-1H-pyrazole

The titled compound was prepared as described in the general procedure for the phosphonate reduction substituting diethyl 1-phenyl-1H-pyrazol-5-ylphosphonate (3.77 g, 13.5 mmol, 1 equiv) for diethylphosphonate, wherein all other reagents were scaled accordingly, and using the air-free work up method B (1.6 mL water, 1.6 mL 15% aqueous sodium hydroxide, 4.6 mL water) (1.95 g, 82% yield). $^1$H NMR (400 MHz, CDCl$_3$) δ ppm 7.75-7.65 (m, 1H), 7.52-7.37 (m, 5H), 6.60 (d, J=1.2 Hz, 1H), 3.92 (d, J=207.8 Hz, 2H). $^{31}$P NMR (CDCl$_3$, 202 MHz) δ ppm −161.3 (s).

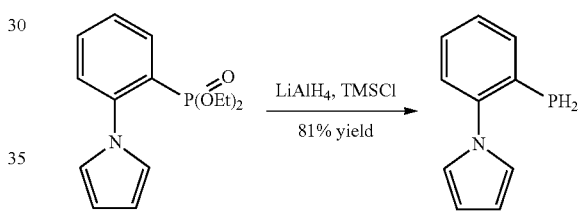

Example 5-n

1-(2-Phosphinophenyl)-1H-pyrrole

The titled compound was prepared as described in the general procedure for the phosphonate reduction substituting diethyl 2-(1H-pyrrol-1-yl)phenylphosphonate (4.00 g, 14.3 mmol, 1 equiv) for diethylphosphonate, wherein all other reagents were scaled accordingly, and using the air-free work up method B (1.6 mL water, 1.6 mL 15% aqueous sodium hydroxide, 4.9 mL water) (2.03 g, 81% yield). $^1$H NMR (400 MHz, CDCl$_3$) δ ppm 7.63-7.52 (m, 1H), 7.43-7.31 (m, 1H), 7.31-7.21 (m, 2H), 6.84-6.74 (m, 2H), 6.37-6.29 (m, 2H), 3.74 (d, J=205.6 Hz, 2H). $^{31}$P NMR (CDCl$_3$ 202 MHz) δ ppm −132.3 (s).

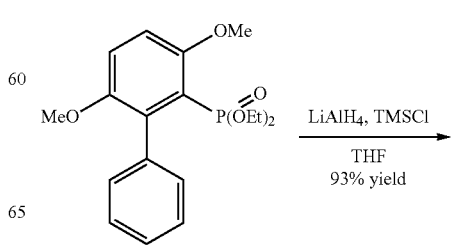

-continued

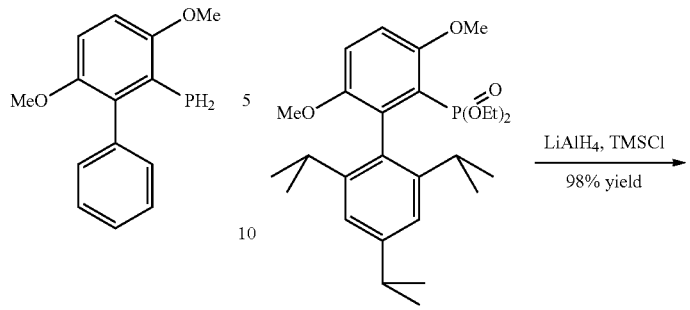

Example 5-o (3,6-Dimethoxybiphenyl-2-yl)phosphine

The titled compound was prepared as described in the general procedure for the phosphonate reduction substituting diethyl 3,6-dimethoxybiphenyl-2-ylphosphonate (2.50 g, 7.14 mmol, 1 equiv) for diethylphosphonate, wherein all other reagents were scaled accordingly, and using the air-free work up method B (0.8 mL water, 0.8 mL 15% aqueous sodium hydroxide, 2.4 mL water) (1.64 g, 93% yield). $^1$H NMR (400 MHz, CDCl$_3$) δ 7.49-7.40 (m, 2H), 7.40-7.33 (m, 1H), 7.26-7.20 (m, 1H), 6.84 (dt, J=8.9, 5.9 Hz, 2H), 3.88 (s, 3H), 3.67 (s, 3H), 3.46 (d, J=215.1 Hz, 2H). $^{31}$P NMR (CDCl$_3$, 202 MHz) δ ppm −154.6 (s).

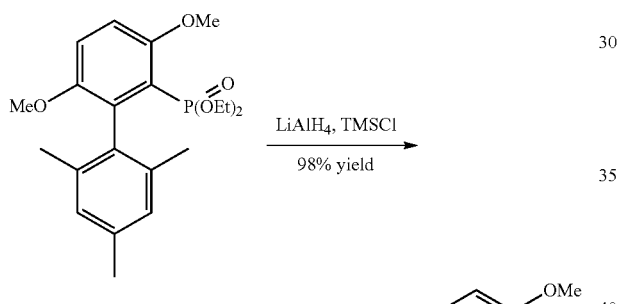

Example 5-p (3,6-Dimethoxy-2',4',6'-trimethylbiphenyl-2-yl)phosphine

The titled compound was prepared as described in the general procedure for the phosphonate reduction substituting diethyl 3,6-dimethoxy-2',4',6'-trimethylbiphenyl-2-yl-phosphonate (3.05 g, 7.77 mmol, 1 equiv) for diethylphosphonate, wherein all other reagents were scaled accordingly, and using the air-free work up method B (0.9 mL water, 0.9 mL 15% aqueous sodium hydroxide, 2.7 mL water) (2.19 g, 98% yield). $^1$H NMR (400 MHz, CDCl$_3$) δ ppm 6.95 (s, 2H), 6.83 (dt, J=8.9, 6.0 Hz, 2H), 3.87 (s, 3H), 3.67 (s, 3H), 3.34 (d, J=214.2 Hz, 2H), 2.34 (s, 3H), 1.94 (s, 6H). $^{31}$P NMR (CDCl$_3$, 202 MHz) δ ppm −160.4 (s).

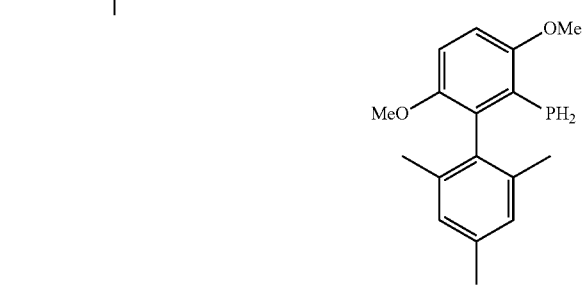

Example 5-q (2',4',6'-Triisopropyl-3,6-dimethoxybiphenyl-2-yl)phosphine

The titled compound was prepared as described in the general procedure for the phosphonate reduction substituting diethyl 2',4',6'-triisopropyl-3,6-dimethoxybiphenyl-2-yl-phosphonate (3.47 g, 7.28 mmol, 1 equiv) for diethylphosphonate, wherein all other reagents were scaled accordingly, and using work up method A (6 mL ethyl acetate, 100 mL 1 M aqueous hydrochloric acid) (2.67 g, 98% yield). $^1$H NMR (CDCl$_3$, 400 MHz) δ ppm 7.05 (d, J=3.2 Hz, 2H), 6.86-6.78 (m, 2H), 3.88 (s, 3H), 3.65 (s, 3H), 3.31 (d, J=215.0 Hz, 2H), 3.01-2.88 (m, 1H), 2.44 (hept, J=6.8 Hz, 2H), 1.31 (d, J=6.9 Hz, 6H), 1.15 (d, J=6.9 Hz, 6H), 1.02 (d, J=6.8 Hz, 6H). $^{31}$P NMR (CDCl$_3$, 202 MHz) δ ppm −156.3 (s).

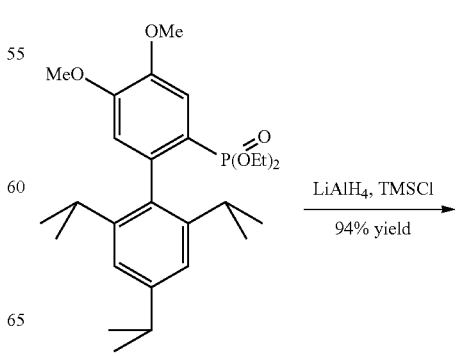

7.11 (m, 3H), 6.45-6.38 (m, 3H), 3.79 (d, J=204.4 Hz, 2H), 3.74 (s, 6H). $^{31}$P NMR (CDCl$_3$, 202 MHz) δ ppm −123.5 (t, $^1J_{PH}$=200 MHz).

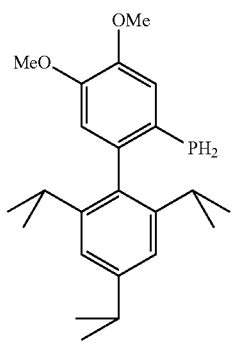

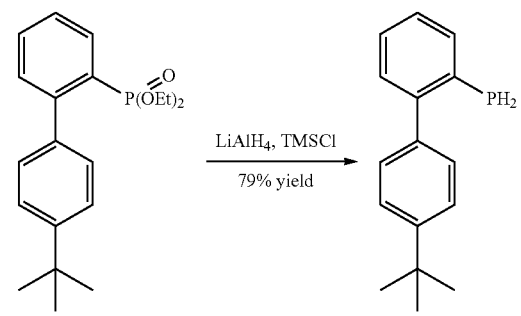

Example 5-r (2',4',6'-Triisopropyl-4,5-dimethoxybiphenyl-2-yl)phosphine

The titled compound was prepared as described in the general procedure for the phosphonate reduction substituting diethyl 2',4',6'-triisopropyl-4,5-dimethoxybiphenyl-2-ylphosphonate (1.10 g, 2.31 mmol, 1 equiv) for diethylphosphonate, wherein all other reagents were scaled accordingly, and using work up method A (1.7 mL ethyl acetate, 32 mL 1 M aqueous hydrochloric acid) (798 mg, 93% yield). $^1$H NMR (400 MHz, CDCl$_3$) δ ppm 7.11-7.03 (m, 3H), 6.69-6.65 (m, 1H), 3.96 (d, J=57.3 Hz, 1H), 3.94 (s, 3H), 3.81 (s, 3H), 3.31 (s, 1H), 3.02-2.89 (m, 1H), 2.56-2.39 (m, 3H), 1.32 (d, J=6.9 Hz, 2H), 1.19 (d, J=6.9 Hz, 2H), 1.04 (d, J=6.8 Hz, 2H). $^{31}$P NMR (CDCl$_3$, 202 MHz) δ ppm −128.9 (s).

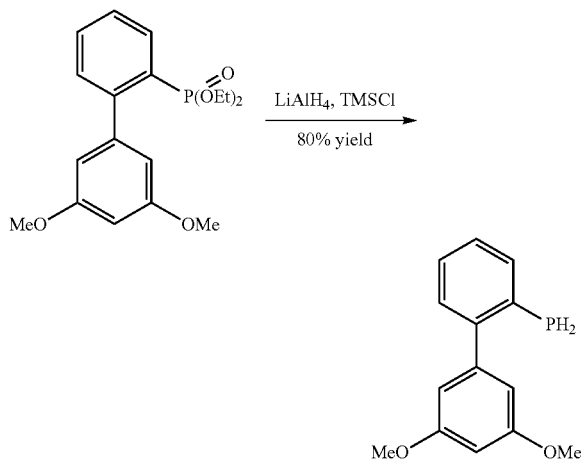

Example 5-s (3',5'-Dimethoxybiphenyl-2-yl)phosphine

The titled compound was prepared as described in the general procedure for the phosphonate reduction substituting diethyl 3',5'-dimethoxybiphenyl-2-ylphosphonate (2.75 g, 7.85 mmol, 1 equiv) for diethylphosphonate, wherein all other reagents were scaled accordingly, and using the air-free work up method B (0.9 mL water, 0.9 mL 15% aqueous sodium hydroxide, 2.7 mL water) (1.54 g, 80% yield). $^1$H NMR (400 MHz, CDCl$_3$) δ ppm 7.55-7.45 (m, 1H), 7.31-

Example 5-t (4'-tert-Butylbiphenyl-2-yl)phosphine

The titled compound was prepared as described in the general procedure for the phosphonate reduction substituting diethyl 4'-tert-butylbiphenyl-2-ylphosphonate (2.52 g, 7.27 mmol, 1 equiv) for diethylphosphonate, wherein all other reagents were scaled accordingly, and using the air-free work up method B (0.8 mL water, 0.8 mL 15% aqueous sodium hydroxide, 2.5 mL water) (1.40 g, 79% yield). $^1$H NMR (400 MHz, CDCl$_3$) δ ppm 7.56-7.46 (m, 1H), 7.41-7.33 (m, 2H), 7.30-7.09 (m, 5H), 3.78 (d, J=204.7 Hz, 2H), 1.30 (s, 9H). $^{31}$P NMR (CDCl$_3$, 202 MHz) δ ppm −121.1 (t, $^1J_{PH}$=204 MHz).

Example 6

General Procedure for the Double Conjugate Addition to Phorone

A 20-mL glass liner equipped with a magnetic stir bar was charged with the primary biarylphosphine (1 equiv) and phorone (2.1 equiv). The glass liner was then placed into a 30-mL Parr Hastelloy C reactor, which was purged with nitrogen gas and sealed under 30 psig of N$_2$. For air sensitive phosphines, the reaction was setup in a nitrogen-atmosphere glovebox and sealed under an atmosphere of N$_2$. The reaction was stirred overnight in an oil bath at 170° C. Upon cooling to room temperature, the Parr reactor was carefully vented and then unsealed. The glass liner was removed from the Parr body and typically contained a yellow solid. Ethanol was added to the crude material and manually slurried with a spatula. If necessary, gentle heating (50° C.) was applied to aid in breaking the solid apart. The product was isolated by filtration and the glass liner and filter cake were washed with cold ethanol (3×).

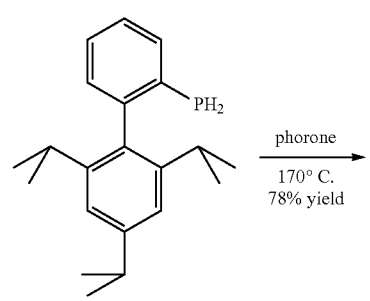

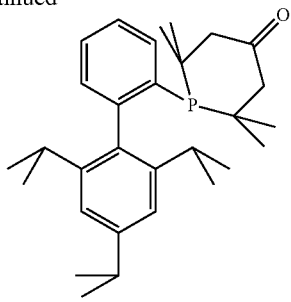

Example 6-a

Alternative Preparation of 2,2,6,6-Tetramethyl-1-(2',4',6'-triisopropylbiphenyl-2-yl)phosphinan-4-one (Example 1-b)

The titled compound was prepared as described in the general procedure for the double conjugate addition to phorone substituting (2',4',6'-triisopropylbiphenyl-2-yl)phosphine (4.0 g, 12.8 mmol, 1 equiv) for biarylphosphine, wherein all other reagents were scaled accordingly, and heating for 20 hours (4.49 g, 92 area % by HPLC, 78% yield). $^1$H NMR (400 MHz, CDCl$_3$) δ ppm 7.91-7.79 (m, 1H), 7.43-7.33 (m, 2H), 7.29-7.21 (m, 1H), 7.02 (s, 2H), 3.04-2.89 (m, 3H), 2.49 (hept, J=6.6 Hz, 2H), 2.29 (dd, J=13.6, 4.9 Hz, 2H), 1.32 (d, J=6.9 Hz, 6H), 1.25-1.15 (m, 12H), 1.02-0.95 (m, 12H). $^{31}$P NMR (CDCl$_3$, 202 MHz) δ ppm 6.1 (s).

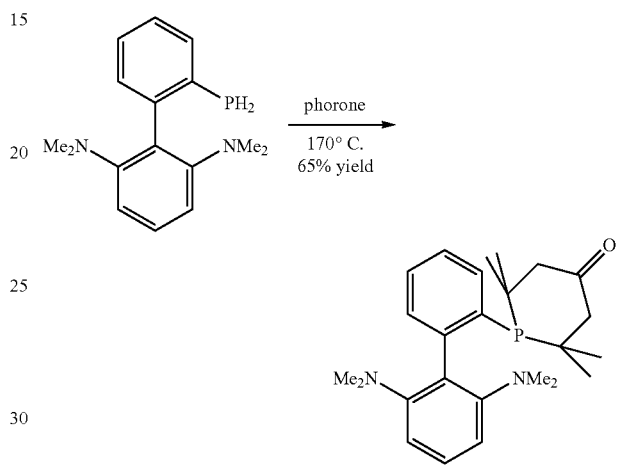

Example 6-b

1-(2'-(Dimethylamino)-6'-methoxybiphenyl-2-yl)-2,2,6,6-tetramethylphospinan-4-one The titled compound was prepared as described in the general procedure for the double conjugate addition to phorone substituting 6-methoxy-N,N-dimethyl-2'-phosphinobiphenyl-2-amine (1.82 g, 7.02 mmol, 1 equiv) for biarylphosphine, wherein all other reagents were scaled accordingly, and heating for 20 hours (2.01 g, >99 area % by HPLC, 72% yield). $^1$H NMR (400 MHz, CDCl$_3$) δ ppm 7.82 (dd, J=5.3, 3.9 Hz, 1H), 7.47-7.40 (m, 1H), 7.36-7.27 (m, 3H), 6.69 (dd, J=8.2, 0.9 Hz, 1H), 6.63 (dd, J=8.3, 0.8 Hz, 1H), 3.63 (s, 3H), 3.03 (d, J=13.8 Hz, 1H), 2.90-2.78 (m, 1H), 2.46 (s, 6H), 2.42-2.33 (m, 1H), 2.18-2.02 (m, 1H), 1.23 (d, J=19.6 Hz, 3H), 1.15 (d, J=9.2 Hz, 3H), 1.00 (d, J=17.8 Hz, 3H), 0.62 (d, J=10.0 Hz, 3H). $^{13}$C NMR (100 MHz, CDCl$_3$) δ ppm 212.1, 157.1, 152.3 (d, J=3 Hz), 145.6 (d, J=36 Hz), 135.8 (d, J=28 Hz), 133.3 (d, J=7 Hz), 133.1 (d, J=4 Hz), 128.3, 128.2, 125.8, 124.1 (d, J=7 Hz), 110.5, 104.1, 55.2, 54.7 (d, J=3 Hz), 52.3, 43.6, 35.8 (d, J=21 Hz), 34.9 (d, J=24 Hz), 33.8 (d, J=39 Hz), 31.2 (d, J=34 Hz), 29.6 (d, J=9 Hz), 29.0 (d, J=7 Hz). $^{31}$P NMR (CDCl$_3$, 202 MHz) δ ppm 0.0 (s). LRMS (ESI$^+$) found for [M+H, C$_{24}$H$_{33}$NO$_2$P]$^+$ 398.2.

Example 6-c

1-(2',6'-Bis(dimethylamino)biphenyl-2-yl)-2,2,6,6-tetramethylphosphinan-4-one The titled compound was prepared as described in the general procedure for the double conjugate addition to phorone substituting N$^2$,N$^2$,N$^6$,N$^6$-tetramethyl-2'-phosphinobiphenyl-2,6-diamine (2.89 g, 10.6 mmol, 1 equiv) for biarylphosphine, wherein all other reagents were scaled accordingly, and heating for 20 hours (2.81 g, 87 area % by HPLC, 65% yield). $^1$H NMR (400 MHz, CDCl$_3$) δ ppm 7.79 (d, J=7.7 Hz, 1H), 7.50-7.35 (m, 2H), 7.35-7.26 (m, 2H), 6.93-6.82 (m, 2H), 2.91 (dd, J=13.9, 2.9 Hz, 2H), 2.46 (s, 12H), 2.30 (ddd, J=14.0, 10.2, 4.1 Hz, 2H), 1.15 (s, 3H), 1.10 (s, 3H), 0.95 (s, 3H), 0.93 (s, 3H). $^{13}$C NMR (100 MHz, CDCl$_3$) δ ppm 212.0, 153.1, 147.6, 135.5 (d, J=29 Hz), 133.9 (d, J=4 Hz), 133.5 (d, J=7 Hz), 132.7-131.8 (m), 128.3, 127.6, 125.5, 114.4, 53.7, 45.5, 35.1, 34.9, 33.4, 33.0, 29.6, 29.5. $^{31}$P NMR (CDCl$_3$, 202 MHz) δ ppm 0.0 (s). HRMS (TOF-ESI$^+$) calcd for [M, C$_{25}$H$_{35}$N$_2$OP]$^+$ 410.2487. found 410.2491.

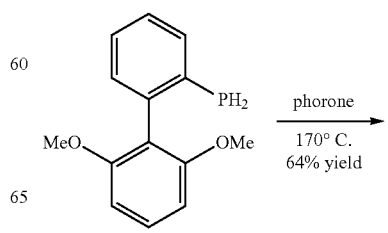

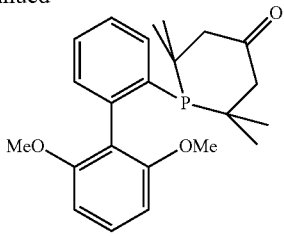

Example 6-d

1-(2',6'-Dimethoxybiphenyl-2-yl)-2,2,6,6-tetramethylphosphinan-4-one

The titled compound was prepared as described in the general procedure for the double conjugate addition to phorone substituting (2',6'-dimethoxybiphenyl-2-yl)phosphine (3.80 g, 15.4 mmol, 1 equiv) for biarylphosphine, wherein all other reagents were scaled accordingly, and heating for 19 hours (2.81 g, 84 area % by HPLC, 65% yield). $^1$H NMR (400 MHz, CDCl$_3$) δ ppm 7.83 (d, J=7.7 Hz, 1H), 7.50-7.41 (m, 1H), 7.41-7.29 (m, 2H), 7.22 (ddd, J=7.5, 3.8, 1.3 Hz, 1H), 6.60 (t, J=9.3 Hz, 2H), 3.69 (s, 6H), 2.91 (dd, J=13.1, 3.9 Hz, 2H), 2.29 (dt, J=21.8, 10.9 Hz, 2H), 1.16 (s, 3H), 1.12 (s, 3H), 0.98 (s, 3H), 0.96 (s, 3H). $^{13}$C NMR (100 MHz, CDCl$_3$) δ ppm 211.7, 156.8 (d, J=2 Hz), 144.0 (d, J=38 Hz), 135.8 (d, J=26 Hz), 132.7 (d, J=4 Hz), 131.6 (d, J=7 Hz), 128.8, 128.5, 126.3, 119.8 (d, J=9 Hz), 103.0, 55.3, 53.7, 35.6, 35.6, 35.4, 35.4, 32.6, 32.2, 29.5 (d, J=7 Hz). $^{31}$P NMR (CDCl$_3$, 202 MHz) δ ppm −0.5 (s). LRMS (ESI$^+$) found for [M+H, C$_{23}$H$_{30}$O$_3$P]$^+$ 385.1.

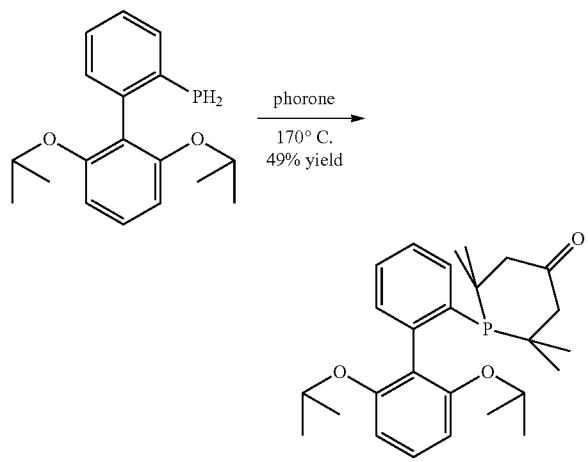

Example 6-e

1-(2',6'-Diisopropoxybiphenyl-2-yl)-2,2,6,6-tetramethylphosphinan-4-one

The titled compound was prepared as described in the general procedure for the double conjugate addition to phorone substituting (2',6'-diisopropoxybiphenyl-2-yl)phosphine (3.93 g, 13.0 mmol, 1 equiv) for biarylphosphine, wherein all other reagents were scaled accordingly, and heating for 15 hours (2.81 g, 83 area % by HPLC, 49% yield). $^1$H NMR (400 MHz, CDCl$_3$) δ ppm 7.77 (dd, J=5.4, 3.7 Hz, 1H), 7.38-7.27 (m, 2H), 7.22 (dd, J=7.3, 4.0 Hz, 1H), 7.10 (ddd, J=7.4, 3.8, 1.7 Hz, 1H), 6.56 (d, J=8.3 Hz, 2H), 4.42 (hept, J=6.1 Hz, 2H), 2.95 (dd, J=13.3, 2.2 Hz, 2H), 2.27 (dd, J=13.3, 4.8 Hz, 2H), 1.18 (dd, J=12.3, 8.6 Hz, 12H), 1.04 (d, J=6.0 Hz, 6H), 0.99 (d, J=9.9 Hz, 6H). $^{31}$P NMR (CDCl$_3$, 202 MHz) δ ppm −1.3 (s). LRMS (ESI$^+$) found for [M+H, C$_{27}$H$_{38}$O$_3$P]$^+$ 441.2.

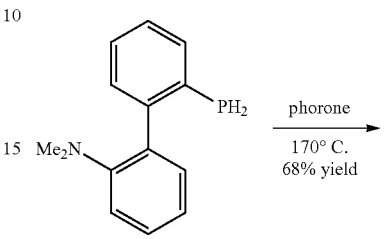

Example 6-f

1-(2'-(Dimethylamino)biphenyl-2-yl)-2,2,6,6-tetramethylphosphinan-4-one

The titled compound was prepared as described in the general procedure for the double conjugate addition to phorone in a nitrogen-atmosphere glovebox substituting N,N-dimethyl-2'-phosphinobiphenyl-2-amine (1.05 g, 4.58 mmol, 1 equiv) for biarylphosphine, wherein all other reagents were scaled accordingly, and heating for 18.5 hours. (1.15 g, 68 area % by HPLC, 68% yield). $^1$H NMR (400 MHz, CDCl$_3$) δ ppm 7.81 (d, J=7.7 Hz, 1H), 7.46 (t, J=7.4 Hz, 1H), 7.39-7.28 (m, 3H), 7.05-6.96 (m, 3H), 3.06 (d, J=13.7 Hz, 1H), 2.83 (d, J=12.6 Hz, 1H), 2.48 (s, 6H), 2.44-2.32 (m, 1H), 2.05 (ddd, J=12.6, 4.6, 1.4 Hz, 1H), 1.33-1.15 (m, 6H), 1.00 (d, J=17.8 Hz, 3H), 0.56 (d, J=9.9 Hz, 3H). $^{31}$P NMR (CDCl$_3$, 202 MHz) δ ppm 9.5 (s). LRMS (ESI$^+$) found for [M+H, C$_{23}$H$_{31}$NOP]$^+$ 368.1.

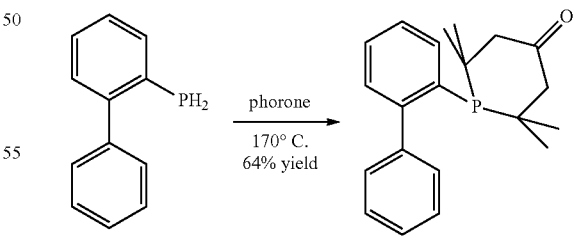

Example 6-g

1-(Biphenyl-2-yl)-2,2,6,6-tetrametramehylphosphinan-4-one

The titled compound was prepared as described in the general procedure for the double conjugate addition to phorone in a nitrogen-atmosphere glovebox substituting biphenyl-2-ylphosphine (2.73 g, 14.7 mmol, 1 equiv) for biarylphosphine, wherein all other reagents were scaled accordingly, and heating for 21 hours (3.05 g, >99 area % by HPLC, 64% yield). $^1$H NMR (400 MHz, CDCl$_3$) δ ppm 7.96-7.86 (m, 1H), 7.52-7.33 (m, 6H), 7.33-7.24 (m, 2H), 3.07-2.86 (m, 2H), 2.32 (dd, J=13.0, 4.9 Hz, 2H), 1.23 (s, 3H), 1.19 (s, 3H), 1.01 (s, 3H), 0.99 (s, 3H). $^{13}$C NMR (100 MHz, CDCl$_3$) δ ppm 211.0, 151.7 (d, J=35 Hz), 142.8 (d, J=8 Hz), 134.0 (d, J=30 Hz), 133.0 (d, J=4 Hz), 130.9 (d, J=6 Hz), 130.3 (d, J=5 Hz), 128.7, 127.1, 126.5, 126.4, 53.4 (d, J=1 Hz), 36.0 (d, J=21 Hz), 32.2, 31.9, 30.1 (d, J=8 Hz). $^{31}$P NMR (CDCl$_3$, 202 MHz) δ ppm −3.9 (s). HRMS (TOF-ESI$^+$) calcd for [M, C$_{21}$H$_{25}$OP]$^+$ 324.1643. found 324.1638.

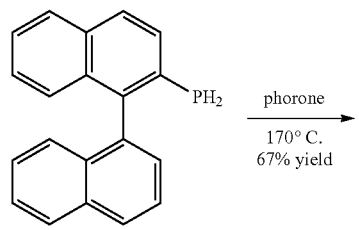

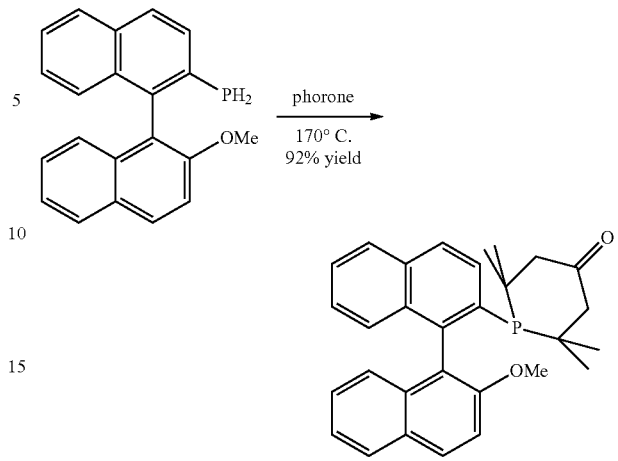

Example 6-i 1-(2'-Methoxy-1,1'-binaphthyl-2-yl)-2,2,6,6-tetramethylphosphinan-4-one The titled compound was prepared as described in the general procedure for the double conjugate addition to phorone in a nitrogen-atmosphere glovebox substituting (2'-methoxy-1,1'-binaphthyl-2-yl)phosphine (808 mg, 2.55 mmol, 1 equiv) for biarylphosphine, wherein all other reagents were scaled accordingly, and heating for 19.5 hours (1.07 g, 92 area % by HPLC, 92% yield). $^1$H NMR (400 MHz, CDCl$_3$) δ ppm 8.11-7.81 (m, 5H), 7.55-7.46 (m, 1H), 7.46-7.38 (m, 1H), 7.35-7.20 (m, 2H), 7.20-7.09 (m, 2H), 6.94-6.84 (m, 1H), 3.76 (d, J=3.7 Hz, 3H), 3.09-2.94 (m, 2H), 2.44-2.23 (m, 2H), 1.19-1.09 (m, 3H), 1.06 (t, J=8.5 Hz, 3H), 0.94-0.85 (m, 6H). $^{13}$C NMR (100 MHz, CDCl$_3$) δ ppm 211.5, 153.6, 145.1 (d, J=38 Hz), 134.1 (d, J=28 Hz), 133.9 (d, J=2 Hz), 133.3, 133.2 (d, J=8 Hz), 129.4, 129.3 (d, J=3 Hz), 128.3, 127.6, 127.4, 127.0 (d, J=3 Hz), 126.9, 126.6, 126.1, 125.9, 125.6, 122.9, 122.3 (d, J=10 Hz), 112.2, 55.6, 54.0, 53.7, 35.7 (d, J=23 Hz), 35.4 (d, J=22 Hz), 32.9 (d, J=37 Hz), 32.5 (d, J=36 Hz), 30.4 (d, J=7 Hz), 29.8 (d, J=7 Hz). $^{31}$P NMR (CDCl$_3$, 202 MHz) δ ppm −1.3 (s). LRMS (ESI$^+$) found for [M+H, C$_{30}$H$_{32}$O$_2$P]$^+$ 455.2.

Example 6-h 1-(1,1'-Binaphthyl-2-yl)-2,2,6,6-tetramethylphosphinan-4-one

The titled compound was prepared as described in the general procedure for the double conjugate addition to phorone in a nitrogen-atmosphere glovebox substituting 1,1'-binaphthyl-2-ylphosphine (1.73 g, 6.04 mmol, 1 equiv) for biarylphosphine, wherein all other reagents were scaled accordingly, and heating for 20 hours (1.71 g, 91 area % by HPLC, 67% yield). $^1$H NMR (400 MHz, CDCl$_3$) δ ppm 8.10-7.86 (m, 5H), 7.66-7.55 (m, 1H), 7.48 (dddd, J=16.4, 8.1, 6.8, 1.2 Hz, 2H), 7.40-7.31 (m, 1H), 7.30-7.20 (m, 2H), 7.14 (t, J=9.3 Hz, 2H), 3.19-2.90 (m, 2H), 2.31 (dddd, J=22.0, 13.0, 4.9, 1.1 Hz, 2H), 1.18-1.08 (m, 3H), 1.07-0.89 (m, 9H). $^{13}$C NMR (100 MHz, CDCl$_3$) δ ppm 211.1, 148.3 (d, J=37 Hz), 138.1 (d, J=10 Hz), 133.6 (d, J=16 Hz), 133.4 (d, J=5 Hz), 133.1, 133.0 (d, J=2 Hz), 133.0, 129.0 (d, J=4 Hz), 128.8 (d, J=3 Hz), 128.0, 127.6-127.4 (m), 127.3 (d, J=11 Hz), 126.7 (d, J=6 Hz), 126.2, 125.4 (d, J=6 Hz), 124.5, 54.1, 53.4, 36.3 (d, J=22 Hz), 35.5 (d, J=22 Hz), 32.7 (d, J=36 Hz), 31.9 (d, J=34 Hz), 30.7 (d, J=7 Hz), 30.0 (d, J=8 Hz). $^{31}$P NMR (CDCl$_3$, 202 MHz) δ ppm −1.1 (s). LRMS (ESI$^+$) found for [M+H, C$_{29}$H$_{30}$OP]$^+$ 425.2.

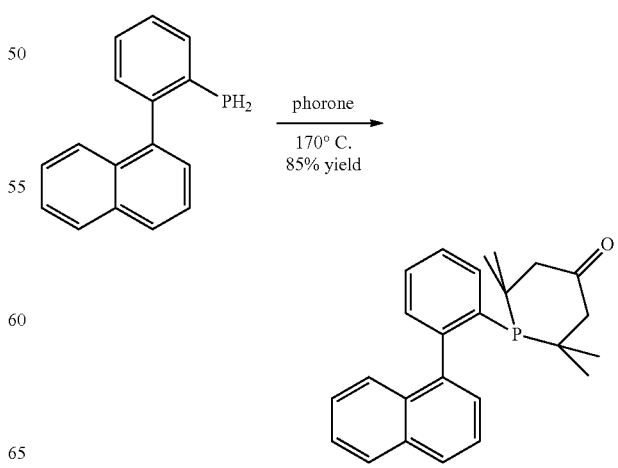

Example 6-j

2,2,6,6-Tetramethyl-1-(2-(naphthalen-1-yl)phenyl)phosphinan-4-one

The titled compound was prepared as described in the general procedure for the double conjugate addition to phorone in a nitrogen-atmosphere glovebox substituting (2-(naphthalen-1-yl)phenyl)phosphine (1.07 g, 4.52 mmol, 1 equiv) for biarylphosphine, wherein all other reagents were scaled accordingly, and heating for 18 hours (1.44 g, 87 area % by HPLC, 85% yield). $^1$H NMR (400 MHz, CDCL$_3$) δ 8.04-7.96 (m, 1H), 7.96-7.87 (m, 2H), 7.61-7.47 (m, 4H), 7.44-7.36 (m, 3H), 7.35-7.27 (m, 1H), 2.99 (ddd, J=13.0, 11.3, 3.1 Hz, 2H), 2.43-2.20 (m, 2H), 1.18-0.96 (m, 12H). $^{13}$C NMR (100 MHz, CDCl$_3$) δ ppm 211.0, 149.5 (d, J=37 Hz), 140.5 (d, J=9 Hz), 135.9 (d, J=29 Hz), 133.3-132.8 (m), 132.4 (d, J=2 Hz), 131.5 (d, J=6 Hz), 128.8, 127.9, 127.8 (d, J=3 Hz), 127.2, 127.0, 126.6, 125.3, 125.2, 124.4, 54.0 (d, J=1 Hz), 52.9 (d, J=1 Hz), 36.2 (d, J=22 Hz), 35.4 (d, J=22 Hz), 32.5 (d, J=35 Hz), 31.5 (d, J=33 Hz), 30.4 (d, J=7 Hz), 30.0 (d, J=8 Hz). $^{31}$P NMR (CDCl$_3$, 202 MHz) δ ppm −4.9 (s). LRMS (ESI$^+$) found for [M+H, C$_{25}$H$_{28}$OP]$^+$ 375.2.

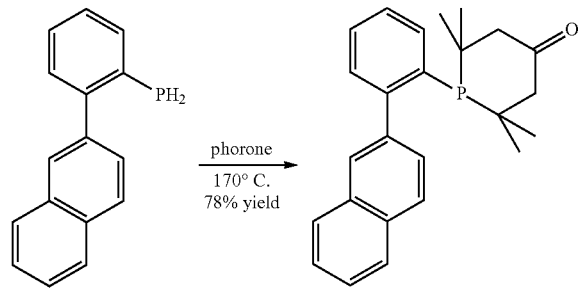

Example 6-k

2,2,6,6-Tetramethyl-1-(2-(naphthalen-2-yl)phenyl)phosphinan-4-one

The titled compound was prepared as described in the general procedure for the double conjugate addition to phorone in a nitrogen-atmosphere glovebox substituting (2-(naphthalen-2-yl)phenyl)phosphine (1.41 g, 5.98 mmol, 1 equiv) for biarylphosphine, wherein all other reagents were scaled accordingly, and heating for 18 hours (1.74 g, 99 area % by HPLC, 78% yield). $^1$H NMR (400 MHz, CDCl$_3$) δ ppm 7.99-7.80 (m, 4H), 7.68 (s, 1H), 7.58-7.37 (m, 6H), 3.07-2.84 (m, 2H), 2.39-2.22 (m, 2H), 1.18 (s, 3H), 1.14 (s, 3H), 1.02 (s, 3H), 0.99 (d, J=9.0 Hz, 3H). $^{13}$C NMR (100 MHz, CDCl$_3$) δ ppm 210.9, 151.6 (d, J=34 Hz), 140.6 (d, J=8 Hz), 134.2 (d, J=30 Hz), 133.0 (d, J=4 Hz), 132.7, 131.9, 131.2 (d, J=6 Hz), 129.3 (d, J=6 Hz), 128.8, 128.6 (d, J=3 Hz), 127.7, 127.5, 126.7, 126.2, 125.8, 125.5, 53.5, 36.2, 36.0, 32.1, 31.8, 30.2, 30.1. $^{31}$P NMR (CDCl$_3$, 202 MHz) δ ppm −6.8 (s).

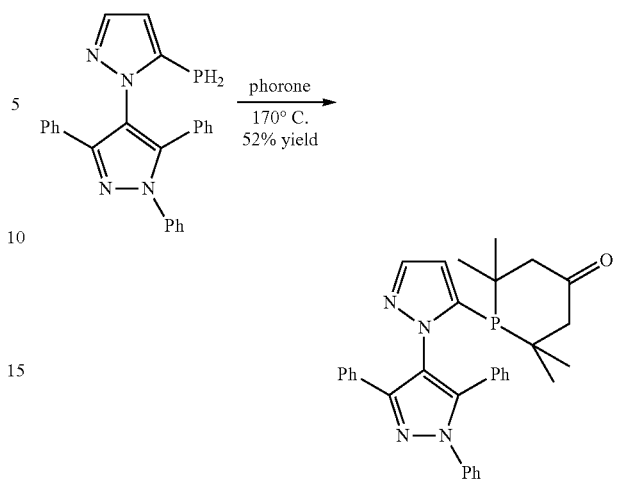

Example 6-l

2,2,6,6-Tetramethyl-1-(1',3',5'-triphenyl-1'H-1,4'-bipyrazol-5-yl)phosphinan-4-one The titled compound was prepared as described in the general procedure for the double conjugate addition to phorone substituting 1',3',5'-triphenyl-5-phosphino-1'H-1,4'-bipyrazole (2.36 g, 5.98 mmol, 1 equiv) for biarylphosphine, wherein all other reagents were scaled accordingly, and heating for 21.5 hours (1.64 g, 80 area % by HPLC, 52% yield). $^1$H NMR (400 MHz, CDCl$_3$) δ ppm 8.20 (d, J=2.0 Hz, 1H), 7.76-7.61 (m, 4H), 7.61-7.28 (m, 13H), 6.80 (t, J=3.3 Hz, 1H), 2.93-2.75 (m, 2H), 2.27-2.12 (m, 2H), 1.12 (dd, J=18.5 Hz, 6H), 0.30 (d, J=12.1 Hz, 3H), 0.01 (d, J=12.0 Hz, 3H). $^{13}$C NMR (100 MHz, CDCl$_3$) δ ppm 210.3, 149.2, 141.9, 141.7, 141.0 (d, J=2 Hz), 140.3 (d, J=2 Hz), 139.6, 131.3, 129.4, 128.6, 128.5, 128.1, 128.1, 128.1, 128.0, 127.3, 127.2, 125.1, 120.4, 111.9 (d, J=5 Hz), 52.7-52.4 (m), 35.5 (d, J=3 Hz), 35.3 (d, J=4 Hz), 30.0 (d, J=7 Hz), 29.6 (d, J=7 Hz), 29.4 (d, J=9 Hz), 28.3 (d, J=9 Hz). $^{31}$P NMR (CDCl$_3$, 202 MHz) δ ppm −21.6 (s). LRMS (ESI$^+$) found for [M+H, C$_{33}$H$_{34}$N$_4$OP]$^+$ 533.2.

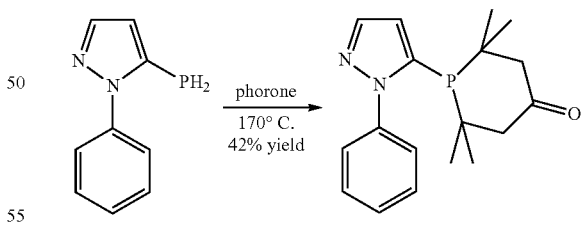

Example 6-m

2,2,6,6-Tetramethyl-1-(1-phenyl-1H-pyrazol-5-yl)phosphinan-4-one

The titled compound was prepared as described in the general procedure for the double conjugate addition to phorone in a nitrogen-atmosphere glovebox substituting 1-phenyl-5-phosphino-1H-pyrazole (1.45 g, 8.23 mmol, 1 equiv) for biarylphosphine, wherein all other reagents were scaled accordingly, and heating for 18 hours (1.08 g, 67 area % by HPLC, 42% yield). $^1$H NMR (400 MHz, CDCl$_3$) δ ppm 7.81 (t, J=3.3 Hz, 1H), 7.49-7.38 (m, 5H), 6.87-6.71 (m, 1H), 3.02-2.87 (m, 2H), 2.25 (dd, J=12.7, 5.6 Hz, 2H), 1.24 (s, 3H), 1.20 (s, 3H), 0.96 (s, 3H), 0.93 (s, 3H). $^{13}$C NMR (100 MHz, CDCl$_3$) δ ppm 210.0, 139.7 (d, J=2 Hz), 138.5 (d, J=28 Hz), 128.3, 128.2, 127.7 (d, J=5 Hz), 112.0 (d, J=5 Hz), 52.7, 52.6, 36.1, 35.9, 30.3, 30.2, 30.2, 29.9. $^{31}$P NMR (CDCl$_3$, 202 MHz) δ ppm −22.0 (s). LRMS (ESI found for [M+H C$_{18}$H$_{24}$N$_2$OP]$^+$ 315.1.

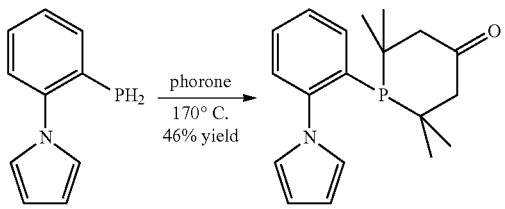

Example 6-n 1-(2-(1H-Pyrrol-1-yl)phenyl)-2,2,6,6-tetramethyl-phosphinan-4-one

The titled compound was prepared as described in the general procedure for the double conjugate addition to phorone in a nitrogen-atmosphere glovebox substituting 1-(2-phosphinophenyl)-1H-pyrrole (2.00 g, 11.4 mmol, 1 equiv) for biarylphosphine, wherein all other reagents were scaled accordingly, and heating for 19 hours (1.65 g, 85 area % by HPLC, 46% yield). $^1$H NMR (400 MHz, CDCl$_3$) δ ppm 7.96-7.83 (m, 1H), 7.54-7.41 (m, 2H), 7.41-7.33 (m, 1H), 6.86-6.73 (m, 2H), 6.37-6.23 (m, 2H), 2.91 (dd, J=13.0, 3.3 Hz, 2H), 2.41-2.26 (m, 2H), 1.25 (s, 3H), 1.20 (s, 3H), 0.98 (s, 3H), 0.96 (s, 3H). $^{13}$C NMR (100 MHz, CDCl$_3$) δ ppm 210.5, 148.4 (d, J=28 Hz), 134.2 (d, J=34 Hz), 133.4 (d, J=4 Hz), 129.9, 128.4 (d, J=3 Hz), 127.4, 123.3 (d, J=3 Hz), 108.4, 53.2, 35.7, 35.5, 32.2, 31.8, 30.0, 29.9. $^{31}$P NMR (CDCl$_3$, 202 MHz) δ ppm −5.4 (s). LRMS (ESI$^+$) found for [M+H, C$_{19}$H$_{25}$NOP]$^+$ 314.1.

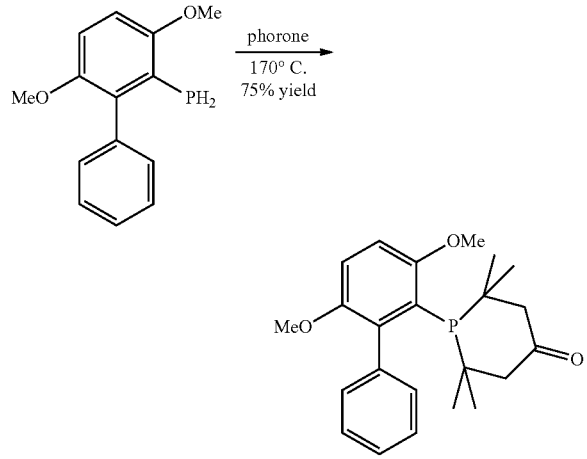

Example 6-o 1-(3,6-Dimethoxybiphenyl-2-yl)-2,2,6,6-tetramethyl-phosphinan-4-one

The titled compound was prepared as described in the general procedure for the double conjugate addition to phorone in a nitrogen-atmosphere glovebox substituting (3,6-dimethoxybiphenyl-2-yl)phosphine (1.58 g, 6.42 mmol, 1 equiv) for biarylphosphine, wherein all other reagents were scaled accordingly, and heating for 18 hours (1.84 g, 87 area % by HPLC, 75% yield). $^1$H NMR (400 MHz, CDCl$_3$) δ ppm 7.44-7.27 (m, 3H), 7.11-7.03 (m, 2H), 7.00 (d, J=8.9 Hz, 1H), 6.87 (dd, J=10.2, 6.9 Hz, 1H), 3.82 (s, 3H), 3.65 (s, 3H), 3.13 (d, J=12.4 Hz, 2H), 2.15 (dd, J=12.6, 5.3 Hz, 2H), 1.12 (s, 3H), 1.07 (s, 3H), 0.95 (s, 3H), 0.93 (s, 3H). $^{13}$C NMR (100 MHz, CDCl$_3$) δ ppm 214.0, 154.2 (d, J=3 Hz), 151.4 (d, J=11 Hz), 142.9 (d, J=42 Hz), 139.2 (d, J=12 Hz), 130.5 (d, J=5 Hz), 126.9, 126.0, 124.6 (d, J=44 Hz), 113.3, 108.5, 56.5, 54.6, 54.6, 54.4, 35.8, 35.5, 34.1, 33.6, 30.4, 30.3. $^{31}$P NMR (CDCl$_3$, 202 MHz) δ ppm 0.1 (s). HRMS (TOF-ESI$^+$) calcd for [M, C$_{23}$H$_{29}$O$_3$P]$^+$ 384.1854. found 384.1860.

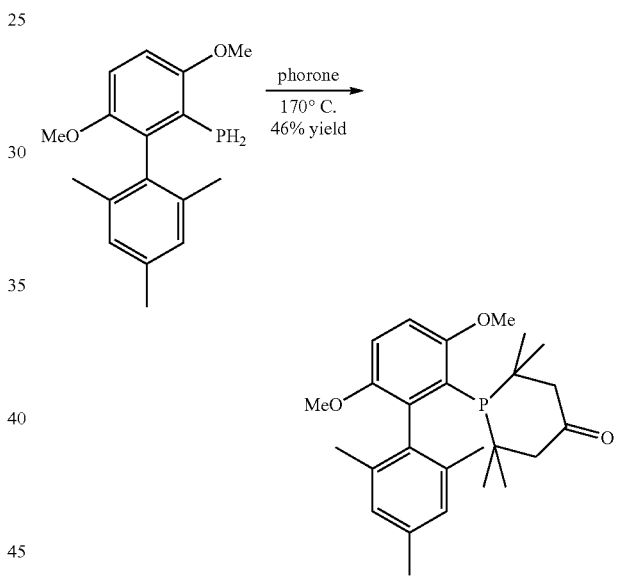

Example 6-p 1-(3,6-Dimethoxy-2',4',6'-trimethylbiphenyl-2-yl)-2,2,6,6-tetramethylphosphinan-4-one The titled compound was prepared as described in the general procedure for the double conjugate addition to phorone substituting (3,6-dimethoxy-2',4',6'-trimethylbiphenyl-2-yl)phosphine (2.08 g, 7.23 mmol, 1 equiv) for biarylphosphine, wherein all other reagents were scaled accordingly, and heating for 19 hours (1.65 g, 88 area % by HPLC, 46% yield). $^1$H NMR (400 MHz, CDCl$_3$) δ ppm 7.03-6.95 (m, 1H), 6.85 (dd, J=12.9, 9.0 Hz, 3H), 3.79 (s, 3H), 3.64 (s, 3H), 2.98 (dd, J=14.3, 4.3 Hz, 2H), 2.33 (s, 3H), 2.31-2.21 (m, 2H), 1.95 (s, 6H), 1.17-1.11 (m, 3H), 1.08 (s, 3H), 0.99 (s, 3H), 0.97 (s, 3H). $^{13}$C NMR (100 MHz, CDCl$_3$) δ ppm 213.4, 154.5, 151.4 (d, J=12 Hz), 140.7 (d, J=41 Hz), 135.7, 135.4 (d, J=3 Hz), 134.5 (d, J=10 Hz), 127.2, 124.2 (d, J=43 Hz), 113.1, 108.5, 56.3, 54.3, 54.3, 54.2, 35.0, 34.5, 34.5, 34.2, 29.0 (d, J=3 Hz), 21.6, 21.4, 21.3. $^{31}$P NMR (CDCl$_3$, 202 MHz) δ ppm 6.8 (s). HRMS (TOF-ESI$^+$) calcd for [M, C$_{26}$H$_{35}$O$_3$P]$^+$ 426.2324. found 426.2327.

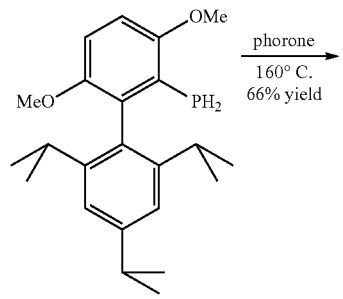

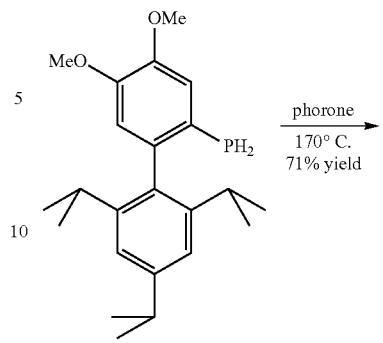

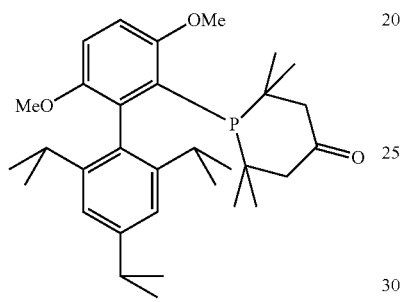

Example 6-q 2,2,6,6-Tetramethyl-1-(2',4',6'-triisopropyl-3,6-dimethoxybiphenyl-2-yl)phosphinan-4-one The titled compound was prepared as described in the general procedure for the double conjugate addition to phorone substituting (2',4',6'-triisopropyl-3,6-dimethoxybiphenyl-2-yl)phosphine (1.80 g, 4.83 mmol, 1 equiv) for biarylphosphine, wherein all other reagents were scaled accordingly, and heating for 19 hours followed by purification via silica gel column chromatography (80-g column; gradient: 2 column volumes heptane, ramp up to 80:20 heptane:ethyl acetate over 8 column volumes, hold at 80:20 for 4 column volumes) (1.63 g, 93 area % by HPLC, 66% yield). $^1$H NMR (CDCl$_3$, 400 MHz) δ ppm 7.00 (s, 2H), 6.98-6.86 (m, 2H), 3.85 (s, 3H), 3.62 (s, 3H), 3.08 (dd, J=12.8, 1.7 Hz, 1H), 2.98 (hept, J=6.7 Hz, 1H), 2.48 (hept, J=6.7 Hz, 1H), 2.21 (dd, J=12.8, 5.0 Hz, 1H), 1.35 (d, J=6.9 Hz, 6H), 1.25 (d, J=6.8 Hz, 6H), 1.16 (d, J=22.8 Hz, 3H), 1.02-0.94 (m, 12H). $^{13}$C NMR (100 MHz, CDCl$_3$) δ ppm 213.8, 154.1 (d, J=2 Hz), 152.2 (d, J=12 Hz), 146.9, 145.6 (d, J=2 Hz), 140.5 (d, J=42 Hz), 132.0 (d, J=10 Hz), 125.4 (d, J=44 Hz), 119.8, 111.4, 107.9, 55.3 (d, J=4 Hz), 54.6, 54.2, 36.4, 36.1, 34.9, 34.4, 34.1, 30.9, 29.4 (d, J=3 Hz), 25.5, 24.3, 23.9. $^{31}$P NMR (CDCl$_3$, 202 MHz) δ ppm 6.2 (br s). HRMS (TOF-ESI$^+$) calcd for [M, C$_{32}$H$_{47}$O$_3$P]$^+$ 510.3263. found 510.3267.

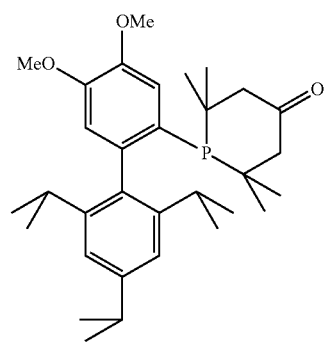

Example 6-r 2,2,6,6-Tetramethyl-1-(2',4',6'-triisopropyl-4,5-dimethoxybiphenyl-2-yl)phosphinan-4-one The titled compound was prepared as described in the general procedure for the double conjugate addition to phorone substituting (2',4',6'-triisopropyl-4,5-dimethoxybiphenyl-2-yl)phosphine (600 mg, 1.61 mmol, 1 equiv) for biarylphosphine, wherein all other reagents were scaled accordingly, and heating for 16 hours. The product was slurried in a mixture of heptane and collected by filtration (581 mg, 97% pure by $^1$H NMR, 71% yield). $^1$H NMR (400 MHz, CDCl$_3$) δ ppm 7.29 (d, J=1.0 Hz, 1H), 7.02 (s, 2H), 6.72 (d, J=3.6 Hz, 1H), 3.94 (d, J=5.2 Hz, 3H), 3.84 (d, J=8.4 Hz, 3H), 3.01-2.85 (m, 3H), 2.65-2.51 (m, 2H), 2.34 (dt, J=14.6, 5.2 Hz, 2H), 1.32 (d, J=6.9 Hz, 6H), 1.26-1.21 (m, 9H), 1.18 (s, 3H), 1.05-0.99 (m, 12H). $^{13}$C NMR (100 MHz, CDCl$_3$) δ ppm 211.0, 148.6 (d, J=1 Hz), 147.4, 146.4, 145.8, 143.0 (d, J=39 Hz), 135.9 (d, J=6 Hz), 126.0 (d, J=29 Hz), 120.3, 115.9 (d, J=3 Hz), 115.3 (d, J=8 Hz), 56.1, 55.8, 53.9 (d, J=1 Hz), 36.3, 36.0, 34.2, 32.9, 32.5, 30.7, 30.2 (d, J=6 Hz), 26.7, 24.3, 23.3. $^{31}$P NMR (CDCl$_3$, 202 MHz) δ ppm −0.9 (s). LRMS (ESI) found for [M+H, C$_{32}$H$_{48}$O$_3$P]$^+$ 511.2.

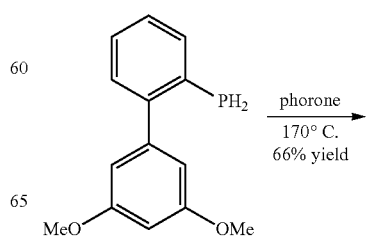

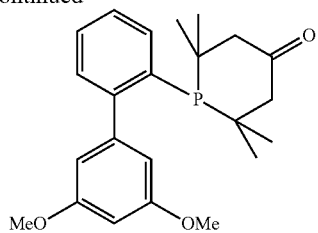

Example 6-s 1-(3',5'-Dimethoxybiphenyl-2-yl)-2,2,6,6-tetramethylphosphinan-4-one The titled compound was prepared as described in the general procedure for the double conjugate addition to phorone in a nitrogen-atmosphere glovebox substituting (3',5'-dimethoxybiphenyl-2-yl)phosphine (1.30 g, 5.28 mmol, 1 equiv) for biarylphosphine, wherein all other reagents were scaled accordingly, and heating for 18 hours (1.33 g, 94 area % by HPLC, 66% yield). $^1$H NMR (400 MHz, CDCl$_3$) δ ppm 7.87 (dt, J=6.2, 1.8 Hz, 1H), 7.46-7.36 (m, 2H), 7.36-7.30 (m, 1H), 6.46 (t, J=2.3 Hz, 1H), 6.39 (d, J=2.3 Hz, 2H), 3.81 (s, 6H), 2.94 (dd, J=13.0, 3.3 Hz, 2H), 2.30 (dd, J=13.0, 4.9 Hz, 2H), 1.22 (s, 3H), 1.17 (s, 3H), 0.99 (s, 3H), 0.96 (s, 3H). $^{13}$C NMR (100 MHz, CDCl$_3$) δ ppm 211.0, 159.3, 151.6 (d, J=36 Hz), 144.8 (d, J=8 Hz), 134.0 (d, J=30 Hz), 132.9 (d, J=4 Hz), 130.4 (d, J=6 Hz), 128.7, 126.6, 108.8 (d, J=4 Hz), 98.6, 55.4, 53.5, 36.1, 35.9, 32.3, 31.9, 30.2 (d, J=7 Hz). $^{31}$P NMR (CDCl$_3$, 202 MHz) δ ppm −3.7 (s). HRMS (TOF-ESI$^+$) calcd for [M, C$_{23}$H$_{29}$O$_3$P]$^+$ 384.1854. found 384.18604.

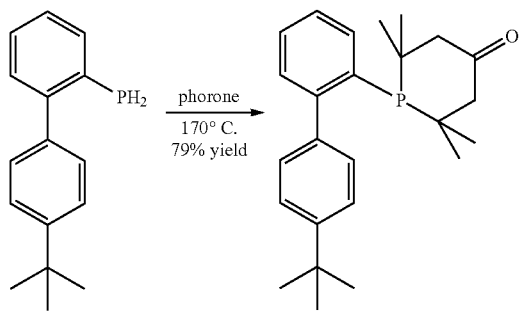

Example 6-t 1-(4'-tert-Butylbiphenyl-2-yl)-2,2,6,6-tetramethylphosphinan-4-one

The titled compound was prepared as described in the general procedure for the double conjugate addition to phorone in a nitrogen-atmosphere glovebox substituting (4'-tert-butylbiphenyl-2-yl)phosphine (1.24 g, 5.10 mmol, 1 equiv) for biarylphosphine, wherein all other reagents were scaled accordingly, and heating for 17 hours followed by purification via silica gel column chromatography (80-g column; gradient: 2 column volumes heptane, ramp up to 85:15 heptane:ethyl acetate over 8 column volumes, hold at 85:15 for 2 column volumes) to afford the air-stable product as a white powder (1.53 g, 74 area % by HPLC, 79% yield).

$^1$H NMR (400 MHz, CDCl$_3$) δ ppm 7.87 (d, J=7.5 Hz, 1H), 7.46-7.36 (m, 4H), 7.36-7.30 (m, 1H), 7.19 (d, J=7.9 Hz, 2H), 2.95 (dd, J=12.9, 2.7 Hz, 2H), 2.28 (dd, J=13.0, 4.8 Hz, 2H), 1.39 (s, 8H), 1.22 (s, 3H), 1.17 (s, 3H), 0.96 (d, J=10.0 Hz, 6H). $^{13}$C NMR (100 MHz, CDCl$_3$) δ ppm 211.3, 151.7 (d, J=34 Hz), 148.8, 139.6 (d, J=8 Hz), 134.1 (d, J=30 Hz), 132.9 (d, J=4 Hz), 131.2 (d, J=6 Hz), 130.1 (d, J=5 Hz), 128.7, 126.3, 124.0, 53.4, 36.2, 35.9, 34.7, 32.3, 31.9, 31.7, 30.2 (d, J=8 Hz). $^{31}$P NMR (CDCl$_3$, 202 MHz) δ ppm −4.3 (br s). HRMS (TOF-ESI$^+$) calcd for [M, C$_{25}$H$_{33}$OP]$^+$ 380.2269. found 380.2282.

Example 7

General Procedure for the Phosphorinone Ketalization

To a round-bottom flask equipped with a magnetic stir bar was added the biaryl phosphorinone (1 equiv) and p-toluenesulfonic acid (0.1 equiv). The flask was purged with nitrogen for 15 minutes, and then anhydrous nitrogen-sparged toluene was added (0.1 M in the phosphorinone), followed by ethylene glycol (10 equiv). The reaction flask was fitted with a Dean-Stark trap and heated to reflux under a N$_2$ atmosphere. The distilled toluene and water were collected in the Dean-Stark trap. Reaction conversion was determined by reverse phase HPLC. Upon completion of the reaction, the solution was cooled to room temperature and quenched with aqueous saturated sodium bicarbonate. The phases were partitioned, and the organic layer was collected. The aqueous layer was then washed with ethyl acetate (3×), and the combined organic fractions were washed once with brine, dried over sodium sulfate, filtered, and concentrated on a rotary evaporator. The resulting crude material was then crystallized from a saturated ethanol solution. The crystalline material was isolated by filtration, washed with ice-cold ethanol, and dried under vacuum at room temperature.

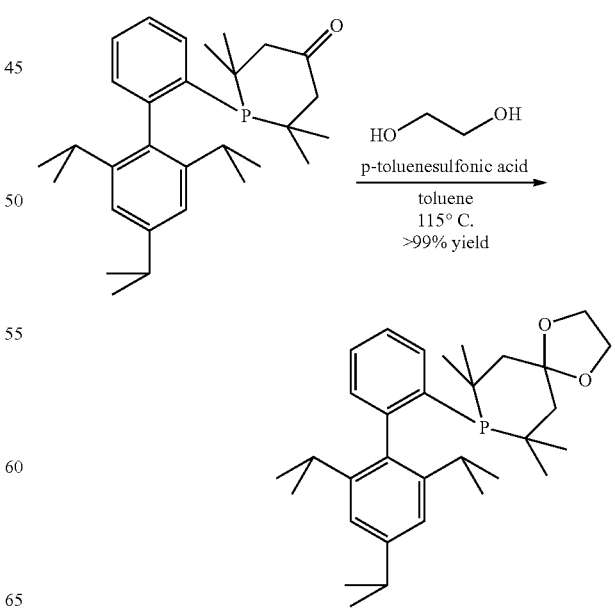

Example 7-a

Alternative Preparation of 7,7,9,9-Tetramethyl-8-(2',4',6'-triisopropylbiphenyl-2-yl)-1,4-dioxa-8-phosphaspiro[4.5]decane (Example 1-d)

The titled compound was prepared as described in the general procedure for the phosphorinone ketalization substituting 2,2,6,6-tetramethyl-1-(2',4',6'-triisopropylbiphenyl-2-yl)phosphinan-4-one (2.79 g, 6.19 mmol, 1 equiv) for biaryl phosphorinone, wherein all other reagents were scaled accordingly, and refluxing for 3 hours, followed by purification via crystallization from a saturated ethanol solution (3.06 g, 95 area % by HPLC, >99% yield). $^1$H NMR (400 MHz, CDCl$_3$) δ ppm 7.79-7.71 (m, 1H), 7.35-7.27 (m, 2H), 7.19-7.12 (m, 1H), 7.00 (s, 2H), 4.09-3.99 (m, 2H), 3.99-3.90 (m, 2H), 2.94 (hept, J=7.0 Hz, 1H), 2.49 (hept, J=6.7 Hz, 2H), 2.15 (d, J=14.3 Hz, 2H), 1.67 (dd, J=14.3, 5.7 Hz, 2H), 1.36-1.29 (m, 9H), 1.28-1.19 (m, 9H), 0.95 (d, J=6.7 Hz, 6H), 0.87 (d, J=10.1 Hz, 6H). $^{13}$C NMR (100 MHz, CDCl$_3$) δ ppm 148.8 (d, J=36 Hz), 147.0, 145.5, 136.7 (d, J=16 Hz), 136.5 (d, J=9 Hz), 133.8 (d, J=3 Hz), 132.3 (d, J=7 Hz), 127.6, 125.8, 120.2, 110.6, 64.9, 63.1, 44.9 (d, J=3 Hz), 34.2, 32.6, 32.3 (d, J=6 Hz), 32.1, 31.3 (d, J=7 Hz), 30.6, 26.3, 24.3, 23.4. $^{31}$P NMR (CDCl$_3$, 202 MHz) δ ppm −9.4 (s). LRMS (ESI$^+$) found for [M+H, C$_{32}$H$_{48}$O$_2$P]$^+$ 495.3.

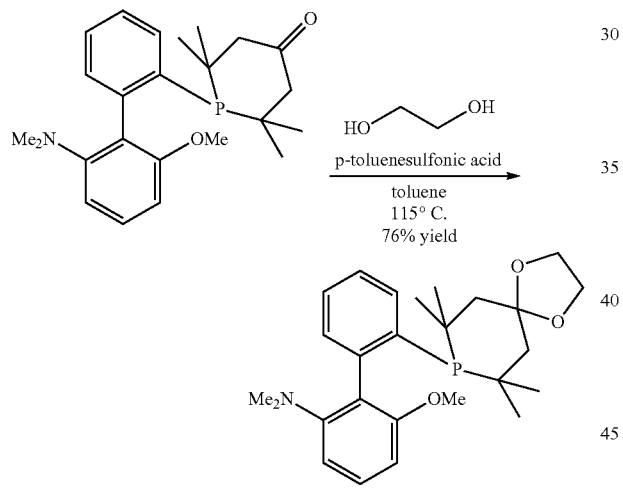

Example 7-b

6-Methoxy-N,N-dimethyl-2'-(7,7,9,9-tetramethyl-1,4-dioxa-8-phosphaspiro[4.5]decan-8-yl)biphenyl-2-amine The titled compound was prepared as described in the general procedure for the phosphorinone ketalization substituting 1-(2'-(dimethylamino)-6'-methoxybiphenyl-2-yl)-2,2,6,6-tetramethylphosphinan-4-one (1.48 g, 3.72 mmol, 1 equiv) for biaryl phosphorinone, wherein all other reagents were scaled accordingly, and refluxing for 5.5 hours, followed by purification via crystallization from a saturated methanol solution (1.24 g, 97 area % by HPLC, 76% yield). $^1$H NMR (400 MHz, CDCl$_3$) δ ppm 7.68-7.58 (m, 1H), 7.34-7.08 (m, 4H), 6.60 (dt, J=5.4, 2.2 Hz, 1H), 6.52 (dd, J=8.3, 0.8 Hz, 1H), 3.98-3.76 (m, 4H), 3.52 (s, 3H), 2.36 (s, 6H), 2.13 (d, J=14.4 Hz, 1H), 1.84 (dd, J=14.2, 1.1 Hz, 1H), 1.74-1.60 (m, 1H), 1.49-1.38 (m, 1H), 1.20 (t, J=12.9 Hz, 3H), 1.05 (t, J=14.9 Hz, 3H), 0.95 (d, J=9.5 Hz, 3H), 0.43 (d, J=10.0 Hz, 3H). $^{13}$C NMR (100 MHz, CDCl$_3$) δ ppm 157.0, 152.3 (d, J=3.0 Hz), 145.2 (d, J=35.4 Hz), 136.9 (d, J=28.6 Hz), 133.5 (d, J=4.3 Hz), 132.9 (d, J=6.6 Hz), 127.8 (d, J=41.7 Hz), 125.5, 124.6 (d, J=7.4 Hz), 111.2, 110.4, 104.0, 64.8, 63.0, 55.2, 45.8 (d, J=2.8 Hz), 43.6, 43.5 (d, J=2.4 Hz), 33.2 (d, J=39.4 Hz), 31.7 (d, J=37.1 Hz), 31.2 (d, J=19.6 Hz), 31.0 (d, J=13.9 Hz), 30.9, 29.8 (d, J=7.2 Hz). $^{31}$P NMR (CDCl$_3$, 202 MHz) δ ppm −5.6 (s). LRMS (ESI$^+$) found for [M+H, C$_{26}$H$_{37}$NO$_3$P]$^+$ 442.2.

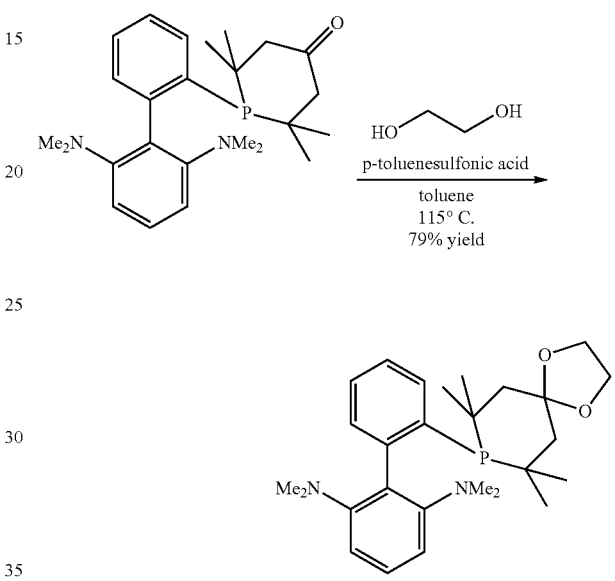

Example 7-c

N$^2$,N$^2$,N$^6$,N$^6$-Tetramethyl-2'-(7,7,9,9-tetramethyl-1,4-dioxa-8-phosphaspiro[4.5]decan-8-yl)biphenyl-2,6-diamine The titled compound was prepared as described in the general procedure for the phosphorinone ketalization substituting 1-(2',6'-bis(dimethylamino)biphenyl-2-yl)-2,2,6,6-tetramethylphosphinan-4-one (2.72 g, 6.63 mmol, 1 equiv) for biaryl phosphorinone, wherein all other reagents were scaled accordingly, and refluxing for 3 hours, followed by purification via crystallization from a saturated ethanol solution (2.37 g, 89 area % by HPLC, 79% yield). $^1$H NMR (400 MHz, CDCl$_3$) δ ppm 7.72 (d, J=7.7 Hz, 1H), 7.40-7.28 (m, 3H), 7.26-7.21 (m, 1H), 6.90 (d, J=8.0 Hz, 2H), 4.05-3.98 (m, 2H), 3.96-3.90 (m, 2H), 2.47 (s, 12H), 2.11 (d, J=14.5 Hz, 2H), 1.69 (dd, J=14.2, 5.6 Hz, 2H), 1.26 (s, 3H), 1.21 (s, 3H), 0.87 (s, 3H), 0.84 (s, 3H). $^{13}$C NMR (100 MHz, CDCl$_3$) δ ppm 153.1, 147.1 (d, J=36 Hz), 136.7 (d, J=29 Hz), 134.0 (d, J=4 Hz), 133.3 (d, J=7 Hz), 128.1, 126.9, 125.3, 114.4, 110.9, 64.8, 63.0, 45.6, 45.3 (d, J=3 Hz), 33.2, 32.8, 31.5, 31.3, 30.6 (d, J=7 Hz). $^{31}$P NMR (CDCl$_3$, 202 MHz) δ ppm −6.0 (s). HRMS (TOF-ESI$^+$) calcd for [M, C$_{27}$H$_{39}$N$_2$O$_2$P]$^+$ 454.2749. found 454.2753.

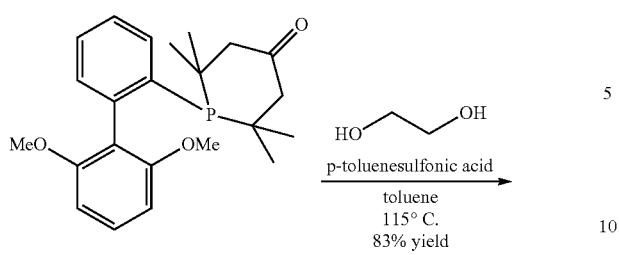

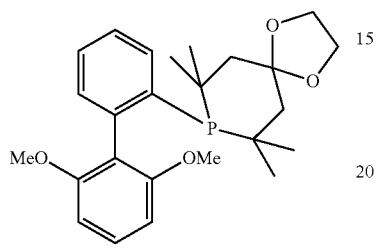

Example 7-d 8-(2',6'-Dimethoxybiphenyl-2-yl)-7,7,9,9-tetramethyl-1,4-dioxa-8-phosphaspiro[4.5]decane The titled compound was prepared as described in the general procedure for the phosphorinone ketalization substituting 1-(2',6'-dimethoxybiphenyl-2-yl)-2,2,6,6-tetramethylphosphinan-4-one (4.22 g, 11.0 mmol, 1 equiv) for biaryl phosphorinone, wherein all other reagents were scaled accordingly, and refluxing for 3 hours, followed by purification via silica gel column chromatography (330-g column; gradient: 1.5 column volumes heptane, ramp up to 78:22 heptane:ethyl acetate over 8.5 column volumes, hold at 78:22 over 6 column volumes) (3.92 g, 92 area % by HPLC, 83% yield). $^1$H NMR (400 MHz, CDCl$_3$) δ ppm 7.88-7.66 (m, 1H), 7.50-7.25 (m, 3H), 7.24-7.12 (m, 1H), 6.61 (dd, J=15.2, 8.3 Hz, 2H), 4.07-4.00 (m, 2H), 3.96 (ddd, J=13.1, 8.7, 3.7 Hz, 2H), 3.72 (s, 6H), 2.11 (dd, J=14.2, 3.1 Hz, 2H), 1.71 (dd, J=14.3, 5.5 Hz, 2H), 1.28 (s, 3H), 1.22 (d, J=10.8 Hz, 3H), 0.91 (s, 3H), 0.89 (s, 3H). $^{13}$C NMR (100 MHz, CDCl$_3$) δ ppm 156.8 (d, J=1.8 Hz), 143.6 (d, J=37.3 Hz), 137.0, 133.2 (d, J=4.3 Hz), 131.1 (d, J=6.8 Hz), 128.3, 128.2, 126.0, 120.3, 116.5 (m), 111.0, 102.9, 64.7, 63.2, 55.3, 44.9, 32.6, 32.2, 31.4, 31.2, 30.6, 30.6. $^{31}$P NMR (CDCl$_3$, 202 MHz) δ ppm −5.6 (s). LRMS (ESI$^+$) found for [M+H, C$_{25}$H$_{34}$O$_4$P]$^+$ 429.2.

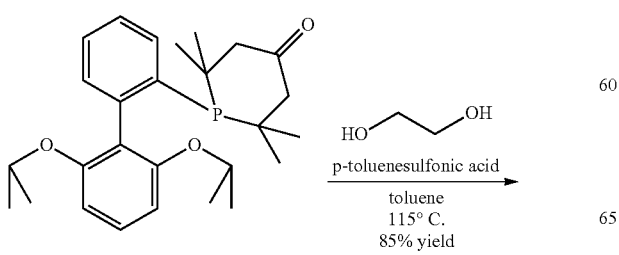

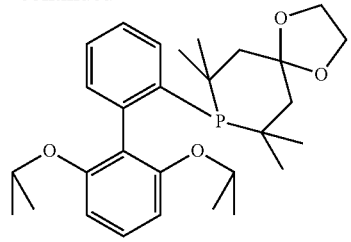

Example 7-e 8-(2',6'-Diisopropoxybiphenyl-2-yl)-7,7,9,9-tetramethyl-1,4-dioxa-8-phosphaspiro[4.5]decane The titled compound was prepared as described in the general procedure for the phosphorinone ketalization substituting 1-(2',6'-diisopropoxybiphenyl-2-yl)-2,2,6,6-tetramethylphosphinan-4-one (2.77 g, 6.29 mmol, 1 equiv) for biaryl phosphorinone, wherein all other reagents were scaled accordingly, and refluxing for 3 hours (2.60 g, >99 area % by HPLC, 85% yield). $^1$H NMR (400 MHz, CDCl$_3$) δ ppm 7.78-7.64 (m, 1H), 7.36-7.17 (m, 3H), 7.10-7.01 (m, 1H), 6.63-6.51 (m, 2H), 4.53-4.36 (m, 2H), 4.10-4.01 (m, 2H), 4.01-3.92 (m, 2H), 2.21-2.03 (m, 2H), 1.70 (dd, J=14.3, 5.6 Hz, 2H), 1.32 (s, 3H), 1.28 (d, J=7.8 Hz, 3H), 1.23 (s, 3H), 1.22 (s, 3H), 1.07 (d, J=3.4 Hz, 3H), 1.05 (s, 3H), 0.93 (s, 3H), 0.90 (d, J=5.3 Hz, 3H). $^{13}$C NMR (100 MHz, CDCl$_3$) δ ppm 155.7, 144.7 (d, J=37 Hz), 137.3 (d, J=26 Hz), 132.7 (d, J=4 Hz), 131.3 (d, J=7 Hz), 127.6 (d, J=24 Hz), 125.3, 123.8, 111.2, 105.8, 70.3, 64.8, 63.0, 44.7 (d, J=3 Hz), 32.6, 32.3, 31.4 (d, J=8 Hz), 31.2 (d, J=19 Hz), 22.5, 22.4. $^{31}$P NMR (CDCl$_3$, 202 MHz) δ ppm −6.7 (s). LRMS (ESI$^+$) found for [M+H, C$_{29}$H$_{42}$O$_4$P]$^+$ 485.2.

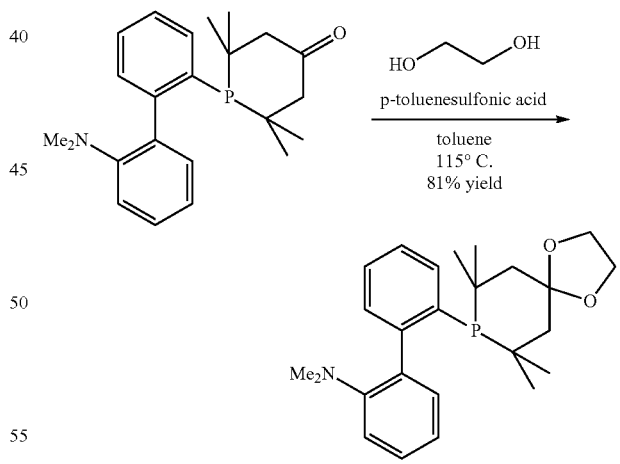

Example 7-f

N,N-Dimethyl-2'-(7,7,9,9-tetramethyl-1,4-dioxa-8-phosphaspiro[4.5]decan-8-yl)biphenyl-2-amine The titled compound was prepared as described in the general procedure for the phosphorinone ketalization substituting 1-(2'-(dimethylamino)biphenyl-2-yl)-2,2,6,6-tetramethylphosphinan-4-one (1.13 g, 3.07 mmol, 1 equiv) for biaryl phosphorinone, wherein all other reagents were scaled accordingly, and refluxing for 5 hours (1.02 g, 98 area % by HPLC, 81% yield). $^1$H NMR (400 MHz, CDCl$_3$) δ ppm 7.73 (dd, J=6.8, 1.5 Hz, 1H), 7.41 (ddd, J=8.1, 2.1, 1.0 Hz, 1H), 7.38-7.23 (m, 3H), 7.01 (td, J=8.2, 2.6 Hz, 3H), 4.14-3.88 (m, 4H), 2.51 (s, 6H), 2.27 (d, J=14.5 Hz, 1H), 1.92 (d, J=14.1 Hz, 1H), 1.81 (ddd, J=14.5, 5.3, 1.5 Hz, 1H), 1.52 (ddd, J=14.2, 5.3, 1.6 Hz, 1H), 1.36 (d, J=19.9 Hz, 3H), 1.17 (d, J=18.9 Hz, 3H), 1.11 (d, J=9.7 Hz, 3H), 0.51 (d, J=9.8 Hz, 3H). $^{13}$C NMR (100 MHz, CDCl$_3$) δ ppm 151.0 (d, J=3.0 Hz), 150.1 (d, J=36 Hz), 136.6 (d, J=23 Hz), 136.5, 133.3 (d, J=5 Hz), 131.9, 130.7 (d, J=7 Hz), 128.6, 127.6, 125.7, 120.7, 117.2, 111.0, 64.8, 63.0, 45.9 (d, J=3 Hz), 43.3, 43.2 (d, J=3 Hz), 33.3, 32.9, 31.9 (d, J=20 Hz), 31.7, 31.3 (d, J=3 Hz), 31.3, 30.9 (d, J=22 Hz), 30.0 (d, J=7 Hz). $^{31}$P NMR (CDCl$_3$, 202 MHz) δ ppm −3.8 (s). LRMS (ESI$^+$) found for [M+H, C$_{25}$H$_{35}$NO$_2$P]$^+$ 412.2.

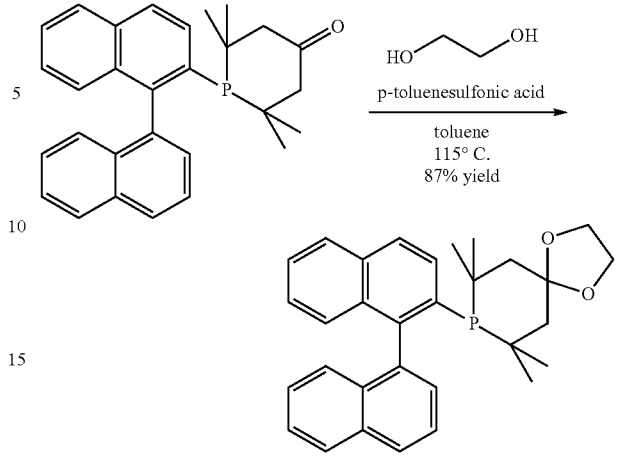

Example 7-g

8-(Biphenyl-2-yl)-7,7,9,9-tetramethyl-1,4-dioxa-8-phosphaspiro[4.5]decane

The titled compound was prepared as described in the general procedure for the phosphorinone ketalization substituting 1-(biphenyl-2-yl)-2,2,6,6-tetramethylphosphinan-4-one (2.00 g, 6.17 mmol, 1 equiv) for biaryl phosphorinone, wherein all other reagents were scaled accordingly, and refluxing for 4 hours (1.81 g, >99 area % by HPLC, 80% yield). $^1$H NMR (400 MHz, CDCl$_3$) δ 7.80 (dd, J=5.3, 3.8 Hz, 1H), 7.51-7.21 (m, 8H), 4.14-4.01 (m, 2H), 4.01-3.87 (m, 2H), 2.13 (dt, J=14.2, 4.0 Hz, 2H), 1.70 (dd, J=14.3, 5.6 Hz, 2H), 1.33 (s, 3H), 1.28 (d, J=5.6 Hz, 3H), 0.91 (s, 3H), 0.88 (s, 3H). $^{13}$C NMR (100 MHz, CDCl$_3$) δ 151.3 (d, J=34 Hz), 143.2 (d, J=8 Hz), 135.3, 133.6 (d, J=4 Hz), 130.5 (d, J=6 Hz), 130.3 (d, J=4 Hz), 128.1, 127.0, 126.1, 110.9, 64.8, 63.2, 44.5 (d, J=2 Hz), 32.2, 31.9, 31.7, 31.5, 31.3, 31.2. $^{31}$P NMR (CDCl$_3$, 202 MHz) δ ppm −8.8 (s). LRMS (ESI$^+$) found for [M+H, C$_{23}$H$_{30}$O$_2$P]$^+$ 369.1.

Example 7-h

8-(1,1'-Binaphthyl-2-yl)-7,7,9,9-tetramethyl-1,4-dioxa-8-phosphaspiro[4.5]decane The titled compound was prepared as described in the general procedure for the phosphorinone ketalization substituting 1-(1,1'-binaphthyl-2-yl)-2,2,6,6-tetramethylphosphinan-4-one (1.66 g, 3.91 mmol, 1 equiv) for biaryl phosphorinone, wherein all other reagents were scaled accordingly, and refluxing for 5 hours (1.60 g, >99 area % by HPLC, 87% yield). $^1$H NMR (400 MHz, CDCl$_3$) δ ppm 7.98-7.88 (m, 3H), 7.85 (dd, J=8.3, 4.4 Hz, 2H), 7.55 (dt, J=11.0, 5.5 Hz, 1H), 7.42 (dddd, J=8.1, 6.9, 5.8, 1.2 Hz, 2H), 7.30 (dd, J=7.0, 1.1 Hz, 1H), 7.18 (dddd, J=22.1, 20.7, 10.3, 4.6 Hz, 3H), 7.05 (d, J=8.1 Hz, 1H), 4.03-3.87 (m, 4H), 2.20 (ddd, J=25.6, 14.2, 1.8 Hz, 2H), 1.81-1.58 (m, 2H), 1.28-1.13 (m, 3H), 1.02 (d, J=19.6 Hz, 3H), 0.89 (dd, J=19.9, 10.0 Hz, 6H). $^{13}$C NMR (100 MHz, CDCl$_3$) δ ppm 147.6 (d, J=37 Hz), 138.6 (d, J=10 Hz), 134.9 (d, J=29 Hz), 133.4 (d, J=7 Hz), 133.1 (d, J=2 Hz), 132.9, 129.6 (d, J=4 Hz), 129.0 (d, J=4 Hz), 127.9, 127.4 (d, J=3 Hz), 127.3, 127.2, 127.0, 126.6, 126.2, 125.8, 125.3, 125.2, 124.5, 110.9, 64.8, 63.2, 45.1, 44.5, 32.7, 32.3, 32.2, 32.0, 31.9, 31.8, 31.2, 31.1, 31.0. $^{31}$P NMR (CDCl$_3$, 202 MHz) δ ppm −8.8 (s). LRMS (ESI$^+$) found for [M+H, C$_{31}$H$_{34}$O$_2$P]$^+$ 469.2.

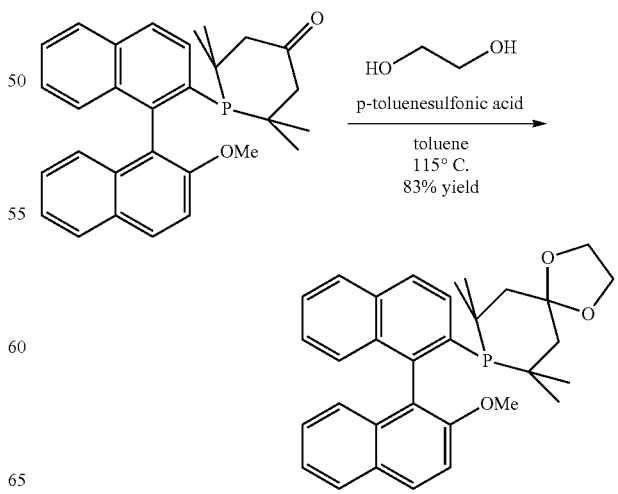

Example 7-i

8-(2'-Methoxy-1,1'-binaphthyl-2-yl)-7,7,9,9-tetramethyl-1,4-dioxa-8-phosphaspiro[4.5]decane The titled compound was prepared as described in the general procedure for the phosphorinone ketalization substituting 1-(2'-methoxy-1,1'-binaphthyl-2-yl)-2,2,6,6-tetramethylphosphinan-4-one (955 mg, 2.19 mmol, 1 equiv) for biaryl phosphorinone, wherein all other reagents were scaled accordingly, and refluxing for 5 hours (910 mg, 95 area % by HPLC, 83% yield). $^1$H NMR (400 MHz, CDCl$_3$) δ ppm 8.10-7.99 (m, 1H), 7.99-7.91 (m, 1H), 7.91-7.80 (m, 2H), 7.53-7.40 (m, 2H), 7.33-7.26 (m, 2H), 7.26-7.19 (m, 1H), 7.19-7.07 (m, 2H), 6.95-6.86 (m, 1H), 4.10-3.91 (m, 4H), 3.79 (s, 3H), 2.34-2.16 (m, 2H), 1.82-1.64 (m, 2H), 1.35-1.19 (m, 3H), 1.10-0.94 (m, 6H), 0.81 (dd, J=12.4, 7.2 Hz, 3H). $^{13}$C NMR (100 MHz, CDCl$_3$) δ ppm 153.6, 144.3 (d, J=37 Hz), 135.5 (d, J=28 Hz), 133.9, 133.2, 133.1, 130.0 (d, J=3 Hz), 129.1, 128.3, 127.4 (d, J=12 Hz), 126.9 (d, J=2 Hz), 126.4, 126.2, 126.1, 125.8, 125.3, 122.8, 122.7 (d, J=10 Hz), 112.2, 111.0, 64.8, 63.2, 55.6, 45.2, 44.9, 33.0, 32.6, 32.2, 31.7, 31.5 (dd, J=7, 4 Hz), 31.3, 30.8 (d, J=7 Hz). $^{31}$P NMR (CDCl$_3$, 202 MHz) δ ppm −6.5 (s). LRMS (ESI$^+$) found for [M+H, C$_{32}$H$_{36}$O$_3$P]$^+$ 499.2.

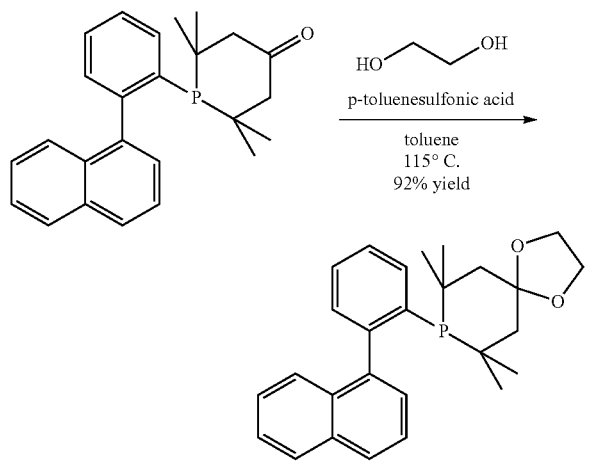

Example 7-j

7,7,9,9-Tetramethyl-8-(4-ml-8-(4-methyl-2-(naphthalen-1-yl)phenyl)-1,4-dioxa-8-phosphaspiro[4.5]decane The titled compound was prepared as described in the general procedure for the phosphorinone ketalization substituting 2,2,6,6-tetramethyl-1-(2-(naphthalen-1-yl)phenyl) phosphinan-4-one (1.39 g, 3.71 mmol, 1 equiv) for biaryl phosphorinone, wherein all other reagents were scaled accordingly, and refluxing for 4 hours (1.43 g, 88 area % by HPLC, 92% yield). $^1$H NMR (400 MHz, CDCl$_3$) δ ppm 7.98-7.83 (m, 3H), 7.58-7.24 (m, 8H), 4.10-3.91 (m, 4H), 2.31-2.04 (m, 2H), 1.78-1.58 (m, 2H), 1.24 (d, J=18.8 Hz, 3H), 1.09 (d, J=19.2 Hz, 3H), 0.94 (dd, J=11.2, 10.4 Hz, 6H). $^{13}$C NMR (100 MHz, CDCl$_3$) δ ppm 149.1 (d, J=36 Hz), 141.0 (d, J=8 Hz), 136.9 (d, J=30 Hz), 133.5 (d, J=4 Hz), 132.9, 132.4, 131.2 (d, J=6 Hz), 128.1, 127.8, 127.8, 127.0, 126.9, 126.6, 125.1 (d, J=11 Hz), 124.3, 110.8, 64.8, 63.1, 45.0 (d, J=2 Hz), 44.1 (d, J=2 Hz), 32.4, 32.0, 31.9, 31.8, 31.7, 31.6, 31.5, 31.5, 31.2, 31.1, 31.0. $^{31}$P NMR (CDCl$_3$, 202 MHz) δ ppm −9.8 (s).

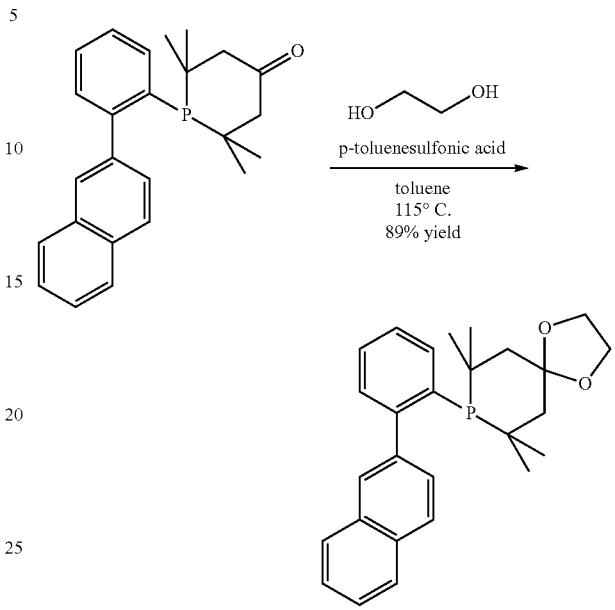

Example 7-k

7,7,9,9-Tetramethyl-8-(2-(naphthalen-2-yl)phenyl)-1,4-dioxa-8-phosphaspiro[4.5]decane The titled compound was prepared as described in the general procedure for the phosphorinone ketalization substituting 2,2,6,6-tetramethyl-1-(2-(naphthalen-2-yl)phenyl) phosphinan-4-one (1.71 g, 4.56 mmol, 1 equiv) for biaryl phosphorinone, wherein all other reagents were scaled accordingly, and refluxing for 15 hours (1.69 g, 99 area % by HPLC, 89% yield). $^1$H NMR (400 MHz, CDCl$_3$) δ ppm 7.93-7.76 (m, 4H), 7.65 (s, 1H), 7.54-7.42 (m, 3H), 7.42-7.29 (m, 3H), 4.06-3.97 (m, 2H), 3.96-3.89 (m, 2H), 2.11 (dd, J=14.3, 2.2 Hz, 2H), 1.67 (dd, J=14.3, 5.6 Hz, 2H), 1.26 (d, J=4.8 Hz, 3H), 1.22 (s, 3H), 0.92 (s, 3H), 0.89 (s, 3H). $^{13}$C NMR (100 MHz, CDCl$_3$) δ 151.2 (d, J=34 Hz), 141.1 (d, J=8 Hz), 135.2 (d, J=31 Hz), 133.6 (d, J=4 Hz), 132.7, 131.8, 130.8 (d, J=6 Hz), 129.5 (d, J=6 Hz), 128.5 (d, J=3 Hz), 128.2, 127.6, 127.5, 126.3, 126.0, 125.6, 125.3, 110.8, 64.8, 63.2, 44.5 (d, J=2 Hz), 32.2, 31.8, 31.8, 31.6, 31.3, 31.3. $^{31}$P NMR (CDCl$_3$, 202 MHz) δ ppm −11.6 (s). HRMS (TOF-ESI$^+$) calcd for [M, C$_{27}$H$_{31}$O$_2$P]$^+$ 418.2062. found 418.2068.

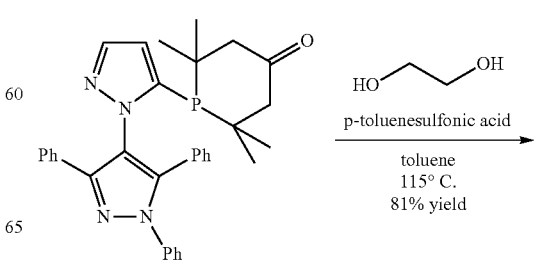

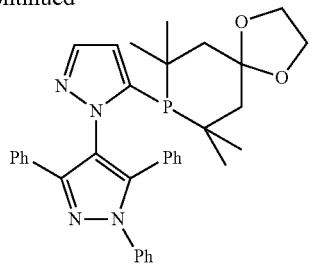

Example 7-l

1',3',5'-Triphenyl-5-(7,7,9,9-tetramethyl-1,4-dioxa-8-phosphaspiro[4.5]decan-8-yl)-1'H-1,4'-bipyrazole The titled compound was prepared as described in the general procedure for the phosphorinone ketalization substituting 2,2,6,6-tetramethyl-1-(1',3',5'-triphenyl-1'H-1,4'-bipyrazol-5-yl)phosphinan-4-one (1.57 g, 2.95 mmol, 1 equiv) for biaryl phosphorinone, wherein all other reagents were scaled accordingly, and refluxing for 4 hours (1.38 g, 95 area % by HPLC, 81% yield). $^1$H NMR (400 MHz, CDCl$_3$) δ ppm 7.91 (d, J=2.0 Hz, 1H), 7.52-7.43 (m, 4H), 7.40-7.28 (m, 3H), 7.28-7.20 (m, 5H), 7.20-7.11 (m, 3H), 6.48 (d, J=2.0 Hz, 1H), 3.95-3.78 (m, 4H), 1.72 (t, J=14.3 Hz, 2H), 1.50-1.31 (m, 2H), 1.02 (dd, J=21.1, 19.0 Hz, 6H), −0.01 (d, J=12.0 Hz, 3H), −0.30 (d, J=11.9 Hz, 3H). $^{13}$C NMR (100 MHz, CDCl$_3$) δ ppm 149.9, 143.2 (d, J=27 Hz), 141.6, 140.5, 140.3, 131.9, 129.9, 129.0, 128.9, 128.7, 128.5, 128.4, 128.3, 128.3, 127.7, 127.6, 125.5, 121.1, 112.6 (d, J=5 Hz), 110.5, 64.7, 62.9, 43.6 (d, J=3.6 Hz), 30.6, 30.5, 30.1, 30.0, 29.5 (d, J=3 Hz), 29.2 (d, J=3 Hz), 29.0, 28.9. $^{31}$P NMR (CDCl$_3$, 202 MHz) δ ppm −16.0 (s). LRMS (ESI$^+$) found for [M+H, C$_{35}$H$_{38}$N$_4$O$_2$P]$^+$ 577.2.

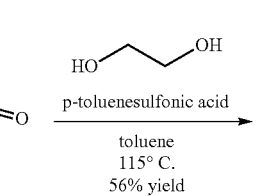

Example 7-m

1-Phenyl-5-(7,7,9,9-tetramethyl-1,4-dioxa-8-phosphaspiro[4.5]decan-8-yl)-1H-pyrazole The titled compound was prepared as described in the general procedure for the phosphorinone ketalization substituting 2,2,6,6-tetramethyl-1-(1-phenyl-1H-pyrazol-5-yl)phosphinan-4-one (1.04 g, 3.30 mmol, 1 equiv) for biaryl phosphorinone, wherein all other reagents were scaled accordingly, and refluxing for 15 hours (659 mg, 94 area % by HPLC, 56% yield). $^1$H NMR (400 MHz, CDCl$_3$) δ ppm 7.75 (t, J=3.2 Hz, 1H), 7.54-7.39 (m, 5H), 6.71 (dd, J=5.7, 1.1 Hz, 1H), 4.09-4.01 (m, 2H), 3.99-3.92 (m, 2H), 2.04 (dd, J=14.6, 5.1 Hz, 2H), 1.75-1.62 (m, 2H), 1.38 (s, 3H), 1.33 (s, 3H), 0.88 (s, 3H), 0.85 (s, 3H). $^{13}$C NMR (100 MHz, CDCl$_3$) δ ppm 140.1 (d, J=126 Hz), 139.3 (d, J=2 Hz), 128.1, 127.9, 127.8, 127.7, 112.5 (d, J=5 Hz), 110.3, 64.9, 63.1, 43.7 (d, J=4 Hz), 31.6, 31.4, 31.3, 31.2, 30.1, 29.7. $^{31}$P NMR (CDCl$_3$, 202 MHz) δ ppm −26.2 (s). HRMS (TOF-ESI$^+$) calcd for [M, C$_{20}$H$_{27}$N$_2$O$_2$P]$^+$ 358.1810. found 358.1814.

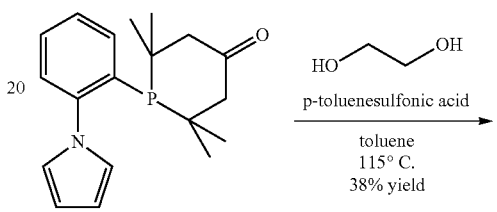

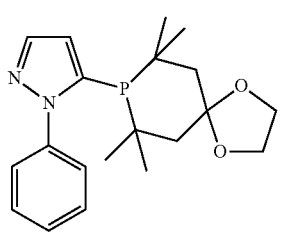

Example 7-n 1-(2-(7,7,9,9-Tetramethyl-1,4-dioxa-8-phosphaspiro[4.5]decan-8-yl)phenyl)-1H-pyrrole The titled compound was prepared as described in the general procedure for the phosphorinone ketalization substituting 1-(2-(1H-pyrrol-1-yl)phenyl)-2,2,6,6-tetramethylphosphinan-4-one (1.32 g, 4.21 mmol, 1 equiv) for biaryl phosphorinone, wherein all other reagents were scaled accordingly, and refluxing for 3 hours, followed by purification via silica gel column chromatography (40-g column; gradient: 1.5 column volumes heptane, ramp up to 85:15 heptane:ethyl acetate over 7 column volumes, hold at 85:15 for 3 column volumes) (572 mg, 98 area % by HPLC, 38% yield). $^1$H NMR (400 MHz, CDCl$_3$) δ ppm 7.67 (dd, J=5.2, 3.8 Hz, 1H), 7.40-7.25 (m, 2H), 7.21 (dddd, J=7.5, 5.7, 4.0, 2.0 Hz, 1H), 6.70 (dd, J=3.8, 2.0 Hz, 2H), 6.21 (t, J=2.1 Hz, 2H), 3.99-3.90 (m, 2H), 3.90-3.77 (m, 2H), 1.96 (dt, J=9.7, 4.9 Hz, 2H), 1.61 (dd, J=14.4, 5.7 Hz, 2H), 1.25 (s, 3H), 1.20 (s, 3H), 0.78 (s, 3H), 0.75 (s, 3H). $^{13}$C NMR (100 MHz, CDCl$_3$) δ 148.1 (d, J=28 Hz), 135.3 (d, J=35 Hz), 133.9 (d, J=4 Hz), 129.2, 128.0 (d, J=3 Hz), 127.0, 123.3 (d, J=3 Hz), 110.7, 108.1, 64.8, 63.2, 44.3 (d, J=2 Hz), 32.2, 31.8, 31.3, 31.1, 31.1, 31.0. $^{31}$P NMR (CDCl$_3$, 202 MHz) δ ppm −13.3 (s). LRMS (ESI$^+$) found for [M+H, C$_{21}$H$_{29}$NO$_2$P]$^+$ 358.1.

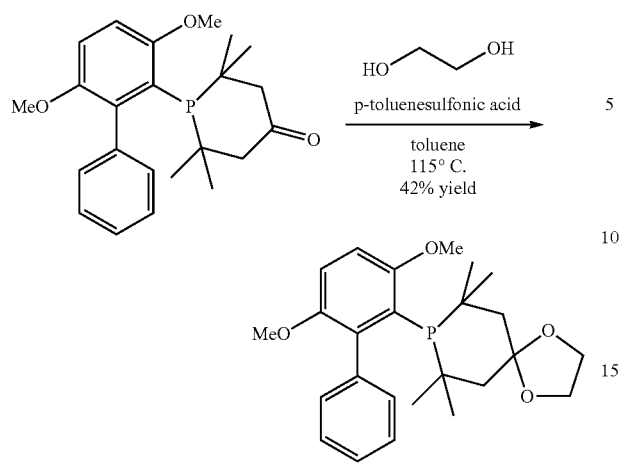

Example 7-o

8-(3,6-Dimethoxybiphenyl-2-yl)-7,7,9,9-tetramethyl-1,4-dioxa-8-phosphaspiro[4.5]decane The titled compound was prepared as described in the general procedure for the phosphorinone ketalization substituting 1-(3,6-dimethoxybiphenyl-2-yl)-2,2,6,6-tetramethylphosphinan-4-one (1.80 g, 4.67 mmol, 1 equiv) for biaryl phosphorinone, wherein all other reagents were scaled accordingly, and refluxing for 5 hours, followed by purification via silica gel column chromatography (80-g column; gradient: 1.5 column volumes heptane, ramp up to 80:20 heptane:ethyl acetate over 8.5 column volumes, hold at 80:20 over 6 column volumes) (1.27 mg, 88 area % by HPLC, 63% yield). $^1$H NMR (400 MHz, CDCl$_3$) δ ppm 7.37 (ddd, J=7.4, 4.4, 1.3 Hz, 2H), 7.33-7.27 (m, 1H), 7.08-7.02 (m, 2H), 6.97-6.90 (m, 1H), 6.79 (d, J=8.9 Hz, 1H), 3.98 (dd, J=9.8, 3.6 Hz, 2H), 3.88 (dd, J=9.6, 3.5 Hz, 1H), 3.80 (s, 3H), 3.63 (s, 3H), 2.21 (d, J=13.3 Hz, 2H), 1.55 (dd, J=13.3, 6.2 Hz, 1H), 1.22 (s, 3H), 1.16 (s, 3H), 0.82 (d, J=9.3 Hz, 6H). $^{13}$C NMR (100 MHz, CDCl$_3$) δ ppm 154.5 (d, J=3 Hz), 151.1 (d, J=11 Hz), 142.7 (d, J=41 Hz), 139.6 (d, J=12 Hz), 130.6 (d, J=5 Hz), 126.8, 126.2 (d, J=45 Hz), 125.8, 112.8, 112.1, 107.8, 64.7, 62.9, 56.5, 54.2, 45.6 (d, J=4 Hz), 33.9, 33.4, 31.7, 31.6 (d, J=1 Hz), 31.4. $^{31}$P NMR (CDCl$_3$, 202 MHz) δ ppm −5.6 (s). HRMS (TOF-ESI$^+$) calcd for [M, C$_{25}$H$_{33}$O$_4$P]$^+$ 428.2117. found 428.2122.

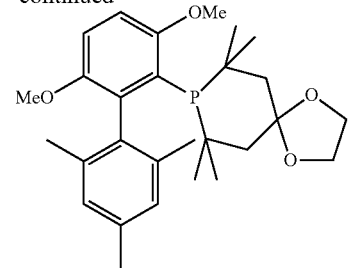

Example 7-p

8-(3,6-Dimethoxy-2',4',6'-trimethylbiphenyl-2-yl)-7,7,9,9-tetramethyl-1,4-dioxa-8-phosphaspiro[4.5]decane The titled compound was prepared as described in the general procedure for the phosphorinone ketalization substituting 1-(3,6-dimethoxy-2',4',6'-trimethylbiphenyl-2-yl)-2,2,6,6-tetramethylphosphinan-4-one (1.39 g, 3.25 mmol, 1 equiv) for biaryl phosphorinone, wherein all other reagents were scaled accordingly, and refluxing for ~14.5 hours, followed by purification via silica gel column chromatography (80-g column; gradient: 1.5 column volumes heptane, ramp up to 80:20 heptane: ethyl acetate over 8.5 column volumes, hold at 80:20 over 4 column volumes) (644 mg, >99 area % by HPLC, 42% yield). $^1$H NMR (400 MHz, CDCl$_3$) δ ppm 6.93 (d, J=8.9 Hz, 1H), 6.85 (s, 2H), 6.79 (d, J=8.9 Hz, 1H), 4.01-3.95 (m, 2H), 3.93-3.86 (m, 2H), 3.79 (s, 3H), 3.62 (s, 3H), 2.33 (s, 3H), 2.21 (d, J=13.5 Hz, 2H), 1.95 (s, 6H), 1.57 (dd, J=13.3, 6.4 Hz, 2H), 1.24 (s, 3H), 1.18 (s, 3H), 0.86 (d, J=8.8 Hz, 6H). $^{13}$C NMR (100 MHz, CDCl$_3$) δ ppm 154.7, 151.3 (d, J=11 Hz), 140.7 (d, J=41 Hz), 135.4, 135.4 (d, J=1 Hz), 134.8 (d, J=10 Hz), 127.1, 126.0 (d, J=45 Hz), 112.5, 111.8, 107.7, 77.3, 77.0, 76.7, 64.6, 62.9, 56.3, 54.1, 46.2 (d, J=4 Hz), 34.5, 34.1, 32.1, 31.9, 30.8 (d, J=4 Hz), 21.6, 21.4 (d, J=3 Hz). $^{31}$P NMR (CDCl$_3$, 202 MHz) δ ppm 0.1 (s). HRMS (TOF-ESI$^+$) calcd for [M, C$_{28}$H$_{39}$O$_4$P]$^+$ 470.2586. found 470.2590.

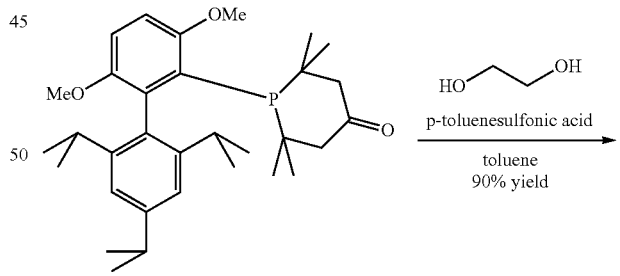

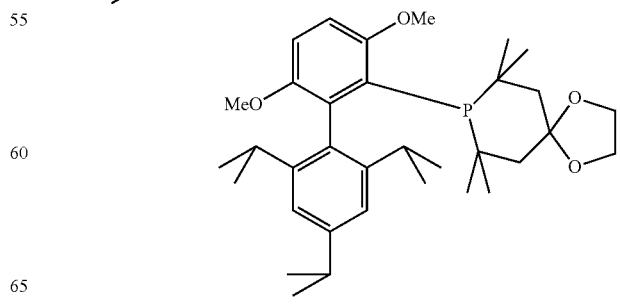

Example 7-q

7,7,9,9-Tetramethyl-8-(2',4',6'-triisopropyl-3,6-dimethoxybiphenyl-2-yl)-1,4-dioxa-8-phosphaspiro[4.5]decane

The titled compound was prepared as described in the general procedure for the phosphorinone ketalization substituting 2,2,6,6-tetramethyl-1-(2',4',6'-triisopropyl-3,6-dimethoxybiphenyl-2-yl)phosphinan-4-one (1.10 g, 2.15 mmol, 1 equiv) for biaryl phosphorinone, wherein all other reagents were scaled accordingly, and refluxing for ~15.6 hours, followed by purification via silica gel column chromatography (80-g column; gradient: 2 column volumes heptane, ramp up to 80:20 heptane:ethyl acetate over 8 column volumes, hold at 80:20 over 6 column volumes) (1.08 g, 94 area % by HPLC, 90% yield). $^1$H NMR (CDCl$_3$, 400 MHz), δ ppm 6.99 (s, 2H), 6.91-6.77 (m, 2H), 4.02 (dd, J=9.6, 3.4 Hz, 2H), 3.92 (dd, J=9.6, 3.5 Hz, 2H), 3.83 (s, 3H), 3.59 (s, 3H), 2.98 (hept, J=6.8 Hz, 1H), 2.51 (hept, J=6.7 Hz, 1H), 2.21 (d, J=13.2 Hz, 2H), 1.59 (dd, J=13.2, 6.4 Hz, 2H), 1.35 (d, J=6.9 Hz, 3H), 1.25 (dd, J=15.1, 8.3 Hz, 6H), 0.96 (d, J=6.7 Hz, 6H), 0.88 (d, J=8.7 Hz, 6H). $^{13}$C NMR (100 MHz, CDCl$_3$) δ ppm 154.2, 152.0 (d, J=12 Hz), 146.4, 145.5 (d, J=2 Hz), 140.3 (d, J=42 Hz), 132.3 (d, J=9 Hz), 127.0 (d, J=46 Hz), 119.8, 111.8), 110.8, 107.2, 64.7, 62.9, 54.6, 54.0, 46.8 (d, J=4 Hz), 34.4, 34.0, 33.9, 32.8, 32.5, 30.7, 30.7, 30.7, 25.5, 24.3, 24.2. $^{31}$P NMR (CDCl$_3$, 202 MHz), δ ppm −0.7 (br s). HRMS (TOF-ESI$^+$) calcd for [M, C$_{34}$H$_{51}$O$_4$P]$^+$554.3525. found 554.3528.

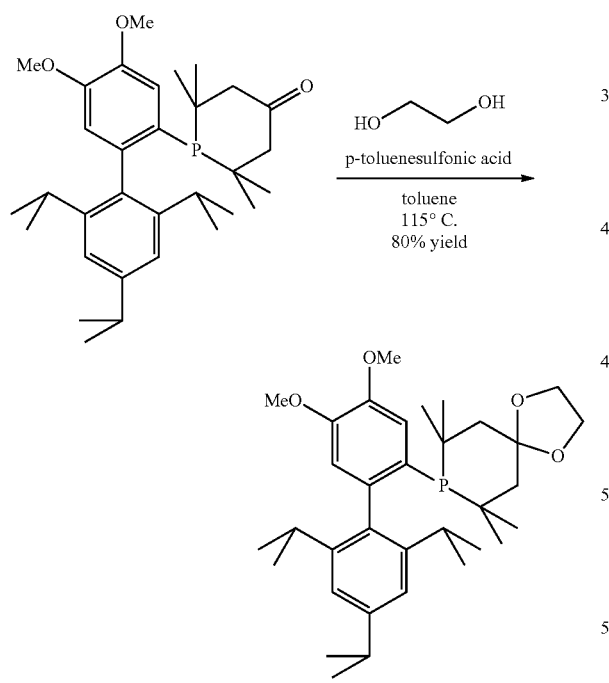

Example 7-r

7,7,9,9-Tetramethyl-8-(2',4',6'-triisopropyl-4,5-dimethoxybiphenyl-2-yl)-1,4-dioxa-8-phosphaspiro[4.5]decane

The titled compound was prepared as described in the general procedure for the phosphorinone ketalization substituting 2,2,6,6-tetramethyl-1-(2',4',6'-triisopropyl-4,5-dimethoxybiphenyl-2-yl)phosphinan-4-one (670 mg, 1.31 mmol, 1 equiv) for biaryl phosphorinone, wherein all other reagents were scaled accordingly, and refluxing for ~15.5 hours, followed by purification via silica gel column chromatography (80-g column; gradient: 2 column volumes heptane, ramp up to 78:22 heptane:ethyl acetate over 8 column volumes, hold at 78:22 over 2 column volumes). The title compound was isolated as a white solid (585 mg, 85 area % by HPLC, 80% yield). $^1$H NMR (CDCl$_3$, 400 MHz), δ ppm 6.99 (s, 2H), 6.91-6.77 (m, 2H), 4.02 (dd, J=9.6, 3.4 Hz, 2H), 3.92 (dd, J=9.6, 3.5 Hz, 2H), 3.83 (s, 3H), 3.59 (s, 3H), 2.98 (hept, J=6.8 Hz, 1H), 2.51 (hept, J=6.7 Hz, 1H), 2.21 (d, J=13.2 Hz, 2H), 1.59 (dd, J=13.2, 6.4 Hz, 2H), 1.35 (d, J=6.9 Hz, 3H), 1.25 (dd, J=15.1, 8.3 Hz, 6H), 0.96 (d, J=6.7 Hz, 6H), 0.88 (d, J=8.7 Hz, 6H). $^{13}$C NMR (100 MHz, CDCl$_3$) δ ppm 148.0, 147.0, 146.1, 145.8, 142.5 (d, J=38 Hz), 136.4 (d, J=6 Hz), 127.4 (d, J=29 Hz), 120.3, 116.0 (d, J=3 Hz), 115.1 (d, J=8 Hz), 110.5, 64.9, 63.2, 56.0, 55.7, 45.5 (d, J=2 Hz), 34.2, 32.6, 32.4, 32.3 (d, J=4 Hz), 32.1, 31.2 (d, J=7 Hz), 30.5, 29.3, 26.6, 24.3, 23.5, 23.0, 14.5. $^{31}$P NMR (CDCl$_3$, 202 MHz), δ ppm −0.7 (br s). HRMS (TOF-ESI$^+$) calcd for [M, C$_{34}$H$_{51}$O$_4$P]$^+$ 554.3525. found 554.3533.

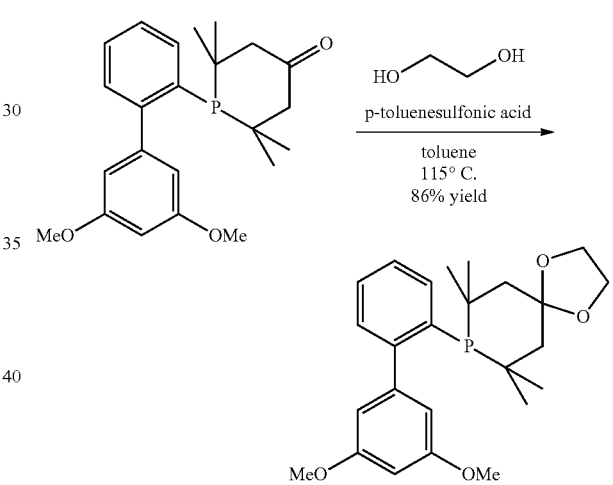

Example 7-s

8-(3',5'-Dimethoxybiphenyl-2-yl)-7,7,9,9-tetramethyl-1,4-dioxa-8-phosphaspiro[4.5]decane

The titled compound was prepared as described in the general procedure for the phosphorinone ketalization substituting 1-(3',5'-dimethoxybiphenyl-2-yl)-2,2,6,6-tetramethylphosphinan-4-one (1.28 g, 3.33 mmol, 1 equiv) for biaryl phosphorinone, wherein all other reagents were scaled accordingly, and refluxing for ~15.5 hours (1.23 g, >99 area % by HPLC, 86% yield). $^1$H NMR (400 MHz, CDCl$_3$) δ ppm 7.82-7.74 (m, 1H), 7.42-7.23 (m, 3H), 6.47 (t, J=2.3 Hz, 1H), 6.41 (d, J=2.3 Hz, 2H), 4.08-4.01 (m, 2H), 4.00-3.94 (m, 2H), 3.84 (s, 6H), 2.12 (dd, J=14.3, 2.4 Hz, 2H), 1.71 (dd, J=14.3, 5.5 Hz, 2H), 1.34 (s, 3H), 1.29 (s, 3H), 0.91 (s, 3H), 0.89 (s, 3H). $^{13}$C NMR (100 MHz, CDCl$_3$) δ ppm 159.2, 151.2 (d, J=35 Hz), 145.3 (d, J=9 Hz), 135.1 (d, J=31 Hz), 133.5 (d, J=4 Hz), 130.0 (d, J=6 Hz), 128.1, 126.2, 110.9, 108.7 (d, J=4 Hz), 98.6, 64.8, 63.2, 55.4, 44.5, 32.3, 31.9, 31.6, 31.4, 31.4, 31.3. $^{31}$P NMR (CDCl$_3$, 202 MHz), δ ppm −8.5 (br s). HRMS (TOF-ESI⁺) calcd for [M, $C_{25}H_{33}O_4P$]⁺ 428.2117. found 428.2121.

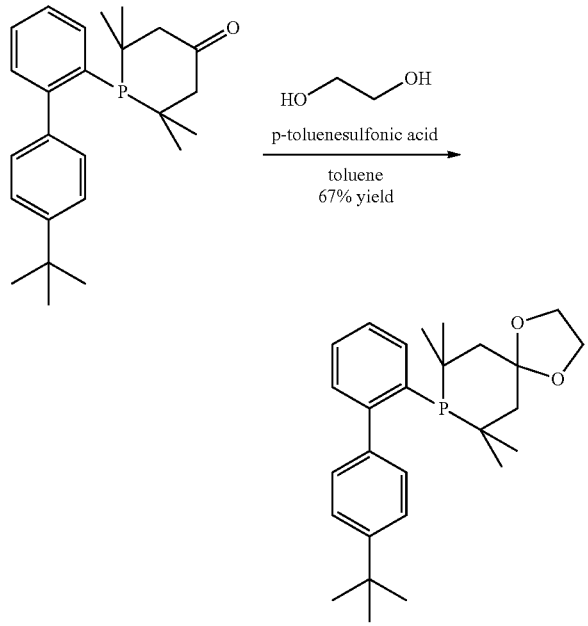

Example 7-t 8-(4'-tert-Butylbiphenyl-2-yl)-7,7,9,9-tetramethyl-1,4-dioxa-8-phosphaspiro[4.5]decane The titled compound was prepared as described in the general procedure for the phosphorinone ketalization substituting 1-(4'-tert-butylbiphenyl-2-yl)-2,2,6,6-tetramethylphosphinan-4-one (1.49 g, 3.92 mmol, 1 equiv) for biaryl phosphorinone, wherein all other reagents were scaled accordingly, and refluxing for ~15 hours (1.12 g, 93 area % by HPLC, 67% yield). ¹H NMR (400 MHz, CDCl₃) δ ppm 7.82-7.75 (m, 1H), 7.42-7.33 (m, 3H), 7.33-7.24 (m, 2H), 7.24-7.17 (m, 2H), 4.12-4.01 (m, 2H), 4.01-3.88 (m, 2H), 2.13 (dd, J=14.3, 1.9 Hz, 2H), 1.69 (dd, J=14.3, 5.5 Hz, 2H), 1.42 (s, 9H), 1.34 (s, 3H), 1.29 (s, 3H), 0.88 (d, J=10.0 Hz, 6H). ¹³C NMR (100 MHz, CDCl₃) δ ppm 151.3 (d, J=34 Hz), 148.4, 140.1 (d, J=8 Hz), 135.1 (d, J=31 Hz), 133.6 (d, J=4 Hz), 130.9 (d, J=6 Hz), 130.1 (d, J=5 Hz), 128.1, 125.9, 123.9, 110.9, 64.8, 63.1, 44.5, 34.7, 32.3, 31.9, 31.7, 31.7, 31.5, 31.3, 31.3. ³¹P NMR (CDCl₃, 202 MHz), δ ppm −9.4 (br s). HRMS (TOF-ESI⁺) calcd for [M, $C_{27}H_{37}O_2P$]⁺ 424.2531. found 424.2539.

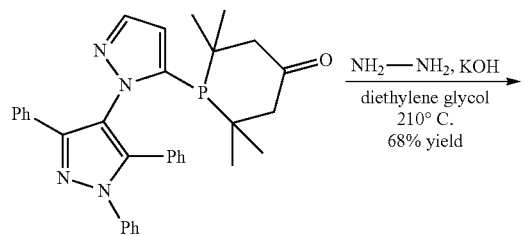

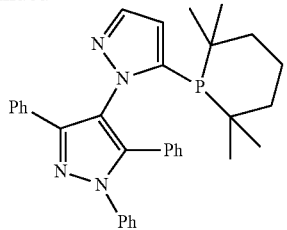

Example 8

1',3',5'-Triphenyl-5-(2,2,6,6-tetramethylphosphinan-1-yl)-1'H-1,4'-bipyrazole

A round bottom flask was charged with 2,2,6,6-tetramethyl-1-(1',3',5'-triphenyl-1'H-1,4'-bipyrazol-5-yl)phosphinan-4-one (1.25 g, 2.35 mmol, 1.0 equiv) and purged with nitrogen for 15 minutes. Then nitrogen-sparged diethylene glycol (12.3 mL, 129 mmol, 55 equiv) was added and the flask was equipped with a Claisen adapter and a Dean-Stark trap. The mixture was charged with hydrazine hydrate (1.07 mL, 11.7 mmol, 5 equiv, 55 wt % hydrazine) and potassium hydroxide (658 mg, 11.7 mmol, 5 equiv). The mixture was immersed in an oil bath at 125° C. under a nitrogen atmosphere. The temperature of the bath was increased to 210° C. over 1 hour and kept at that temperature for 7 hours. The reaction mixture was cooled to room temperature under a positive pressure of nitrogen, and then diluted with heptane (10 mL) and ethyl acetate (10 mL). The phases were partitioned, and the aqueous layer was collected. The aqueous layer was then washed with ethyl acetate (2×20 mL), and the combined organic fractions were washed once with aqueous saturated sodium chloride (50 mL), dried over sodium sulfate, filtered, and concentrated on a rotary evaporator. The crude concentrate was dissolved in a minimal amount of hot ethanol, and the solution was allowed to cool, effecting the crystallization of the product as a white solid. (826 mg, 95 area % by HPLC, 68% yield). ¹H NMR (400 MHz, CDCl₃) δ ppm 7.91 (d, J 1.9 Hz, 1H), 7.52-7.42 (m, 4H), 7.38-7.26 (m, 3H), 7.25-7.19 (m, 5H), 7.19-7.11 (m, 3H), 6.61 (d, J=1.8 Hz, 1H), 1.53 (dd, J=14.1, 12.0 Hz, 5H), 1.21 (ddd, J=24.9, 11.7, 5.7 Hz, 2H), 0.85 (dd, J=24.4, 18.8 Hz, 6H), 0.01 (d, J=11.6 Hz, 3H), −0.27 (d, J=11.5 Hz, 3H). ¹³C NMR (100 MHz, CDCl₃) δ ppm 149.3 (d, J=2 Hz), 145.0, 143.2 (d, J=27 Hz), 141.0 (d, J=2 Hz), 139.8, 139.6 (d, J=2 Hz), 131.5, 129.5, 128.5, 128.3, 128.0, 127.9, 127.8, 127.3, 127.2, 125.1, 120.9, 113.0 (d, J=5 Hz), 37.1 (dd, J=8, 2 Hz), 29.9, 29.8, 29.3 (d, J=2 Hz), 29.2 (d, J=2 Hz), 29.1 (d, J=2 Hz), 28.8 (d, J=2 Hz), 28.8 (d, J=8 Hz), 20.2. ³¹P NMR (CDCl₃, 202 MHz) δ ppm −17.0 (s). LRMS (ESI⁺) found for [M+H, $C_{33}H_{36}N_4P$]⁺ 519.2.

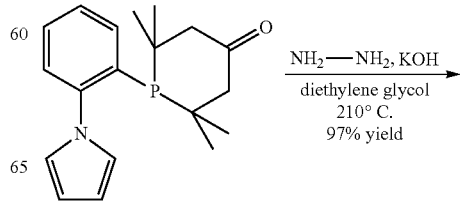

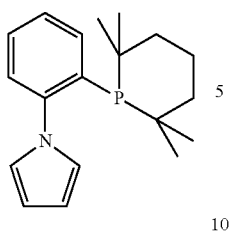

Example 9

1-(2-(2,2,6,6-Tetramethylphosphinan-1-yl)phenyl)-1H-pyrrole

A round bottom flask was charged with 1-(2-(1H-pyrrol-1-yl)phenyl)-2,2,6,6-tetramethylphosphinan-4-one (878 mg, 2.80 mmol, 1.0 equiv) and purged with nitrogen for 15 minutes. Then nitrogen-sparged diethylene glycol (14.7 mL, 154 mmol, 55 equiv) was added and the flask was equipped with a Claisen adapter and a Dean-Stark trap. The flask was further charged with hydrazine hydrate (1.24 mL, 14.0 mmol, 5 equiv, 55 wt % hydrazine) and potassium hydroxide (786 mg, 14.0 mmol, 5 equiv), and the mixture was immersed in an oil bath at 60° C. The temperature of the bath was gradually increased to 210° C. over 1 hour and kept at that temperature for 7 hours. The reaction mixture was cooled to room temperature under a positive pressure of nitrogen and then diluted with water (50 mL) and ethyl acetate (20 mL). The phases were partitioned, and the organic layer was collected. The aqueous layer was washed with ethyl acetate (4×20 mL), and the combined organic fractions were washed once with aqueous saturated sodium chloride, dried over sodium sulfate, filtered, and concentrated on a rotary evaporator to afford the title compound as a pale yellow solid (811 mg, 91 area % by HPLC, 97% yield). $^1$H NMR (400 MHz, CDCl$_3$) δ ppm 7.96-7.83 (m, 1H), 7.35-7.22 (m, 2H), 7.22-7.17 (m, 1H), 6.72-6.66 (m, 2H), 6.20 (t, J=2.1 Hz, 2H), 1.87-1.71 (m, 2H), 1.71-1.56 (m, 2H), 1.50-1.33 (m, 2H), 1.11 (s, 3H), 1.06 (s, 3H), 0.76 (d, J=9.7 Hz, 6H). $^{13}$C NMR (100 MHz, CDCl$_3$) δ ppm 149.4-146.8 (m), 134.7 (d, J=4 Hz), 129.0, 127.8 (d, J=3 Hz), 126.5, 123.3 (d, J=3 Hz), 107.9, 37.6, 31.4, 31.1, 30.2 (d, J=7 Hz), 29.6 (d, J=18 Hz), 20.5. $^{31}$P NMR (CDCl$_3$, 202 MHz) δ ppm −7.6 (s).

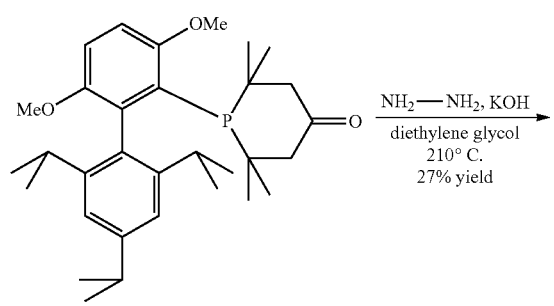

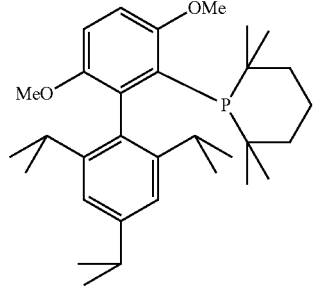

Example 10

2,2,6,6-Tetramethyl-1-(2',4',6'-triisopropyl-3,6-dimethoxybiphenyl-2-yl)phosphinane

A round bottom flask was charged with 2,2,6,6-tetramethyl-1-(2',4',6'-triisopropyl-3,6-dimethoxybiphenyl-2-yl)phosphinan-4-one (1.03 g, 2.02 mmol, 1.0 equiv) and purged with nitrogen for 15 minutes. Then nitrogen-sparged diethylene glycol (10.6 mL, 111 mmol, 55 equiv) was added and the flask was equipped with a Claisen adapter and a Dean-Stark trap. The flask was charged with hydrazine hydrate (0.892 mL, 10.1 mmol, 5 equiv, 55 wt % hydrazine) and potassium hydroxide (918 mg, 10.1 mmol, 5 equiv). The mixture was immersed in an oil bath at 170° C. The temperature of the bath was gradually increased to 210° C. over 1 hour and kept at that temperature for 7 hours. The reaction mixture was cooled to room temperature under a positive pressure of nitrogen. Reaction material that had condensed on the Claisen adapter was washed down into the reaction flask with ethyl acetate (5 mL). The phases were partitioned, and the organic layer was collected. The aqueous layer was washed with ethyl acetate (2×20 mL). The combined organic fractions were washed once with aqueous saturated sodium chloride, dried over sodium sulfate, filtered, and concentrated on a rotary evaporator. Purification of the crude material by silica gel column chromatography on an Isco CombiFlash system (40-g column; gradient: 2 column volumes heptane, ramp up to 85:15 heptane:ethyl acetate over 8 column volumes, hold at 85:15 for 4 column volumes) afforded the title compound as a white solid (266 mg, >99 area % by HPLC, 27% yield). $^1$H NMR (400 MHz, CDCl$_3$) δ ppm 6.95 (s, 2H), 6.85 (d, J=8.8 Hz, 1H), 6.79 (d, J=8.8 Hz, 1H), 3.82 (s, 3H), 3.56 (s, 3H), 2.95 (hept, J=6.9 Hz, 1H), 2.49 (hept, J=6.7 Hz, 2H), 2.10-1.89 (m, 2H), 1.71-1.51 (m, 2H), 1.45-1.26 (m, 8H), 1.21 (d, J=6.8 Hz, 6H), 1.14 (s, 3H), 1.08 (s, 3H), 0.93 (d, J=6.7 Hz, 6H), 0.80 (d, J=8.6 Hz, 6H). $^{13}$C NMR (100 MHz, CDCl$_3$) δ ppm 154.3, 151.9 (d, J=11 Hz), 146.3, 145.5 (d, J=2 Hz), 140.1 (d, J=42 Hz), 132.5 (d, J=9 Hz), 127.7 (d, J=46 Hz), 119.7, 110.6, 107.1, 54.3 (d, J=62 Hz), 40.8 (d, J=4 Hz), 34.0 (d, J=5 Hz), 33.4, 30.7, 30.3 (d, J=24 Hz), 30.1 (d, J=3 Hz), 25.5, 24.2 (d, J=13 Hz), 20.8. $^{31}$P NMR (CDCl$_3$, 202 MHz) δ ppm −6.0 (br s). HRMS (TOF-ESI$^+$) calcd for [M, C$_{32}$H$_{49}$O$_2$P]$^+$ 496.3470. found 496.3465.

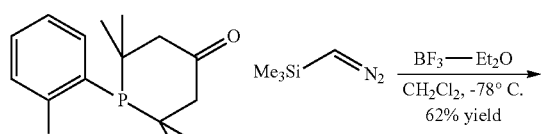 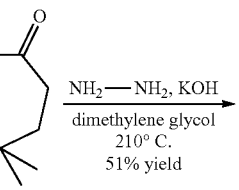

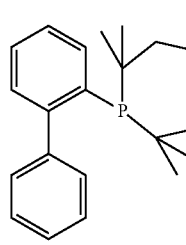 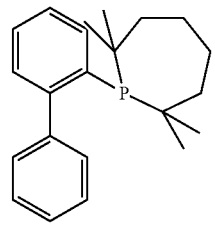

Example 11

1-(Biphenyl-2-yl)-2,2,7,7-tetramethylphosphepan-4-one

To a 40-mL scintillation vial equipped with a magnetic stir bar was added 1-(biphenyl-2-yl)-2,2,6,6-tetramethylphosphinan-4-one (900 mg, 2.77 mmol, 1 equiv). The vial was sealed with a septa-top cap and then purged with nitrogen gas for 10 minutes. The solid was then dissolved with anhydrous, degassed dichloromethane (9 mL). In a separate 250-mL round bottom flask was added anhydrous, degassed dichloromethane (31 mL) which was cooled to −78° C. Boron trifluoride diethyl etherate (527 μL, 4.16 mmol, 1.5 equiv) was then added to the flask. The phosphine solution was transferred by cannula to the reaction flask over the course of 3 minutes using a positive pressure of nitrogen gas. After stirring the solution for 5 minutes, (trimethylsilyl)diazomethane (2.1 mL, 4.16 mmol, 1.5 equiv, 2 M in hexane) was added slowly over 3 minutes The bright yellow solution was stirred at −78° C. for an hour, and then diluted with 1 M aqueous hydrochloric acid (50 mL). The slurry was warmed to room temperature overnight. The solution was charged into a separatory funnel and the phases were partitioned. The dichloromethane layer was collected, and the aqueous layer was washed with dichloromethane (3×20 mL). The combined organic layers were then washed with aqueous saturated sodium bicarbonate (50 mL), dried over sodium sulfate, filtered, and concentrated in a rotary evaporator. Purification of the crude product oil by silica gel column chromatography on an Isco CombiFlash system (120-g column; gradient: 1.5 column volumes heptane, ramp up to 98:2 heptane:methyl tert-butyl ether over 0.5 column volumes, hold at 98:2 for 2 column volumes, ramp up to 75:25 heptane:methyl tert-butyl ether over 8 column volumes, hold at 75:25 for 2 column volumes) afforded the title compound as a white solid (578 mg, 98 area % by HPLC, 62% yield). $^1$H NMR (400 MHz, CDCl$_3$) δ ppm 7.88 (dt, J=7.8, 1.5 Hz, 1H), 7.47-7.32 (m, 5H), 7.32-7.27 (m, 1H), 7.26-7.20 (m, 2H), 2.91 (dd, J=12.2, 7.6 Hz, 1H), 2.67-2.46 (m, 3H), 2.17-2.04 (m, 1H), 1.91 (dddd, J=21.9, 15.4, 6.4, 4.7 Hz, 1H), 1.20 (d, J=5.0 Hz, 3H), 1.16 (d, J=5.5 Hz, 3H), 1.02 (d, J=13.6 Hz, 3H), 0.98 (d, J=13.6 Hz, 3H). $^{13}$C NMR (100 MHz, CDCl$_3$) δ ppm 211.3, 151.5 (d, J=34 Hz), 143.2, 134.6 (d, J=3 Hz), 133.1 (d, J=29 Hz), 130.5 (d, J=6 Hz), 130.0 (d, J=4 Hz), 128.7, 126.9, 126.3, 125.7, 55.7 (d, J=17 Hz), 41.5, 37.0 (d, J=18 Hz), 35.2, 35.0, 33.2, 32.9, 32.6, 32.3, 31.9, 31.6, 27.3, 26.3. $^{31}$P NMR (CDCl$_3$, 202 MHz) δ ppm 15.1 (s). HRMS (TOF-ESI$^+$) calcd for [M, C$_{22}$H$_{27}$OP]$^+$ 338.1800. found 338.1805.

Example 12

1-(Biphenyl-2-yl)-2,2,7,7-tetramethylphosphepane

A round bottom flask was charged with 1-(biphenyl-2-yl)-2,2,7,7-tetramethylphosphepan-4-one (520 mg, 1.54 mmol, 1.0 equiv) and purged with nitrogen for 15 minutes. Then nitrogen-sparged diethylene glycol (8.0 mL, 85 mmol, 55 equiv) was added and the flask was equipped with a Claisen adapter and a Dean-Stark trap. The mixture was charged with hydrazine hydrate (0.680 mL, 7.68 mmol, 5 equiv, 55 wt % hydrazine) and potassium hydroxide (431 mg, 7.68 mmol, 5 equiv). The mixture was immersed in an oil bath at 175° C. The temperature of the bath was gradually increased to 210° C. over 30 minutes and kept at that temperature for 7 hours. The reaction mixture was cooled to room temperature under a positive pressure of nitrogen, and the reaction mixture was diluted with water (10 mL) and heptane (30 mL). The phases were partitioned, and the organic layer was collected. The aqueous layer was washed with heptane (2×20 mL). The combined organic fractions were washed once with aqueous saturated sodium chloride (20 mL), dried over sodium sulfate, filtered, and concentrated on a rotary evaporator. The crude product was crystallized from a saturated solution of ethanol and isolated by filtration to afford an off-white solid (254 mg, 90 area % by HPLC, 51% yield). $^1$H NMR (400 MHz, CDCl$_3$) δ ppm 8.03-7.95 (m, 1H), 7.47-7.27 (m, 8H), 1.88-1.54 (m, 8H), 1.26 (d, J=4.0 Hz, 6H), 0.96 (s, 3H), 0.92 (s, 3H). $^{13}$C NMR (100 MHz, CDCl$_3$) δ ppm 150.8 (d, J=34 Hz), 143.5 (d, J=7 Hz), 136.3 (d, J=3 Hz), 134.8 (d, J=32 Hz), 130.3 (d, J=4 Hz), 130.2 (d, J=6 Hz), 127.9, 126.7, 125.9, 125.3, 45.1 (d, J=18 Hz), 35.2, 34.9, 32.3, 32.0, 28.1 (d, J=3 Hz), 25.6 (d, J=3 Hz). $^{31}$P NMR (CDCl$_3$, 202 MHz) δ ppm 14.4 (s). HRMS (TOF-ESI$^+$) calcd for [M, C$_{22}$H$_{29}$P]$^+$ 324.2007. found 324.2004.

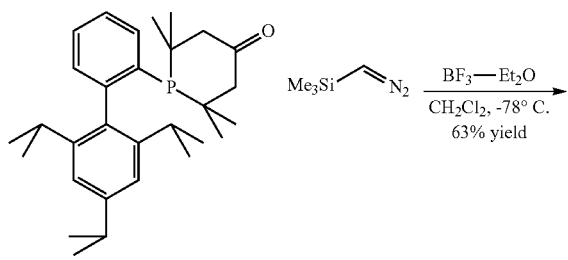

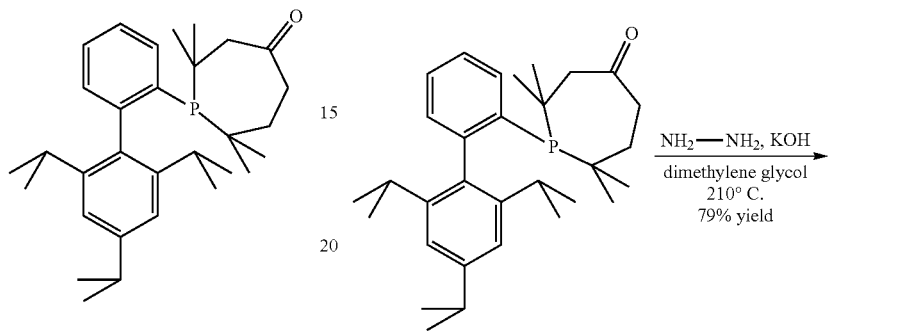

Example 13

2,2,7,7-Tetramethyl-1-(2',4',6'-triisopropylbiphenyl-2-yl)phosphepan-4-one

To a 40-mL scintillation vial equipped with a magnetic stir bar was added 2,2,6,6-tetramethyl-1-(2',4',6'-triisopropylbiphenyl-2-yl)phosphinan-4-one (1.38 g, 3.06 mmol, 1 equiv). The vial was sealed with a septa-top cap and then purged with nitrogen gas for 10 minutes The solid was then dissolved with anhydrous, degassed dichloromethane (10 mL). In a separate 250-mL round bottom flask was added anhydrous, degassed dichloromethane (36 mL) which was cooled to −78° C. Boron trifluoride diethyl etherate (582 µL, 4.59 mmol, 1.5 equiv) was then added to the flask. The phosphine solution was transferred by cannula to the reaction flask over the course of 3 minutes using a positive pressure of nitrogen gas. After stirring the solution for 5 minutes, (trimethylsilyl)diazomethane (2.3 mL, 4.59 mmol, 1.5 equiv, 2 Min hexane) was added slowly over 3 minutes The bright yellow solution was stirred at −78° C. for an hour, then diluted with 1 M aqueous hydrochloric acid (50 mL). The slurry was warmed to room temperature overnight. The solution was charged into a separatory funnel and the phases were partitioned. The organic layer was collected and washed with aqueous saturated sodium bicarbonate (50 mL), dried over sodium sulfate, filtered, and concentrated in a rotary evaporator. Purification of the crude colorless oil by silica gel column chromatography on an Isco CombiFlash system (120-g column; gradient: 1.5 column volumes heptane, ramp up to 98:2 heptane:methyl tert-butyl ether over 0.5 column volumes, hold at 98:2 for 2 column volumes, ramp up to 80:20 heptane:methyl tert-butyl ether over 8 column volumes, hold at 80:20 for 2 column volumes) afforded the title compound as a white solid (900 mg, 90 area % by HPLC, 63% yield). $^1$H NMR (400 MHz, CDCl$_3$) δ ppm 8.00-7.90 (m, 1H), 7.43-7.29 (m, 2H), 7.28-7.21 (m, 1H), 7.00 (s, 2H), 3.10-2.86 (m, 2H), 2.73-2.37 (m, 5H), 2.34-2.18 (m, 1H), 1.95-1.77 (m, 1H), 1.31 (d, J=6.9 Hz, 5H), 1.23 (d, J=6.8 Hz, 3H), 1.20 (d, J=6.8 Hz, 3H), 1.15 (d, J=6.6 Hz, 3H), 1.10 (d, J=6.4 Hz, 3H), 1.08-1.03 (m, 4H), 1.02-0.98 (m, 4H), 0.95 (d, J=6.7 Hz, 3H). $^{13}$C NMR (100 MHz, CDCl$_3$) δ ppm 211.3, 148.6 (d, J=35 Hz), 147.5, 145.8 (d, J=16 Hz), 136.1 (d, J=6 Hz), 135.5 (d, J=31 Hz), 134.3 (d, J=2 Hz), 132.6 (d, J=7 Hz), 127.8, 125.5, 120.1 (d, J=5 Hz), 56.5 (d, J=10 Hz), 41.5, 36.3 (d, J=10 Hz), 35.0 (d, J=24 Hz), 34.3, 33.3 (d, J=27 Hz), 32.2 (d, J=31 Hz), 31.9 (dd, J=6, 2 Hz), 30.7, 29.5 (d, J=5 Hz), 29.3 (d, J=3 Hz), 26.7 (d, J=33 Hz), 24.3 (d, J=8 Hz), 22.9 (d, J=9 Hz). $^{31}$P NMR (CDCl$_3$, 202 MHz) δ ppm 18.3 (s). HRMS (TOF-ESI$^+$) calcd for [M, C$_{31}$H$_{45}$OP]$^+$ 464.3208. found 464.3216.

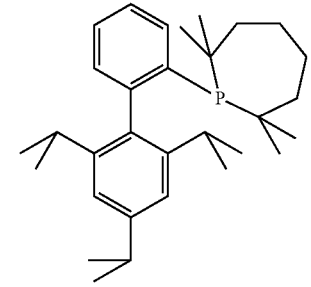

Example 14

2,2,7,7-Tetramethyl-1-(2',4',6'-triisopropylbiphenyl-2-yl)phosphepane

A round bottom flask was charged with 2,2,7,7-tetramethyl-1-(2',4',6'-triisopropylbiphenyl-2-yl)phosphepan-4-one (1.06 g, 2.29 mmol, 1.0 equiv) and purged with nitrogen for 15 minutes. Nitrogen-sparged diethylene glycol (12.0 mL, 126 mmol, 55 equiv) was added and the flask was equipped with a Claisen adapter and a Dean-Stark trap. The mixture was charged with hydrazine hydrate (1.01 mL, 11.4 mmol, 5 equiv, 55 wt % hydrazine) and potassium hydroxide (641 mg, 11.4 mmol, 5 equiv). The mixture was immersed in an oil bath at 175° C. under a nitrogen atmosphere. The temperature of the bath was gradually increased to 210° C. over 40 minutes and kept at that temperature for 7 hours. The reaction mixture was cooled to room temperature under a positive pressure of nitrogen and then the reaction mixture was diluted with heptane (20 mL) and ethyl acetate (20 mL). The phases were partitioned, and the organic layer was collected. The aqueous layer was washed with ethyl acetate (3×20 mL). The combined organic fractions were washed once with aqueous saturated sodium chloride (50 mL), dried over sodium sulfate, filtered, and concentrated on a rotary evaporator. The crude product was purified by silica gel column chromatography (80-g column; gradient: 1.5 column volumes heptane, ramp up to 92:8 heptane:ethyl acetate over 8.5 column volumes, hold at 92:8 for 2 column volumes) to afford the title compound as a white solid (810 mg, >99 area % by HPLC, 79% yield). $^1$H NMR (400 MHz, CDCl$_3$) δ ppm 8.00-7.83 (m, 1H), 7.33-7.26 (m, 2H), 7.22-7.13 (m, 1H), 6.97 (s, 2H), 2.91 (hept, J=6.9 Hz, 1H), 2.48 (hept, J=6.7 Hz, 2H), 1.77-1.60 (m, 6H), 1.60-1.47 (m, 2H), 1.29 (d, J=6.9 Hz, 6H), 1.21 (dd, J=8.2, 4.4 Hz, 12H), 0.96 (d, J=6.7 Hz, 6H), 0.82 (s, 3H), 0.78 (s, 3H). $^{13}$C NMR (100 MHz, CDCl$_3$) δ ppm 148.0, 147.7, 147.2, 145.8, 137.0 (d, J=34 Hz), 136.7, 136.2 (d, J=2 Hz), 131.7 (d, J=7 Hz), 126.9, 125.1, 119.9, 46.3 (d, J=17 Hz), 35.1, 34.8, 34.3, 32.1, 31.9, 31.1 (d, J=3 Hz), 28.8 (d, J=3 Hz), 26.7, 26.2 (d, J=3 Hz), 24.4, 22.9 (d, J=2 Hz). $^{31}$P NMR (CDCl$_3$, 202 MHz) δ ppm 20.1 (s). HRMS (TOF-ESI$^+$) calcd for [M, C$_{31}$H$_{47}$P]$^+$ 450.3415. found 450.3429.

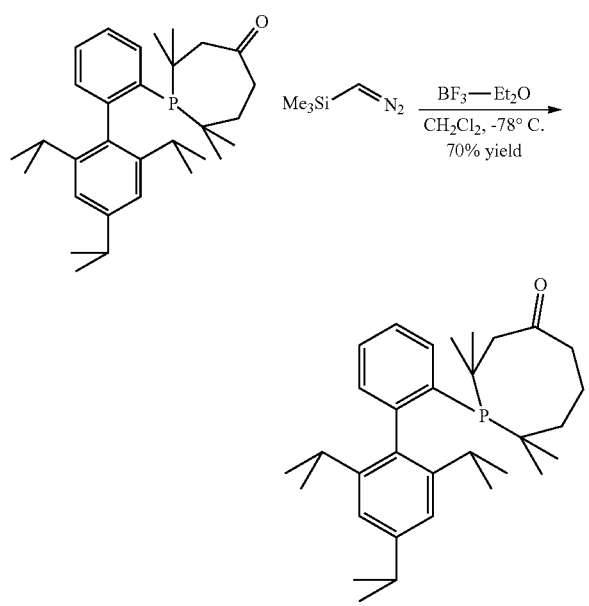

Example 15

2,2,8,8-Tetramethyl-1-(2',4',6'-triisopropylbiphenyl-2-yl)phosphocan-4-one

To a 250-mL round bottom flask equipped with a magnetic stir bar was added 2,2,7,7-tetramethyl-1-(2',4',6'-triisopropylbiphenyl-2-yl)phosphepan-4-one (1.24 g, 2.67 mmol, 1 equiv). The flask was sealed with a septum and purged with nitrogen gas for 10 minutes The solid was dissolved with anhydrous, degassed dichloromethane (38 mL), and the solution was cooled to −78° C. Boron trifluoride diethyl etherate (507 μL, 4.00 mmol, 1.5 equiv) was added to the flask over the course of 3 minutes After stirring the solution for 5 minutes, (trimethylsilyl)diazomethane (2.0 mL, 4.00 mmol, 1.5 equiv, 2 M in hexane) was added slowly over 3 minutes The bright yellow solution was stirred at −78° C. for an hour, then diluted with 1 M aqueous hydrochloric acid (50 mL). The slurry was warmed to room temperature overnight. The solution was charged into a separatory funnel and the phases were partitioned. The organic layer was collected, and the aqueous layer was washed with dichloromethane (2×20 mL). The combined organic fractions were then washed with aqueous saturated sodium bicarbonate (30 mL), dried over sodium sulfate, filtered, and concentrated via a rotary evaporator. Purification by silica gel column chromatography on an Isco CombiFlash system (120-g column; gradient: 1.5 column volumes heptane, ramp up to 90:10 heptane:ethyl acetate over 8.5 column volumes, hold at 90:10 for 4 column volumes) afforded the title compound as a white solid (905 mg, >99 area % by HPLC, 71% yield). $^1$H NMR (400 MHz, CDCl$_3$) δ ppm 7.87-7.80 (m, 1H), 7.37-7.27 (m, 2H), 7.22 (ddd, J=4.2, 3.3, 1.9 Hz, 1H), 6.97 (dd, J=7.3, 1.8 Hz, 2H), 3.09-2.97 (m, 1H), 2.92 (dq, J=13.7, 6.9 Hz, 1H), 2.75-2.54 (m, 2H), 2.46-2.30 (m, 2H), 2.24 (dq, J=15.0, 5.7 Hz, 1H), 1.98-1.77 (m, 2H), 1.65 (tdd, J=13.5, 9.4, 3.9 Hz, 1H), 1.55-1.41 (m, 4H), 1.30 (d, J=6.9 Hz, 6H), 1.27 (t, J=4.5 Hz, 6H), 1.17 (d, J=6.8 Hz, 3H), 1.01 (d, J=6.6 Hz, 3H), 0.95 (d, J=6.7 Hz, 3H), 0.90 (d, J=12.2 Hz, 3H), 0.74 (d, J=16.4 Hz, 3H). $^{13}$C NMR (100 MHz, CDCl$_3$) δ ppm 213.9, 148.5, 148.1, 147.4, 145.9, 145.6, 136.9 (d, J=2 Hz), 136.1 (d, J=5 Hz), 134.9, 134.6, 132.2 (d, J=7 Hz), 127.6, 124.9, 120.0 (d, J=14 Hz), 59.7 (d, J=27 Hz), 42.9 (d, J=12 Hz), 42.6, 36.9 (d, J=31 Hz), 36.0 (d, J=28 Hz), 34.3, 31.8 (d, J=14 Hz), 31.2 (d, J=4 Hz), 31.0, 30.3 (d, J=26 Hz), 29.0 (d, J=4 Hz), 27.1, 26.4-26.0 (m), 24.4 (d, J=7 Hz), 23.2-22.8 (m), 21.3 (d, J=7 Hz). $^{31}$P NMR (CDCl$_3$, 202 MHz) δ ppm 10.5 (s). HRMS (TOF-ESI$^+$) calcd for [M, C$_{32}$H$_{47}$OP]$^+$ 478.3365. found 478.3369.

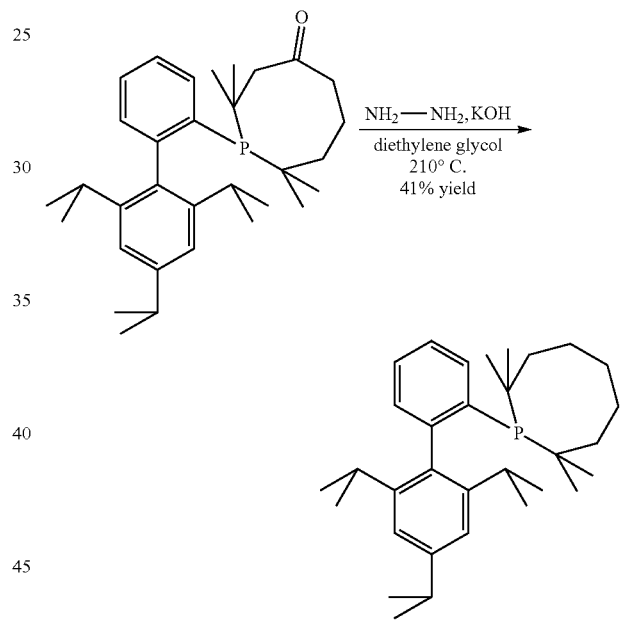

Example 16

2,2,8,8-Tetramethyl-1-(2',4',6'-triisopropylbiphenyl-2-yl)phosphocane

A round bottom flask was charged with 2,2,8,8-tetramethyl-1-(2',4',6'-triisopropylbiphenyl-2-yl)phosphocan-4-one (1.25 g, 2.61 mmol, 1.0 equiv) and purged with nitrogen for 15 minutes. Nitrogen-sparged diethylene glycol (13.7 mL, 144 mmol, 55 equiv) was added, and the flask was equipped with a Claisen adapter and a Dean-Stark trap. The mixture was charged with hydrazine hydrate (1.16 mL, 13.1 mmol, 5 equiv, 55 wt % hydrazine) and potassium hydroxide (733 mg, 13.1 mmol, 5 equiv). The mixture was immersed in an oil bath at 160° C. under a nitrogen atmosphere. The temperature of the bath was gradually increased to 210° C. over 30 minutes and kept at that temperature for 7 hours. The reaction mixture was cooled to room temperature under a positive pressure of nitrogen overnight. The Claisen adapter was washed with ethyl acetate (30 mL). The phases were partitioned, and the organic layer was collected. The aqueous layer was washed with ethyl acetate (3×20 mL), and the combined organic fractions were washed once with water (50 mL) and aqueous saturated sodium chloride (50 mL), dried over sodium sulfate, filtered, and concentrated on a rotary evaporator. The purified product was triturated from hot methanol and collected by filtration to afford the title compound as a white solid (499 mg, 92 area % by HPLC, 41% yield). $^1$H NMR (400 MHz, CDCl$_3$) δ ppm 7.96-7.87 (m, 1H), 7.33-7.26 (m, 2H), 7.23-7.17 (m, 1H), 6.97 (s, 2H), 3.00-2.85 (m, 1H), 2.61-2.44 (m, 2H), 1.91-1.61 (m, 5H), 1.61-1.41 (m, 5H), 1.39 (d, J=2.5 Hz, 6H), 1.31 (d, J=6.9 Hz, 6H), 1.23 (d, J=6.8 Hz, 6H), 0.98 (d, J=6.7 Hz, 6H), 0.74 (d, J=15.0 Hz, 6H). $^{13}$C NMR (100 MHz, CDCl$_3$) δ ppm 148.2 (d, J=35 Hz), 147.1, 145.8, 137.3, 136.8 (d, J=8 Hz), 136.6 (d, J=21 Hz), 132.0 (d, J=7 Hz), 126.9, 124.6, 119.8, 43.8 (d, J=18 Hz), 36.3 (d, J=30 Hz), 34.3, 31.1, 31.0 (d, J=18 Hz), 28.3 (d, J=4 Hz), 26.8 (d, J=11 Hz), 26.7, 24.4, 23.1 (d, J=2 Hz), 22.4 (d, J=6 Hz). $^{31}$P NMR (CDCl$_3$, 202 MHz) δ ppm 10.5 (s). HRMS (TOF-ESI) calcd for [M, C$_{32}$H$_{49}$P]$^+$ 464.3572. found 464.3584.

Assay Yield Calculation for Examples 17-29.

Product standards were determined using commercially available or purified material. The product standard of interest was weighed into a volumetric flask (Wt$_{std}$) and dissolved in the appropriate volume of acetonitrile (Vol$_{std}$). A sample was injected into an HPLC instrument and the area corresponding to the product was recorded (A$_{std}$). The mass of the crude reaction solution following filtration and rinse was obtained (Wt$_{pdt}$). A sample of known mass (Wt$_{sample}$) was taken from the bulk solution and added to a volumetric flask, then diluted in acetonitrile (Vol$_{soln}$). A sample was then injected into an HPLC instrument, recording the area corresponding to the product (A$_{soln}$). The assay yield of product was then determined using the following formula.

$$\text{Assay yield (\%)} = \frac{A_{soln} \times Vol_{soln} \times Wt_{std} \times Wt_{pdt} \times 100}{A_{std} \times Wt_{sample} \times Vol_{std} \times \text{theoretical yield}}$$

Unless noted otherwise, the following HPLC method was used for reaction analyses for Examples 17-29.

Mobile phase A: 0.1% HClO$_4$ in water (volume/volume).

Mobile phase B: acetonitrile.

Column: Ascentis® Express C8 2.7 μm, 4.6 mm×150 mm.

Flow rate: 1.25 mL/minute.

Column temperature: 40° C.

Monitor at 210 nm.

| Time (minutes) | % A | % B |
|---|---|---|
| 0 | 40% | 60% |
| 6 | 5% | 95% |
| 10 | 5% | 95% |
| 11 | 40% | 60% |

Example 17-1

Palladium-Catalyzed C—N Cross-Coupling of an Aryl Nonaflate with Methylsulfonamide

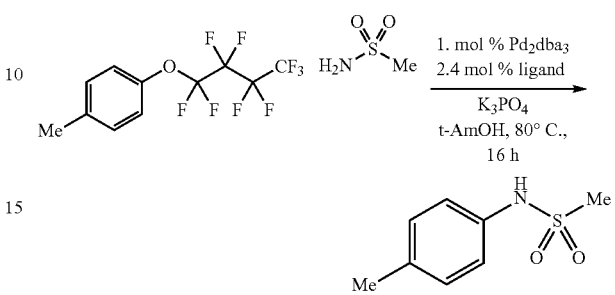

N-p-tolylmethanesulfonamide

In a nitrogen-atmosphere glovebox, a microwave vial equipped with a magnetic stir bar was charged with potassium phosphate (71.6 mg, 0.337 mmol, 1.1 equivalents), tris(dibenzylideneacetone)dipalladium(0) (Pd$_2$dba$_3$) (2.8 mg, 0.00307 mmol, 0.01 equivalents) and phosphine ligand (0.00736 mmol, 0.024 equivalents). t-Amyl alcohol (1.1 mL) was syringed into the vial and the mixture was stirred for 30 minutes at 80° C. After cooling to room temperature, methanesulfonamide (35.0 mg, 0.368 mmol, 1.2 equivalents) and p-methylbenzene nonaflate (100 mg, 0.307 mmol, 1 equivalent) were added to the reaction solution. The vial was sealed with a crimp top and placed in a heating block at 80° C. After 16 hours, the reaction was cooled to room temperature and brought out of the glovebox. The reaction solution was diluted with CH$_2$Cl$_2$ (2 mL) and filtered through a pad of diatomaceous earth. The vial was rinsed with CH$_2$Cl$_2$ (2×2 mL), then the filter cake was washed with CH$_2$Cl$_2$ (2×2 mL). The filtrate was transferred to a tared flask and concentrated on a rotary evaporator to furnish an orange oil. The crude concentrate was sampled for a wt % analysis. Purified material could be isolated as an off-white solid by silica gel flash column chromatography (30 g silica gel, gradient from 85:15 to 70:30 heptane:ethyl acetate) (literature reference: Shekhar S, et al. J. Org. Chem. 2011; 76: 4552-4563). $^1$H NMR (400 MHz, CDCl$_3$) δ ppm 7.22-7.07 (m, 4H), 6.57 (br s, 1H), 2.99 (s, 3H), 2.34 (s, 3H).

| Ligand | Assay Yield (%)$^a$ |
|---|---|
| 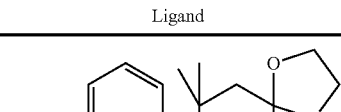 | >99 (92) |

| Ligand | Assay Yield (%)ᵃ |
|---|---|
| 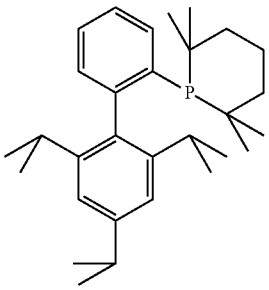 [SMILES: CC(C)c1cc(C(C)C)c(-c2ccccc2P2C(C)(C)CCCC2(C)C)c(C(C)C)c1] | >99 |
| | 87 |
| Ligand | Assay Yield (%)ᵃ |
|---|---|
| 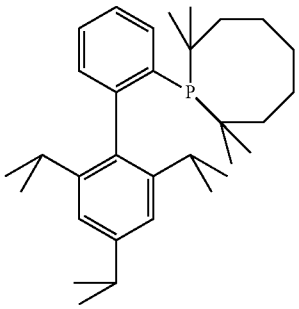 [SMILES: CC(C)c1cc(C(C)C)c(-c2ccccc2P2C(C)(C)CCCCCC2(C)C)c(C(C)C)c1] | 79 |
Other examples of palladium-catalyzed coupling reactions of aryl and alkyl primary sulfonamides with various aryl and heteroaryl nonaflates catalyzed by the disclosed ligands include the following:
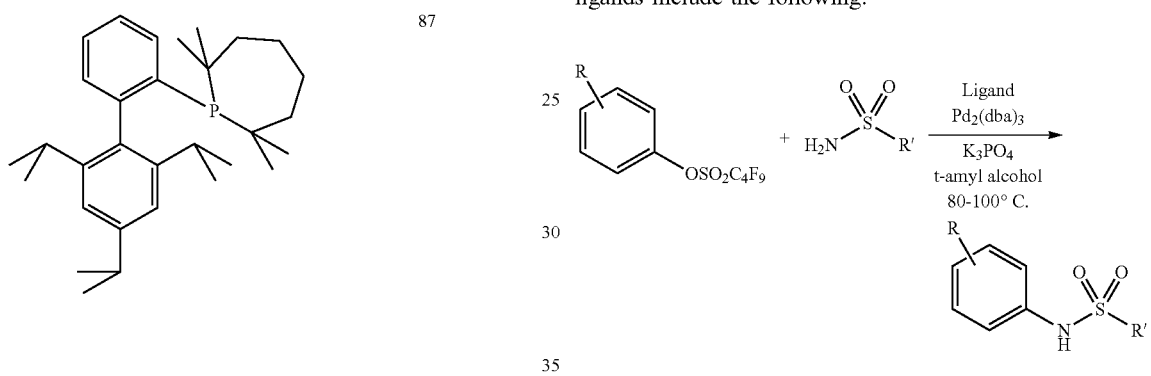
| Example | R | R' | Product | Yield |
|---|---|---|---|---|
| 17-2 | Me | 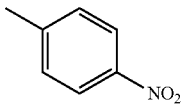 | 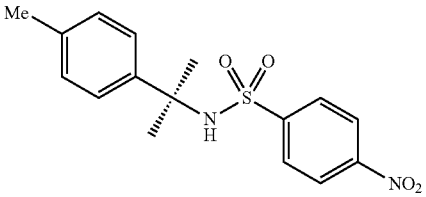 | 82% |
| 17-3 | Me | 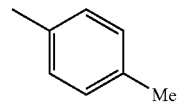 | 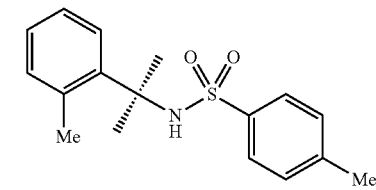 | 96% |
| 17-4 | 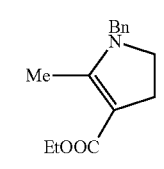 | 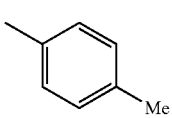 | 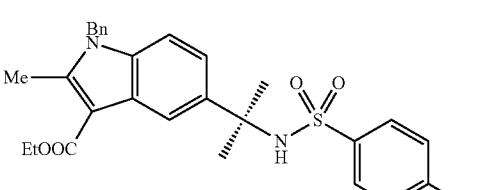 | 88% |

-continued

| Example | R | R' | Product | Yield |
|---|---|---|---|---|
| 17-5 | Me | 4-hydroxyphenyl | | 83% |
| 17-6 | BocHN | 4-methylphenyl | | 92% |
| 17-7 | pyridin-3-yl | 4-methylphenyl | | 80% |
| 17-8 and 17-9 | R = H, R = Me | 4-methylphenyl | | R = H, 82% R = Me, 86% |
| 17-10 | Me | tert-butyl | | 86% |

Example 17-11

Preparation of N-(6-(3-tert-butyl-5-(2,4-dioxo-3,4-dihydropyrimidin-1 (2H)-yl)-2-methoxyphenyl) naphthalen-2-yl)methanesulfonamide (compound (A-1))

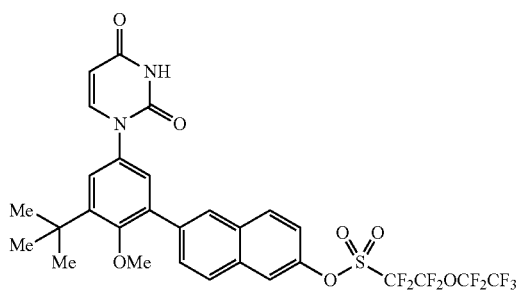

+

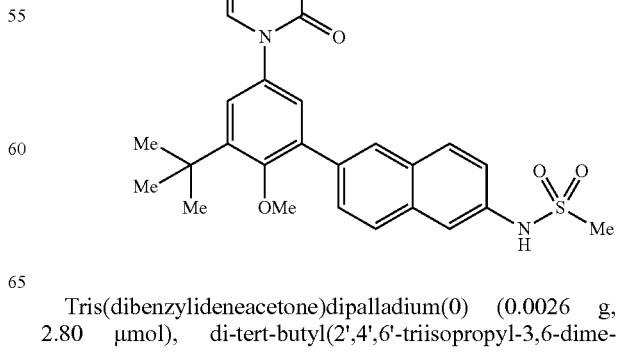

Tris(dibenzylideneacetone)dipalladium(0) (0.0026 g, 2.80 μmol), di-tert-butyl(2',4',6'-triisopropyl-3,6-dimethoxybiphenyl-2-yl)phosphine (0.0033 g, 6.72 μmol) and milled potassium phosphate tribasic (0.131 g, 0.616 mmol) were charged to a 40-mL reaction vial inside an inert atmosphere glove box. 2-Methyltetrahydrofuran (1.5 mL) was added, the vial was capped, and the contents were heated to 80° C. and stirred at this temperature for 30 minutes. The reaction mixture was cooled down to room temperature. 6-(3-tert-Butyl-5-(2,4-dioxo-3,4-dihydropyrimidin-1 (2H)-yl)-2-methoxyphenyl)naphthalen-2-yl 1,1,2,2-tetrafluoro-2-(perfluoroethoxy)ethanesulfonate (0.4 g, 0.560 mmol, Example 3-7, compound (5f)), methanesulfonamide (0.064 g, 0.672 mmol) and ethyl acetate (3 mL) were added to the 40-mL reaction vial. The temperature of the closed vial was raised to 90° C. and the contents were magnetically stirred for 16 hours. HPLC analysis of the reaction mixture showed that the product was formed in 97 area % at 210 nm.

Example 17-12

Alternative Preparation of N-(6-(3-tert-butyl-5-(2,4-dioxo-3,4-dihydropyrimidin-1 (2H)-yl)-2-methoxyphenyl)naphthalen-2-yl)methanesulfonamide (compound (A-1))

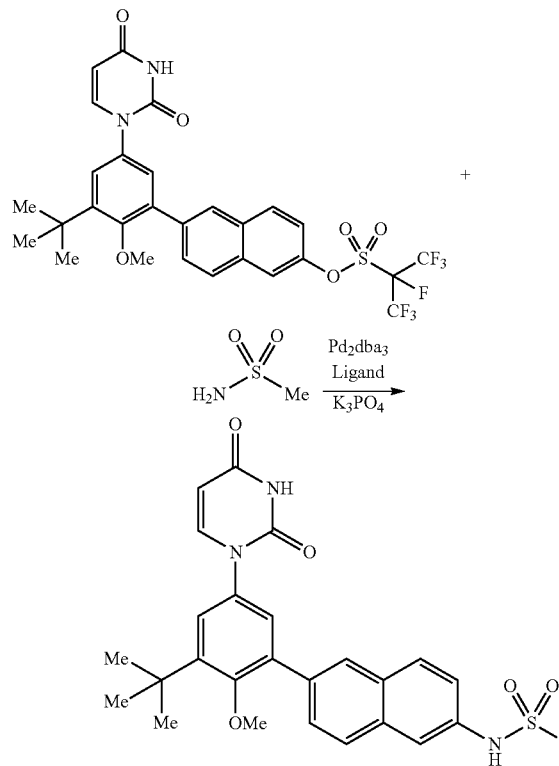

Tris(dibenzylideneacetone)dipalladium(0) (0.0071 g, 7.71 μmol), di-tert-butyl(2',4',6'-triisopropyl-3,6-dimethoxybiphenyl-2-yl)phosphine (0.0089 g, 19.0 μmol) and milled potassium phosphate tribasic (0.360 g, 1.696 mmol) were charged to a 40-mL reaction vial inside an inert atmosphere glove box. 2-Methyltetrahydrofuran (4 mL) was added, and the closed vial and its contents were heated to 80° C. with magnetic stirring for 30 minutes. The reaction mixture was cooled down to room temperature. 6-(3-tert-Butyl-5-(2,4-dioxo-3,4-dihydropyrimidin-1 (2H)-yl)-2-methoxyphenyl)naphthalen-2-yl 1,1,1,2,3,3,3-heptafluoropropane-2-sulfonate (1.0 g, 1.542 mmol, Example 3-4, compound (5c)), methanesulfonamide (0.176 g, 1.850 mmol) and ethyl acetate (8 mL) were added to the 40-mL reaction vial. The temperature of the closed vial and its contents was raised to 90° C. and stirred for 20 hours. HPLC analysis of the reaction mixture showed that the product was formed in 95 area % at 210 nm.

Example 17-13

Alternative Preparation of N-(6-(3-tert-butyl-5-(2,4-dioxo-3,4-dihydropyrimidin-1 (2H)-yl)-2-methoxyphenyl)naphthalen-2-yl)methanesulfonamide (compound (A-1))

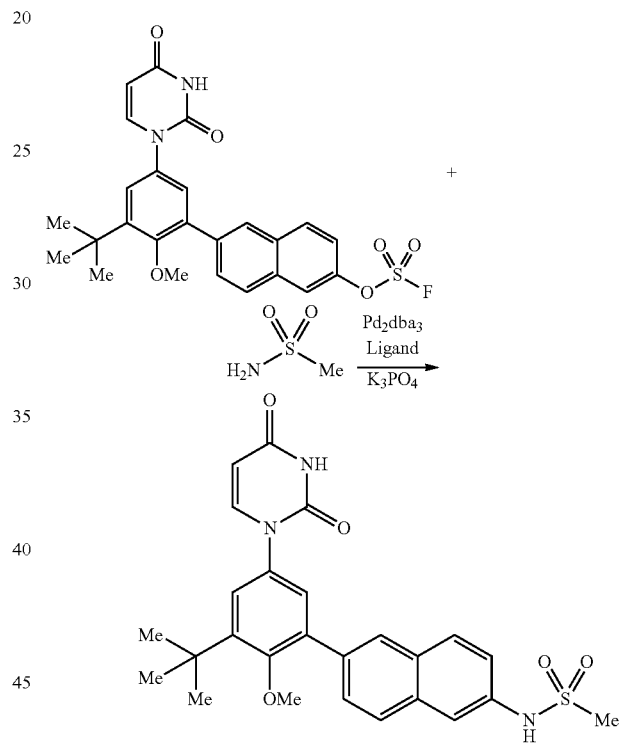

Tris(dibenzylideneacetone)dipalladium(0) (0.0055 g, 6.02 μmol), di-tert-butyl(2',4',6'-triisopropyl-3,6-dimethoxybiphenyl-2-yl)phosphine (0.0070 g, 14.0 μmol) and milled potassium phosphate tribasic (0.281 g, 1.324 mmol) were charged to a 40-mL reaction vial inside an inert atmosphere glove box. 2-Methyltetrahydrofuran (3.4 mL) was added, and the closed vial and its contents were heated to 80° C. with magnetic stirring for 30 minutes. The reaction mixture was cooled down to room temperature. 6-(3-tert-Butyl-5-(2,4-dioxo-3,4-dihydropyrimidin-1(2H)-yl)-2-methoxyphenyl)naphthalen-2-yl sulfofluoridate (0.6 g, 1.204 mmol, Example 3-8, compound (5 g)), methanesulfonamide (0.137 g, 1.444 mmol) and ethyl acetate (6.7 mL) were added to the 40-mL reaction vial. The temperature of the closed reaction vial and its contents was raised to 90° C. and the contents were stirred for 20 hours. HPLC analysis of the reaction mixture showed that the product was formed in 79 area % at 210 nm.

Example 17-14

Alternative Preparation of N-(6-(3-tert-butyl-5-(2,4-dioxo-3,4-dihydropyrimidin-1 (2H)-yl)-2-methoxyphenyl)naphthalen-2-yl)methanesulfonamide (compound (A-I))

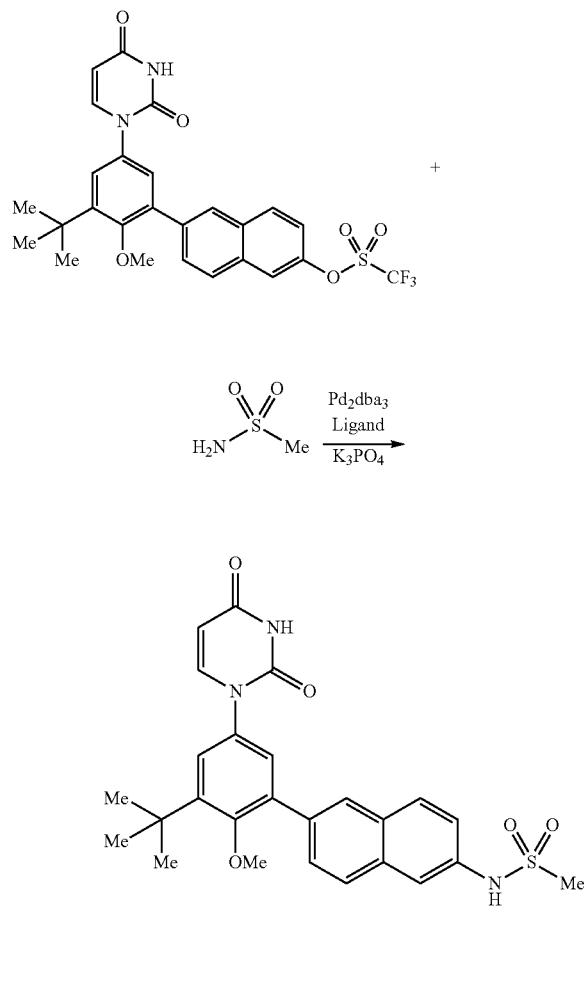

Example 17-15

Alternative Preparation of N-(6-(3-tert-butyl-5-(2,4-dioxo-3,4-dihydropyrimidin-1 (2H)-yl)-2-methoxyphenyl)naphthalen-2-yl)methanesulfonamide (compound (A-1))

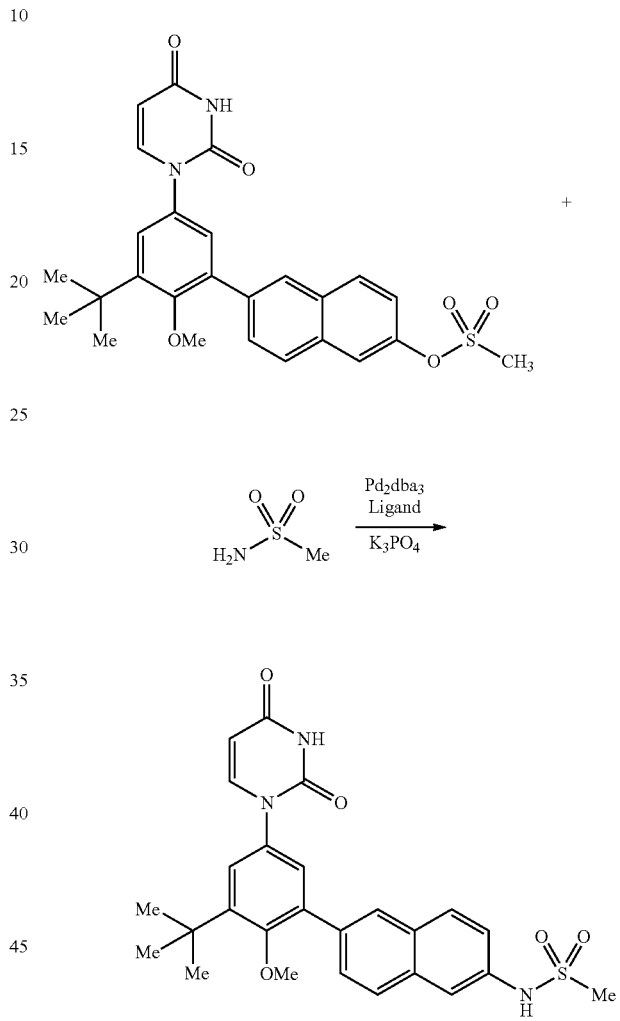

Tris(dibenzylideneacetone)dipalladium(0) (0.0042 g, 4.56 µmol), di-tert-butyl(2',4',6'-triisopropyl-3,6-dimethoxybiphenyl-2-yl)phosphine (0.0053 g, 12.0 µmol) and milled potassium phosphate tribasic (0.213 g, 1.003 mmol) were charged to a 40-mL reaction vial inside an inert atmosphere glove box. 2-Methyltetrahydrofuran (1.9 mL) was added, and the closed vial and its contents were heated to 80° C. with magnetic stirring for 30 minutes. The reaction mixture was cooled down to room temperature. 6-(3-tert-Butyl-5-(2,4-dioxo-3,4-dihydropyrimidin-1 (2H)-yl)-2-methoxyphenyl)naphthalen-2-yl trifluoromethanesulfonate (0.5 g, 0.912 mmol, Example 3-6, compound (5e)), methanesulfonamide (0.104 g, 1.094 mmol) and ethyl acetate (5.7 mL) were added to the 40-mL reaction vial. The temperature of the closed vial and its contents was raised to 90° C. and stirred for 14 hours. HPLC analysis of the reaction mixture showed that the product was formed in 91 area % at 210 nm.

Tris(dibenzylideneacetone)dipalladium(0) (0.0037 g, 4.04 µmol), di-tert-butyl(2',4',6'-triisopropyl-3,6-dimethoxybiphenyl-2-yl)phosphine (0.0047 g, 9.7 µmol) and milled potassium phosphate tribasic (0.094 g, 0.445 mmol) were charged to a 40-mL reaction vial inside an inert atmosphere glove box. tert-Amyl alcohol (1.0 mL) was added, the contents were heated to 80° C. and stirred at this temperature for 30 minutes. The reaction mixture was cooled down to room temperature. 6-(3-tert-Butyl-5-(2,4-dioxo-3,4-dihydropyrimidin-1(2H)-yl)-2-methoxyphenyl) naphthalen-2-yl methanesulfonate (0.2 g, 0.404 mmol), methanesulfonamide (0.046 g, 0.485 mmol) and tert-amyl alcohol (1.5 mL) were added to a 40-mL reaction vial. The reaction temperature was raised to 110° C., and the contents were stirred for 14 hours. HPLC analysis of the reaction mixture showed that the titled compound was formed in 7 area % at 210 nm.

Example 17-16

Alternative Preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

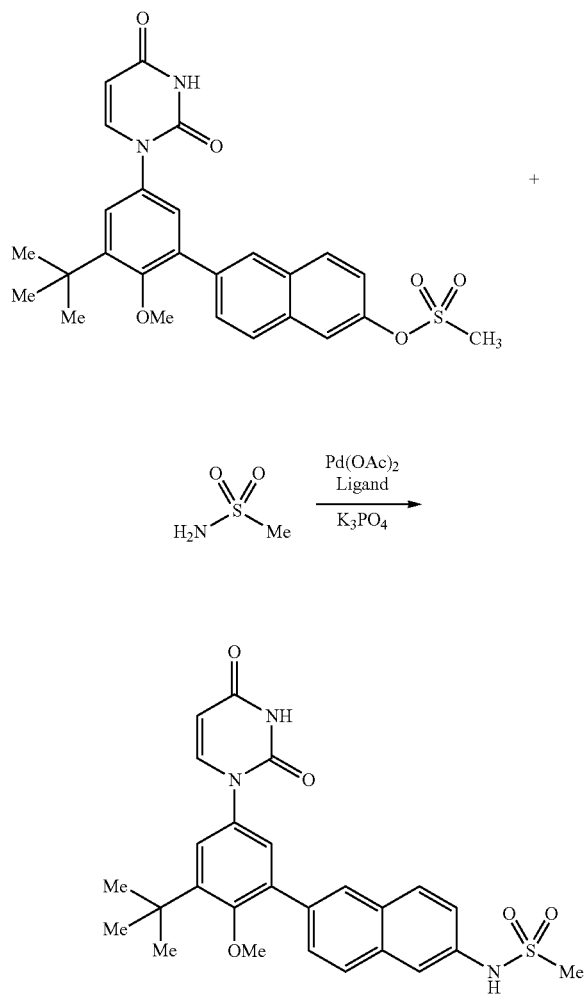

Palladium acetate (0.0018 g, 8.09 μmol), di-tert-butyl(2',4',6'-triisopropyl-3,6-dimethoxybiphenyl-2-yl)phosphine (0.0086 g, 0.018 mmol) and water (0.6 μL, 0.032 mmol) were charged to a 40-mL reaction vial inside an inert atmosphere glove box. tert-Amyl alcohol (1.0 mL) was added, and the contents were heated to 80° C. and stirred at this temperature for 15 minutes. The reaction mixture was cooled down to room temperature. Potassium phosphate tribasic (0.094 g, 0.445 mmol), 6-(3-tert-butyl-5-(2,4-dioxo-3,4-dihydropyrimidin-1(2H)-yl)-2-methoxyphenyl)naphthalen-2-yl methanesulfonate (0.2 g, 0.404 mmol), methanesulfonamide (0.046 g, 0.485 mmol) and tert-amyl alcohol (1.5 mL) were added to the 40-mL reaction vial. The reaction temperature was raised to 110° C., and the contents were stirred for 14 hours. HPLC analysis of the reaction mixture showed that the titled compound was formed in 5 area % at 210 nm.

Example 18

Palladium-Catalyzed C—O Cross-Coupling of a Primary Alcohol with an Aryl Chloride

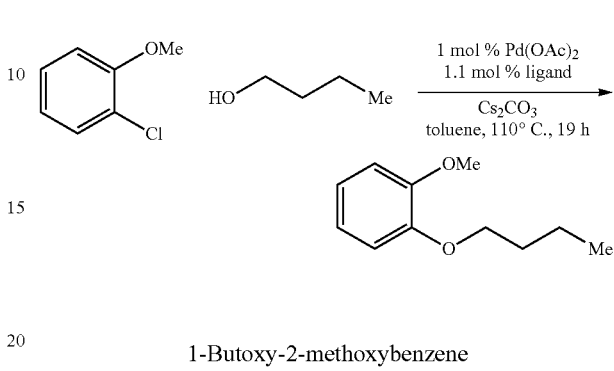

1-Butoxy-2-methoxybenzene

In a nitrogen-atmosphere glovebox, a 40-mL scintillation vial equipped with a magnetic stir bar was charged with palladium(II) acetate (3.2 mg, 0.014 mmol, 0.01 equivalents), 7,7,9,9-tetramethyl-8-(2',4',6'-triisopropyl-3,6-dimethoxybiphenyl-2-yl)-1,4-dioxa-8-phosphaspiro[4.5]decane (8.6 mg, 0.015 mmol, 0.011 equivalents) and cesium carbonate (686 mg, 2.10 mmol, 1.5 equivalents). The solids were then slurried in toluene (2.8 mL) and n-butanol (385 μL, 4.21 mmol, 3 equivalents). 2-Chloroanisole (178 μL, 1.40 mmol, 1 equivalent) was added by syringe, then the vial was sealed with a polytetrafluoroethylene (PTFE) screw cap septum and heated to 110° C. for 19 hours. After cooling the reaction to room temperature, the vial was brought outside the glovebox. The reaction mixture was diluted with ethyl acetate (2 mL) and filtered through a pad of diatomaceous earth. After the vial was rinsed with ethyl acetate (2×2 mL) and filtered, the filter cake was washed with ethyl acetate (2 mL). The ethyl acetate was carefully removed on a rotary evaporator. A weight percent (wt %) analysis was then performed on the crude concentrate to determine an assay yield of 62% (literature reference: Wolter M, et al. Org. Lett. 2002; 4: 973-976). $^1$H NMR (400 MHz, CDCl$_3$) δ ppm 6.96-6.84 (m, 4H), 4.03 (t, J=6.8 Hz, 2H), 3.87 (s, 3H), 1.91-1.78 (m, 2H), 1.57-1.44 (m, 2H), 0.99 (t, J=7.4 Hz, 3H).

| Ligand | Assay Yield (%)[a] |
|---|---|
| (structure shown) | 62 |

[a] Assay yield was determined by weight percent analysis versus isolated, characterized product.

Example 19

Palladium-catalyzed phenylurea coupling 4-chlorotoluene

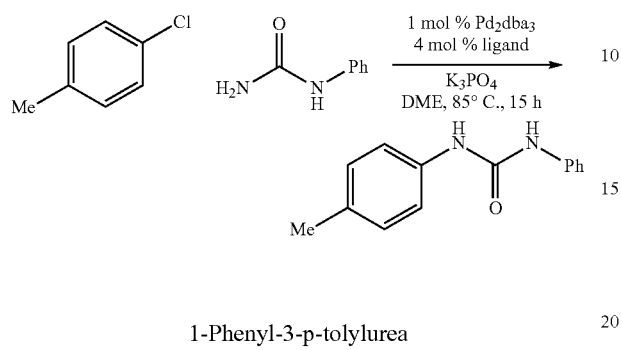

1-Phenyl-3-p-tolylurea

In a nitrogen-atmosphere glovebox, a microwave vial equipped with a magnetic stir bar was charged with phenylurea (100 mg, 0.734 mmol, 1 equivalent), potassium phosphate (234 mg, 1.10 mmol, 1.5 equivalents), tris(dibenzylideneacetone)dipalladium(0) (Pd$_2$dba$_3$) (6.7 mg, 0.00734 mmol, 0.01 equivalents) and phosphine ligand (0.029 mmol, 0.04 equivalents). Then 1,2-dimethoxyethane (1.34 mL) was syringed into the vial. After stirring the mixture for 1 hour at room temperature, 4-chlorotoluene (96 µL, 0.808 mmol, 1.1 equivalents) was added. The vial was sealed with a crimp top and placed in a heating block at 85° C. After 15 hours, the reaction vial was cooled to room temperature and brought out of the glovebox. The reaction solution was diluted with dimethylformamide (0.6 mL) and stirred for 15 minutes. The slurry was then filtered through a pad of diatomaceous earth. The vial was rinsed with dimethylformamide (0.6 mL) before passing through the filter. The combined filtrate was concentrated on a rotary evaporator to furnish an orange oil. A 1:1 mixture of methanol:water (3.5 mL) was added dropwise to the crude concentrate, leading to the precipitation of product. The solids were collected by filtration and washed with 1:1 methanol:water (3 mL). The isolated product urea was dried in a vacuum oven for 6 hours at 60° C./150 mm Hg. (literature reference: Kotecki B J, et al. Org. Lett. 2009; 11: 947-950). $^1$H NMR (400 MHz, DMSO-d$_6$) δ ppm 8.52 (t, J=22.7 Hz, 2H), 7.42 (dd, J=8.5, 1.0 Hz, 2H), 7.31 (t, J=5.4 Hz, 2H), 7.26 (dd, J=10.7, 5.2 Hz, 2H), 7.07 (d, J=8.2 Hz, 2H), 6.95 (dd, J=10.5, 4.2 Hz, 1H), 2.24 (s, 3H).

| Ligand | Conversion (%)[a] | Yield (%)[b] |
|---|---|---|
| 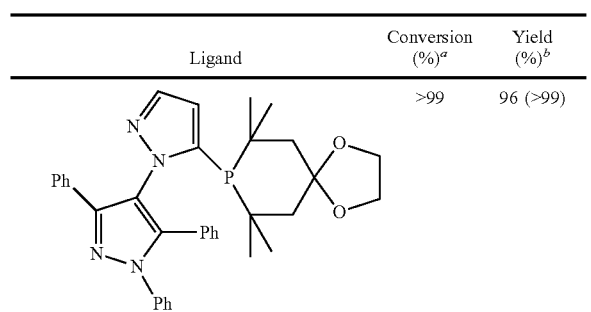 | >99 | 96 (>99) |
| 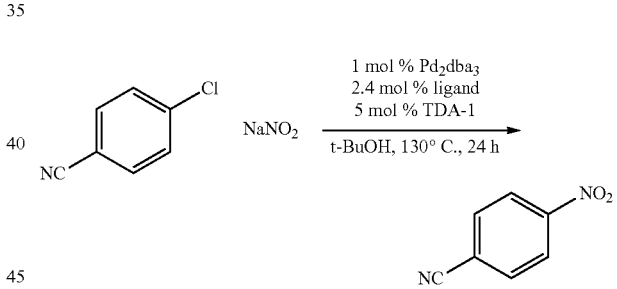 | >99 | 98 (>99) |
| (second structure in image 2) | 96[c] | — |

[a]Reaction conversion determined by reverse phase HPLC versus isolated, characterized product. The conversion is a ratio of ((desired)/(starting material + desired)).
[b]Isolated yields. Values in parentheses are the assay yields of the crude reaction mixtures measured by weight percent analyses.
[c]Reaction conversion measured after 22 hours at 85° C.

Example 20

Palladium-Catalyzed Nitration of an Aryl Chloride

4-Nitrobenzonitrile

In a nitrogen-atmosphere glovebox, a microwave vial equipped with a magnetic stir bar was charged with 4-chlorobenzonitrile (100 mg, 0.727 mmol, 1 equivalent), sodium nitrite (100 mg, 1.45 mmol, 2 equivalents), tris(dibenzylideneacetone)dipalladium(0) (Pd$_2$dba$_3$) (6.7 mg, 0.00727 mmol, 0.01 equivalents) and phosphine ligand (0.017 mmol, 0.024 equivalents). The solids were slurried in t-butyl alcohol (1.3 mL) before adding tris[2-(2-methoxyethoxy)ethyl]amine (TDA-1) (12 µL, 0.036 mmol, 0.05 equivalents). The vial was sealed with a crimp top and placed in a heating block at 130° C. After 24 hours, the reaction vial was cooled to room temperature and brought out of the glovebox. The reaction solution was diluted with tetrahydrofuran (2 mL) and filtered through a pad of diatomaceous earth into a tared 125-mL Erlenmeyer flask. The vial was rinsed with tetrahydrofuran (3×1 mL) before the filter cake was washed with tetrahydrofuran (2 mL). A wt % analysis was performed on the filtrate and an assay yield was measured (literature reference: Fors B P, et al. J. Am. Chem. Soc. 2009; 131: 12898-12899).

| Ligand | Assay Yield (%)[a] |
|---|---|
| (structure: biphenyl with OMe, MeO, diisopropyl/triisopropyl groups and phosphaspiro[4.5]decane with dioxolane) | 92 |
| (structure: biphenyl with diisopropyl groups and phosphaspiro[4.5]decane with dioxolane) | 32 |

[a]Assay yields were determined by weight percent analyses versus commercially available 4-nitrobenzonitrile.

4-Nitrobenzophenone

In a nitrogen-atmosphere glovebox, a microwave vial equipped with a magnetic stir bar was charged with 4-chlorobenzophenone (100 mg, 0.462 mmol, 1 equivalent), sodium nitrite (63.7 mg, 0.923 mmol, 2 equivalents), tris(dibenzylideneacetone)dipalladium(0) (Pd₂dba₃) (0.005 or 0.0025 equivalents) and 7,7,9,9-tetramethyl-8-(2',4',6'-triisopropyl-3,6-dimethoxybiphenyl-2-yl)-1,4-dioxa-8-phosphaspiro[4.5]decane (0.012 or 0.006 equivalents, respectively). The solids were slurried in t-butyl alcohol (0.84 mL) before adding tris[2-(2-methoxyethoxy)ethyl]amine (TDA-1) (7.4 μL, 0.023 mmol, 0.05 equivalents). The vial was sealed with a crimp top and placed in a heating block at 130° C. After indicated reaction time, the vial was cooled to room temperature and brought out of the glovebox. The reaction solution was diluted with tetrahydrofuran (2 mL) and filtered through a pad of diatomaceous earth into a tared 125-mL Erlenmeyer flask. The vial was rinsed with tetrahydrofuran (5×1 mL) before the filter cake was washed with tetrahydrofuran (5 mL). A wt % analysis was performed on the filtrate and an assay yield was measured.

| Ligand | mol % Pd₂dba₃ | mol % ligand | Time (h) | Assay Yield (%) |
|---|---|---|---|---|
| (structure: biphenyl with OMe, MeO, diisopropyl groups and phosphaspiro[4.5]decane with dioxolane) | 0.5% | 1.2% | 22 | 93 |
| | 0.25% | 0.6% | 24 | 96 |

[a]Assay yields were determined by weight percent analyses versus commercially available 4-nitrobenzophenone.

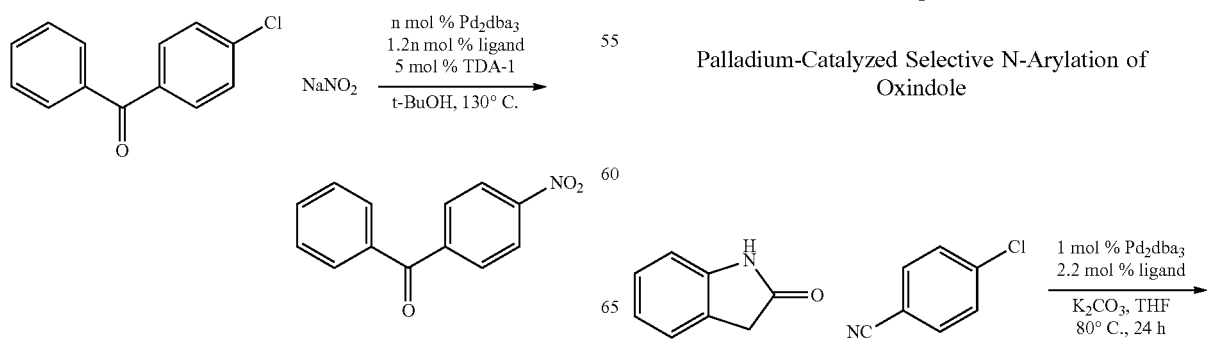

Example 21

Palladium-Catalyzed Selective N-Arylation of Oxindole

159
-continued

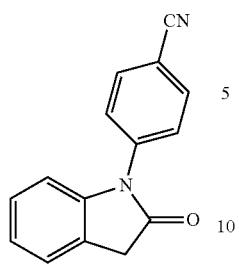

4-(2-Oxoindolin-1-yl)benzonitrile

In a nitrogen-atmosphere glovebox, a microwave vial equipped with a magnetic stir bar was charged with oxindole (40 mg, 0.300 mmol, 1 equivalent), 4-chlorobenzonitrile (50 mg, 0.361 mmol, 1.2 equivalents), potassium carbonate (83 mg, 0.601 mmol, 2 equivalents), tris(dibenzylideneacetone)dipalladium(0) ($Pd_2dba_3$) (2.8 mg, 0.0030 mmol, 0.01 equivalents) and 2,2,7,7-tetramethyl-1-(2',4',6'-triisopropylbiphenyl-2-yl)phosphepane (3.0 mg, 0.0066 mmol, 0.022 equivalents). Then tetrahydrofuran (0.3 mL) was syringed into the vial. The vial was sealed with a crimp top and placed in a heating block at 80° C. After 24 hours, the vial was removed from the heating block, cooled to room temperature and brought out of the glovebox. The reaction solution was diluted with tetrahydrofuran (2 mL) and filtered into a tared 125-mL Erlenmeyer flask. The vial was rinsed with tetrahydrofuran (2×2.5 mL), followed by washing of the filter cake with tetrahydrofuran (5 mL). A wt % analysis was performed on the filtered solution and an assay yield of 71% was measured (literature reference: Altman R A, et al. J. Am. Chem. Soc. 2008; 130: 9613-9620). $^1$H NMR (400 MHz, $CDCl_3$) δ ppm 7.90-7.82 (m, 2H), 7.68-7.60 (m, 2H), 7.41-7.34 (m, 1H), 7.32-7.25 (m, 1H), 7.21-7.13 (m, 1H), 6.93 (dd, J=9.8, 2.1 Hz, 1H), 3.79 (s, 2H).

| Ligand | Assay Yield (%)[a] |
|---|---|
| (structure) | 71 |

[a]Assay yield was determined by weight percent analysis versus isolated, characterized product.

160

Example 22

Palladium-Catalyzed Alkyl Suzuki-Miyaura Cross-Coupling with an Aryl Bromide

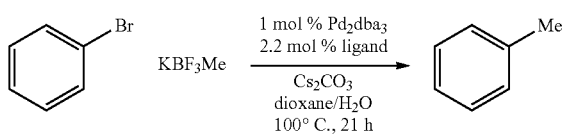

Toluene

In a nitrogen-atmosphere glovebox, a microwave vial equipped with a magnetic stir bar was charged with potassium trifluoromethylborate (140 mg, 1.15 mmol, 1.2 equivalents), cesium carbonate (934 mg, 2.87 mmol, 3 equivalents), tris(dibenzylideneacetone)dipalladium(0) ($Pd_2dba_3$) (8.8 mg, 0.00955 mmol, 0.01 equivalents), and phosphine ligand (0.021 mmol, 0.022 equivalents). Dioxane (1.7 mL) was added to the vial and the resulting slurry was stirred for 1 hour before adding water (190 μL) and bromobenzene (101 μL, 0.955 mmol, 1 equivalent). The vial was sealed with a crimp top and placed in a heating block at 100° C. After 21 hours, the reaction was cooled to room temperature and brought out of the glovebox. The reaction solution was filtered into a tared 125-mL Erlenmeyer flask. The vial was rinsed with dioxane (5×1 mL), followed by washing of the filter cake with dioxane (5 mL). A wt % analysis was performed on the filtrate to obtain an assay yield for toluene.

| Ligand | Assay Yield (%)[a] |
|---|---|
| (structure) | 68 |
| (structure) | 72 |

[a]Assay yields were determined by weight percent analyses versus a toluene standard.

Example 23

Palladium-Catalyzed Borylation of an Aryl Chloride

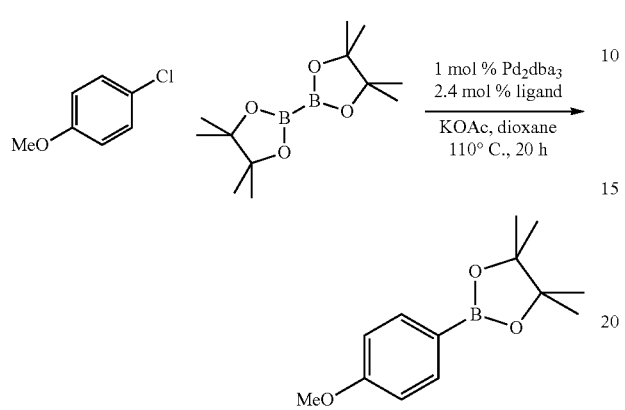

4-Methoxyphenylboronic acid pinacol ester

In a nitrogen-atmosphere glovebox, a microwave vial equipped with a magnetic stir bar was charged bis(pinacolato)diboron (107 mg, 0.421 mmol, 1.2 equivalents), potassium acetate (68.8 mg, 0.701 mmol, 2 equivalents), tris(dibenzylideneacetone)dipalladium(0) (Pd$_2$dba$_3$) (3.2 mg, 0.00351 mmol, 0.01 equivalents), and 8-(2',6'-diisopropoxybiphenyl-2-yl)-7,7,9,9-tetramethyl-1,4-dioxa-8-phosphaspiro[4.5]decane (4.1 mg, 0.00842 mmol, 0.024 equivalents). Then dioxane (0.7 mL) was syringed into the vial, followed by 4-chloroanisole (43 µL, 0.351 mmol, 1 equivalent). The vial was sealed with a crimp top and placed in a heating block at 110° C. After 20 hours, the reaction vial was removed from the heating block, cooled to room temperature and brought out of the glovebox. The reaction solution was filtered into a tared 125-mL Erlenmeyer flask. The vial was rinsed with dioxane (5×1 mL), followed by washing of the filter cake with dioxane (5 mL). A wt % analysis was performed on the filtered solution to obtain an assay yield of 73%.

| Ligand | Assay Yield (%)[a] |
|---|---|
| 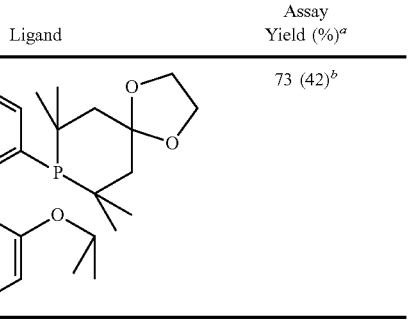 | 73 (42)[b] |

[a]Assay yields were determined by weight percent analyses versus commercially available material.
[b]Value in parentheses is the assay yield of the borylation when 0.25 mol % tris(dibenzylideneacetone)dipalladium(0) (Pd$_2$dba$_3$) and 0.6 mol % ligand were used under the same reaction conditions.

Example 24

Palladium-Catalyzed Fluorination of an Aryl Trifluoromethanesulfonate

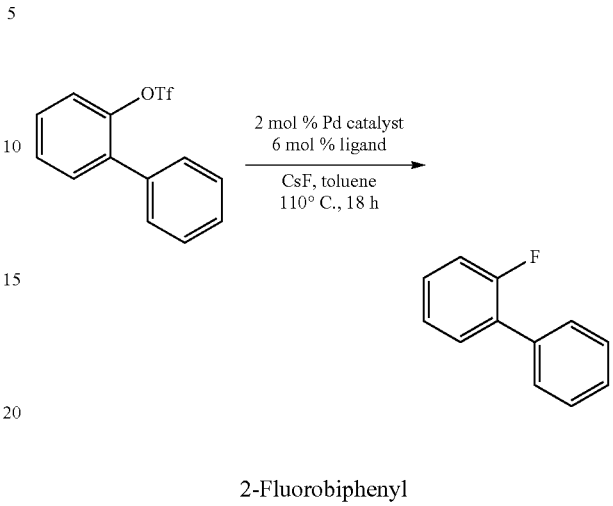

2-Fluorobiphenyl

In a nitrogen-atmosphere glovebox, a microwave vial equipped with a magnetic stir bar was charged with cesium fluoride (101 mg, 0.662 mmol, 2 equivalents), palladium catalyst (0.00662 mmol, 0.02 equivalents), 7,7,9,9-tetramethyl-8-(2',4',6'-triisopropyl-3,6-dimethoxybiphenyl-2-yl)-1,4-dioxa-8-phosphaspiro[4.5]decane (11.0 mg, 0.020 mmol, 0.06 equivalents) and biphenyl-2-yl trifluoromethanesulfonate (Wang J-Q, et al. Tetrahedron 2002; 58: 5927-5931) (100 mg, 0.331 mmol, 1 equivalent). After adding toluene (1.65 mL) the vial was sealed with a crimp top and placed in a heating block at 110° C. After 18 hours, the vial was removed from the heating block, cooled to room temperature and brought out of the glovebox. The reaction solution was diluted with tetrahydrofuran (2 mL) and filtered into a tared 125-mL Erlenmeyer flask. The vial was rinsed with tetrahydrofuran (5×1 mL), followed by washing of the filter cake with tetrahydrofuran (5 mL). A wt % analysis was performed on the filtered solution and an assay yield was measured against commercially available 2-fluorobiphenyl (literature reference: Watson D A, et al. Science 2009; 325: 1661-1664).

| Ligand | Pd catalyst | Assay Yield (%)[a] |
|---|---|---|
| 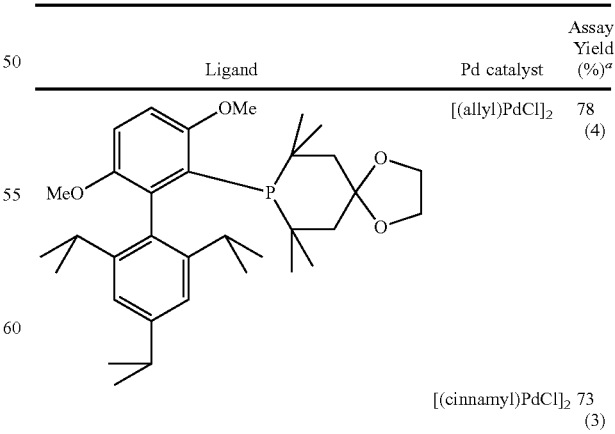 | [(allyl)PdCl]$_2$ | 78 (4) |
| | [(cinnamyl)PdCl]$_2$ | 73 (3) |

[a]Assay yields were determined by weight percent analyses versus commercially available material. Values in parentheses are the measured assay yields of biphenyl formed via reduction of starting triflate.

Example 25

Palladium-Catalyzed Arylation of a Secondary Amine

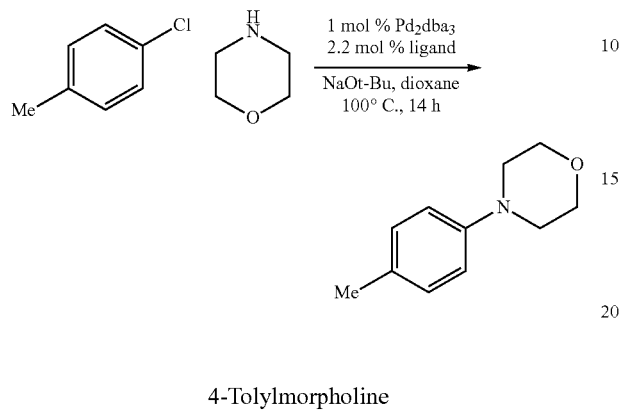

4-Tolylmorpholine

In a nitrogen-atmosphere glovebox, a microwave vial equipped with a magnetic stir bar was charged with sodium tert-butoxide (56.9 mg, 0.592 mmol, 1.5 equivalents), tris(dibenzylideneacetone)dipalladium(0) ($Pd_2dba_3$) (3.62 mg, 0.00395 mmol, 0.01 equivalents), phosphine ligand (0.00869 mmol, 0.022 equivalents) and dioxane (0.79 mL). To the slurry was added 4-chlorotoluene (47 μL, 0.395 mmol, 1 equivalents) and morpholine (42 μL, 0.474 mmol, 1.2 equivalents). The vial was sealed with a crimp top and stirred at 100° C. After 14 hours, the vial was removed from the heating block, cooled to room temperature and brought out of the glovebox. To assay the crude reaction, an aliquot (7 μL) was taken and diluted in acetonitrile (1.5 mL), then injected onto an HPLC instrument. For isolation purposes, the reaction solution was worked up by diluting with $CH_2Cl_2$ (2 mL) and filtering into a round-bottom flask. The vial was rinsed with $CH_2Cl_2$ (5 mL), followed by washing of the filter cake with $CH_2Cl_2$ (2 mL). The volatiles were removed on a rotary evaporator and the crude concentrate was purified by silica gel column chromatography (25 g silica gel, 85:15 heptane:ethyl acetate). The purified product was isolated as a beige solid. $^1$H NMR (400 MHz, $CDCl_3$) δ ppm 7.10 (d, J=8.2 Hz, 1H), 6.88-6.81 (m, 2H), 3.87 (dd, J=5.7, 3.9 Hz, 4H), 3.15-3.09 (m, 4H), 2.29 (s, 3H).

| Ligand | Conversion (%)[a] | Area%[b] |
|---|---|---|
| (biphenyl phosphine with dioxolane) | >99 | 87.8 (93%)[c] |
| (2,4,6-triisopropylbiphenyl phosphine with dioxolane) | >99 | 74.3 |
| (2,6-diethoxybiphenyl phosphine with dioxolane) | >99 | 75.1 |
| (2,6-dimethoxybiphenyl phosphine with dioxolane) | >99 | 81.9 (83%)[c] |
| (2-NMe2-6-OMe biphenyl phosphine with dioxolane) | >99 | 77.6 |

[a] Reaction conversion determined by reverse phase HPLC versus isolated, characterized product. The conversion is a ratio of ((desired)/(starting material + desired)).
[b] Area % of desired product in the crude reaction solution measured at 210 nm by HPLC.
[c] Isolated yield of product following column chromatography.

Example 26

Palladium-Catalyzed Coupling of Bromobenzene with a Thiol

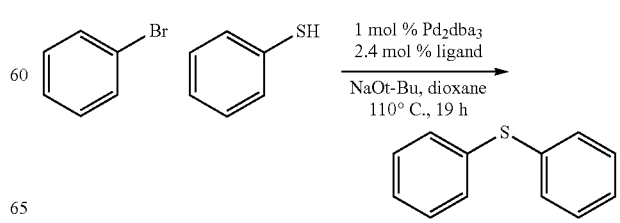

Diphenylsulfide

In a nitrogen-atmosphere glovebox, a microwave vial equipped with a magnetic stir bar was charged with sodium tert-butoxide (33.7 mg, 0.350 mmol, 1.1 equivalents), tris(dibenzylideneacetone)dipalladium(0) (Pd$_2$dba$_3$) (2.9 mg, 0.00318 mmol, 0.01 equivalents), 7,7,9,9-tetramethyl-8-(2',4',6'-triisopropylbiphenyl-2-yl)-1,4-dioxa-8-phosphaspiro[4.5]decane (3.8 mg, 0.00764 mmol, 0.024 equivalents) and dioxane (0.48 mL). The slurry was stirred at room temperature for 1 hour before adding bromobenzene (34 μL, 0.318 mmol, 1 equivalent) and benzenethiol (33 μL, 0.318 mmol, 1 equivalent). The vial was sealed with a crimp top and stirred at 110° C. After 19 hours, the vial was removed from the heating block, cooled to room temperature and brought out of the glovebox. The reaction solution was diluted with tetrahydrofuran (2 mL) and filtered into a tared 125-mL Erlenmeyer flask. The vial was rinsed with tetrahydrofuran (5×1 mL), followed by washing of the filter cake with tetrahydrofuran (5 mL). A wt % analysis was performed on the filtered solution and an assay yield of 88% was measured against commercially available diphenylsulfide.

| Ligand | Assay Yield (%)[a] |
|---|---|
| (structure) | 88 |

[a] Assay yield was determined by weight percent analysis versus commercially available material.

Example 27

Palladium-Catalyzed Suzuki-Miyaura Coupling

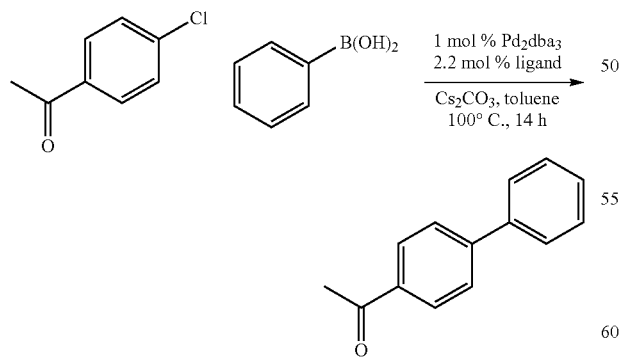

4-Acetylbiphenyl

In a nitrogen-atmosphere glovebox, a microwave vial equipped with a magnetic stir bar was charged with phenylboronic acid (59 mg, 0.485 mmol, 1.5 equivalents), cesium carbonate (316 mg, 0.970 mmol, 3 equivalents), tris(dibenzylideneacetone)dipalladium(0) (Pd$_2$dba$_3$) (3.0 mg, 0.00323 mmol, 0.01 equivalents), phosphine ligand (0.00712 mmol, 0.022 equivalents) and toluene (0.65 mL). The slurry was stirred at room temperature for 1 hour before adding 4'-chloroacetophenone (42 μL, 0.323 mmol, 1 equivalents). The vial was sealed with a crimp top and stirred at 100° C. After 14 hours, the vial was removed from the heating block, cooled to room temperature and brought out of the glovebox. The reaction solution was diluted with tetrahydrofuran (2 mL) and filtered into a tared 125-mL Erlenmeyer flask. The vial was rinsed with tetrahydrofuran (3×2 mL), followed by washing of the filter cake with tetrahydrofuran (5 mL). A wt % analysis was performed on the filtered solution and an assay yield was measured versus commercially available 4-acetylbiphenyl. A modified solvent gradient was utilized in the HPLC method for the weight % analyses. On an Ascentis® Express C8 (2.7 μm, 4.6 mm×150 mm) column at 40° C. with a flow rate of 1.5 mL/minute, the following gradient was used: starting at 60% A (0.1% HClO$_4$ in water) and 40% B (acetonitrile), ramped up to 5% A and 95% B over 8 minutes, followed by a 2 minute hold, and ramp down to 60% A and 40% B over 1 minute.

| Ligand | Assay Yield (%)[a] |
|---|---|
| (structure) | 80 |
| (structure) | 85 |
| (structure) | 87 |

[a] Assay yields were determined by weight percent analyses versus commercially available material.

Example 28

Palladium-Catalyzed Cyanation of an Aryl Bromide

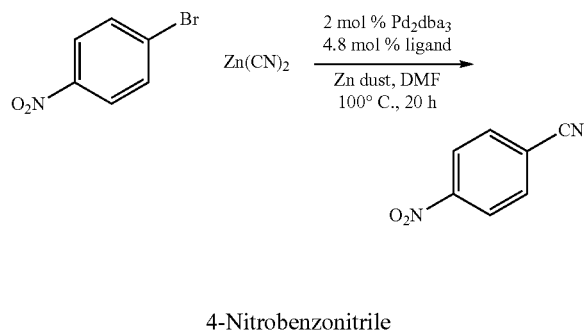

4-Nitrobenzonitrile

In a nitrogen-atmosphere glovebox, a microwave vial equipped with a magnetic stir bar was charged with 1-bromo-4-nitrobenzene (50 mg, 0.248 mmol, 1 equivalent), zinc cyanide (16.0 mg, 0.136 mmol, 0.55 equivalents), zinc dust (1.6 mg, 0.025 mmol, 0.1 equivalents), tris(dibenzylideneacetone)dipalladium(0) (Pd$_2$dba$_3$) (4.5 mg, 0.00495 mmol, 0.02 equivalents), phosphine ligand (0.012 mmol, 0.048 equivalents) and dimethylformamide (0.55 mL). The vial was sealed with a crimp top and stirred at 100° C. After 20 hours, the vial was removed from the heating block, cooled to room temperature and brought out of the glovebox. The reaction solution was diluted with tetrahydrofuran (2 mL) and filtered into a tared 50-mL Erlenmeyer flask. The vial was rinsed with tetrahydrofuran (5×1 mL), followed by washing of the filter cake with tetrahydrofuran (5 mL). A wt % analysis was performed on the filtered solution and an assay yield was measured versus commercially available 4-nitrobenzonitrile.

| Ligand | Assay Yield (%)[a] |
|---|---|
| 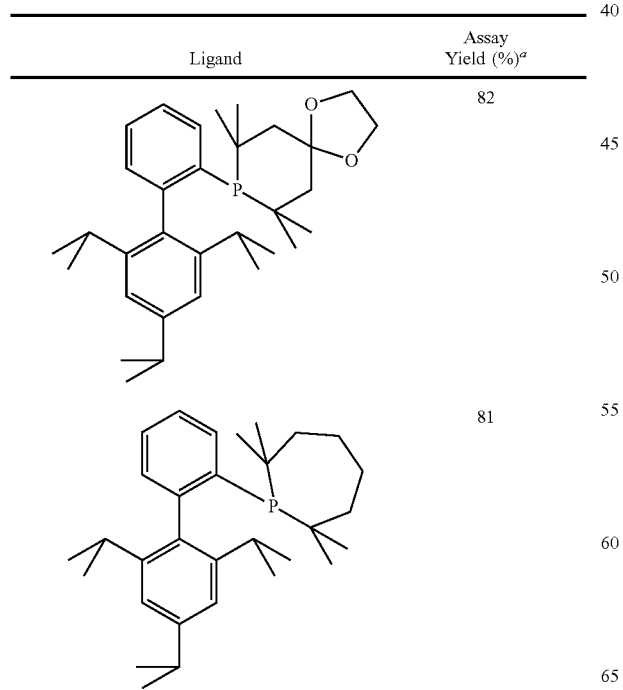 | 82 |
| | 81 |
| | 78 |
| | 81 |
| | 77 |
| | 74 |

[a]Assay yields were determined by weight percent analyses versus commercially available material.

Example 29

Palladium-Catalyzed Coupling of Diethylphosphite with Bromobenzene

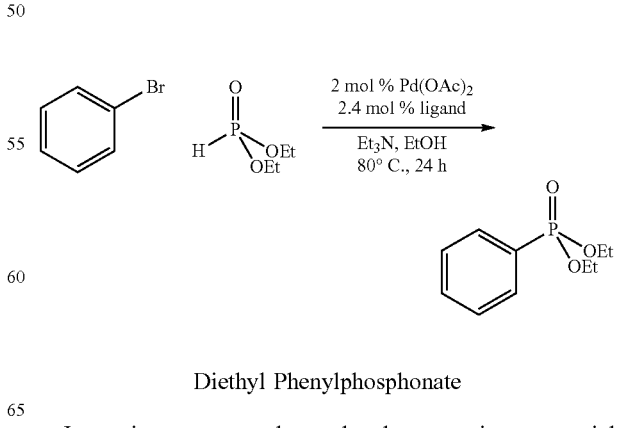

Diethyl Phenylphosphonate

In a nitrogen-atmosphere glovebox, a microwave vial equipped with a magnetic stir bar was charged with palladium(II) acetate (1.4 mg, 0.00637 mmol, 0.02 equivalents), 8-(1,1'-binaphthyl-2-yl)-7,7,9,9-tetramethyl-1,4-dioxa-8-phosphaspiro[4.5]decane (3.6 mg, 0.00764 mmol, 0.024 equivalents) and ethanol (0.64 mL). To the slurry were added triethylamine (67 µL, 0.478 mmol, 1.5 equivalents), bromobenzene (34 µL, 0.318 mmol, 1 equivalent) and diethylphosphite (49 µL, 0.382 mmol, 1.2 equivalents). The vial was sealed with a crimp top and stirred at 80° C. After 24 hours, the vial was removed from the heating block, cooled to room temperature and brought out of the glovebox. The reaction solution was diluted with tetrahydrofuran (2 mL) and filtered into a tared 125-mL Erlenmeyer flask. The vial was rinsed with tetrahydrofuran (5×1 mL), followed by washing of the filter cake with tetrahydrofuran (5 mL). A wt % analysis was performed on the filtrate and an assay yield of 59% was measured versus commercially available diethyl phenylphosphonate.

| Ligand | Assay Yield (%)[a] |
|---|---|
|  | 59 |

[a] Assay yield was determined by weight percent analysis versus commercially available material.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. A compound having a structure corresponding to formula (I), or a salt thereof, $$R^1-Ar^1-X$$
$$R^2-Ar^2$$
(I)

wherein $Ar^1$ and $Ar^2$ are each independently aryl or heteroaryl, and wherein $Ar^1$ and $Ar^2$ are each independently optionally substituted with one or more $R^1$ and $R^2$, respectively;

$R^1$ and $R^2$ are independently selected at each occurrence from the group consisting of hydrogen; amino; hydroxyl; cyano; halo; alkyl; alkenyl; alkynyl; haloalkyl; haloalkoxy; oxoalkyl; alkoxy; aryloxy; heteroaryloxy; arylamino; heteroarylamino; alkylamino; dialkylamino; cycloalkyl optionally substituted with alkyl, alkenyl, alkynyl, alkoxy, cyano, halo, haloalkyl or haloalkoxy; cycloalkyloxy optionally substituted with alkyl, alkenyl, alkynyl, alkoxy, cyano, halo, haloalkyl or haloalkoxy; 5- or 6-membered heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; hydroxyalkoxy; alkoxyalkyl; aminoalkyl; N-alkylaminoalkyl; N,N-dialkylaminoalkyl; N,N,N-trialkylammoniumalkyl; $L^1C(O)-OR^{1'}$, $L^1P(O)-(OR^{1'})_2$, or $L^1-S(O)_2-OR^{1'}$, wherein $L^1$ is a bond or alkylene, and $R^{1'}$ is selected from the group consisting of hydrogen, alkyl and hydroxyalkyl; $L^2-O-C(O)-R^{2'}$, wherein $L^2$ is a bond or alkylene, and $R^{2'}$ is alkyl or hydroxyalkyl; $L^3-C(O)-NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4-NR^{5'}C(O)-R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; sulfate; alkylthio; thioalkyl; and a ring containing an alkylene or $-O-(CH_2)_m-O-$ formed by the joining together of any two $R^1$ or any two $R^2$ or an $R^1$ and an $R^2$, wherein m is 1, 2, 3 or 4;

X is a phosphine of formula (Ia):

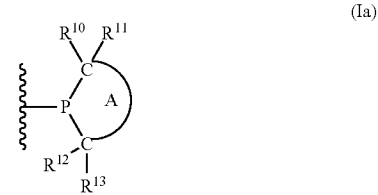
(Ia)

wherein ring A includes 0 to 9 ring atoms in addition to the phosphorus and 2 carbon ring atoms of formula (Ia), wherein said ring atoms are each independently selected from the group consisting of carbon, oxygen, nitrogen, phosphorus and sulfur; and wherein the ring atoms of ring A are each independently optionally substituted with one or more substituents selected from the group consisting of alkenyl; alkoxy; alkoxyalkyl; alkyl; alkylamino; alkylthio; alkynyl; aminoalkyl; N-alkylaminoalkyl; N,N-dialkylaminoalkyl; N,N,N-trialkylammoniumalkyl; arylalkyl optionally substituted with alkyl, alkenyl, alkynyl, alkoxy, cyano, halo, haloalkyl or haloalkoxy; cycloalkyl optionally substituted with alkyl, alkenyl, alkynyl, alkoxy, cyano, halo, haloalkyl or haloalkoxy; dialkylamino; halo; haloalkyl; fluoroalkyl; heteroaryl optionally substituted with alkyl, alkenyl, alkynyl, alkoxy, cyano, halo, haloalkyl or haloalkoxy; heterocycloalkyl optionally substituted with alkyl, alkenyl, alkynyl, alkoxy, cyano, halo, haloalkyl or haloalkoxy; hydroxy; hydroxyalkyl; oxo; an exocyclic double bond optionally substituted with alkyl, alkenyl, alkynyl, aryl, cycloalkyl, heterocyclyl, or heteroaryl; a 3- to 7-membered spiro ring containing zero, one, or two heteroatoms; phenyl optionally substituted with alkyl, alkenyl, alkynyl, alkoxy, cyano, halo, haloalkyl or haloalkoxy; $L^1-C(O)-OR''$, $L^1-P(O)-(OR^{1'})_2$, or $L^1S(O)_2-OR^{1'}$, wherein $L^1$ is a bond or alkylene, and $R^{1'}$ is selected from the group consisting of hydrogen, alkyl or hydroxyalkyl; $L^2-O-C(O)-R^{2'}$, wherein $L^2$ is a bond or alkylene, and $R^{2'}$ is alkyl or hydroxyalkyl; $L^3-C$ (O)—NR$^{3'}$R$^{4'}$, wherein L$^3$ is a bond or alkylene, and R$^{3'}$ and R$^{4'}$ are each independently selected from the group consisting of hydrogen, alkyl, and hydroxyalkyl; L$^4$-NR$^{5'}$C(O)—R$^{6'}$, wherein L$^4$ is a bond or alkylene, R$^{5'}$ is hydrogen or alkyl, and R$^{6'}$ is alkyl or hydroxyalkyl; and L$^7$-NR$^{8'}$—S(O)$_2$—R$^{9'}$, wherein L$^7$ is a bond or alkylene, R$^{8'}$ is hydrogen or alkyl, and R$^{9'}$ is alkyl or hydroxyalkyl; and as to R$^{10}$, R$^{11}$, R$^{12}$, and R$^{13}$, i. R$^{10}$ or R$^{11}$ together with R$^{12}$ or R$^{13}$ form a ring; or ii. R$^{10}$ and R$^{11}$ together with the carbon atom to which they are attached form a spirocyclic ring and/or R$^{12}$ and R$^{13}$ together with the carbon atom to which they are attached form a spirocyclic ring;

wherein, any of substituents R$^{10}$, R$^{11}$, R$^{12}$, and R$^{13}$ that do not form the ring set forth in (i) or (ii) are each independently selected from the group consisting of hydrogen; alkyl; alkenyl; haloalkyl; alkynyl; oxoalkyl; cycloalkyl optionally substituted with alkyl, alkenyl, alkynyl, alkoxy, cyano, halo, haloalkyl or haloalkoxy; heterocyclyl optionally substituted with alkyl, alkenyl, alkynyl, alkoxy, cyano, halo, haloalkyl or haloalkoxy; heteroaryl optionally substituted with alkyl, alkenyl, alkynyl, alkoxy, cyano, halo, haloalkyl or haloalkoxy; phenyl optionally substituted with alkyl, alkenyl, alkynyl, alkoxy, cyano, halo, haloalkyl or haloalkoxy; hydroxyalkyl; alkoxyalkyl; aminoalkyl; N-alkylaminoalkyl; N,N-dialkylaminoalkyl; N,N,N-trialkylammoniumalkyl; thioalkyl; L$^{13}$-C(O)—OR$^{14'}$, L$^{13}$-P(O)—(OR$^{14'}$)$_2$, or L$^{13}$-S(O)$_2$—OR$^{14'''}$, wherein L$^{13}$ is a bond or alkylene, and R$^{14''}$ is selected from the group consisting of hydrogen, alkyl and hydroxyalkyl; L$^{15}$-O—C(O)—R$^{16'}$, wherein L$^{15}$ is alkylene and R$^{16'}$ is alkyl or hydroxyalkyl; L$^{17}$-C(O)—NR$^{18'}$R$^{19'}$, wherein L$^{17}$ is a bond or alkylene, and R$^{18}$ and R$^{19'}$ are each independently selected from the group consisting of hydrogen, alkyl, and hydroxyalkyl; and L$^{20}$-NR$^{2''}$—C(O)—R$^{22'}$, wherein L$^{20}$ is alkylene, R$^{2'''}$ is hydrogen or alkyl, and R$^{22'}$ is alkyl or hydroxyalkyl.

2. The compound or salt of claim 1, wherein the compound has a structure corresponding to a structure of a formula selected from the group consisting of formulae (I-1)-(I-42):

(I-1)

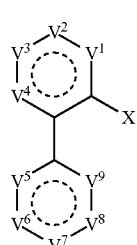

(I-2)

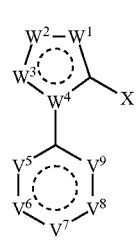

(I-3)

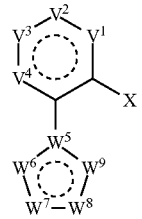

(I-4)

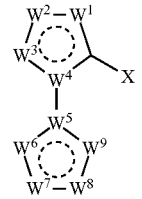

(I-5)

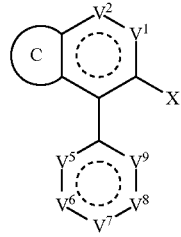

(I-6)

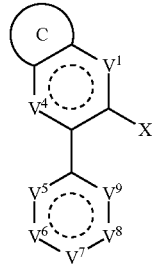

(I-7)

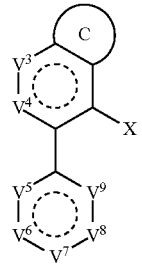

(I-8)

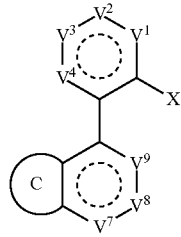

(I-9) 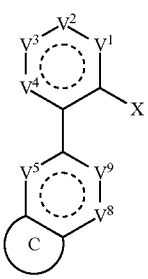
(I-10) 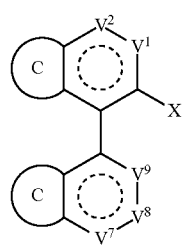
(I-11) 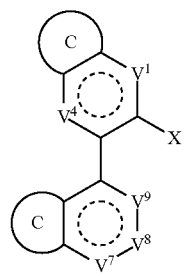
(I-12) 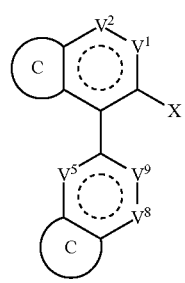
(I-13) 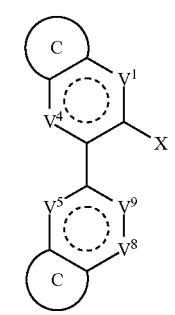
(I-14) 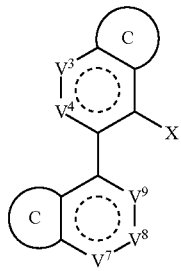
(I-15) 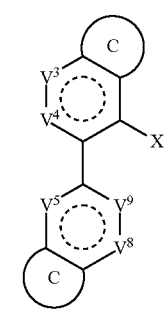
(I-16) 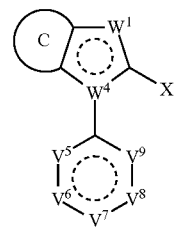
(I-17) 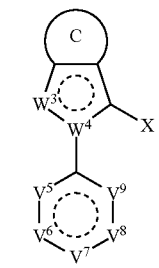
(I-18) 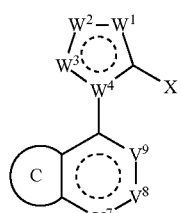
(I-19) 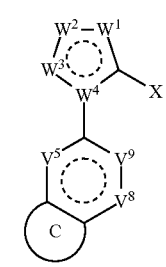

-continued
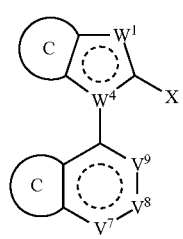 (I-20)
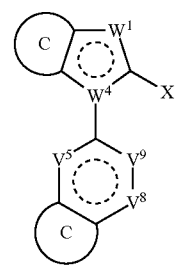 (I-21)
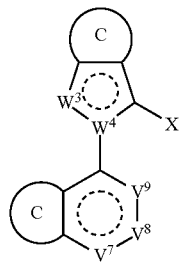 (I-22)
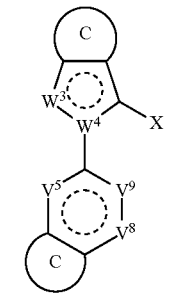 (I-23)
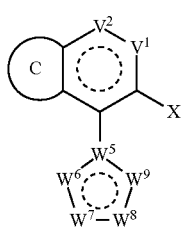 (I-24)
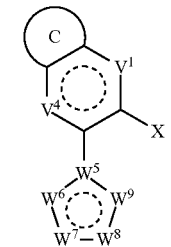 (I-25)
-continued
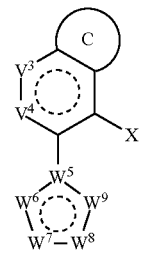 (I-26)
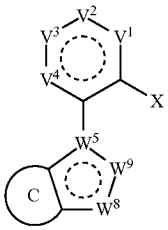 (I-27)
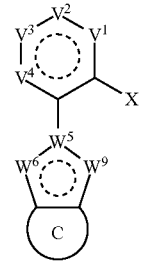 (I-28)
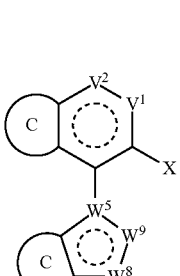 (I-29)
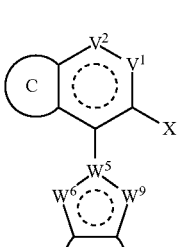 (I-30)
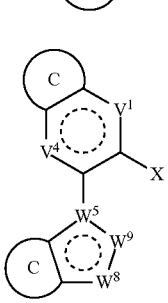 (I-31)

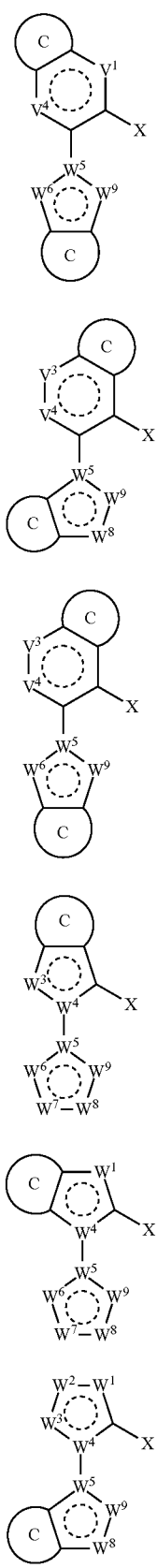
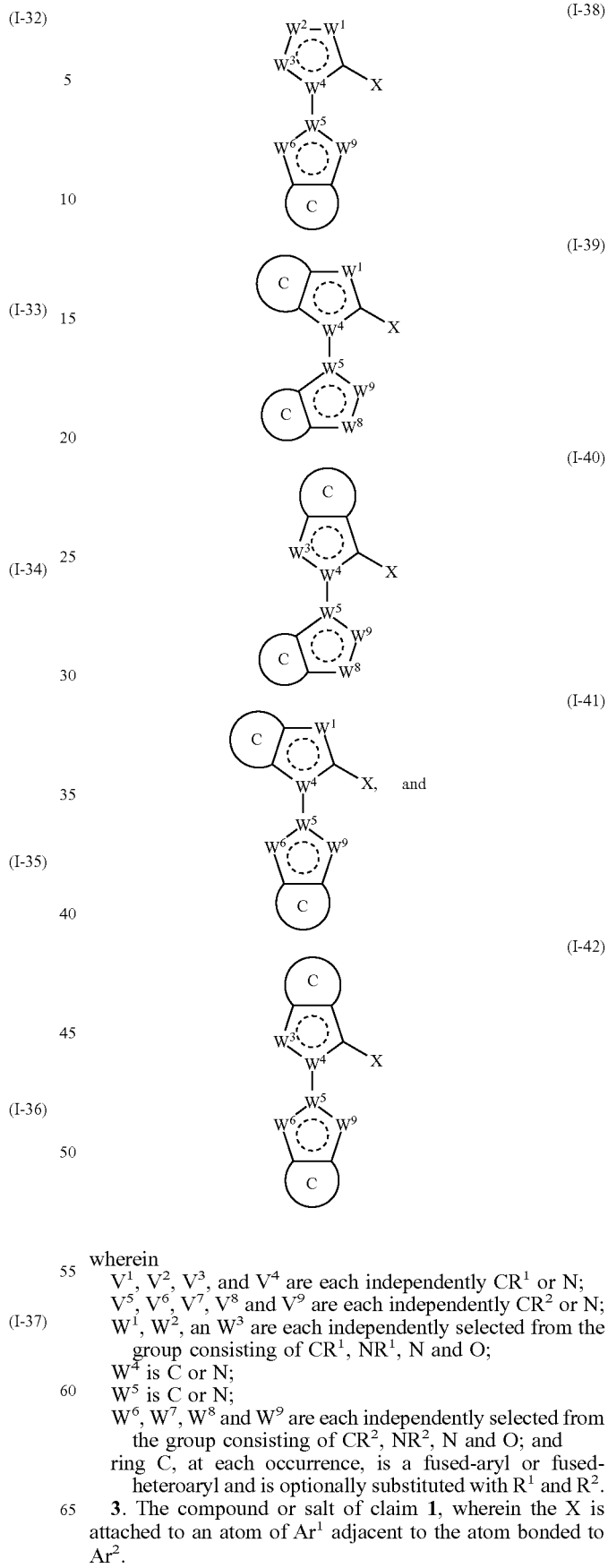

wherein
$V^1$, $V^2$, $V^3$, and $V^4$ are each independently $CR^1$ or N;
$V^5$, $V^6$, $V^7$, $V^8$ and $V^9$ are each independently $CR^2$ or N;
$W^1$, $W^2$, an $W^3$ are each independently selected from the group consisting of $CR^1$, $NR^1$, N and O;
$W^4$ is C or N;
$W^5$ is C or N;
$W^6$, $W^7$, $W^8$ and $W^9$ are each independently selected from the group consisting of $CR^2$, $NR^2$, N and O; and
ring C, at each occurrence, is a fused-aryl or fused-heteroaryl and is optionally substituted with $R^1$ and $R^2$.

3. The compound or salt of claim 1, wherein the X is attached to an atom of $Ar^1$ adjacent to the atom bonded to $Ar^2$.

4. The compound or salt of claim 1, wherein $Ar^1$ and $Ar^2$ are each aryl.

5. The compound or salt of claim 1, wherein $Ar^2$ is substituted with three $R^2$.

6. The compound or salt of claim 1, wherein $R^2$ is alkyl.

7. The compound or salt of claim 1, wherein $R^2$ is isopropyl.

8. The compound or salt of claim 1, wherein X is a phosphine having a structure corresponding to a formula selected from the group consisting of:

1-23
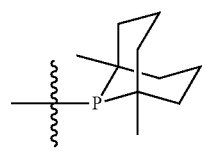

1-24
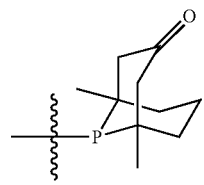

1-25
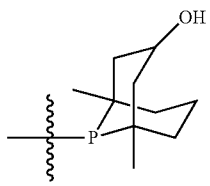

1-26
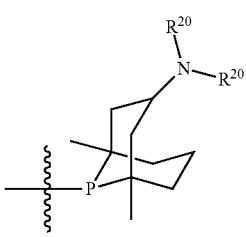

1-27
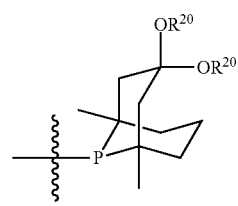

1-28
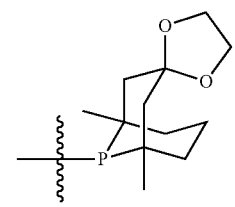

1-29
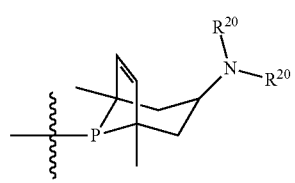

-continued 1-30
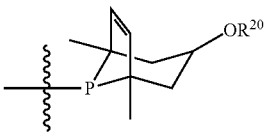

1-31
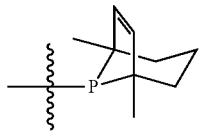

1-32
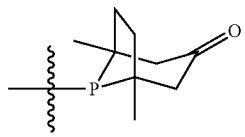

1-33
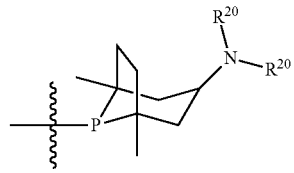

1-34
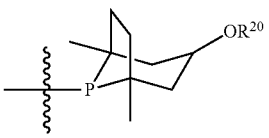

1-35
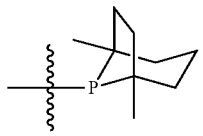

1-36
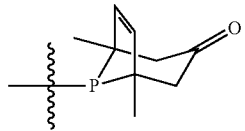

1-37
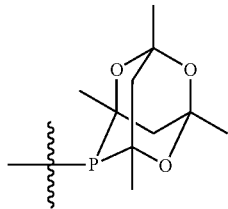

1-38
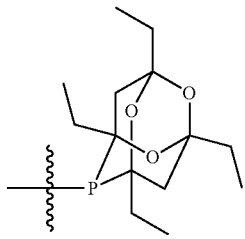

1-39 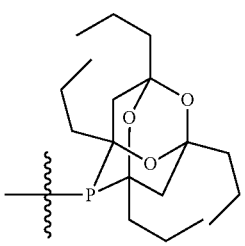

1-40 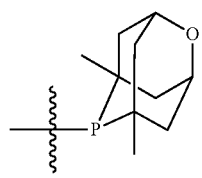

1-41 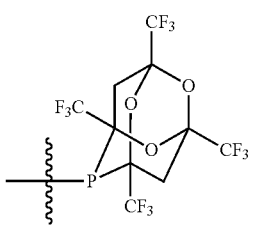

1-45 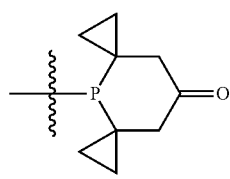

1-46 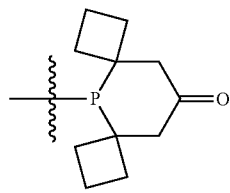

1-47 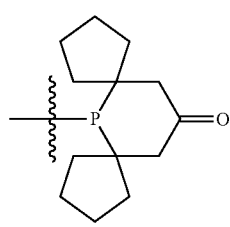

1-48 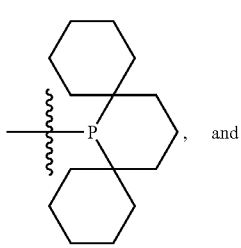, and 1-49 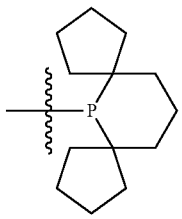

wherein $R^{20}$ is hydrogen, alkyl, aryl, heteroaryl, arylalkyl or heteroarylalkyl, wherein the aryl, heteroaryl, aryl of arylalkyl and heteroaryl of heteroarylalkyl are optionally substituted with alkyl, alkenyl, alkynyl, alkoxy, cyano, halo, haloalkyl or haloalkoxy.

9. The compound or salt of claim 1, wherein X is a phosphine of formula 1-37

1-37 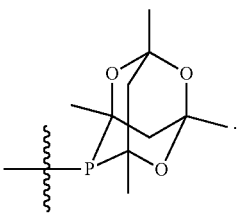

10. A compound or salt thereof, wherein the compound has a structure corresponding to formula (I-1), (I-1) 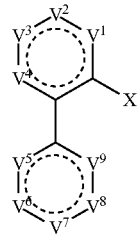

wherein
X is a phosphine of formula 1-37

1-37 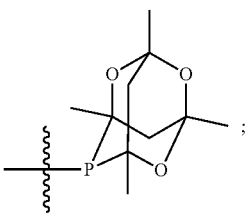;

$V^1$, $V^2$, $V^3$ and $V^4$ are each $CR^1$, wherein $R^1$ is, at each occurrence, hydrogen;
$V^5$ and $V^9$ are $CR^2$, wherein $R^2$ is independently, at each occurrence, hydrogen or alkyl;
$V^6$ and $V^8$ are $CR^2$, wherein $R^2$, at each occurrence, is hydrogen;
$V^7$ is $CR^2$, wherein $R^2$ is hydrogen or alkyl.

11. The compound or salt of claim 10, wherein the compound is selected from the group consisting of:
1,3,5,7-tetramethyl-8-(2',4',6'-triisopropylbiphenyl-2-yl)-2,4,6-trioxa-8-phosphatricyclo[3.3.1.1$^{3,7}$]decane; and
8-(biphenyl-2-yl)-1,3,5,7-tetramethyl-2,4,6-trioxa-8-phosphatricyclo[3.3.1.1$^{3,7}$]decane.

12. A catalyst composition comprising a transition metal catalyst precursor and a compound according to claim 10.

13. The catalyst composition according to claim 12, wherein the transition metal catalyst precursor is selected from the group consisting of palladium, rhodium, ruthenium, platinum, gold, cobalt, iridium, copper and nickel.

14. The catalyst composition according to claim 12, wherein the transition metal catalyst precursor contains palladium.

15. A heterogeneous catalyst composition comprising a compound according to claim 10 covalently bonded to a solid catalyst support.

16. A method for synthesizing a secondary organic sulfonamide, comprising reacting an aryl nonaflate with a primary sulfonamide in the presence of a palladium catalyst precursor and a compound of claim 10.

17. A method of performing a bond-forming reaction comprising catalyzing said reaction with a compound of claim 10, wherein the bond-forming reaction is selected from the group consisting of carbon-nitrogen, carbon-oxygen, carbon-carbon, carbon-sulfur, carbon-phosphorus, carbon-boron, carbon-fluorine and carbon-hydrogen.

18. A method of forming a bond in a chemical reaction comprising catalyzing said reaction with a compound of claim 10, wherein the bond is selected from the group consisting of a carbon-nitrogen bond, a carbon-oxygen bond, a carbon-carbon bond, a carbon-sulfur bond, a carbon-phosphorus bond, a carbon-boron bond, a carbon-fluorine bond and a carbon-hydrogen bond.

19. A process for preparing compound (A), comprising: coupling a sulfonamide with compound (5) in the presence of a catalyst composition:

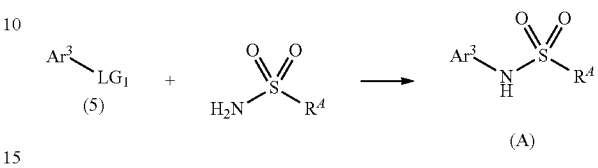

wherein
Ar$^3$ is optionally substituted aryl or optionally substituted heteroaryl;
LG$_1$ is —OSO$_2$R$^{1a}$, wherein R$^{1a}$ is fluoroalkyl;
R$^4$ is optionally substituted aryl or alkyl; and
the catalyst composition comprises a transition metal catalyst precursor and a compound or salt of claim 10.

20. The process of claim 19, wherein the catalyst composition comprises a compound selected from the group consisting of:
1,3,5,7-tetramethyl-8-(2',4',6'-triisopropylbiphenyl-2-yl)-2,4,6-trioxa-8-phosphatricyclo[3.3.1.1$^{3,7}$]decane; and
8-(biphenyl-2-yl)-1,3,5,7-tetramethyl-2,4,6-trioxa-8-phosphatricyclo[3.3.1.13'7]decane.

* * * * *